(12) United States Patent
Kim et al.

(10) Patent No.: US 9,865,820 B2
(45) Date of Patent: Jan. 9, 2018

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Hyungsun Kim, Suwon-si (KR); Byungku Kim, Suwon-si (KR); Youngkwon Kim, Suwon-si (KR); Changwoo Kim, Suwon-si (KR); Changju Shin, Suwon-si (KR); Seungjae Lee, Suwon-si (KR); Eunsun Yu, Suwon-si (KR); Byoungki Choi, Hwaseong-si (KR); Kyuyoung Hwang, Ansan-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 297 days.

(21) Appl. No.: 14/596,645

(22) Filed: Jan. 14, 2015

(65) Prior Publication Data
US 2015/0200371 A1 Jul. 16, 2015

(30) Foreign Application Priority Data
Jan. 14, 2014 (KR) ........................ 10-2014-0004687

(51) Int. Cl.
*H01L 51/00* (2006.01)
*H01L 51/50* (2006.01)
(Continued)

(52) U.S. Cl.
CPC ........ *H01L 51/0067* (2013.01); *C07D 493/04* (2013.01); *C07D 495/04* (2013.01);
(Continued)

(58) Field of Classification Search
None
See application file for complete search history.

(56) References Cited

U.S. PATENT DOCUMENTS 6,687,266 B1 2/2004 Ma et al.
7,154,144 B2 12/2006 Kim et al.
(Continued)

FOREIGN PATENT DOCUMENTS

JP 1999-144867 A 5/1999
KR 10-2013-0016163 A 2/2013
(Continued)

OTHER PUBLICATIONS

Machine English translation of Byun et al. (KR 10-2014-0006201). Jan. 26, 2017.*

(Continued)

*Primary Examiner* — J. L. Yang
(74) *Attorney, Agent, or Firm* — Cantor Colburn LLP

(57) ABSTRACT

A condensed cyclic compound represented by Formula 1, (Continued)

10

| 19 |
|---|
| 15 |
| 11 | wherein, in Formula 1, $L_1$, $E_1$, $R_1$, $X_{11}$ to $X_{13}$, $X_{21}$ to $X_{26}$, a1, and b1 are described in the specification.

24 Claims, 1 Drawing Sheet

(51) Int. Cl.
  *C07D 493/04* (2006.01)
  *C07D 495/04* (2006.01)
  *C07D 498/04* (2006.01)
  *C09K 11/06* (2006.01)
  *C09B 57/00* (2006.01)

(52) U.S. Cl.
  CPC ............ *C07D 498/04* (2013.01); *C09B 57/00* (2013.01); *C09K 11/06* (2013.01); *H01L 51/0071* (2013.01); *H01L 51/5012* (2013.01); *H01L 51/5056* (2013.01); *H01L 51/5072* (2013.01); *C09K 2211/185* (2013.01); *H01L 51/5016* (2013.01); *H01L 2251/5384* (2013.01)

(56) References Cited

U.S. PATENT DOCUMENTS

| | | | |
|---|---|---|---|
| 7,429,426 | B2 | 9/2008 | Brown et al. |
| 7,585,573 | B2 | 9/2009 | Lee et al. |
| 2007/0001166 | A1 | 1/2007 | Tao et al. |
| 2011/0136755 | A1 | 6/2011 | Rieger et al. |
| 2011/0278555 | A1 | 11/2011 | Inoue et al. |
| 2012/0138911 | A1 | 6/2012 | Inoue et al. |
| 2014/0197386 | A1* | 7/2014 | Kim .................. H01L 51/0067 257/40 |
| 2014/0374724 | A1* | 12/2014 | Kim .................. H01L 51/0072 257/40 |
| 2015/0228909 | A1 | 8/2015 | Kim et al. |

FOREIGN PATENT DOCUMENTS

| | | | |
|---|---|---|---|
| KR | 10-2013-0064001 | A | 6/2013 |
| KR | 10-2014-0006201 | * | 1/2014 |
| WO | 2012039561 | A1 | 3/2012 |
| WO | 2013081416 | A1 | 6/2013 |
| WO | 2013085339 | A2 | 6/2013 |
| WO | 2013085339 | A3 | 6/2013 |
| WO | WO-2014/003336 | A1 * | 1/2014 |
| WO | 2014065498 | A1 | 5/2014 |

OTHER PUBLICATIONS

Extended European Search Report issued by the European Patent Office dated Apr. 21, 2015.

Hans-J. Teuber et al. "Pyrazolo[3.4-c]carbazole aus Cyclohexandion-(1.4)-bis-phenylhydrazon", Chem. Ber. 1970, 103 (10), 3302-3318.

Hirotaka Kudo et al. "Angular Polycyclic Thiophenes Containing Two Thiophene Rings. I.", J. Heterocyclic Chem. 1984, 21, 185-192.

Izvestiya Vysshikh Uchebnykh Zavedenii, Khimiya i Khimicheskaya Tekhnologiya 1990, 33(6), 108-114.

Izvestiya Vysshikh Uchebnykh Zavedenii, Khimiya i Khimicheskaya Tekhnologiya 1990, 33(9), 3-6.

Carlo Bonini et al. "Novel N-(2-benzo[b]thienyl)iminophosphoranes and their use in the synthesis of benzo[b]thieno [2,3-b]pyridines", 2002, 58, 3507-3512.

T.E. Khoshtariya et al. "Synthesis of Benzo[b]Thieno-[3,2-e]Benzimidazoles, First Representatives of a New Heterocyclic System", Chemistry of Heterocyclic Compounds, 2008, 44(8), 1024-1026.

* cited by examiner

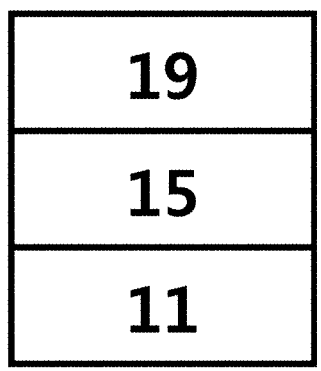

CONDENSED CYCLIC COMPOUND AND ORGANIC LIGHT-EMITTING DEVICE INCLUDING THE SAME

CROSS-REFERENCE TO RELATED APPLICATIONS

This application claims priority to Korean Patent Application No. 10-2014-0004687, filed on Jan. 14, 2014, in the Korean Intellectual Property Office, and all the benefits accruing therefrom under 35 U.S.C. §119, the content of which is incorporated herein in its entirety by reference.

BACKGROUND

1. Field

One or more embodiments of the present disclosure relate to a condensed cyclic compound and an organic light-emitting device including the same.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

A typical organic light-emitting device may include an anode, a cathode, and an organic layer, including an emission layer, disposed between the anode and the cathode. The organic light-emitting device may include a hole transport region between the anode and the emission layer, and an electron transport region between the emission layer and the cathode. Holes injected from the anode move to the emission layer via the hole transport region, while electrons injected from the cathode move to the emission layer via the electron transport region. Carriers such as the holes and electrons recombine in the emission layer to generate excitons. When the excitons drop from an excited state to a ground state, light is emitted.

Various types of organic light emitting devices are known. However, there still remains a need in OLEDs having low driving voltage, high efficiency, high brightness, and long lifespan.

SUMMARY

One or more embodiments of the present disclosure include a novel condensed cyclic compound and an organic light-emitting device including the same.

Additional aspects will be set forth in part in the description which follows and, in part, will be apparent from the description, or may be learned by practice of the presented embodiments.

According to one or more embodiments of the present disclosure, there is provided a condensed cyclic compound represented by Formula 1:

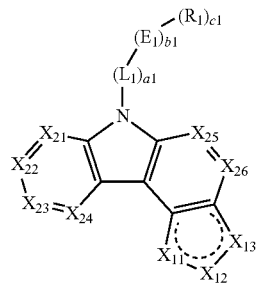

Formula 1 wherein, in Formula 1, $X_{11}$ is S, O, N, C—[$(L_{11})_{a11}$-$(E_{11})_{b11}$-$(R_{11})_{c11}$], or Si-[$(L_{11})_{a11}$-$(E_{11})_{b11}$-$(R_{11})_{c11}$];

$X_{12}$ is S, O, N, C-[$(L_{12})_{a12}$-$(E_{12})_{b12}$-$(R_{12})_{c12}$], or Si-[$(L_{12})_{a12}$-$(E_{12})_{b12}$-$(R_{12})_{c12}$];

$X_{13}$ is S, O, N, C-[$(L_{13})_{a13}$-$(E_{13})_{b13}$-$(R_{13})_{c13}$], or Si-[$(L_{13})_{a13}$-$(E_{13})_{b13}$-$(R_{13})_{c13}$];

$X_{21}$ is N or C-[$(L_{21})_{a21}$-$(E_{21})_{b21}$-$(R_{21})_{c21}$];

$X_{22}$ is N or C-[$(L_{22})_{a22}$-$(E_{22})_{b22}$-$(R_{22})_{c22}$];

$X_{23}$ is N or C-[$(L_{23})_{a23}$-$(E_{23})_{b23}$-$(R_{23})_{c23}$];

$X_{24}$ is N or C-[$(L_{24})_{a24}$-$(E_{24})_{b24}$-$(R_{24})_{c24}$];

$X_{25}$ is N or C-[$(L_{25})_{a25}$-$(E_{25})_{b25}$-$(R_{25})_{c25}$];

$X_{26}$ is N or C-[$(L_{26})_{a26}$-$(E_{26})_{b26}$-$(R_{26})_{c26}$];

$L_1$, $L_{11}$ to $L_{13}$, and $L_{21}$ to $L_{26}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent nonaromatic condensed polycyclic group, and a substituted or unsubstituted divalent nonaromatic condensed heteropolycyclic group;

a1, a11 to a13, and a21 to a26 are each independently an integer selected from 0 to 5;

$E_1$, $E_{11}$ to $E_{13}$, and $E_{21}$ to $E_{26}$ are each independently selected from a substituted or unsubstituted nitrogen-containing electron transporting moiety;

b1, b11 to b13, and b21 to b26 are each independently an integer selected from 0 to 5, provided that at least one of $E_1$, $E_{11}$ to $E_{13}$, and $E_{21}$ to $E_{26}$ is present in Formula 1;

$R_1$, $R_{11}$ to $R_{13}$, and $R_{21}$ to $R_{26}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent nonaromatic condensed polycyclic group, a substituted or unsubstituted monovalent nonaromatic condensed heteropolycyclic group, —$N(Q_1)(Q_2)$, —$Si(Q_3)(Q_4)(Q_5)$, and —$B(Q_6)(Q_7)$;

c1, c11 to c13, and c21 to c26 are each independently an integer selected from 1 to 5;

wherein at least one of substituents of the substituted nitrogen-containing electron transporting moiety, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent nonaromatic condensed polycyclic group, and the substituted monovalent nonaromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{10}$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C$—$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent nonaromatic condensed polycyclic group, and a monovalent nonaromatic condensed heteropolycyclic group.

According to one or more embodiments of the present disclosure, an organic light-emitting device includes:
a first electrode;
a second electrode; and
an organic layer disposed between the first electrode and the second electrode, wherein the organic layer includes an emission layer (EML) and at least one condensed cyclic compound of Formula 1 defined above.

The at least one condensed cyclic compound of Formula 1 may be in the emission layer, and the emission layer may further include a dopant, wherein the at least one condensed cyclic compound of Formula 1 in the emission layer may serve as a host.

The emission layer of the organic light-emitting device may include a first host, a second host, and a dopant, wherein the first host and the second host may be different from each other, the at least one condensed cyclic compound represented by Formula 1 may be in the emission layer, the first host may include the at least one condensed cyclic compound of Formula 1, and the second host may include at least one of a first compound represented by Formula 41, a second compound represented by Formula 61, and a third compound represented by Formula 31:

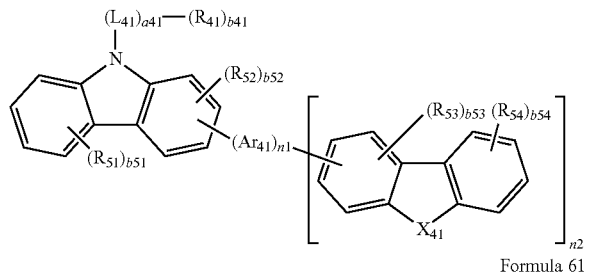

Formula 41

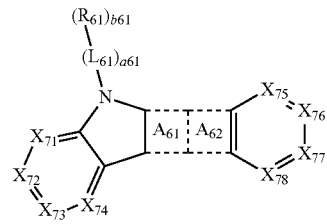

Formula 61

Formula 61A

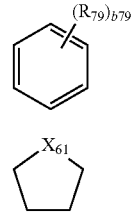

Formula 61B

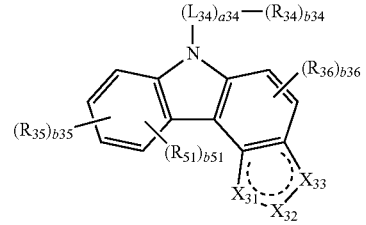

Formula 31 wherein, in Formulae 41, 61, 61A, 61B, and 31, $X_{41}$ may be N-[$(L_{42})_{a42}$-$(R_{42})_{b42}$], S, O, S(=O), S(=O)$_2$, C(=O), C($R_{43}$)($R_{44}$), Si($R_{43}$)($R_{44}$), P($R_{43}$), P(=O)($R_{43}$), or C=N($R_{43}$);

ring $A_{61}$ in Formula 61 may be represented by Formula 61A;

ring $A_{62}$ in Formula 61 may be represented by Formula 61B;

$X_{61}$ may be N-[$(L_{62})_{a62}$-$(R_{62})_{b62}$], S, O, S(=O), S(=O)$_2$, C(=O), C($R_{63}$)($R_{64}$), Si($R_{63}$)($R_{64}$), P($R_{63}$), P(=O)($R_{63}$), or C=N($R_{63}$);

$X_{71}$ may be C($R_{71}$) or N;
$X_{72}$ may be C($R_{72}$) or N;
$X_{73}$ may be C($R_{73}$) or N;
$X_{74}$ may be C($R_{74}$) or N;
$X_{75}$ may be C($R_{76}$) or N;
$X_{76}$ may be C($R_{76}$) or N;
$X_{77}$ may be C($R_{77}$) or N;
$X_{78}$ may be C($R_{78}$) or N;

$X_{31}$ may be S, O, N, C-[$(L_{31})_{a31}$-$(R_{31})_{b31}$], or Si-[$(L_{31})_{a31}$-$(R_{31})_{b31}$];

$X_{32}$ may be S, O, N, C-[$(L_{32})_{a32}$-$(R_{32})_{c32}$], or Si-[$(L_{32})_{a32}$-$(R_{32})_{b32}$];

$X_{33}$ may be S, O, N, C-[$(L_{33})_{a33}$-$(R_{33})_{b33}$], or Si-[$(L_{33})_{a33}$-$(R_{33})_{c33}$];

$Ar_{41}$, $L_{41}$, $L_{42}$, $L_{61}$, and $L_{62}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent nonaromatic condensed polycyclic group, and a substituted or unsubstituted divalent nonaromatic condensed heteropolycyclic group;

$L_{31}$ to $L_{34}$ may be each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent nonaromatic condensed polycyclic group;

n1 and n2 may be each independently an integer selected from 0 to 3;

a41, a42, a61, a62, and a31 to a34 may be each independently an integer selected from 0 to 3;

$R_{41}$ to $R_{44}$, $R_{51}$ to $R_{54}$, $R_{61}$ to $R_{64}$, and $R_{71}$ to $R_{79}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent nonaromatic condensed polycyclic group, a substituted or unsubstituted monovalent nonaromatic condensed heteropolycyclic group, —N($Q_1$)($Q_2$), —Si($Q_3$)($Q_4$)($Q_5$), and —B($Q_6$)($Q_7$);

$R_{31}$ to $R_{36}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group, or a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group;

b41, b42, b51 to b54, b61, b62, b79, and b31 to b34 are each independently an integer selected from 1 to 3;

b35 may be an integer selected from 1 to 3; and b36 may be 1 or 2, wherein at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent nonaromatic condensed polycyclic group, and the substituted monovalent nonaromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —$N(Q_{11})(Q_{12})$, —$Si(Q_{13})(Q_{14})(Q_{15})$, and —$B(Q_{16})(Q_{17})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group, each substituted with at least one of a deuterium atom, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —$N(Q_{21})(Q_{22})$, —$Si(Q_{23})(Q_{24})(Q_{25})$, and —$B(Q_{26})(Q_{27})$, and —$N(Q_{31})(Q_{32})$, —$Si(Q_{33})(Q_{34})(Q_{35})$, and —$B(Q_{36})(Q_{37})$, wherein $Q_1$ to $Q_7$, $Q_{11}$ to $C_{17}$, $C_{21}$ to $C_{27}$, and $Q_{31}$ to $C_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group.

BRIEF DESCRIPTION OF THE DRAWINGS

These and/or other aspects will become apparent and more readily appreciated from the following description of the embodiments, taken in conjunction with the accompanying drawings in which:

The FIGURE a schematic cross-sectional view of an organic light-emitting device according to an embodiment of the present disclosure.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an embodiment of the present disclosure, there is provided a condensed cyclic compound represented by Formula 1 below:

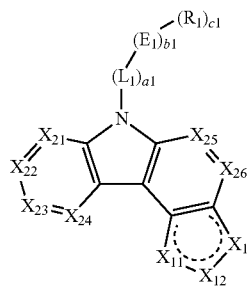

Formula 1

In Formula 1 above, $X_{11}$ may be S, O, N, C-[$(L_{11})_{a11}$-$(E_{11})_{b11}$-$(R_{11})_{c11}$], or Si-[$(L_{11})_{a11}$-$(E_{11})_{b11}$-$(R_{11})_{c11}$];

$X_{12}$ may be S, O, N, C-[$(L_{12})_{a12}$-$(E_{12})_{b12}$-$(R_{12})_{c12}$], or Si-[$(L_{12})_{a12}$-$(E_{12})_{b12}$-$(R_{12})_{c12}$];

$X_{13}$ may be S, O, N, C-[$(L_{13})_{a13}$-$(E_{13})_{b13}$-$(R_{13})_{c13}$], or Si-[$(L_{13})_{a13}$-$(E_{13})_{b13}$-$(R_{13})_{c13}$];

$X_{21}$ may be N or C-[$(L_{21})_{a21}$-$(E_{21})_{b21}$-$(R_{21})_{c21}$];

$X_{22}$ may be N or C-[$(L_{22})_{a22}$-$(E_{22})_{b22}$-$(R_{22})_{c22}$];

$X_{23}$ may be N or C-[$(L_{23})_{a23}$-$(E_{23})_{b23}$-$(R_{23})_{c23}$];

$X_{24}$ may be N or C-[$(L_{24})_{a24}$-$(E_{24})_{b24}$-$(R_{24})_{c24}$];

$X_{25}$ may be N or C-[$(L_{25})_{a25}$-$(E_{25})_{b25}$-$(R_{25})_{c25}$]; and $X_{26}$ may be N or C-[$(L_{26})_{a26}$-$(E_{26})_{b26}$-$(R_{26})_{c26}$].

In some embodiments, in Formula 1 above, $X_{11}$ may be S or O, and $X_{13}$ may be N.

In some other embodiments, in Formula 1 above, $X_{11}$ may be S or O, and $X_{13}$ may be C-[$(L_{13})_{a13}$-$(E_{13})_{b13}$-$(R_{13})_{c13}$].

In Formula 1 above, $L_1$, $L_{11}$ to $L_{13}$, and $L_{21}$ to $L_{26}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent nonaromatic condensed polycyclic group, and a substituted or unsubstituted divalent nonaromatic condensed heteropolycyclic group.

In some embodiments, $L_1$, $L_{11}$ to $L_{13}$, and $L_{21}$ to $L_{26}$ in Formula 1 above may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolynene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group, each substituted with at least one of a deuterium atom, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a $C_1$-$C_{60}$ heteroaryl group, a monovalent nonaromatic condensed polycyclic group, a monovalent nonaromatic condensed heteropolycyclic group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group. However, embodiments of the present disclosure are not limited thereto.

In some other embodiments, $L_1$, $L_{11}$ to $L_{13}$, and $L_{21}$ to $L_{26}$ in Formula 1 above may be each independently one of the groups represented by Formulae 2-1 to 2-34:

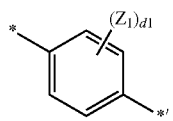

Formula 2-1

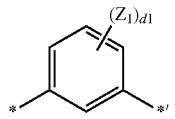

Formula 2-2

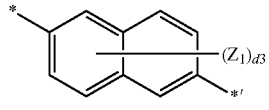

Formula 2-3

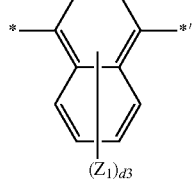

Formula 2-4

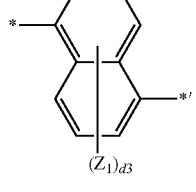

Formula 2-5

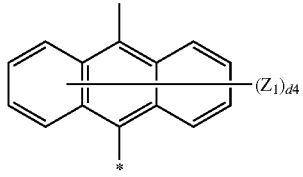

Formula 2-6

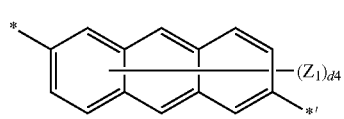

Formula 2-7

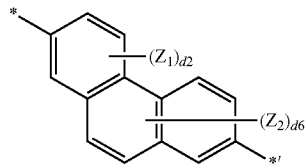

Formula 2-8

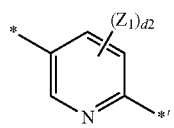

Formula 2-9

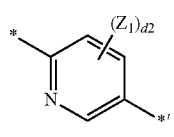

Formula 2-10

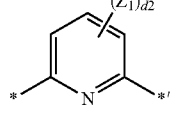

Formula 2-11

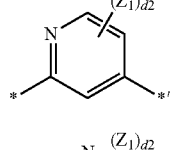

Formula 2-12

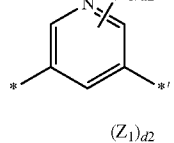

Formula 2-13

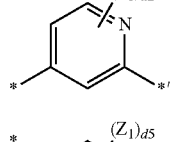

Formula 2-14

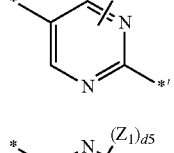

Formula 2-15

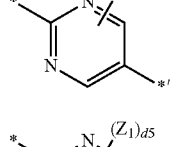

Formula 2-16

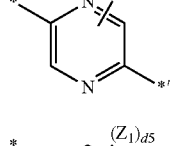

Formula 2-17

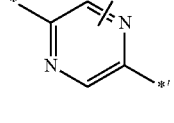

Formula 2-18

-continued

Formula 2-19
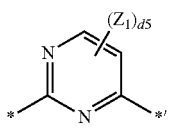

Formula 2-20
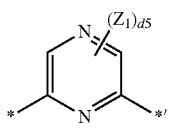

Formula 2-21
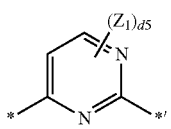

Formula 2-22
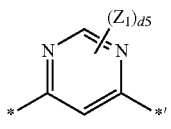

Formula 2-23
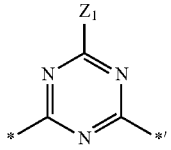

Formula 2-24
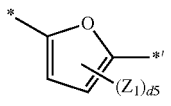

Formula 2-25
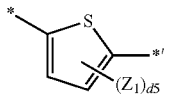

Formula 2-26
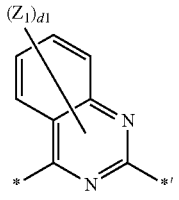

Formula 2-27
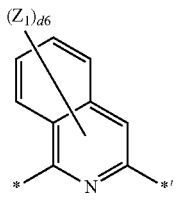

Formula 2-28
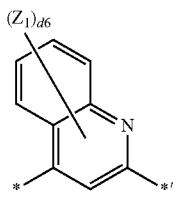

Formula 2-29
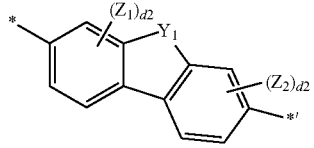

Formula 2-30
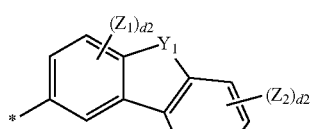

Formula 2-31
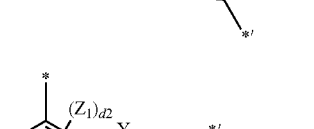

Formula 2-32
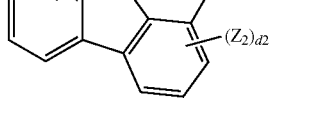

Formula 2-33
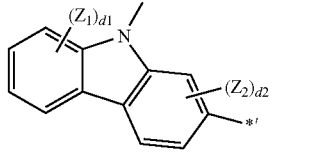

Formula 2-34
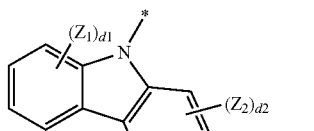

In Formulae 2-1 to 2-34 above, $Y_1$ may be O, S, S(=O), S(=O)$_2$, C($Z_3$)($Z_4$), N($Z_5$), or Si($Z_6$)($Z_7$);

$Z_1$ to $Z_7$ may be each independently selected from a hydrogen, a deuterium, —F, —Cl, —Br, —I, a hydroxyl group, a cyano group, a nitro group, an amino group, an amidino groups, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, or —Si($Q_{33}$)($Q_{34}$)($Q_{35}$), where $Q_{33}$ to $Q_{35}$ may be each independently a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 may be an integer of 1 to 4;

d2 may be an integer of 1 to 3;

d3 may be an integer of 1 to 6;

d4 may be an integer of 1 to 8;

d5 may be 1 or 2;

d6 may be an integer of 1 to 5; and

* and *' indicate a binding site with an adjacent atom.

In some other embodiments, $L_1$, $L_{11}$ to $L_{13}$, and $L_{21}$ to $L_{26}$ in Formula 1 above may be each independently selected from the groups represented by Formulae 3-1 to 3-21 below, but are not limited thereto:

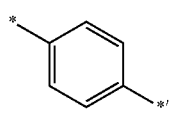

Formula 3-1

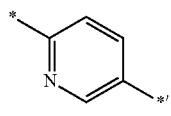

Formula 3-2

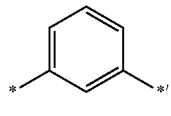

Formula 3-3

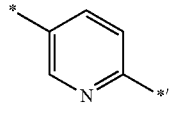

Formula 3-4

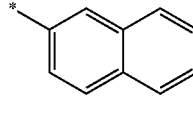

Formula 3-5

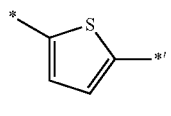

Formula 3-6

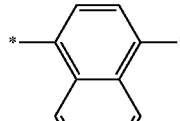

Formula 3-7

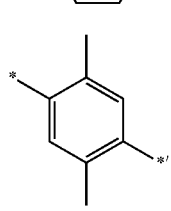

Formula 3-8

-continued

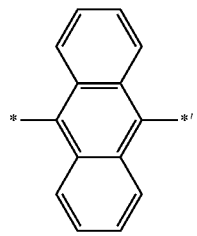

Formula 3-9

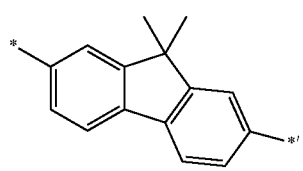

Formula 3-10

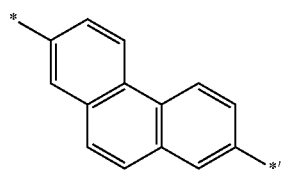

Formula 3-11

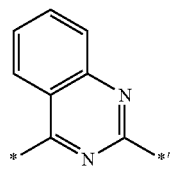

Formula 3-12

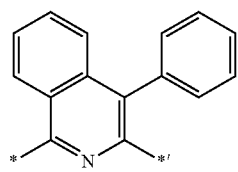

Formula 3-13

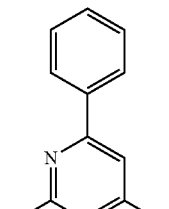

Formula 3-14

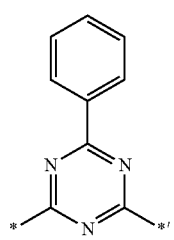

Formula 3-15

-continued

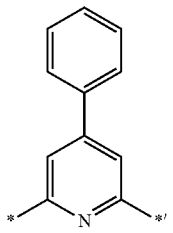
Formula 3-16

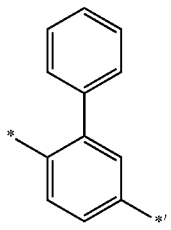
Formula 3-17

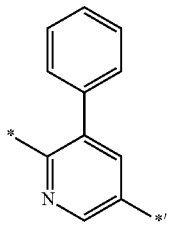
Formula 3-18

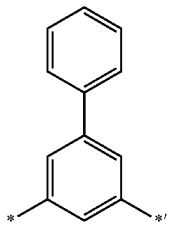
Formula 3-19

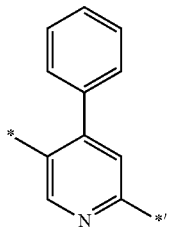
Formula 3-20

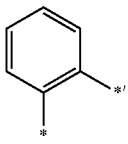
Formula 3-21

In Formulae 3-1 to 3-21 above,

* indicates a binding site with a core in Formula 1 or a binding site with an adjacent group of $L_1$, $L_{11}$ to $L_{13}$, and $L_{21}$ to $L_{26}$ in Formula 1; and

*' indicates a binding site with an adjacent group of $L_1$, $L_{11}$ to $L_{13}$, and $L_{21}$ to $L_{26}$ in Formula 1, a binding site with an adjacent group of $E_1$, $E_{11}$ to $E_{13}$, and $E_{21}$ to $E_{26}$ in Formula 1, or a binding site with one of $R_1$, $R_{11}$ to $R_{13}$, and $R_{21}$ to $R_{26}$ in Formula 1.

In Formula 1 above, a1, which indicates the number of groups $L_1$, may be 0, 1, 2, 3, 4, or 5. For example, a1 may be 0, 1, or 2, and in some embodiments, may be 0 or 1. When a1 is 0, $L_1$ may be a single bond. When a1 is 2 or greater, the at least two groups $L_1$ may be identical to or different from each other. $L_{11}$ to $L_{13}$, and $L_{21}$ to $L_{26}$ in Formula 1 may be understood based on the description of $L_1$ and the structure of Formula 1.

In some embodiments, a1, a11 to a13, and a21 to a26 in Formula 1 above may be each independently 0, 1, or 2.

In Formula 1 above, $E_1$, $E_{11}$ to $E_{13}$, and $E_{21}$ to $E_{26}$ may be each independently selected from a substituted or unsubstituted nitrogen-containing electron transporting moiety. The substituted or unsubstituted nitrogen-containing electron transporting moiety may be a cyclic moiety including nitrogen as a member element of the cyclic moiety. For example, the substituted or unsubstituted nitrogen-containing electron transporting moiety may include one, two, or three nitrogen atoms as member elements of the ring.

For example, $E_1$, $E_{11}$ to $E_{13}$, and $E_{21}$ to $E_{26}$ in Formula 1 above may be each independently selected from a substituted or unsubstituted nitrogen-containing $C_1$-$C_{10}$ heterocycloalkylene group, a substituted or unsubstituted nitrogen-containing $C_1$-$C_{10}$ heterocycloalkenylene group, a substituted or unsubstituted nitrogen-containing $C_1$-$C_{60}$ heteroarylene group, and a substituted or unsubstituted nitrogen-containing divalent nonaromatic condensed heteropolycyclic group, wherein any of the $E_1$, $E_{11}$ to $E_{13}$, and $E_{21}$ to $E_{26}$ is not a substituted or unsubstituted a carbazolylene group.

In some embodiments, $E_1$, $E_{11}$ to $E_{13}$, and $E_{21}$ to $E_{26}$ in Formula 1 above may be each independently, but are not limited to, selected from a substituted or unsubstituted pyrrolylene group, a substituted or unsubstituted imidazolylene group, a substituted or unsubstituted pyrazolylene group, a substituted or unsubstituted thiazolylene group, a substituted or unsubstituted isothiazolylene group, a substituted or unsubstituted oxazolylene group, a substituted or unsubstituted isooxazolylene group, a substituted or unsubstituted pyridinylene group, a substituted or unsubstituted pyrazinylene group, a substituted or unsubstituted pyrimidinylene group, a substituted or unsubstituted pyridazinylene group, a substituted or unsubstituted isoindolylene group, a substituted or unsubstituted indolylene group, a substituted or unsubstituted indazolylene group, a substituted or unsubstituted quinolinylene group, a substituted or unsubstituted isoquinolinylene group, a substituted or unsubstituted benzoquinolinylene group, a substituted or unsubstituted quinoxalinylene group, a substituted or unsubstituted quinazolinylene group, a substituted or unsubstituted phenanthridinylene group, a substituted or unsubstituted acridinylene group, a substituted or unsubstituted phenanthrolinylene group, a substituted or unsubstituted phenazinylene group, a substituted or unsubstituted benzoimidazolylene group, a substituted or unsubstituted isobenzothiazolylene group, a substituted or unsubstituted benzooxazolylene group, a substituted or unsubstituted isobenzooxazolylene group, a substituted or unsubstituted triazolylene group, a substituted or unsubstituted oxadiazolylene group, a substituted or unsubstituted thiadiazolylene group, a substituted or unsubstituted triazinylene group, a substituted or unsubstituted imidazopyridinylene group, and a substituted or unsubstituted imidazopyrimidinylene group, wherein at least one of substituents of the substituted pyrrolylene group, the substituted imidazolylene group, the substituted pyrazolylene group, the substituted thiazolylene group, the substituted isothiazolylene group, the substituted oxazolylene group, the substituted isooxazolylene group, the substituted pyridinylene group, the substituted pyrazinylene group, the substituted pyrimidinylene group, the substituted pyridazinylene group, the substituted isoindolylene group, the substituted indolylene group, the substituted indazolylene group, the substituted quinolinylene group, the substituted isoquinolinylene group, the substituted benzoquinolinylene group, the substituted quinoxalinylene group, the substituted quinazolinylene group, the substituted phenanthridinylene group, the substituted acridinylene group, the substituted phenanthrolinylene group, the substituted phenazinylene group, the substituted benzoimidazolylene group, the substituted isobenzothiazolylene group, the substituted benzooxazolylene group, the substituted isobenzooxazolylene group, the substituted triazolylene group, the substituted oxadiazolylene group, the substituted thiadiazolylene group, the substituted triazinylene group, the substituted imidazopyridinylene group, and the substituted imidazopyrimidinylene group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{23}$)($Q_{24}$)($Q_{25}$), and —Si($Q_{33}$)($Q_{34}$)($Q_{35}$), wherein $Q_{23}$ to $Q_{25}$, and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

In some other embodiments, $E_1$, $E_{11}$ to $E_{13}$, and $E_{21}$ to $E_{26}$ in Formula 1 above may be each independently, but are not limited to, selected from a substituted or unsubstituted imidazolylene group, a substituted or unsubstituted pyridinylene group, a substituted or unsubstituted pyrimidinylene group, a substituted or unsubstituted quinolinylene group, a substituted or unsubstituted isoquinolinylene group, a substituted or unsubstituted quinazolinylene group, a substituted or unsubstituted phenanthrolinylene group, a substituted or unsubstituted benzoimidazolylene group, a substituted or unsubstituted triazolylene group, a substituted or unsubstituted oxadiazolylene group, a substituted or unsubstituted thiadiazolylene group, a substituted or unsubstituted triazinylene group, a substituted or unsubstituted imidazopyridinylene group, and a substituted or unsubstituted imidazopyrimidinylene group, wherein at least one of substituents of the substituted imidazolylene group, the substituted pyridinylene group, the substituted pyrimidinylene group, the substituted quinolinylene group, the substituted isoquinolinylene group, the substituted quinazolinylene group, the substituted phenanthrolinylene group, the substituted benzoimidazolylene group, the substituted triazolylene group, the substituted oxadiazolylene group, the substituted thiadiazolylene group, the substituted triazinylene group, the substituted imidazopyridinylene group, and the substituted imidazopyrimidinylene group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{23}$)($Q_{24}$)($Q_{25}$), and —Si($Q_{33}$)($Q_{34}$)($Q_{35}$), wherein $Q_{23}$ to $Q_{25}$, and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

In some other embodiments, $E_1$, $E_{11}$ to $E_{13}$, and $E_{21}$ to $E_{26}$ in Formula 1 above may be each independently one of the groups represented by Formulae 10-1 to 10-27:

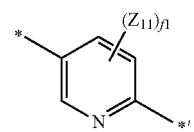

Formula 10-1

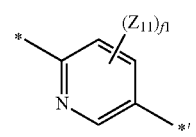

Formula 10-2

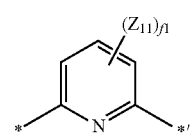

Formula 10-3

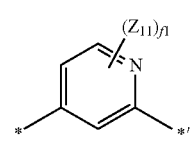

Formula 10-4

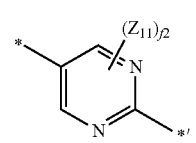

Formula 10-5

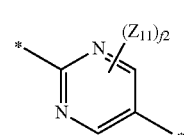

Formula 10-6

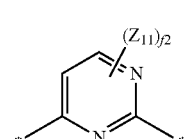

Formula 10-7

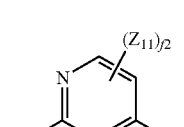

Formula 10-8

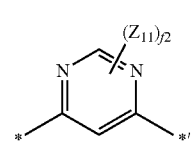

Formula 10-9

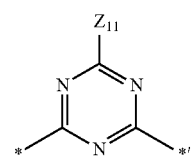

Formula 10-10

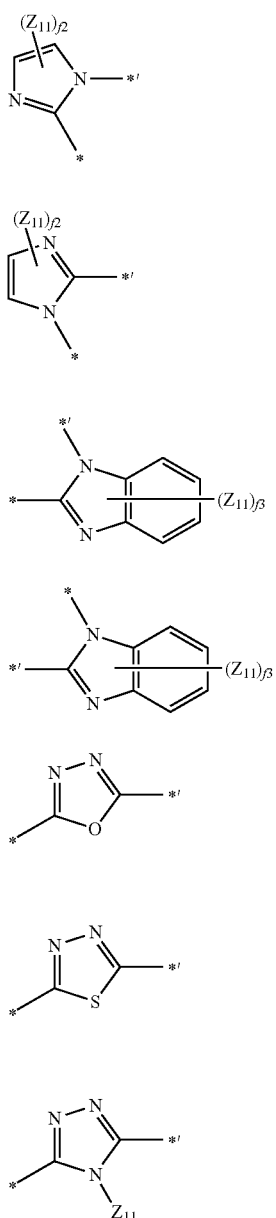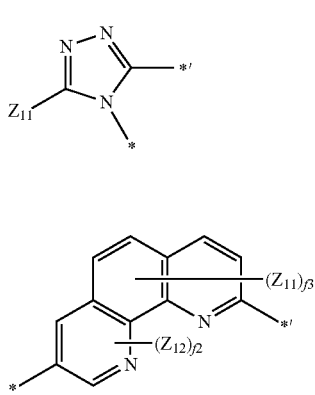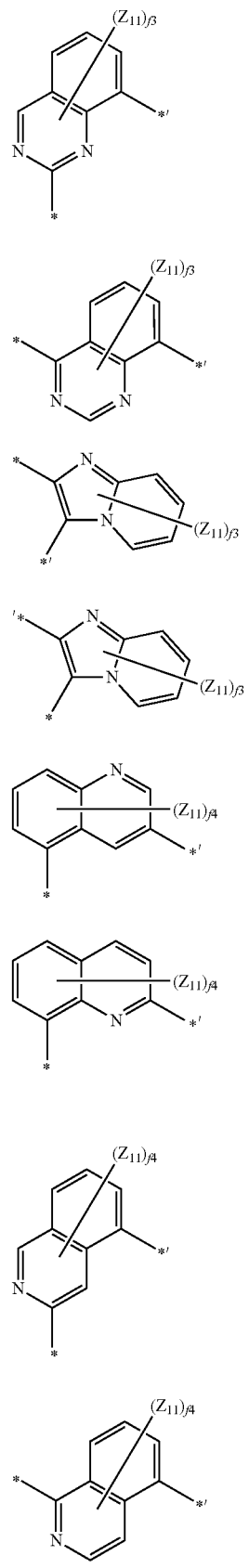

In Formulae 10-1 to 10-27 above, $Z_{11}$ and $Z_{12}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, an anthracenyl group, a triphenylenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, a phenyl group, a naphthyl group, an anthracenyl group, a triphenylenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{23}$)($Q_{24}$)($Q_{25}$); and —Si($Q_{33}$)($Q_{34}$)($Q_{35}$), wherein $Q_{23}$ to $Q_{25}$, and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

f1 may be an integer selected from 1 to 3;

f2 may be 1 or 2;

f3 may be an integer selected from 1 to 4;

f4 may be an integer selected from 1 to 5;

* indicates a binding site with a core in Formula 1, a binding site with an adjacent group of $L_1$, $L_{11}$ to $L_{13}$, and $L_{21}$ to $L_{26}$ in Formula 1, or a binding site with an adjacent group of $E_1$, $E_{11}$ to $E_{13}$, and $E_{21}$ to $E_{26}$ in Formula 1; and

*' indicates a binding site with an adjacent group of $E_1$, $E_{11}$ to $E_{13}$, and $E_{21}$ to $E_{26}$ in Formula 1, or a binding site with an adjacent group of $R_1$, $R_{11}$ to $R_{13}$, and $R_{21}$ to $R_{26}$ in Formula 1.

In Formula 1 above, b1, which indicates the number of groups $E_1$, may be 0, 1, 2, 3, 4, or 5. For example, b1 may be 1 or 2. When b1 is 2 or greater, the at least two groups $E_1$ may be identical to or different from each other.

In Formula 1 above, b1, which indicates the number of groups $E_{11}$, may be 0, 1, 2, 3, 4, or 5. For example, b11 may be 0, 1, or 2, and in some embodiments, may be 0 or 1. When b11 is 0, $E_{11}$ may be a single bond. When b11 is 2 or greater, the at least two groups $E_{11}$ may be identical to or different from each other. b12, b13, and b21 to b26 in Formula 1 above may be understood based on the above description of b11 and the structure of Formula 1 above.

In Formula 1 above, b1, b11 to b13, and b21 to b26 may be each independently an integer selected from 0 to 5.

Furthermore, at least one of $E_1$, $E_{11}$ to $E_{13}$, and $E_{21}$ to $E_{26}$ is present in Formula 1 above.

In some embodiments, b1 in Formula 1 above may be selected from an integer of 1 to 5. In other words, b1 in Formula 1 above is not 0, and $E_1$ has to be present in Formula 1 above. However, embodiments of the present disclosure are not limited thereto.

In some embodiments, $X_{22}$ in Formula 1 above may be C-[$(L_{22})_{a22}$-$(E_{22})_{b22}$-$(R_{22})_{c22}$], and b22 may be an integer selected from 1 to 5. For example, b22 may be 1.

In some other embodiments, $X_{23}$ in Formula 1 above may be C-[$(L_{23})_{a23}$-$(E_{23})_{b23}$-$(R_{23})_{c23}$], and b23 may be an integer selected from 1 to 5. For example, b23 may be 1.

In some embodiments, $R_1$, $R_{11}$ to $R_{13}$, and $R_{21}$ to $R_{26}$ in Formula 1 above may be each independently selected from a hydrogen, a deuterium, a fluoro group (—F), a chloro group (—Cl), a bromo group (—Br), an iodo group (—I), a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

In some embodiments, $R_1$, $R_{11}$ to $R_{13}$, and $R_{21}$ to $R_{26}$ in Formula 1 above may be each independently, but are not limited to, selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group and a salt thereof, a phosphoric acid group or a salt thereof, a $C_1$-$C_{20}$ alkyl group, or a $C_1$-$C_{20}$ alkoxy group, a $C_1$-$C_{20}$ alkyl group and a $C_1$-$C_{20}$ alkoxy group, each substituted with at least one of a deuterium atom, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{35}$), and —Si($Q_3$)($Q_4$)($Q_5$), wherein $R_{11}$ to $R_{13}$ may be not —Si($Q_3$)($Q_4$)($Q_5$); and $Q_3$ to $Q_5$, and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In some other embodiments, $R_1$, $R_{11}$ to $R_{13}$, and $R_{21}$ to $R_{26}$ in Formula 1 above may be each independently, but are not limited thereto, selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a group represented by one of Formulae 4-1 to 4-31, and —Si($Q_3$)($Q_4$)($Q_5$), wherein $Q_3$ to $Q_5$ may be each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

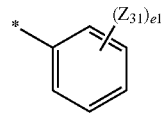

Formula 4-1

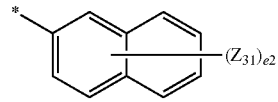

Formula 4-2

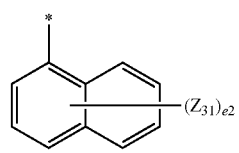

Formula 4-3

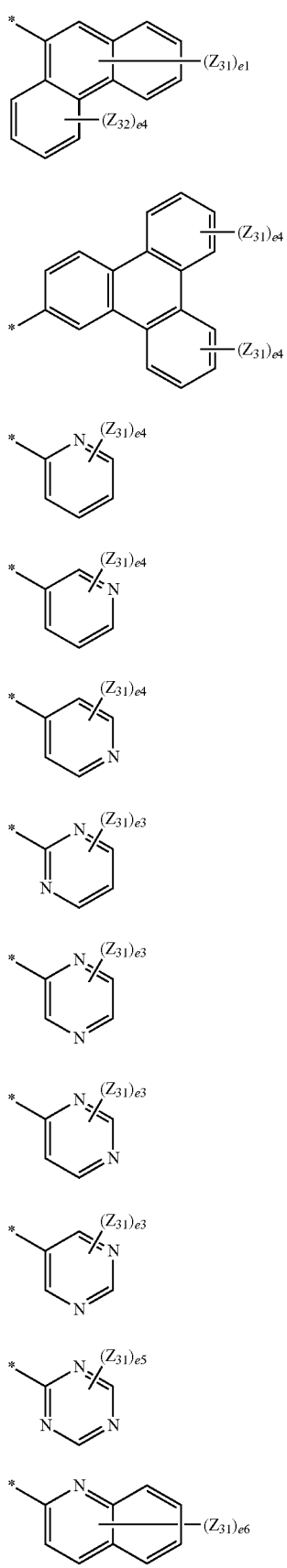
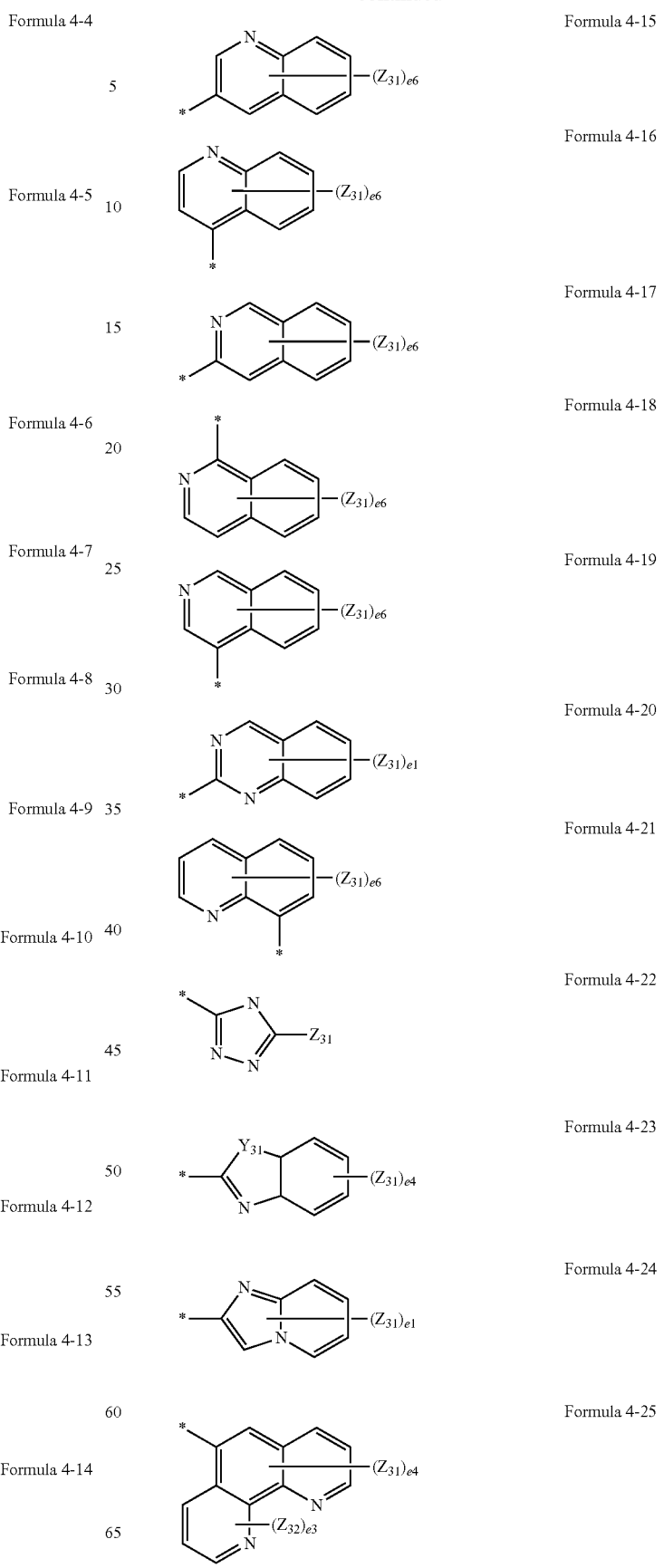

-continued

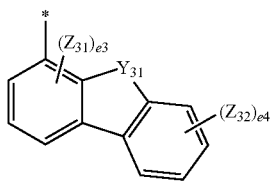
Formula 4-26

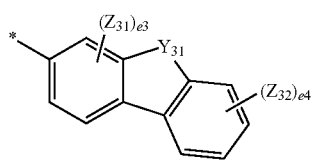
Formula 4-27

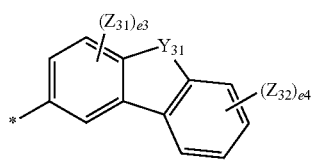
Formula 4-28

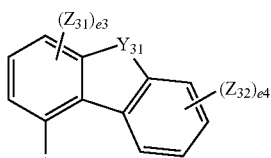
Formula 4-29

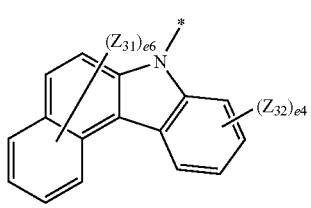
Formula 4-30

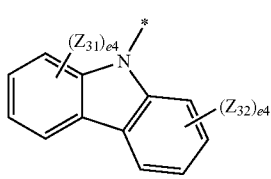
Formula 4-31

In Formulae 4-1 to 4-31 above, $Y_{31}$ may be O, S, $C(Z_{33})(Z_{34})$, $N(Z_{35})$, or $Si(Z_{36})(Z_{37})$;

$Z_{31}$ to $Z_{37}$ may be each independently selected from a hydrogen, a deuterium, —F, —Cl, —Br, —I, a hydroxyl group, a cyano group, a nitro group, an amino group, an amidino groups, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —$Si(Q_{33})(Q_{34})(Q_{35})$, wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 may be an integer of 1 to 5;

e2 may be an integer of 1 to 7;

e3 may be an integer of 1 to 3;

e4 may be an integer of 1 to 4;

e5 may be 1 or 2;

e6 may be an integer of 1 to 6;

* indicates a binding site with a core in Formula 1, a binding site with an adjacent group of $L_1$, $L_{11}$ to $L_{13}$, and $L_{21}$ to $L_{26}$ in Formula 1, or a binding site with an adjacent group of $E_1$, $E_{11}$ to $E_{13}$, and $E_{21}$ to $E_{26}$ in Formula 1.

In some other embodiments, $R_1$, $R_{11}$ to $R_{13}$, and $R_{21}$ to $R_{26}$ in Formula 1 above may be each independently, but are not limited to, selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a group represented by one of Formulae 5-1 to 5-27, and —$Si(Q_3)(Q_4)(Q_5)$, wherein $Q_3$ to $Q_5$ may be each independently selected from a hydrogen, a $C_1$-$C_{20}$ alkyl group, a $C_1$-$C_{20}$ alkoxy group, a phenyl group, and a naphthyl group.

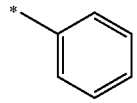
Formula 5-1

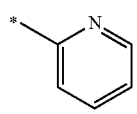
Formula 5-2

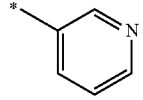
Formula 5-3

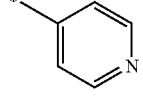
Formula 5-4

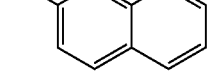
Formula 5-5

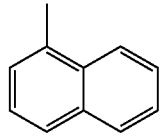
Formula 5-6

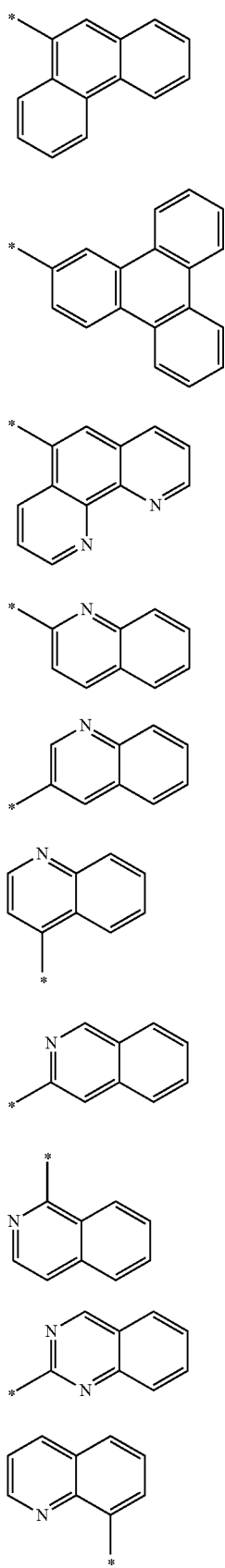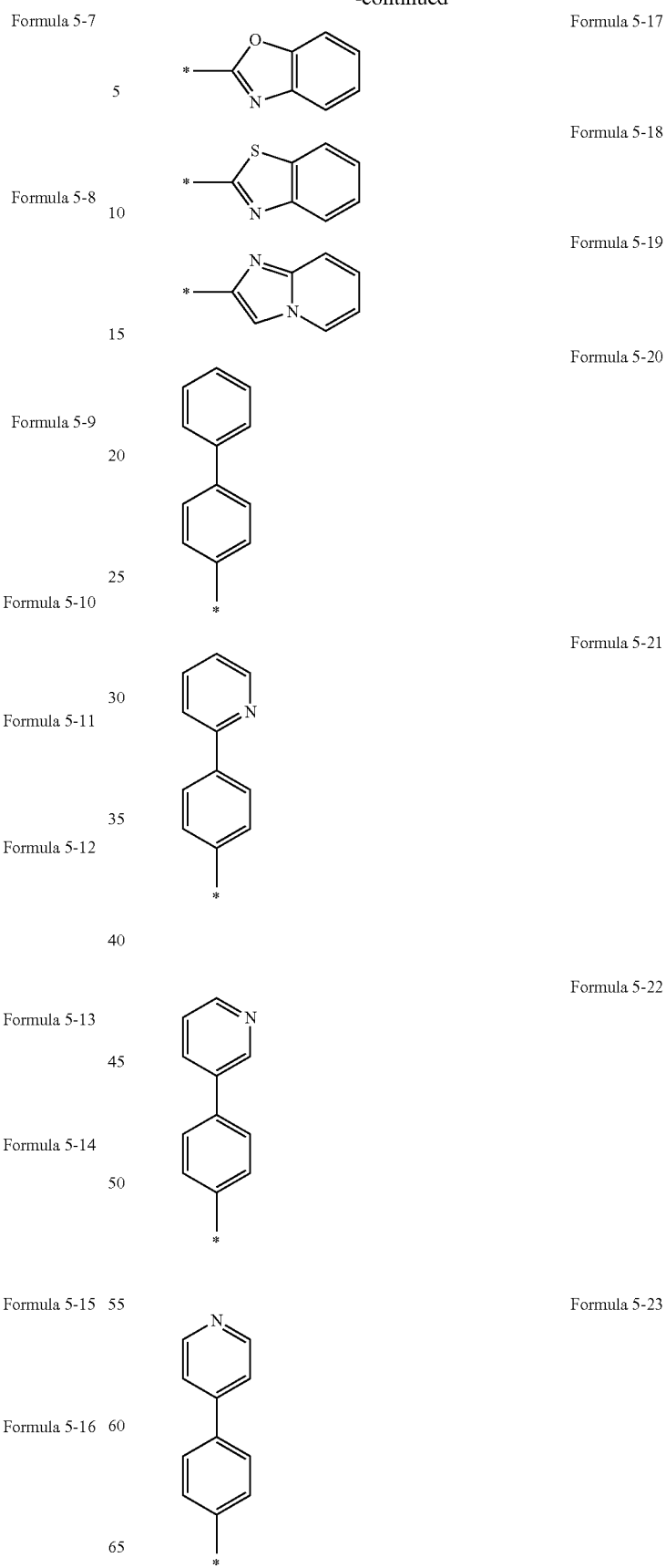

Formula 5-24

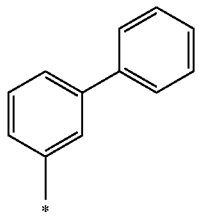

Formula 5-25

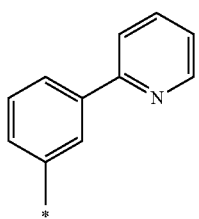

Formula 5-26

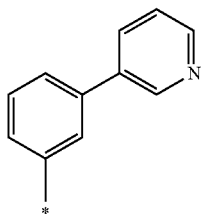

Formula 5-27

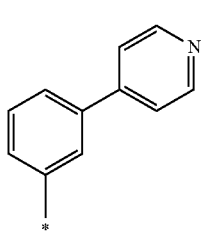

In Formulae 5-1 to 5-27 above, * indicates a binding site with a core in Formula 1, a binding site with an adjacent group of $L_1$, $L_{11}$ to $L_{13}$, and $L_{21}$ to $L_{26}$ in Formula 1, or a binding site with an adjacent group of $E_1$, $E_{11}$ to $E_{13}$, and $E_{21}$ to $E_{26}$ in Formula 1.

In some embodiments, in Formula 1 above, $X_{21}$ may be C-[$(L_{21})_{a21}$-$(E_{21})_{b21}$-$(R_{21})_{c21}$];

$X_{22}$ may be C-[$(L_{22})_{a22}$-$(E_{22})_{b22}$-$(R_{22})_{c22}$];

$X_{23}$ may be C-[$(L_{23})_{a23}$-$(E_{23})_{b23}$-$(R_{23})_{c23}$];

$X_{24}$ may be C-[$(L_{24})_{a24}$-$(E_{24})_{b24}$-$(R_{24})_{c24}$];

$X_{25}$ may be C-[$(L_{25})_{a25}$-$(E_{25})_{b25}$-$(R_{25})_{c25}$];

$X_{26}$ may be C-[$(L_{26})_{a26}$-$(E_{26})_{b26}$-$(R_{26})_{c26}$];

a21 to a26, and b21 to b26 may be 0;

$R_{21}$ to $R_{26}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group a naphthyl group, and —Si($Q_3$)($Q_4$)($Q_5$);

c21 to c26 may be 1;

wherein $Q_3$ to $Q_5$ may be each independently selected from a hydrogen, a $C_1$-$C_{20}$ alkyl group, a $C_1$-$C_{20}$ alkoxy group, a phenyl group, and a naphthyl group.

In some other embodiments, in Formula 1, b1 may be 1, and at least one of c1 number of groups $R_1$ (for example, at least two of c1 number of groups $R_1$) may be selected from a substituted or unsubstituted $C_6$-$C_{20}$ aryl group, a substituted or unsubstituted $C_1$-$C_{20}$ heteroaryl group, a substituted or unsubstituted monovalent nonaromatic condensed polycyclic group, and a substituted or unsubstituted monovalent nonaromatic condensed heteropolycyclic group. However, embodiments of the present disclosure are not limited thereto.

For example, in Formula 1 above, b1 may be 1, and at least one of c1 number of groups $R_1$ (for example, at least two of c1 number of groups $R_1$) may be a group represented by one of Formulae 4-1 to 4-31 above, for example, a group represented by one of Formulae 5-1 to 5-27 above. However, embodiments of the present disclosure are not limited thereto.

In Formula 1 above, c1, which indicates the number of groups $R_1$, may be an integer of 1 to 5, for example, may be an integer selected from 1 to 3. In some embodiments, c1 may be 1 or 2, for example, may be 1. When c1 is 2 or greater, the at least two groups $R_1$ may be identical to or different from each other. c11 to c13, and c21 to c26 in Formula 1 above may be understood based on the above description of c1 and the structure of Formula 1 above.

The condensed cyclic compound of Formula 1 above may be a compound represented by one of Formulae 1A to 1D below:

Formula 1A

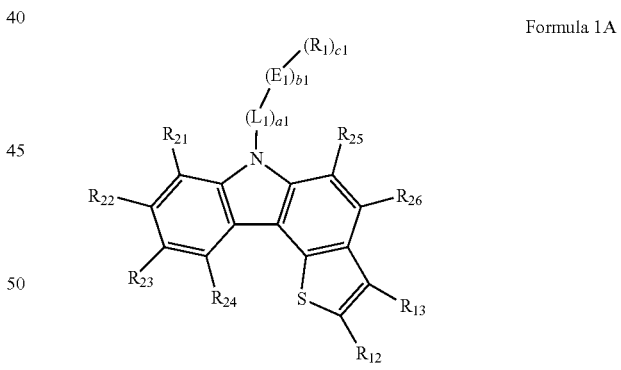

Formula 1B

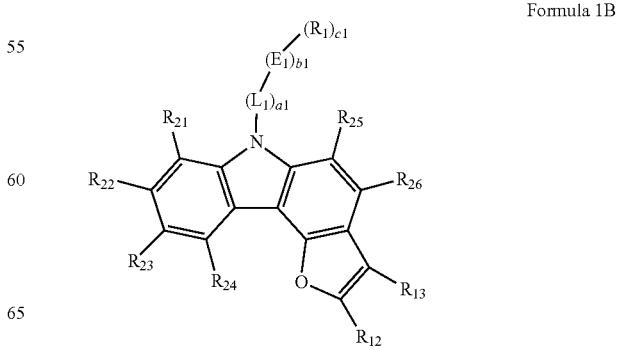

Formula 1C

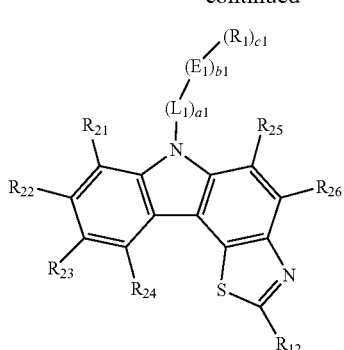

Formula 1D

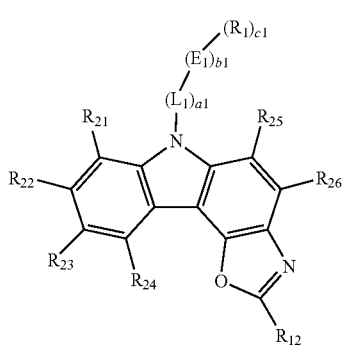

In Formulae 1A to 1D above, $L_1$, a1, $E_1$, $R_1$, $R_{12}$, $R_{13}$, $R_{21}$ to $R_{26}$, and c1 may be the same as those defined herein, and b1 may be an integer selected from 1 to 5. That is, $E_1$ as defined therein has to be present in each of Formulae 1A to 1D above.

In some embodiments, the condensed cyclic compound may be represented by one of Formulae 1A to 1D above, but is not limited thereto.

For example, the condensed cyclic compound of Formula 1 above may be a compound represented by one of Formulae 1A to 1D,
wherein $L_1$ may be a group represented by one of Formulae 2-1 to 2-33;
a1 may be 0, 1, or 2;
$E_1$ may be selected from a substituted or unsubstituted imidazolylene group, a substituted or unsubstituted pyridinylene group, a substituted or unsubstituted pyrimidinylene group, a substituted or unsubstituted quinolinylene group, a substituted or unsubstituted isoquinolinylene group, a substituted or unsubstituted quinazolinylene group, a substituted or unsubstituted phenanthrolinylene group, a substituted or unsubstituted benzoimidazolylene group, a substituted or unsubstituted triazolylene group, a substituted or unsubstituted oxadiazolylene group, a substituted or unsubstituted thiadiazolylene group, a substituted or unsubstituted triazinylene group, a substituted or unsubstituted imidazopyridinylene group, and a substituted or unsubstituted imidazopyrimidinylene group;
at least one of substituents of the substituted imidazolylene group, the substituted pyridinylene group, the substituted pyrimidinylene group, the substituted quinolinylene group, the substituted isoquinolinylene group, the substituted quinazolinylene group, the substituted phenanthrolinylene group, the substituted benzoimidazolylene group, the substituted triazolylene group, the substituted oxadiazolylene group, the substituted thiadiazolylene group, the substituted triazinylene group, the substituted imidazopyridinylene group, and the substituted imidazopyrimidinylene group may be selected from
a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, phenyl group, a naphthyl group, an anthracenyl group, a triphenylenyl group, a
pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group,
a phenyl group, a naphthyl group, an anthracenyl group, a triphenylenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, phenyl group, a naphthyl group, an anthracenyl group, a triphenylenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{23}$)($Q_{24}$)($Q_{25}$), and
—Si($Q_{33}$)($Q_{34}$)($Q_{35}$),
wherein $Q_{23}$ to $Q_{25}$ and $Q_{33}$ to $Q_{35}$ may be each independently selected from a hydrogen, $C_1$-$C_{20}$ alkyl group, a $C_1$-$C_{20}$ alkoxy group, phenyl group, a naphthyl group, an anthracenyl group, a triphenylenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, dibenzofuranyl group, a quinoxalinyl group, a cinnolinyl group, and a quinazolinyl group;
b1 may be 1 or 2;
$R_1$, $R_{12}$, $R_{13}$, and $R_{21}$ to $R_{26}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a group represented by one of Formulae 4-1 to 4-31 above, and —Si($Q_3$)($Q_4$)($Q_5$),
wherein $Q_3$ to $Q_5$ may be each independently selected from a hydrogen, a $C_1$-$C_{20}$ alkyl group, a $C_1$-$C_{20}$ alkoxy group, phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group; and c1 may be 1 or 2.

In some other embodiments, the condensed cyclic compound of Formula 1 above may be a compound represented by one of Formulae 1A to 1D, wherein $L_1$ may be a group represented by one of Formulae 3-1 to 3-21 above;

a1 may be 0, 1, or 2;

E may be a group represented by one of Formulae 10-1 to 10-27 above;

$R_1$, $R_{12}$, $R_{13}$, and $R_{21}$ to $R_{26}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a group represented by one of Formulae 5-1 to 5-27 above, and —Si($Q_3$)($Q_4$)($Q_5$), wherein at least one of c1 number of groups $R_1$ may be a group represented by one of Formulae 5-1 to 5-27, and $Q_3$ to $Q_5$ may be each independently selected from a hydrogen, $C_1$-$C_{20}$ alkyl group, a $C_1$-$C_{20}$ alkoxy group, phenyl group, and a naphthyl group; and c1 may be 1 or 2.

For example, the condensed cyclic compound of Formula 1 above may be one of Compounds 1 to 504 below, but is not limited thereto.

1

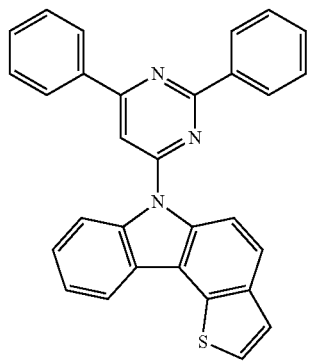

2

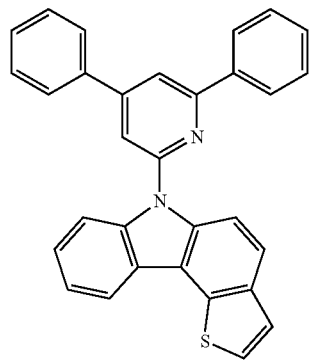

3

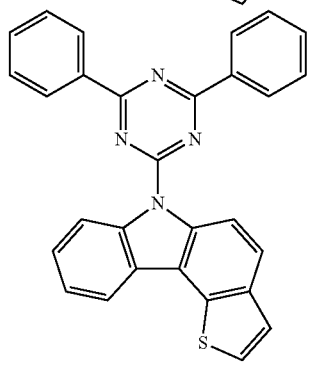

4

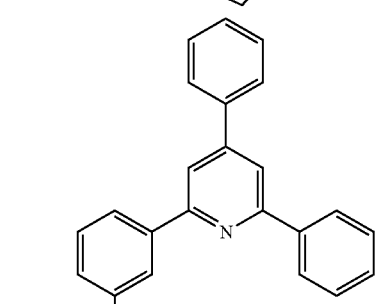

5

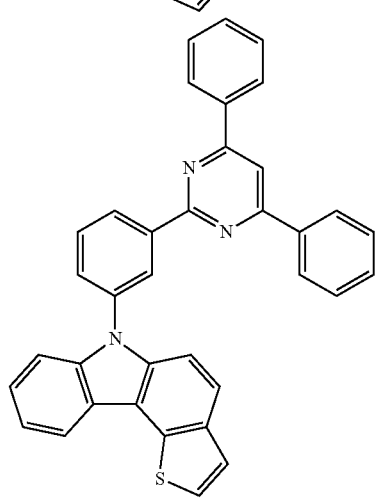

6

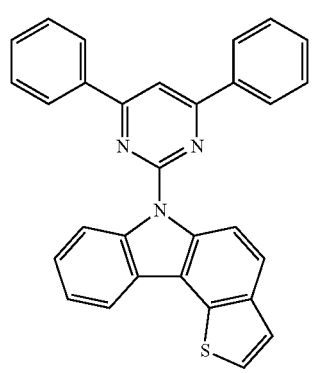

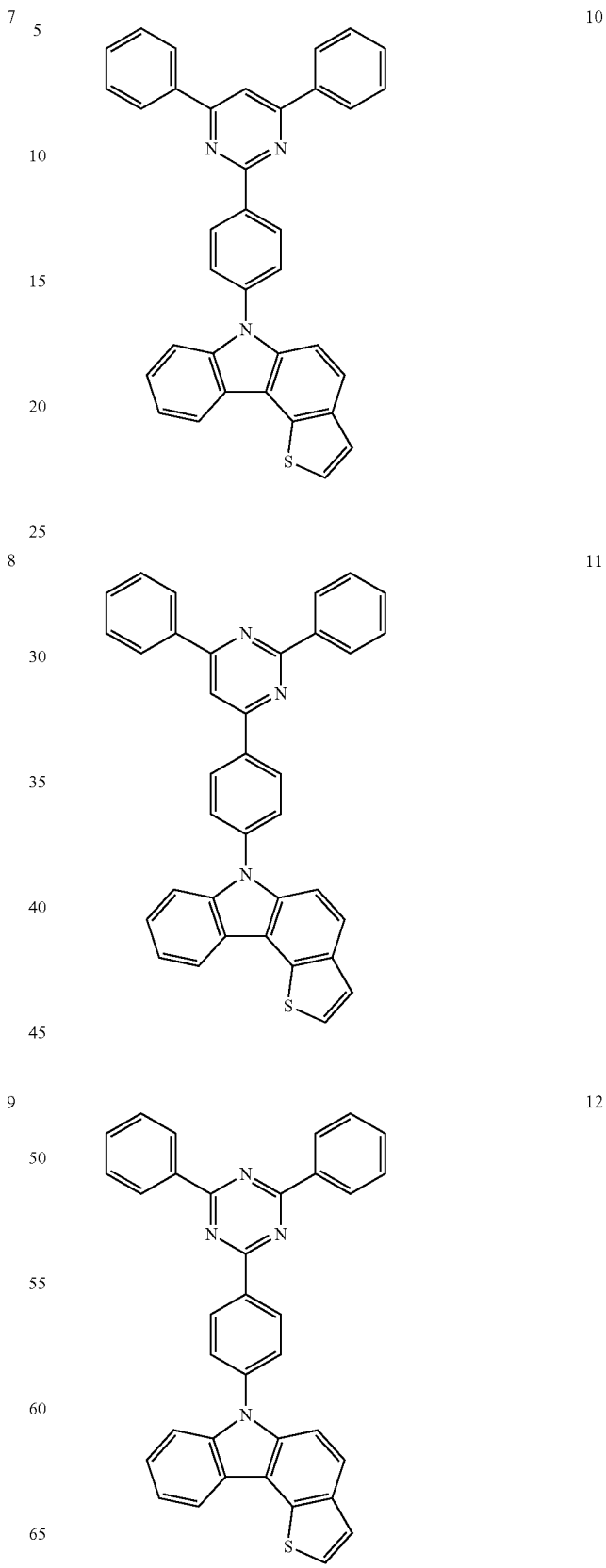

13
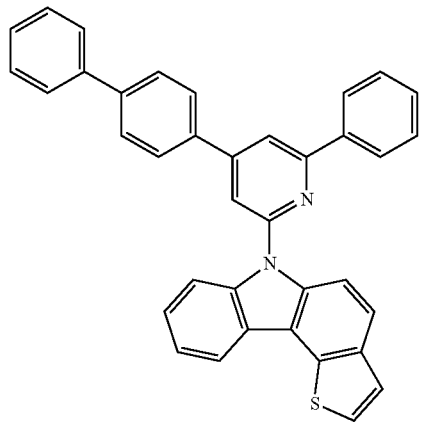
14
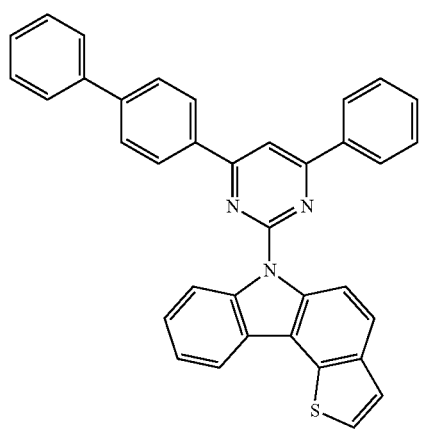
15
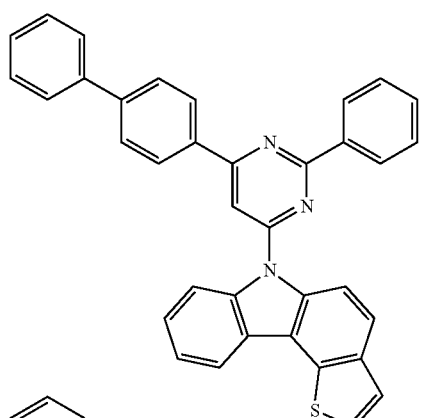
16
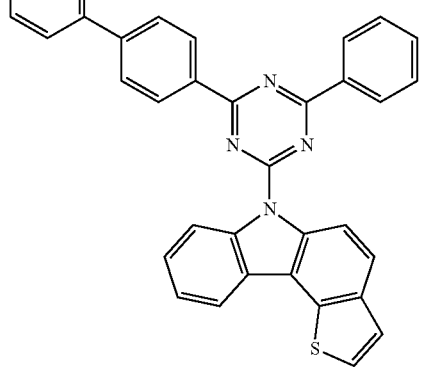
17
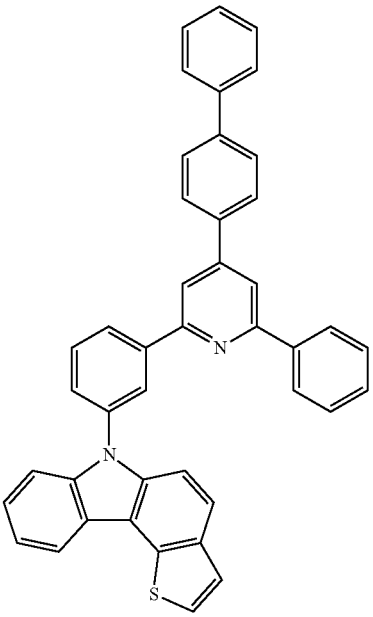
18
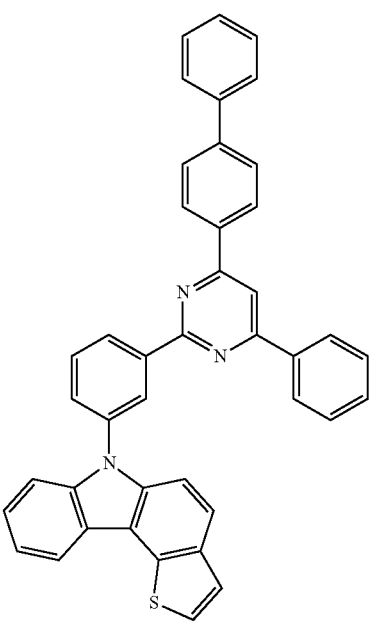

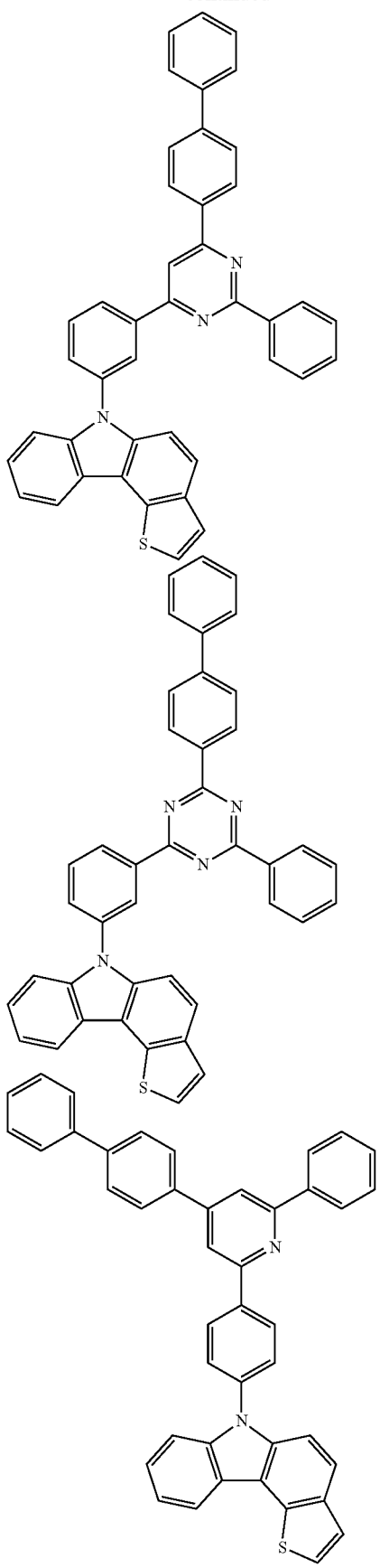
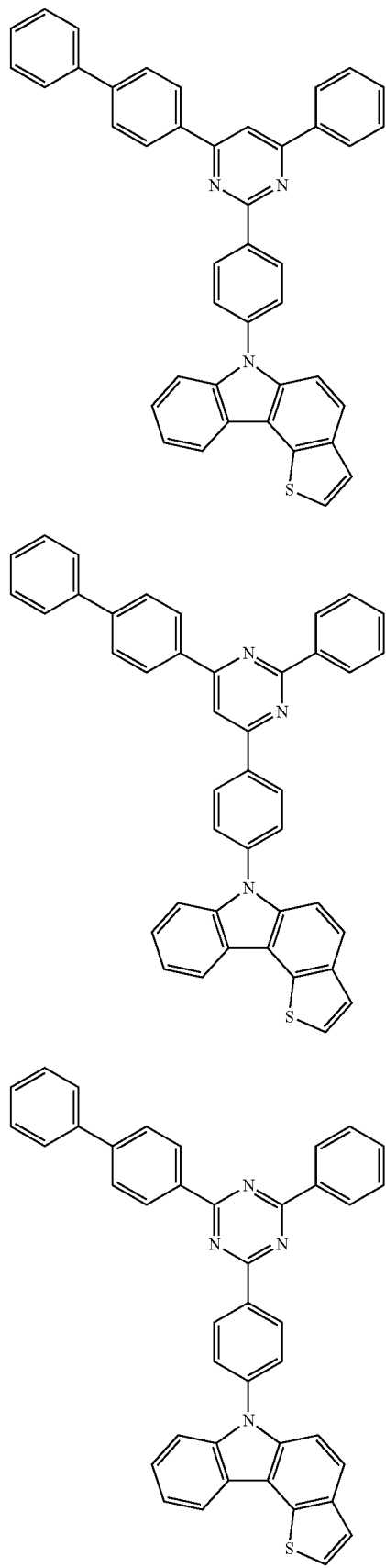

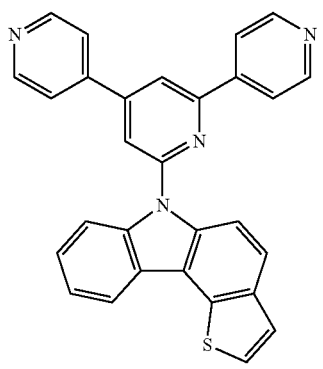
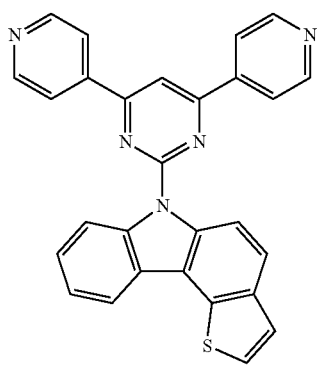
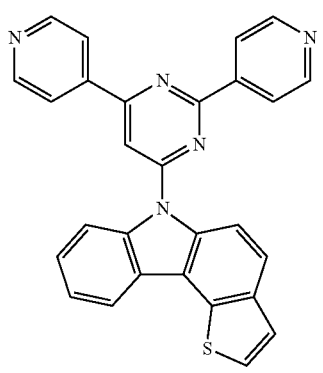
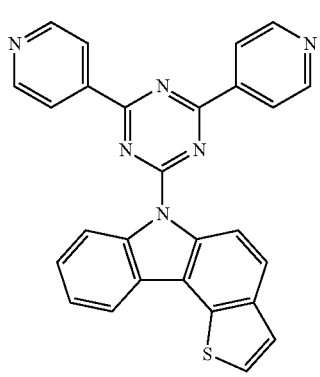
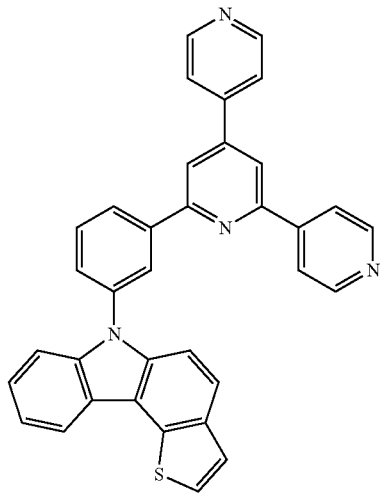
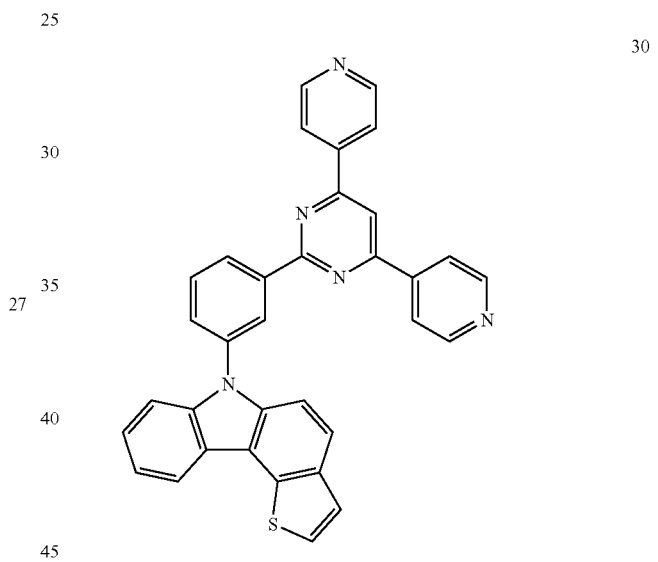
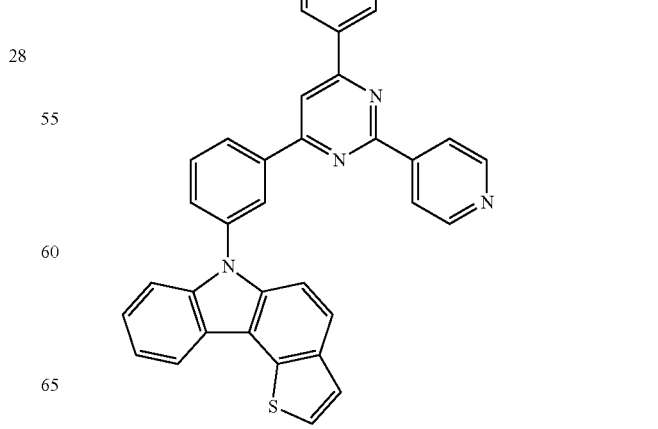

32
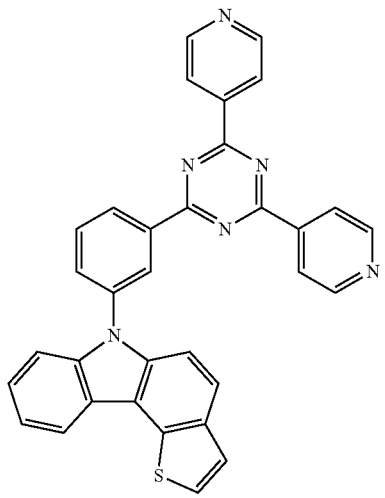
33
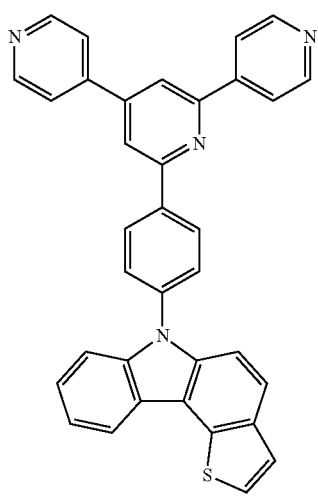
34
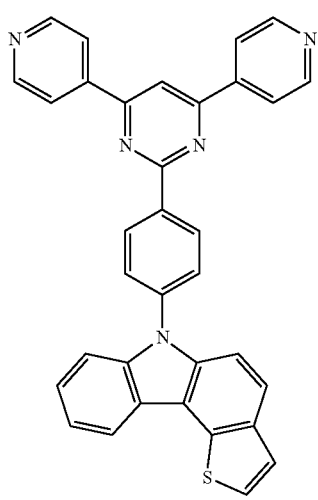
35
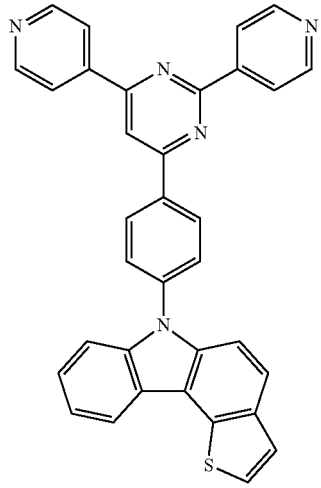
36
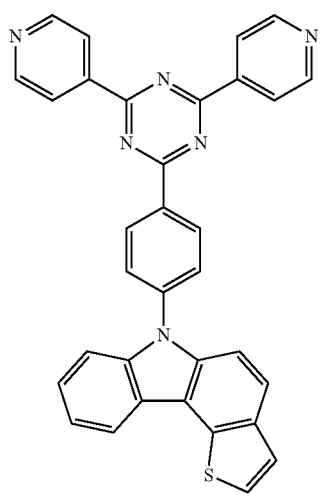
37
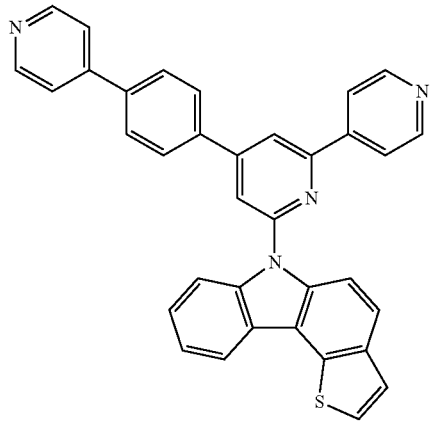

51
-continued
38
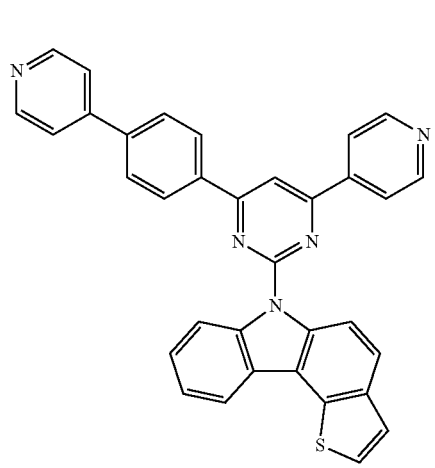
39
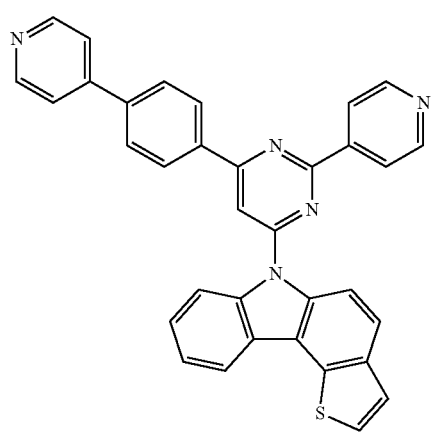
40
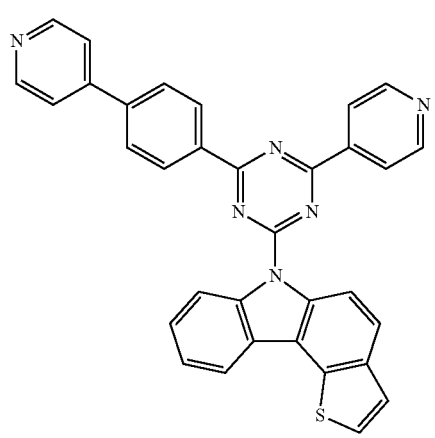
52
-continued
41
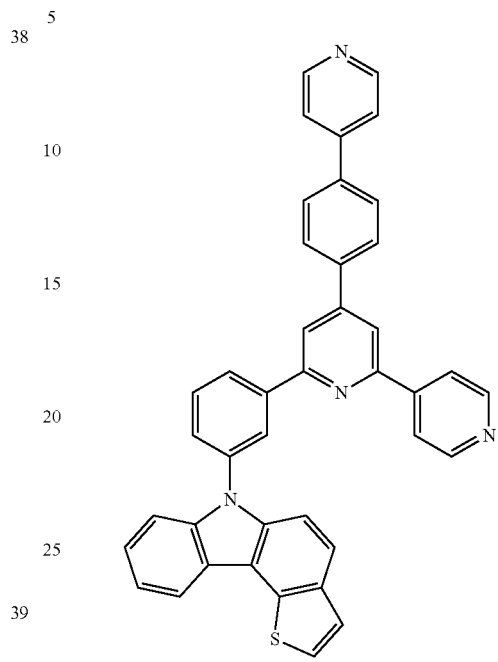
42
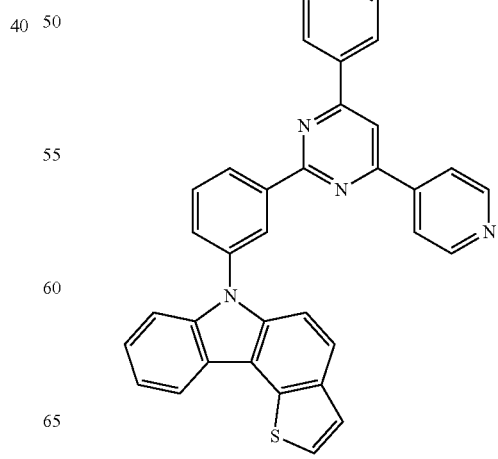

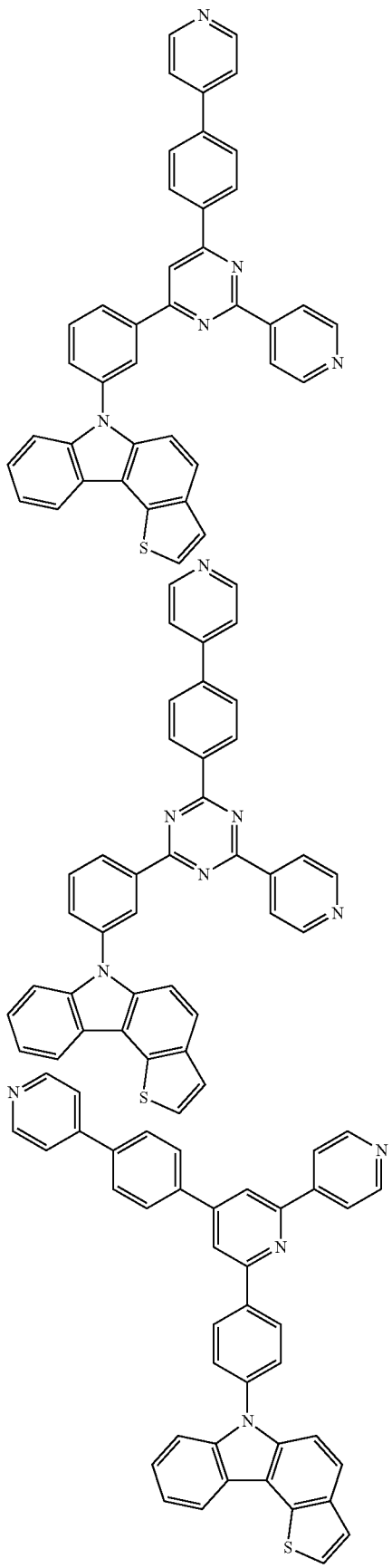
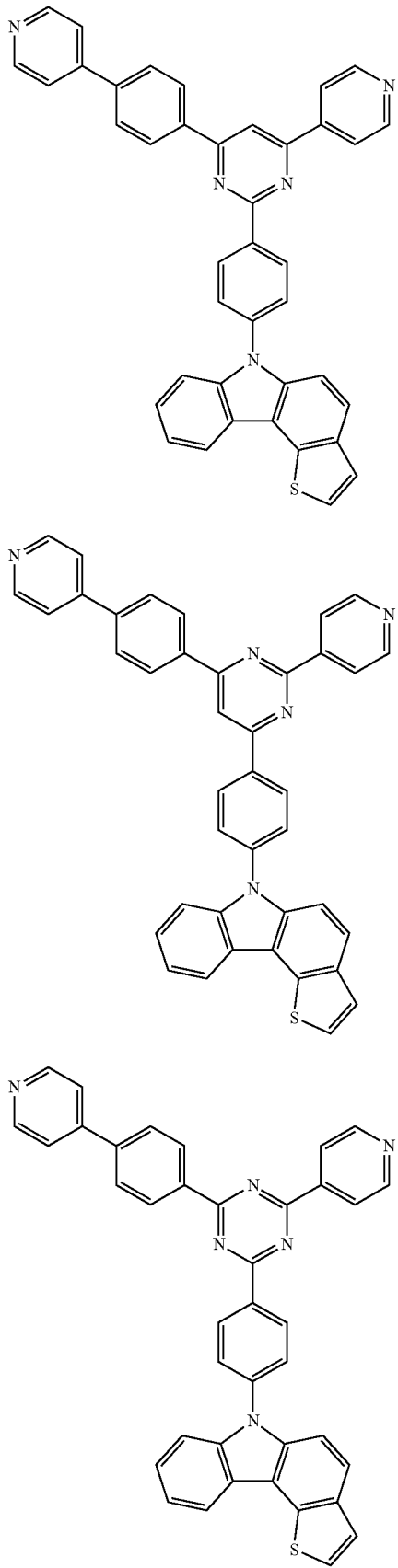

49
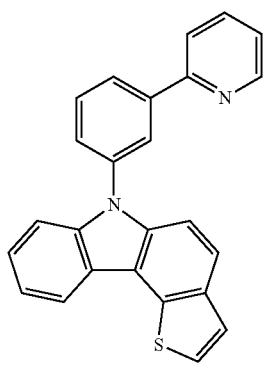
50
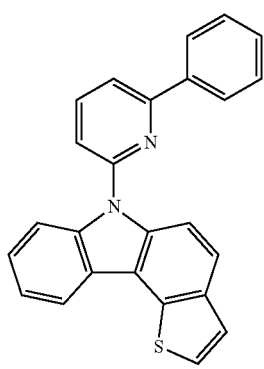
51
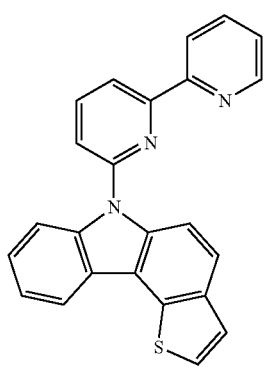
52
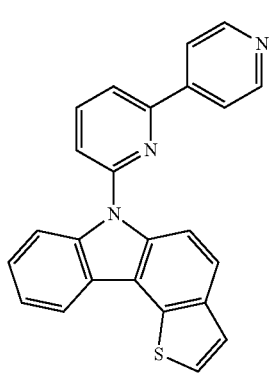
53
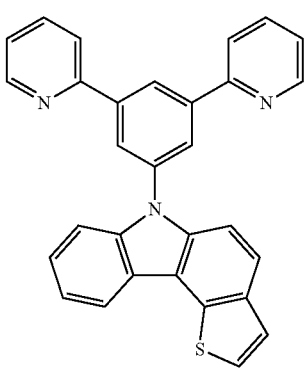
54
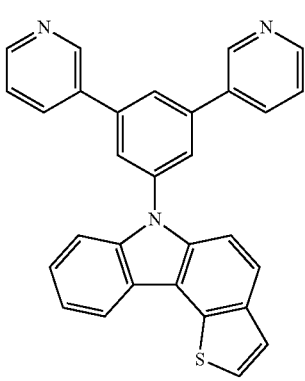
55
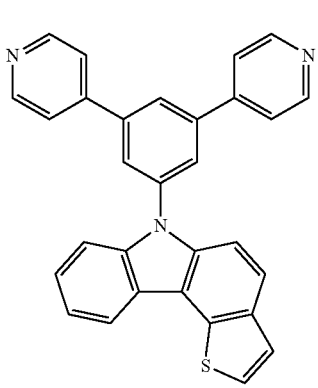
56
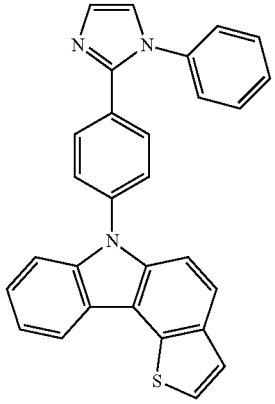

57
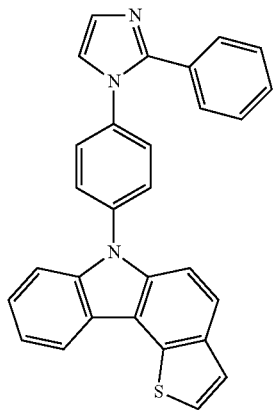
58
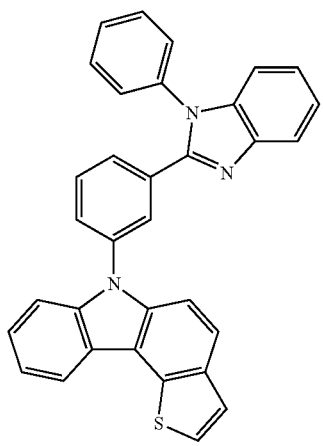
59
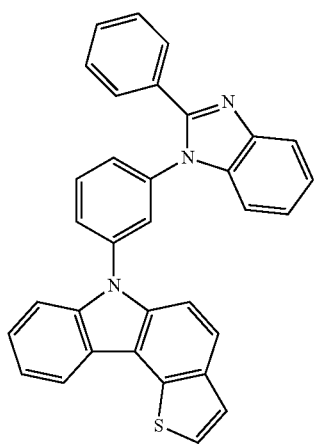
57
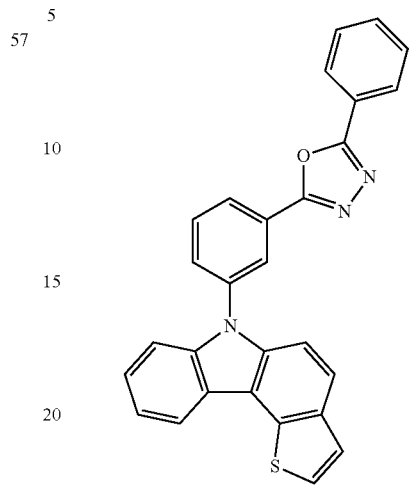
58
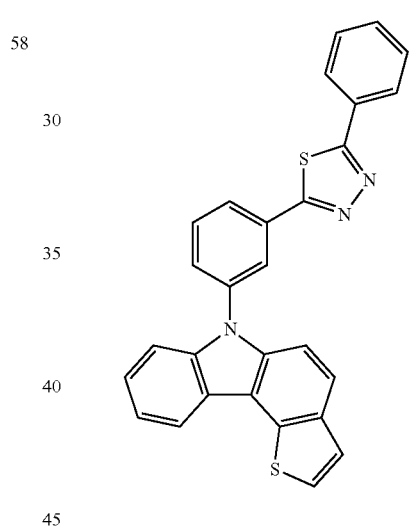
60
61
62
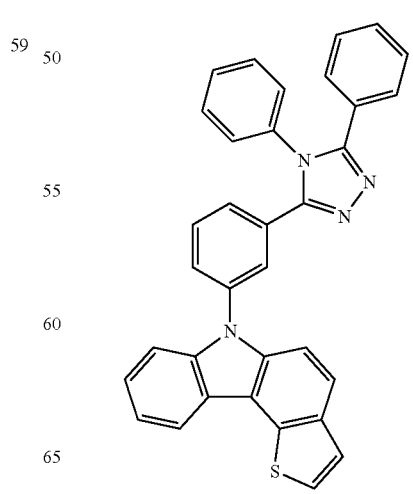

63
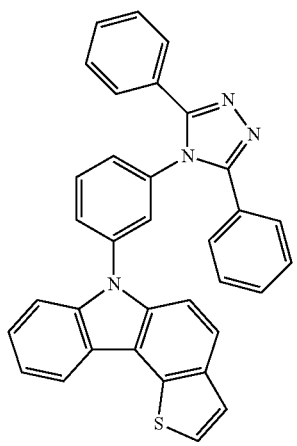
64
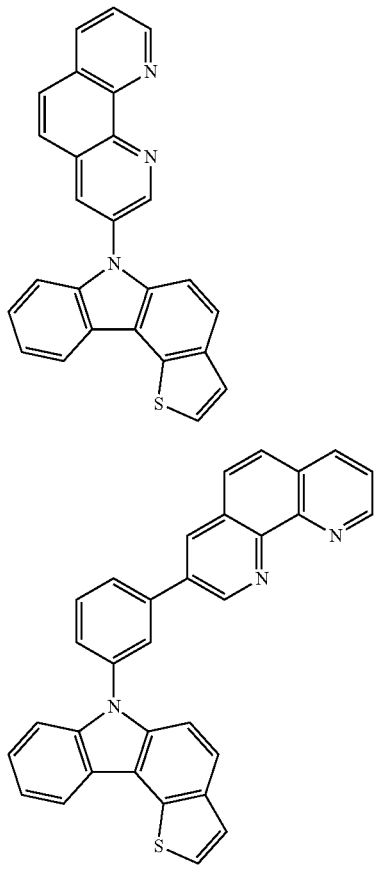
65
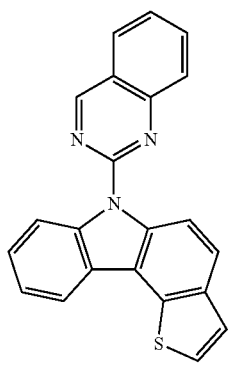
67
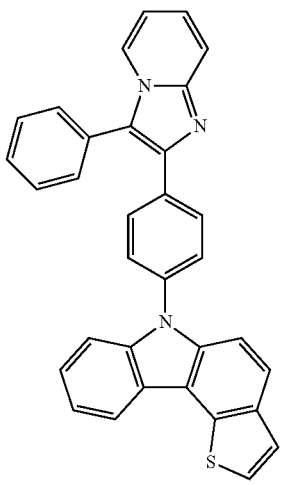
68
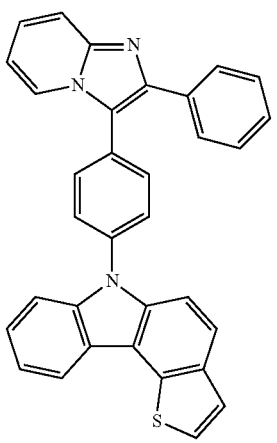
69
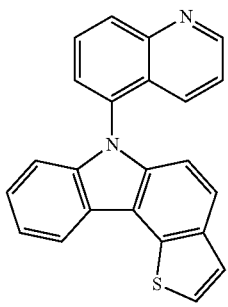
70
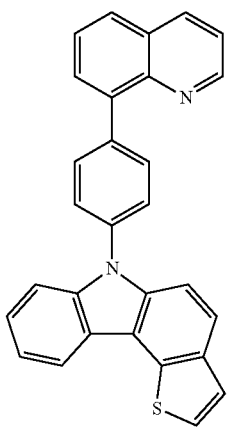

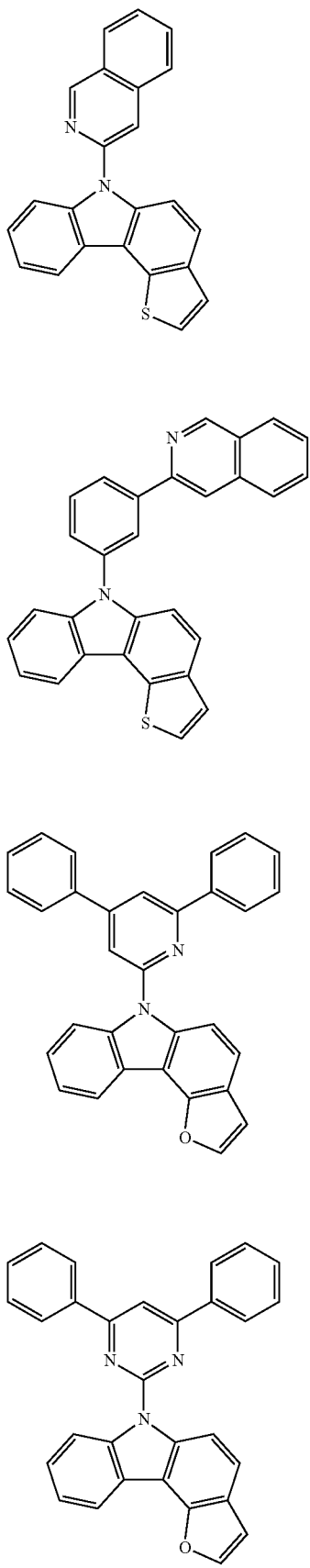
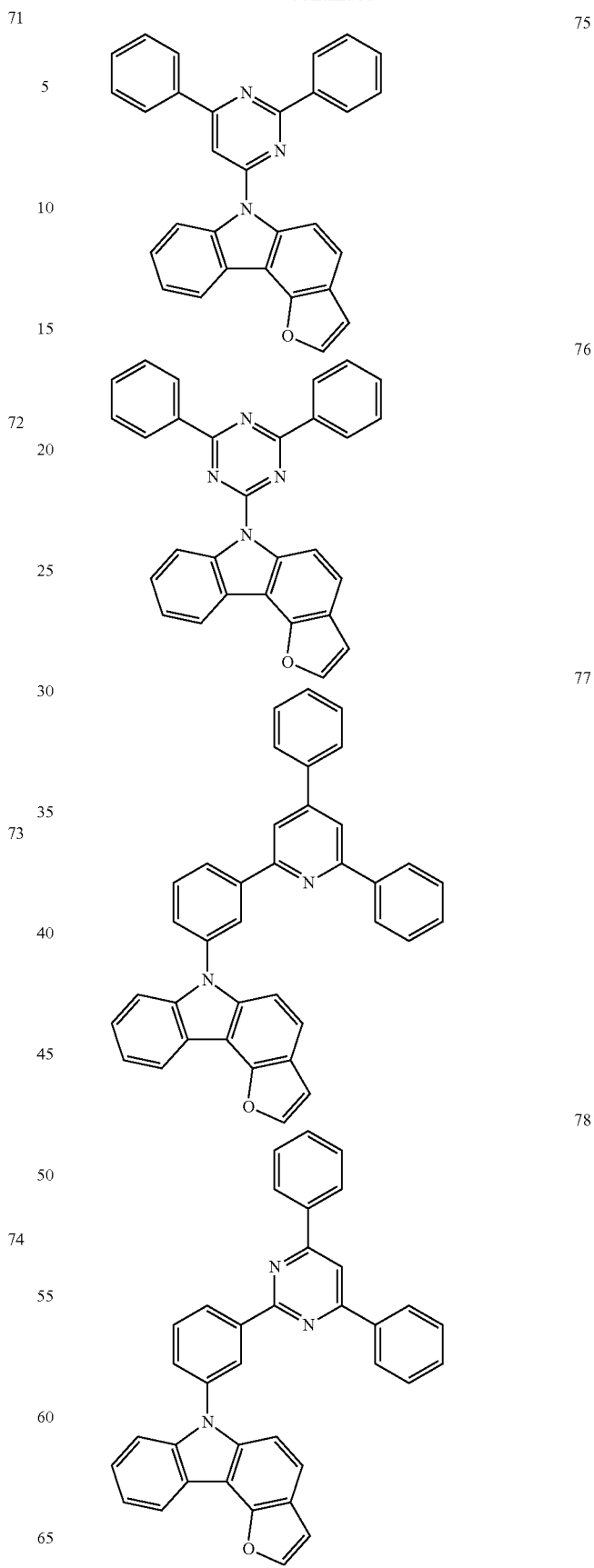

63
-continued
79
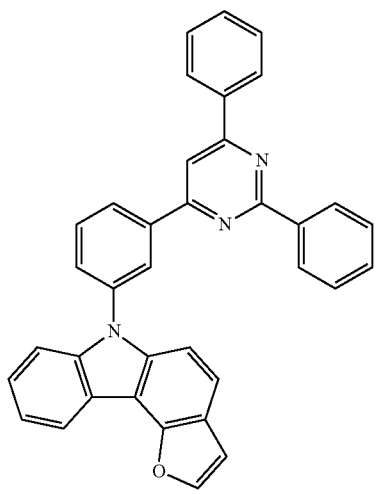
80
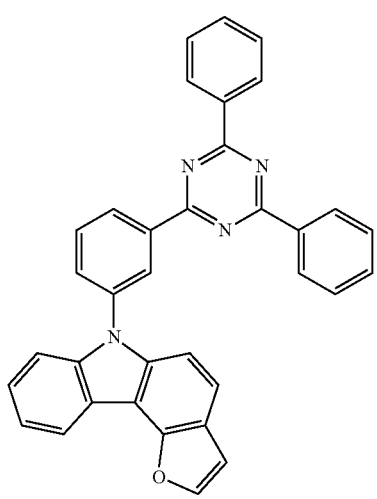
81
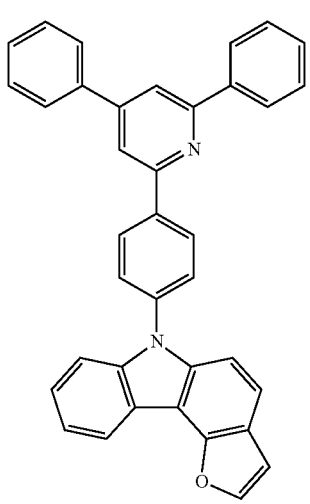
64
-continued
82
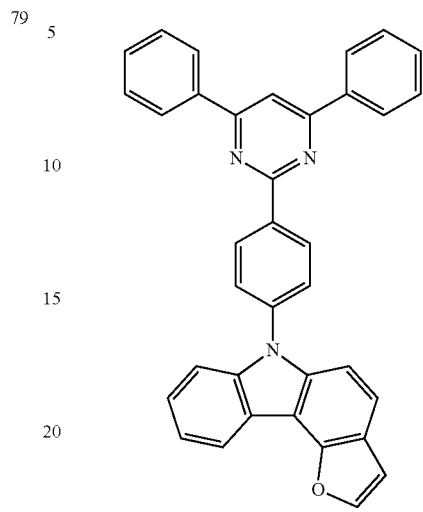
83
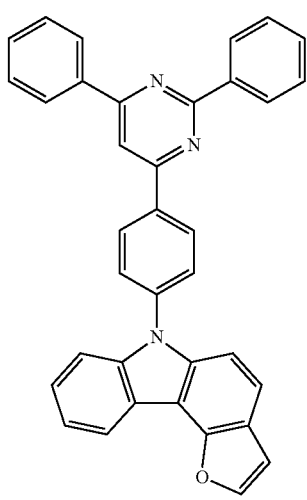
84
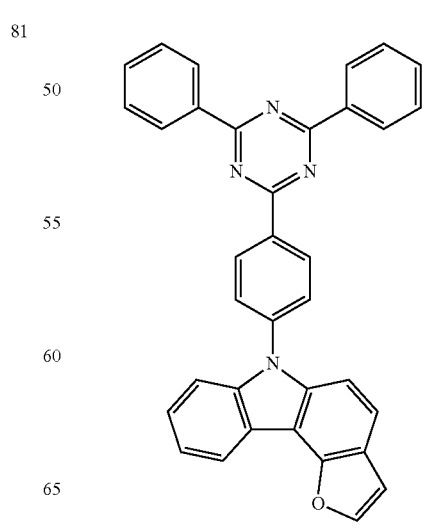

85
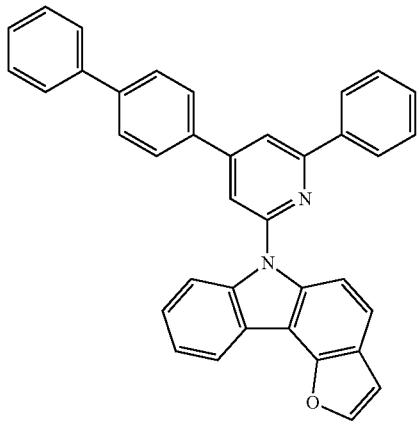
86
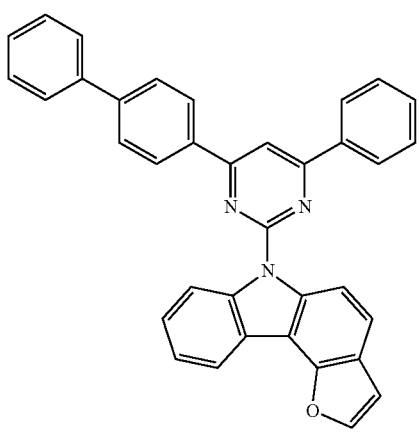
87
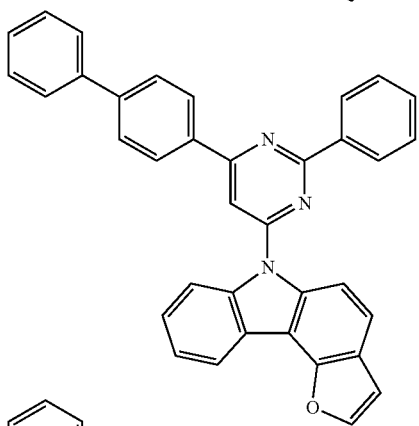
88
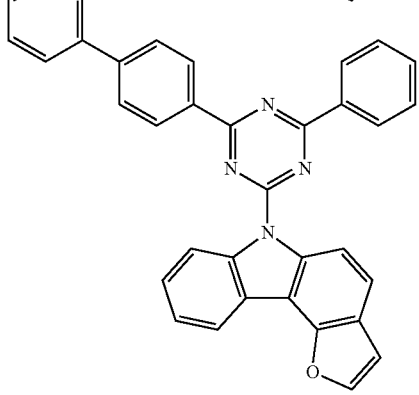
89
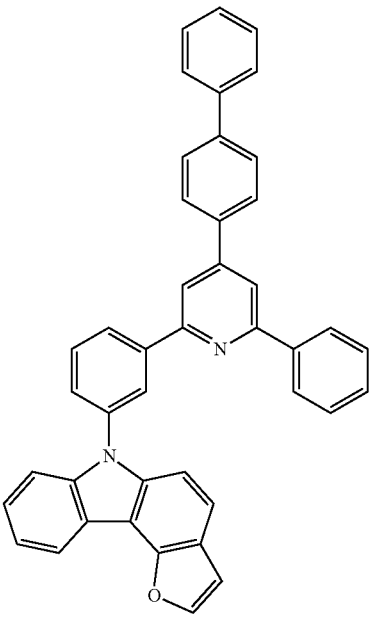
90
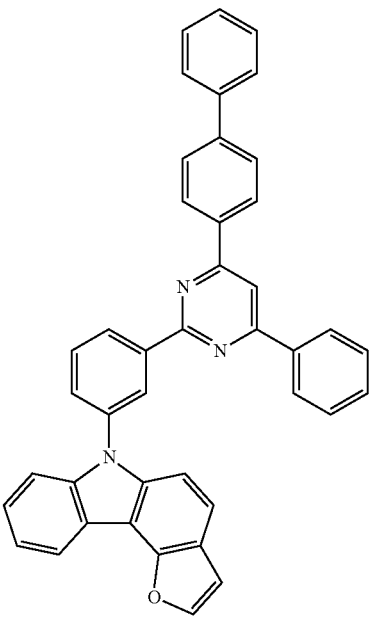

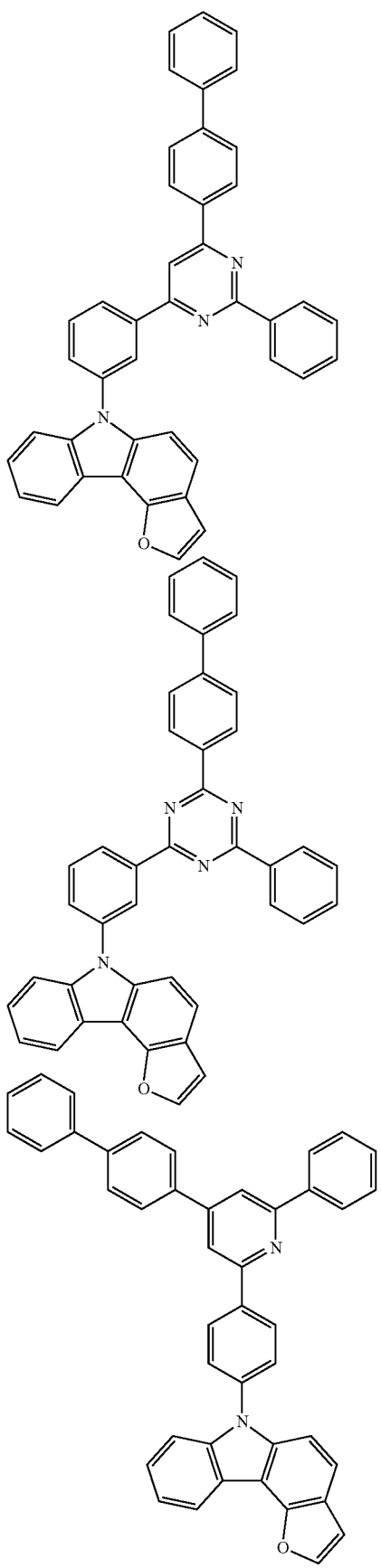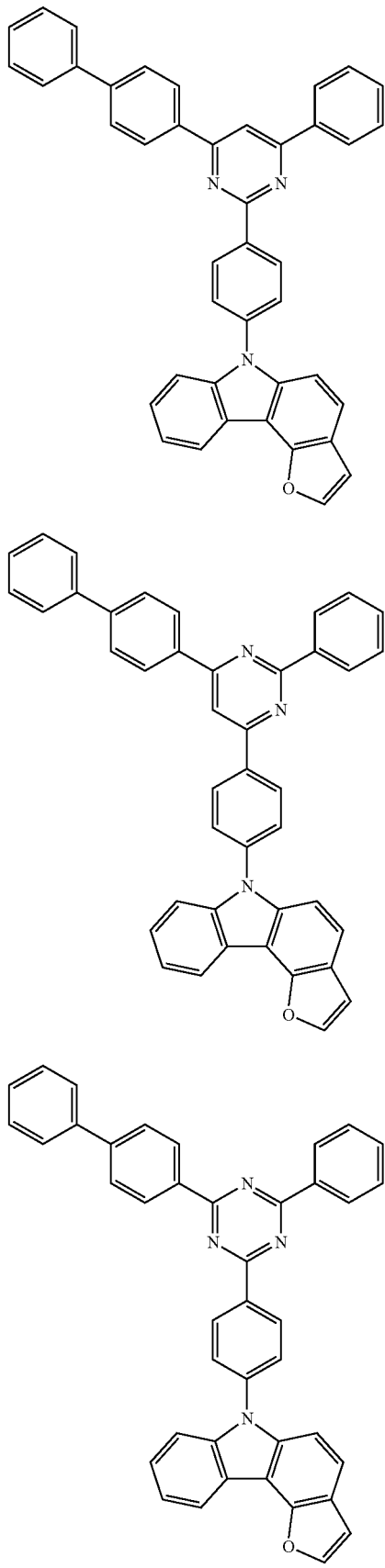

97
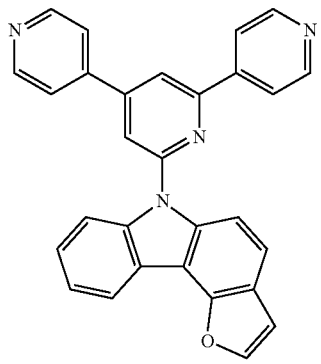
98
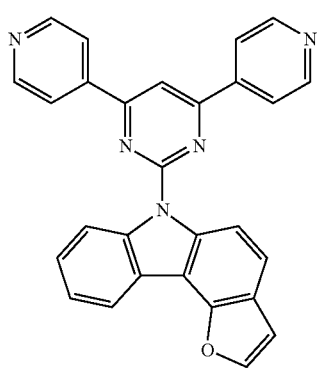
99
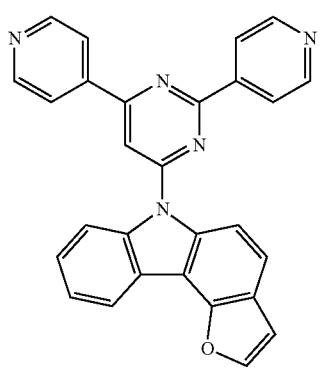
100
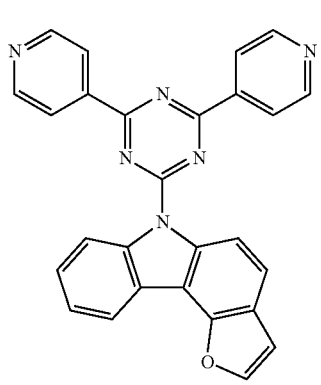
101
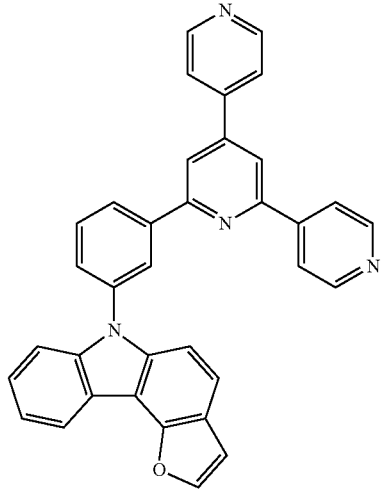
102
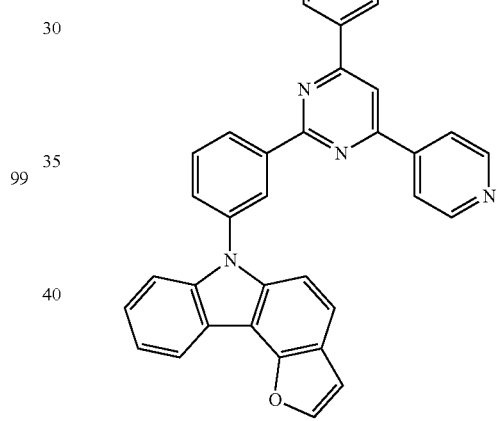
103
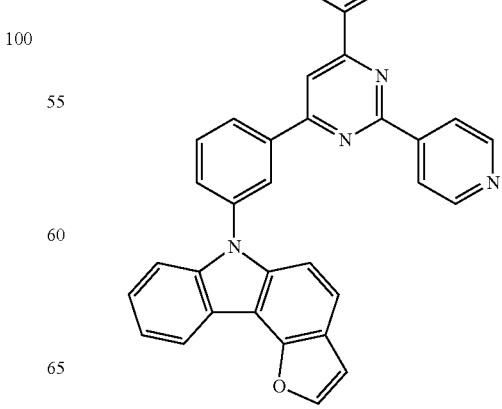

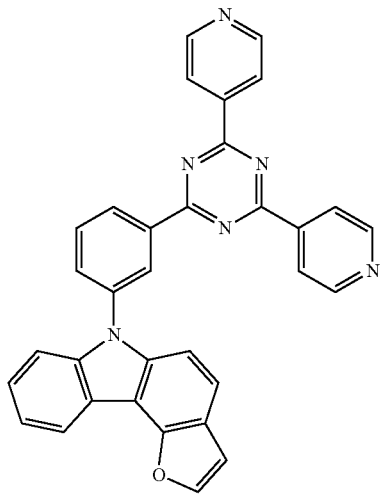
104
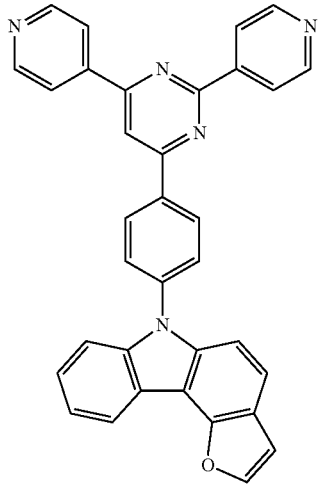
107
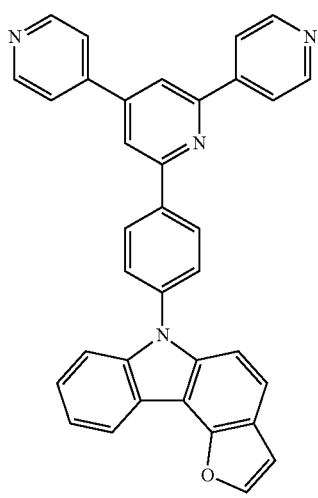
105
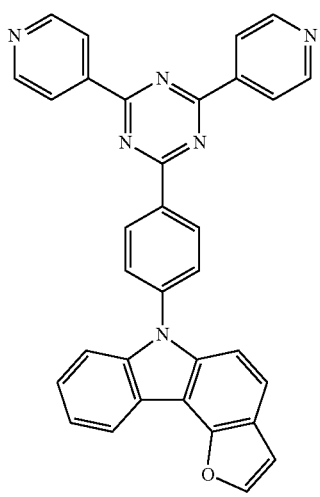
108
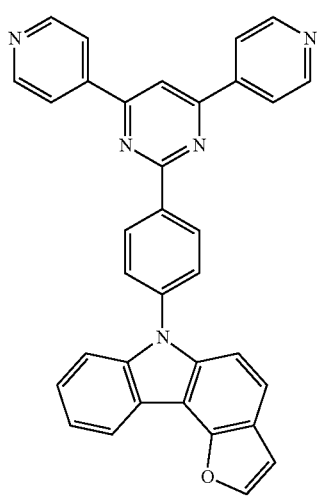
106
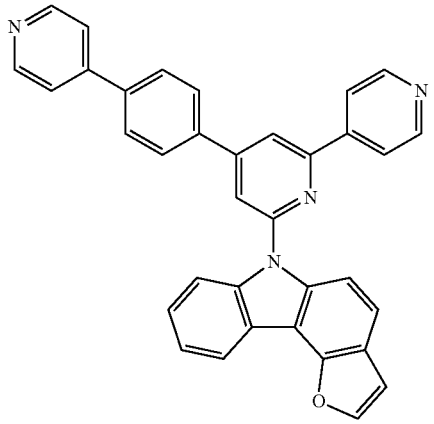
109

73
-continued
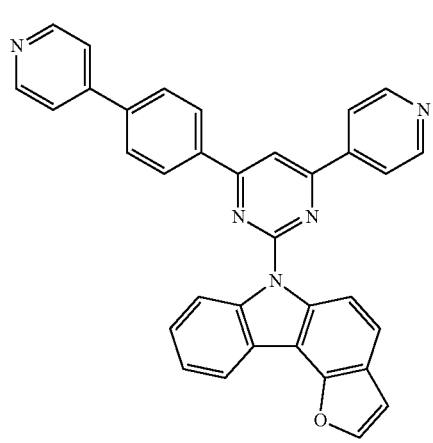
110
111
112
74
-continued
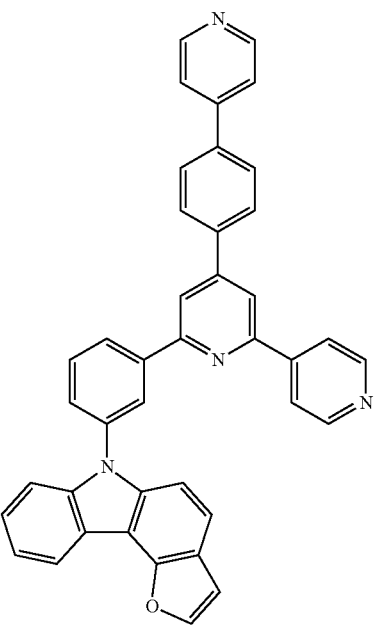
113
114
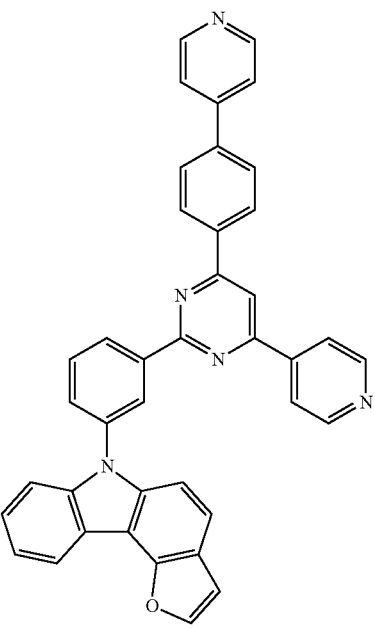

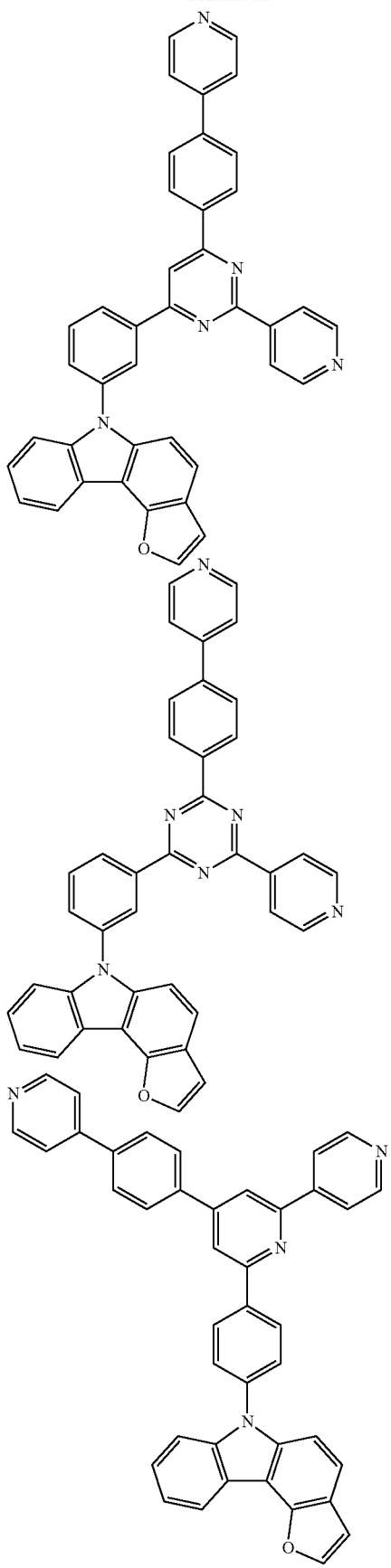
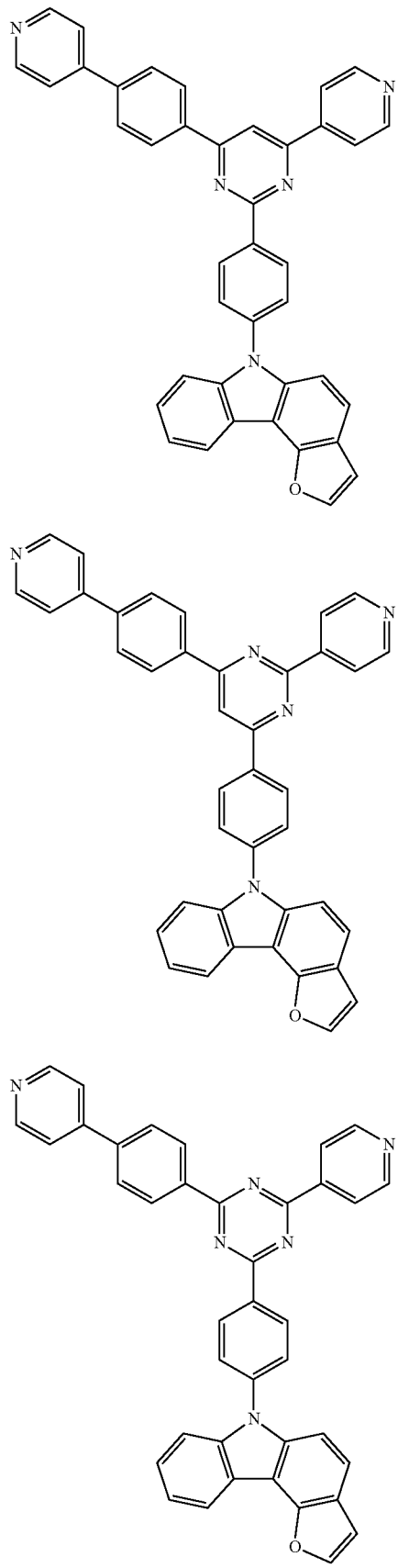

121 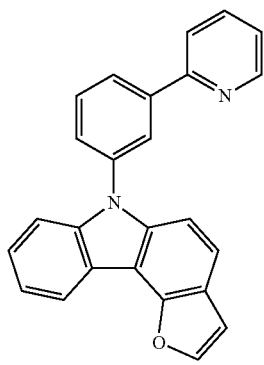
125 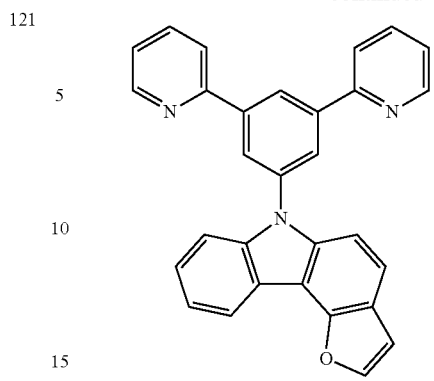
122 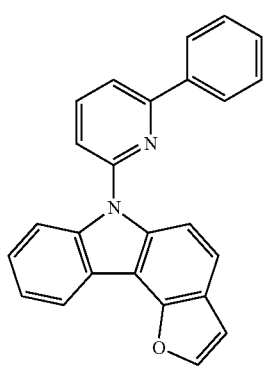
126 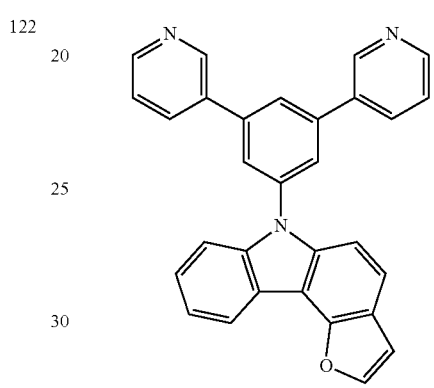
123 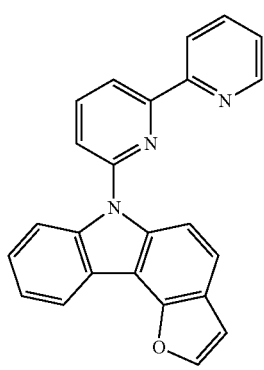
127 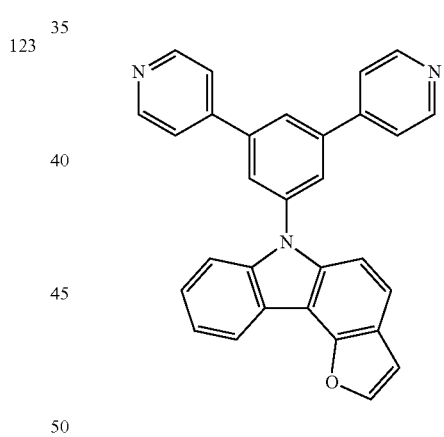
124 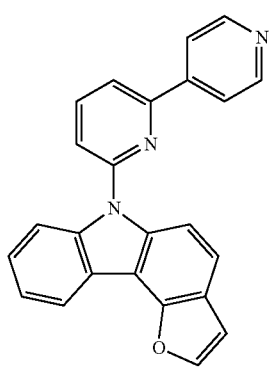
128 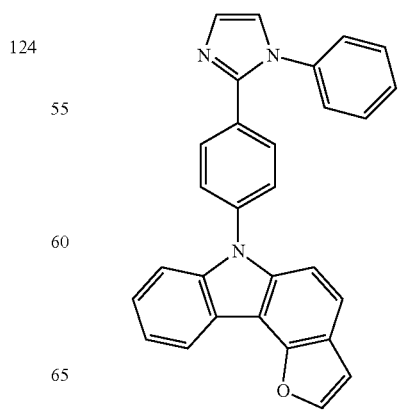

129 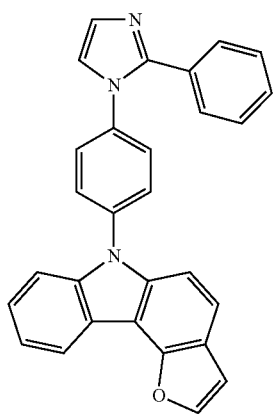
130 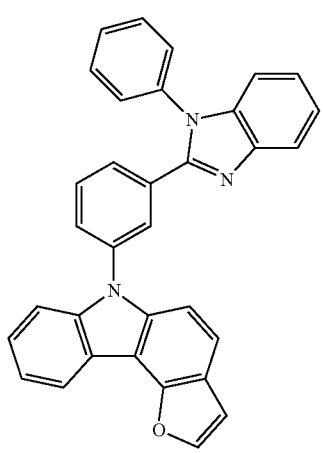
131 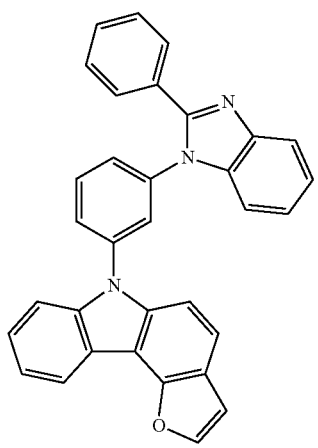
132 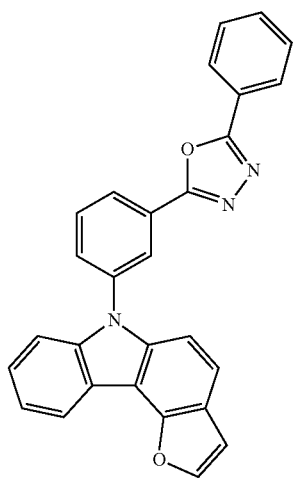
133 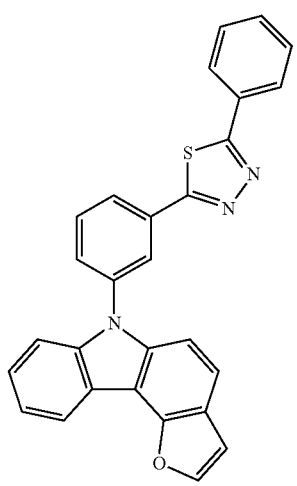
134 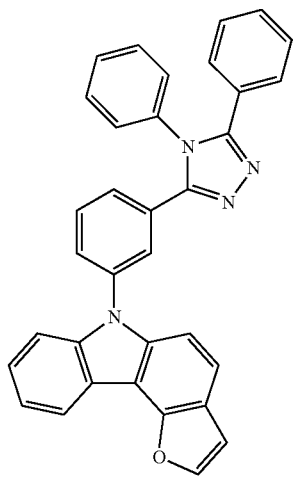

135 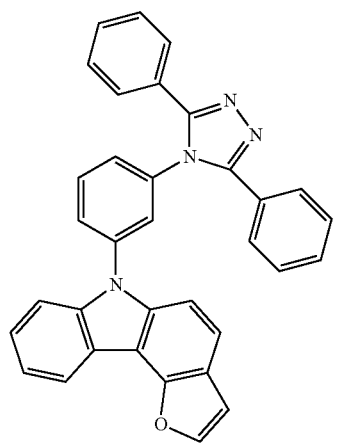
136 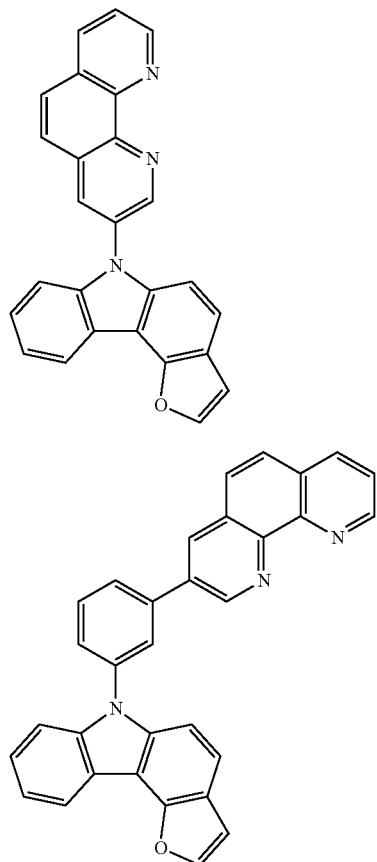
137 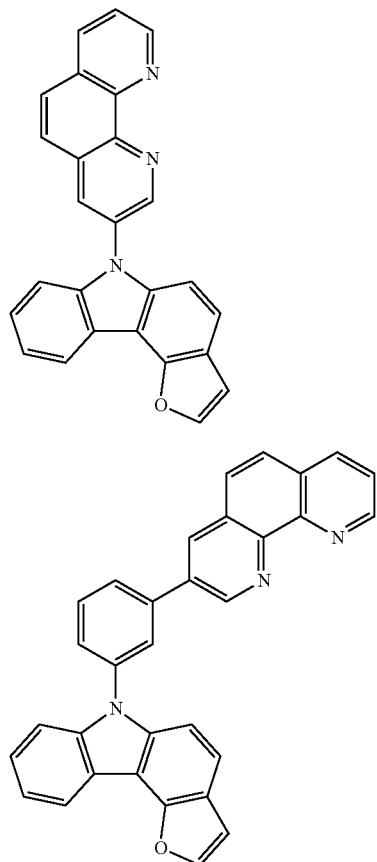
138 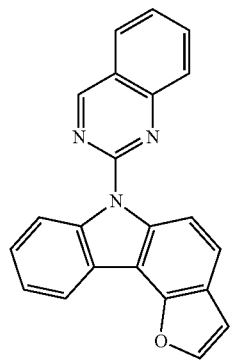
139 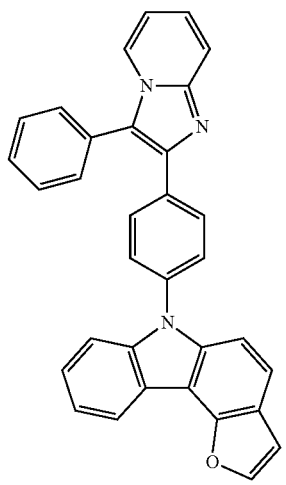
140 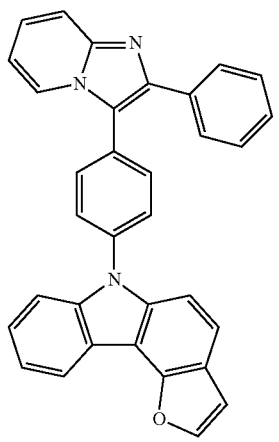
141 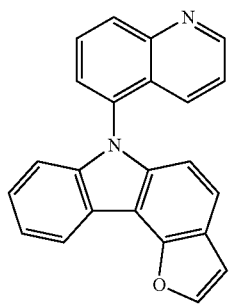
142 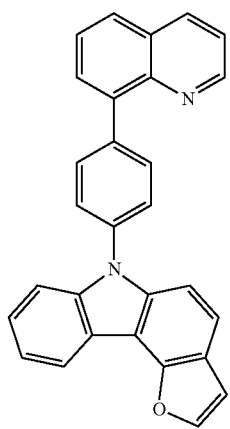

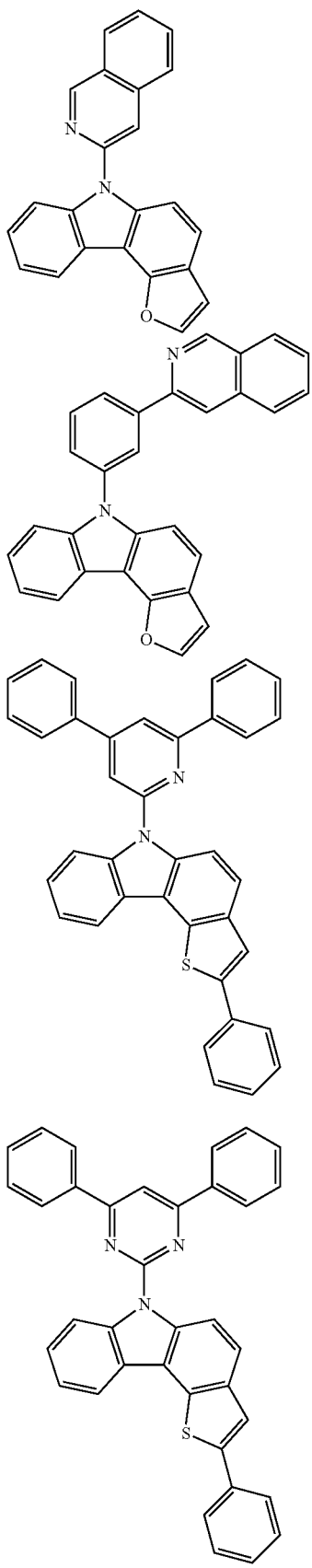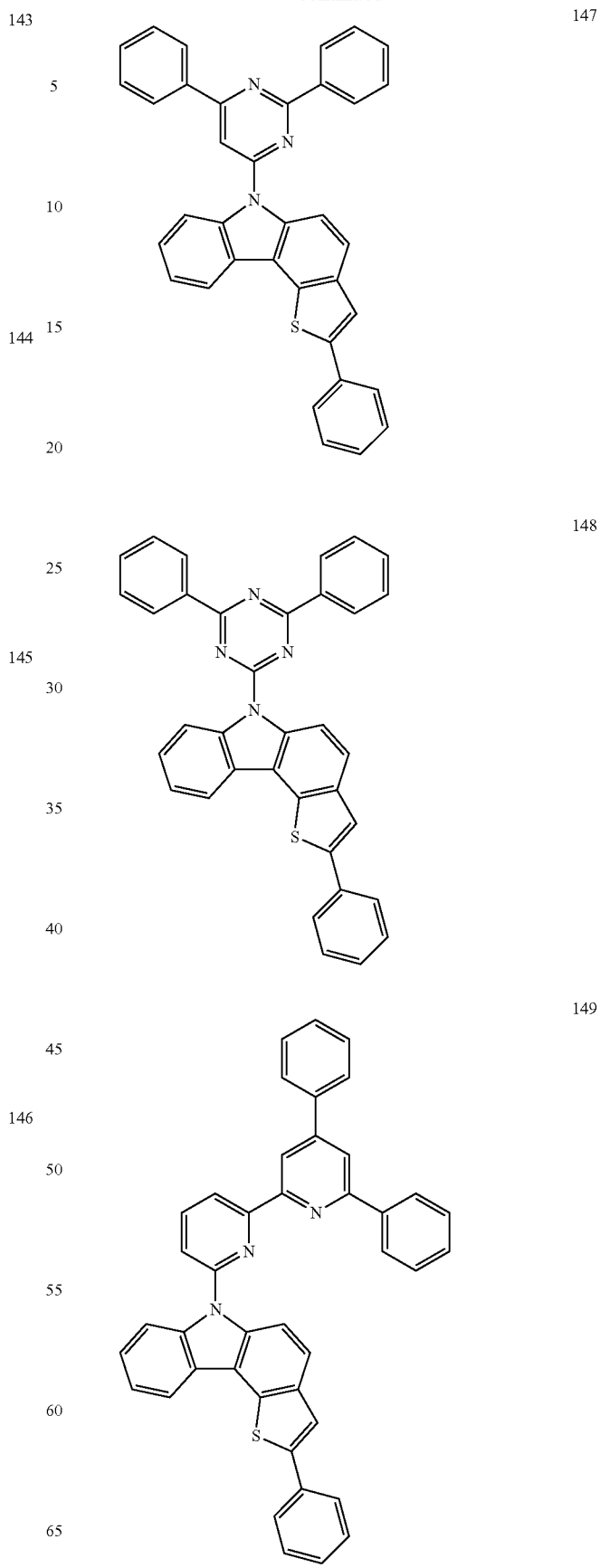

150 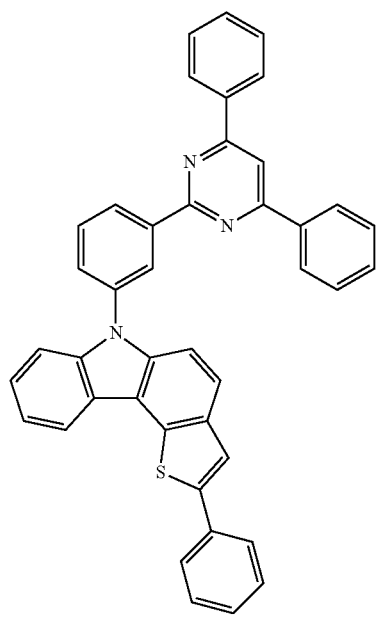
152 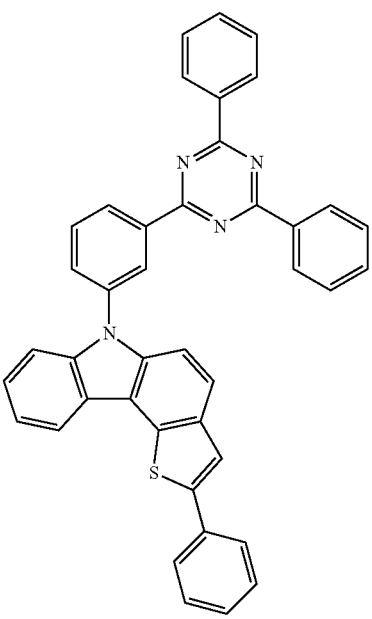
151 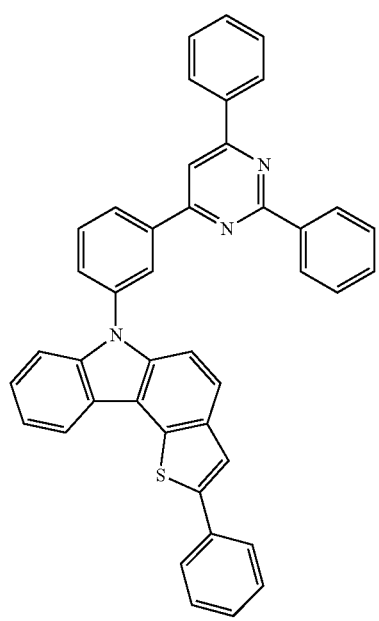
153 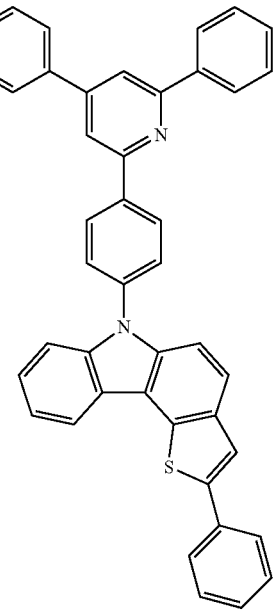

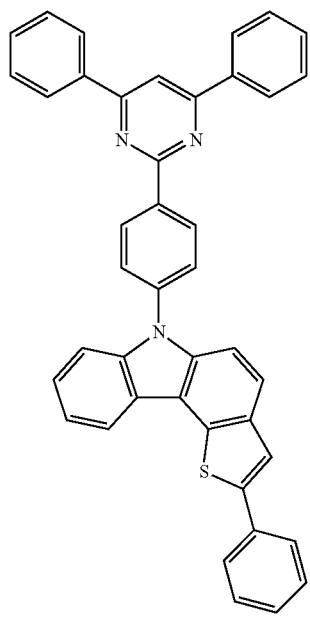
154
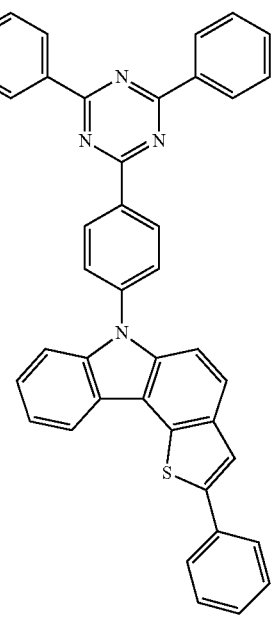
157
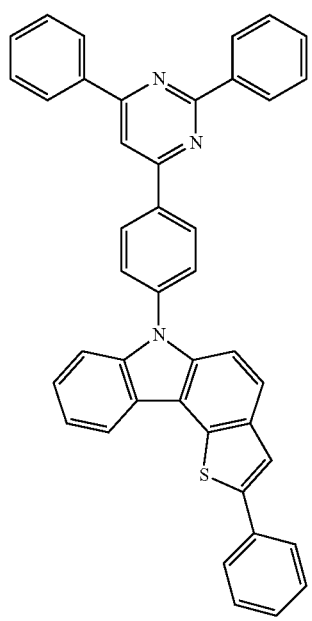
155
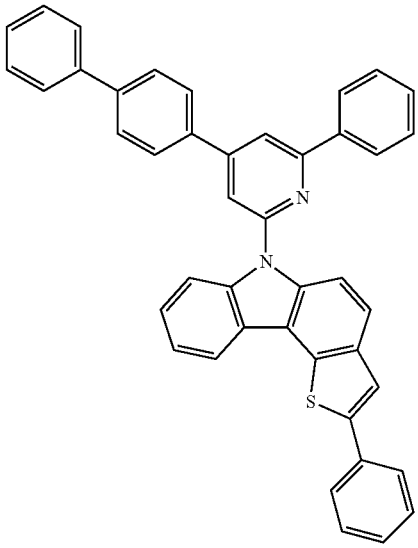
157

158
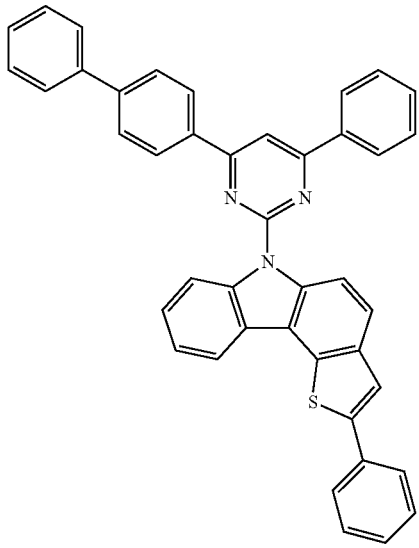
159
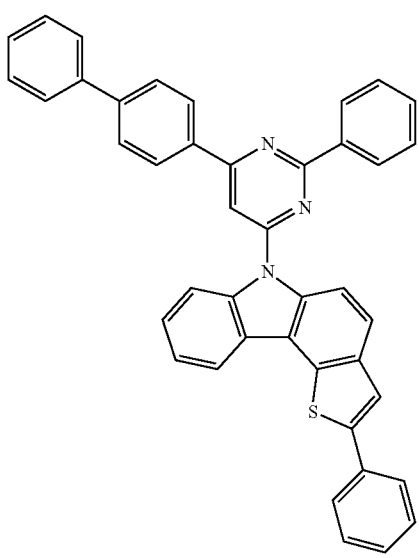
160
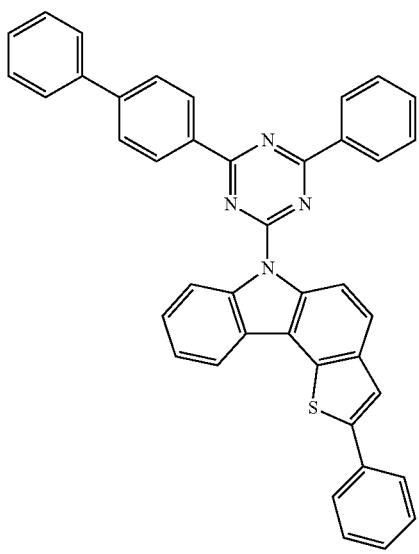
161
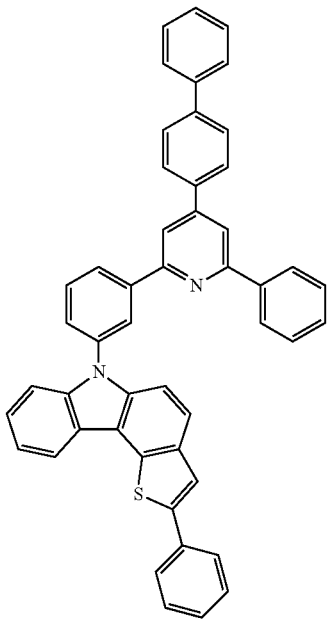
162
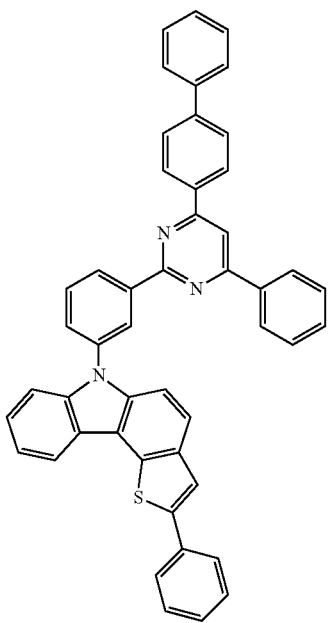

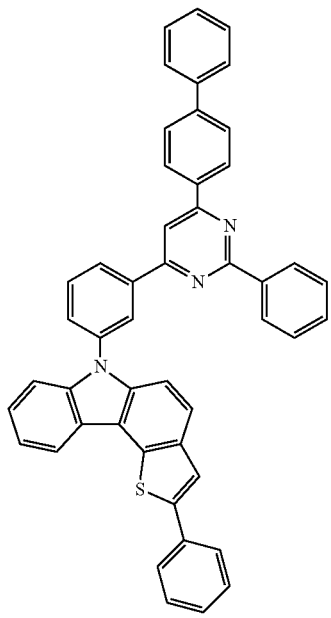
163
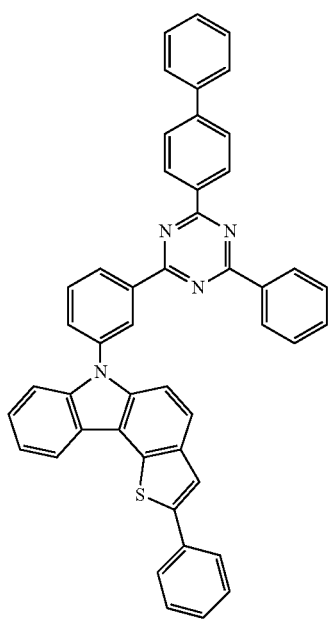
164
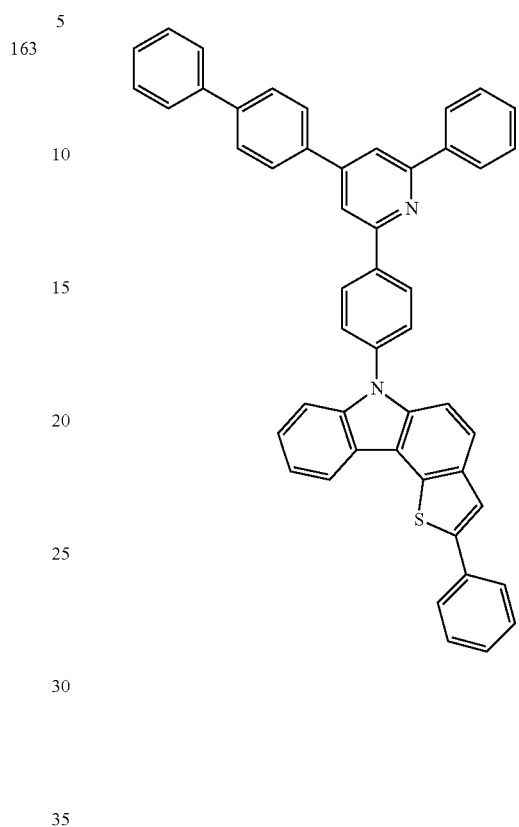
165
166

167
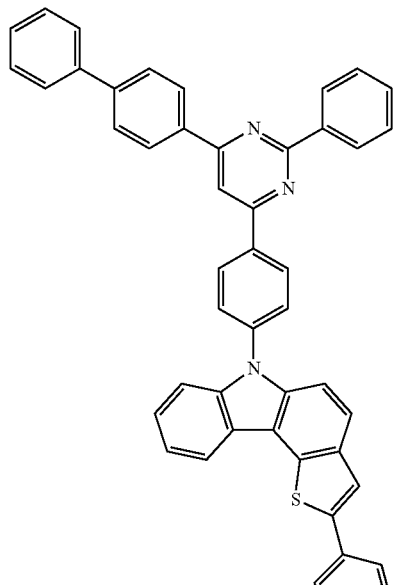
168
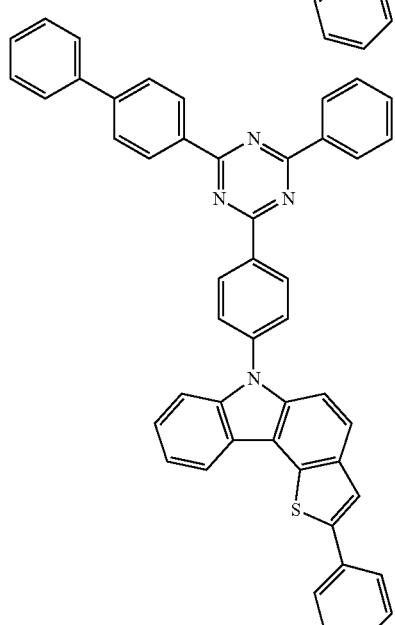
169
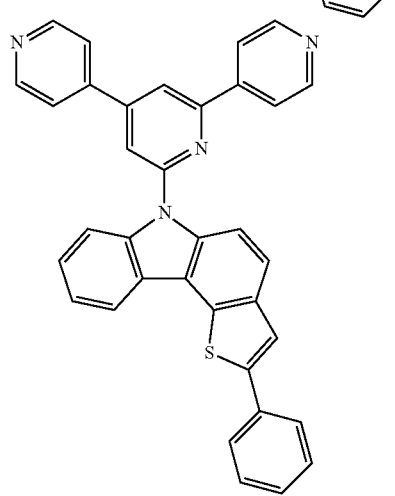
170
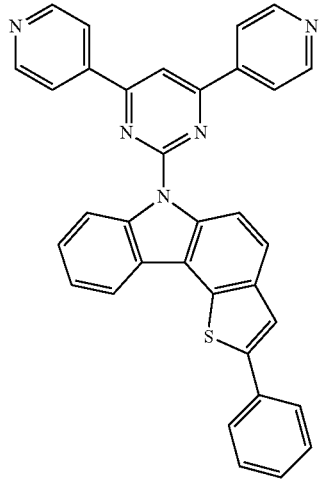
171
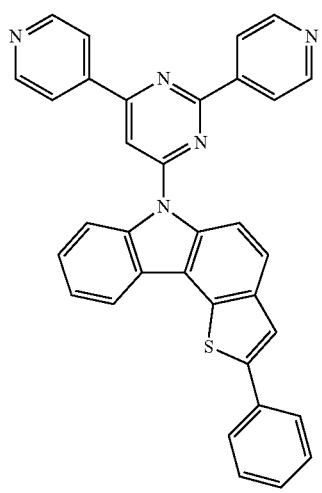
172
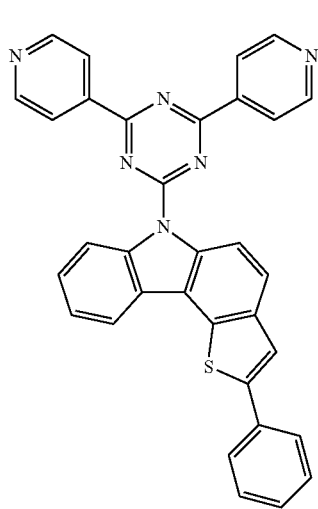

173 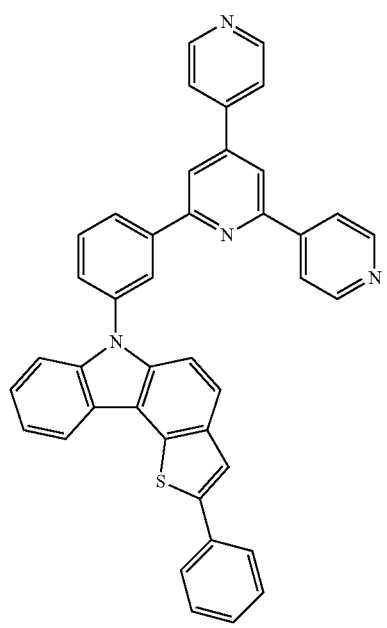
175 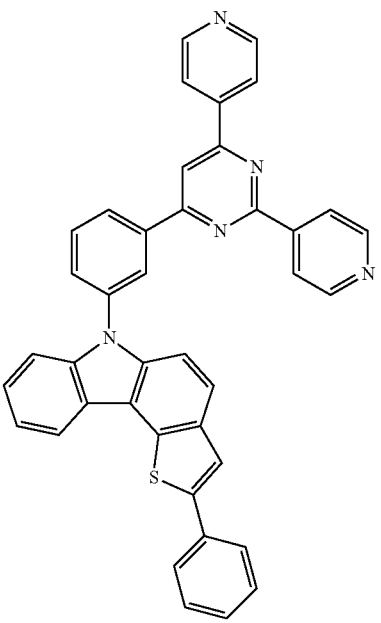
174 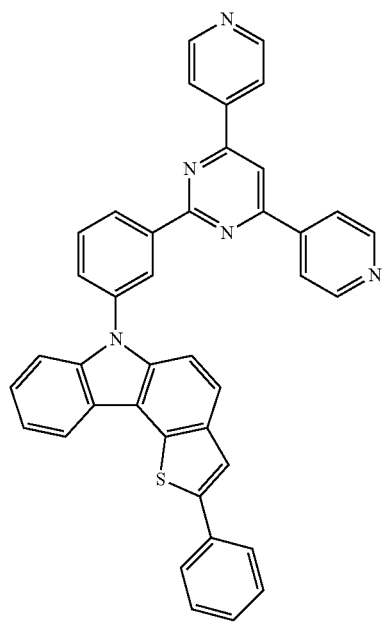
176 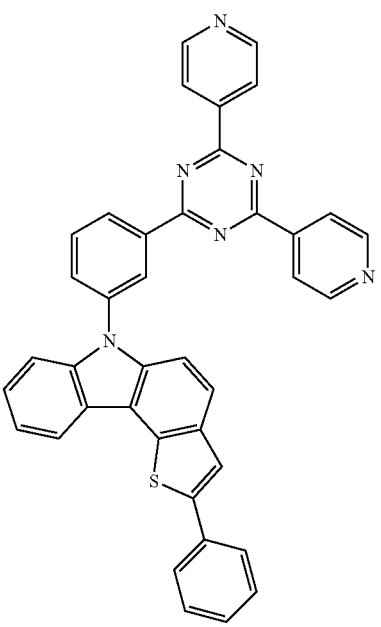

97
-continued
177
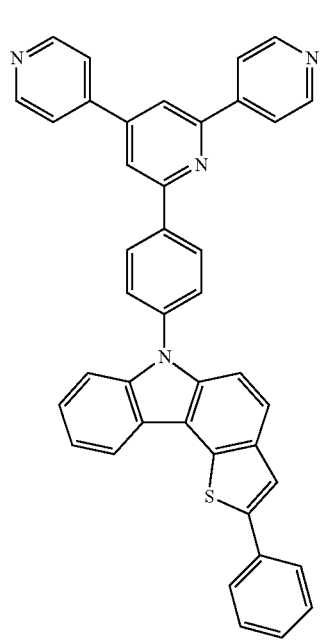
178
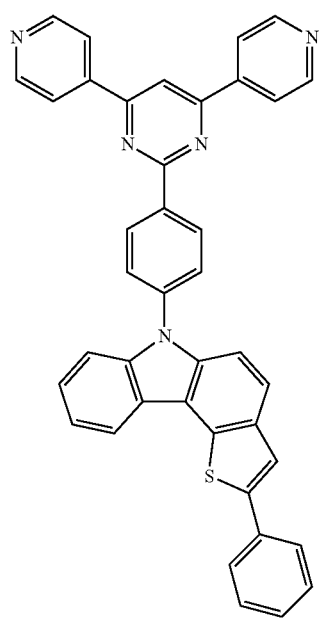
98
-continued
179
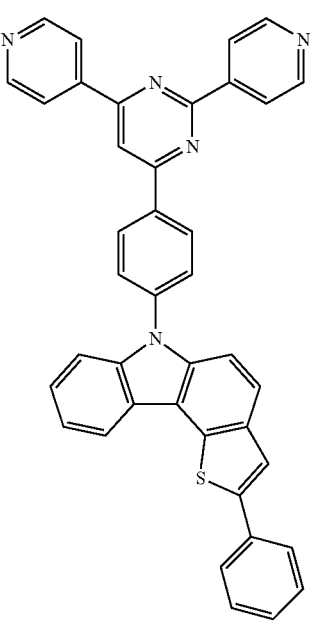
180
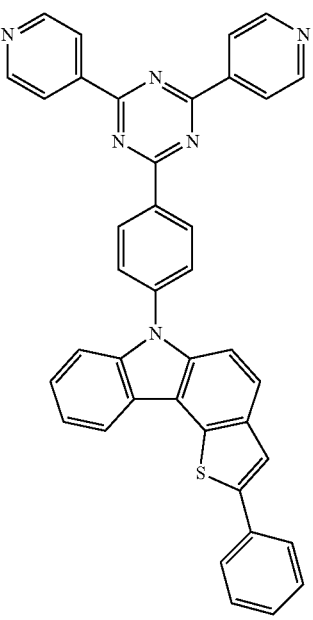

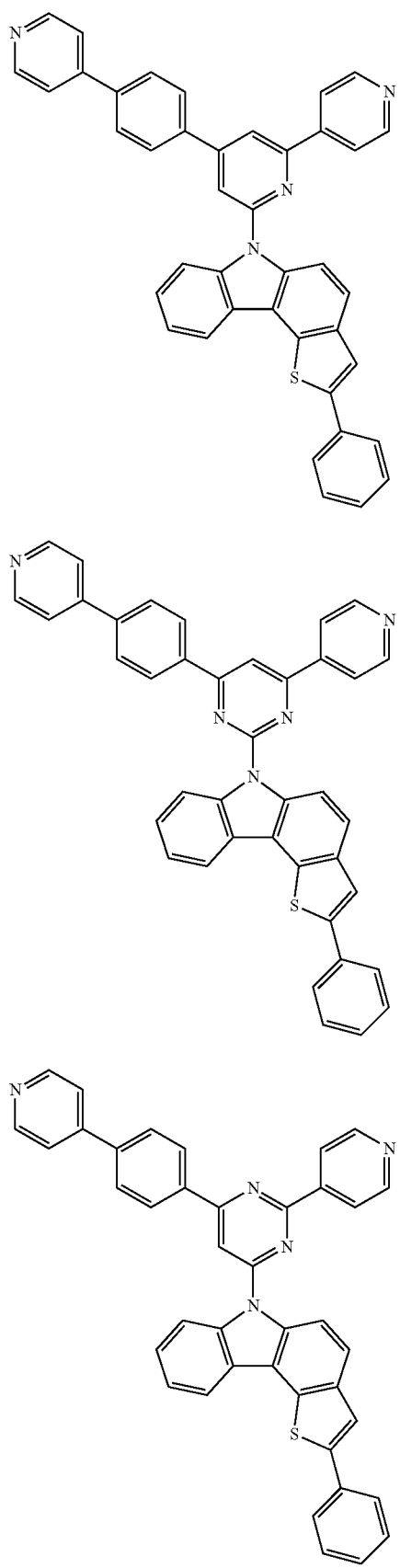
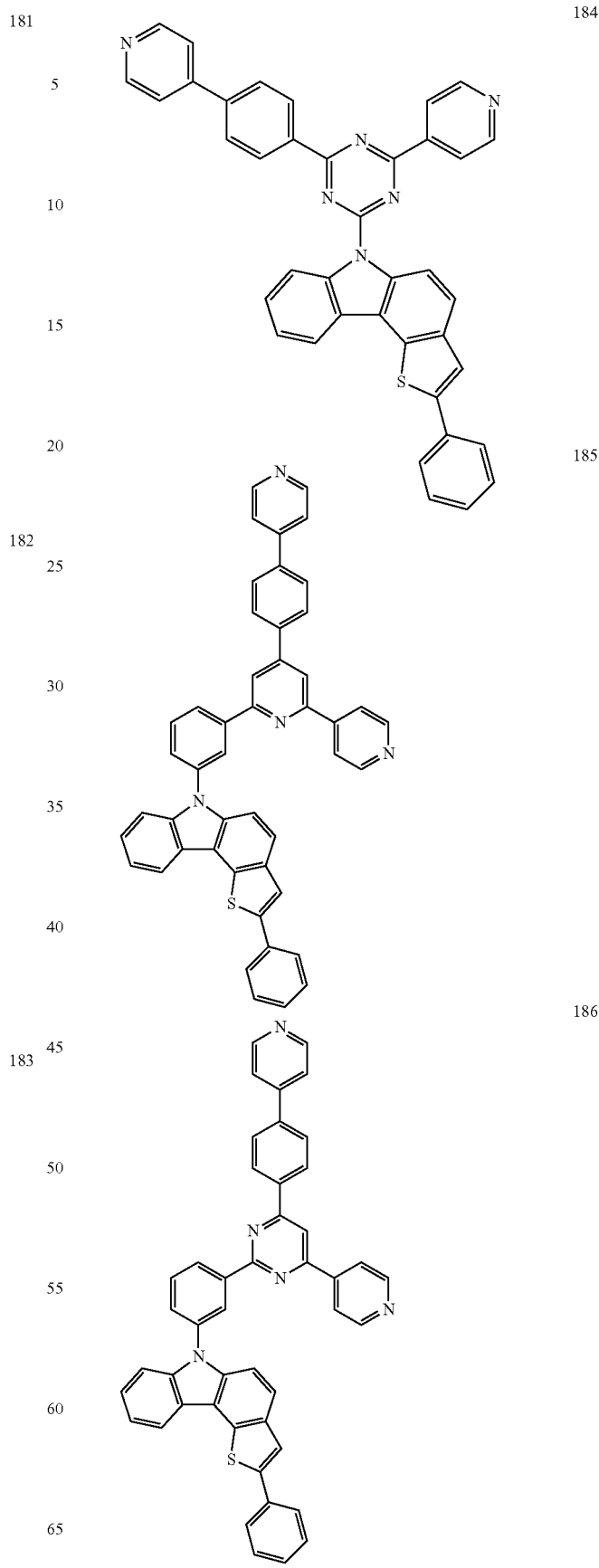

187 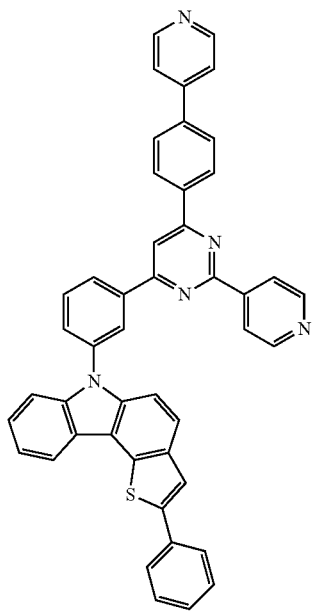
188 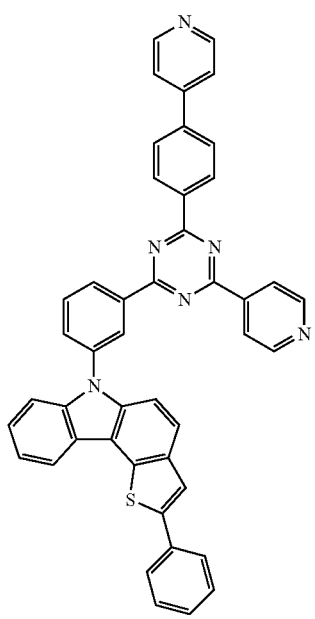
189 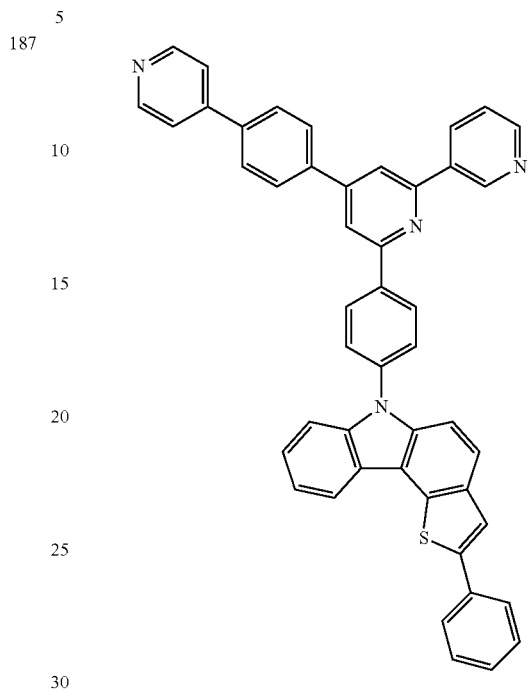
190 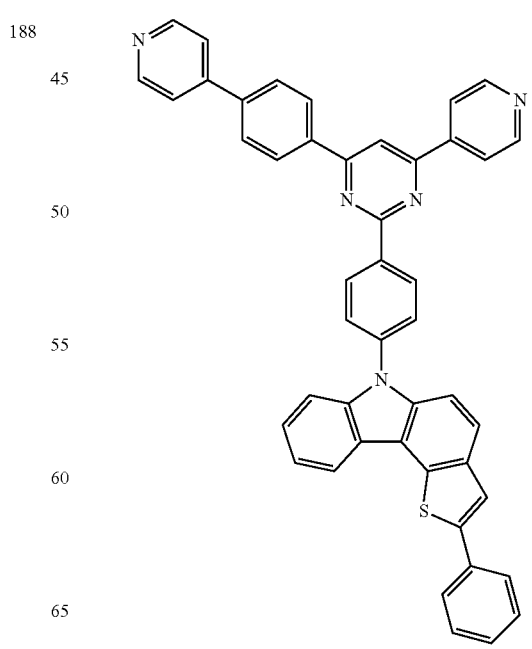

103
-continued
191
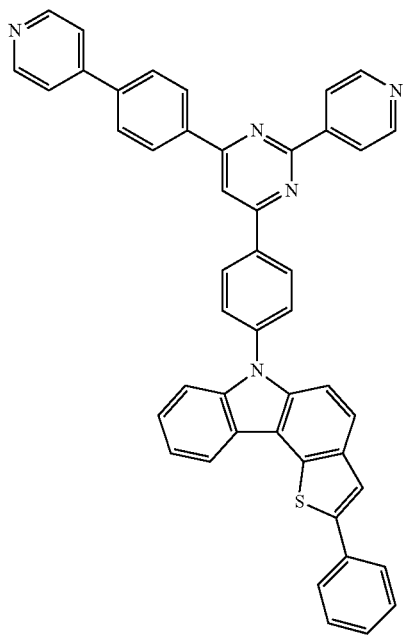
192
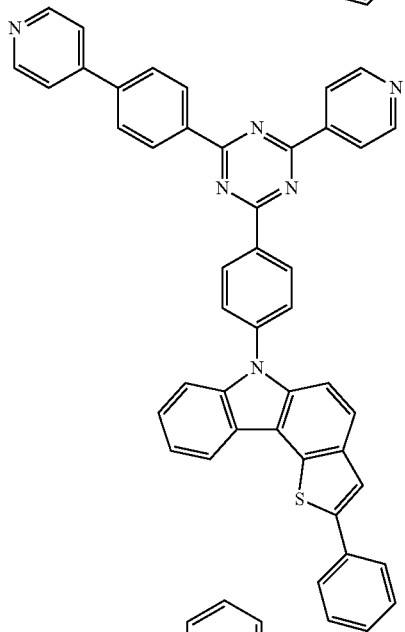
193
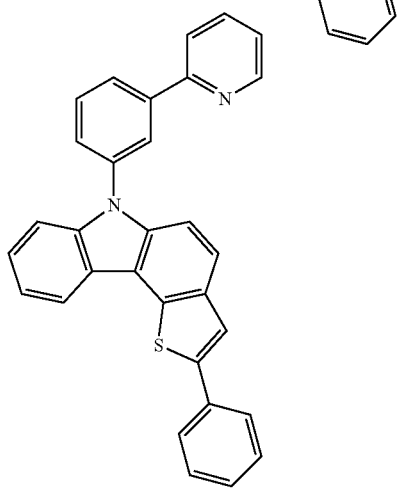
104
-continued
194
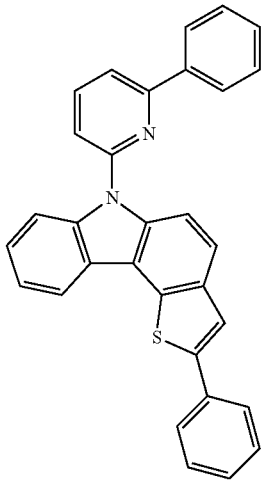
195
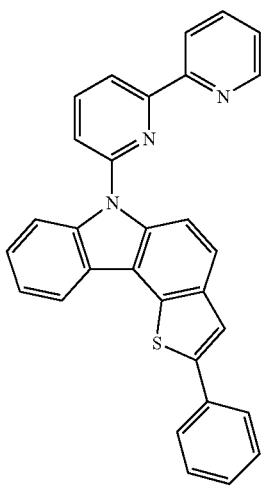
196
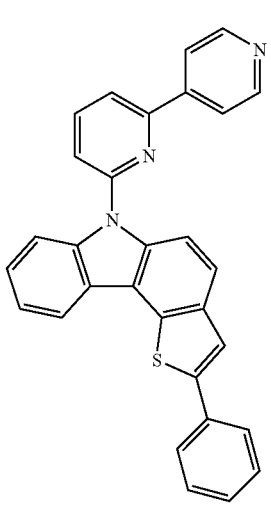

197
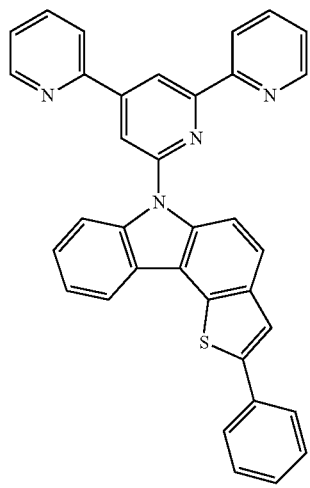
198
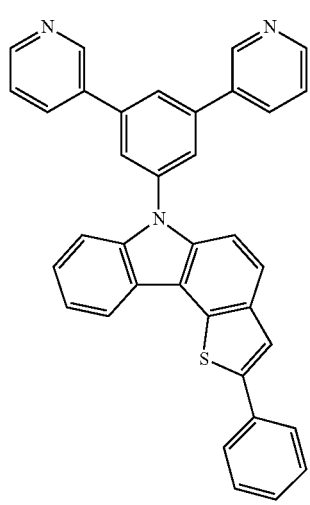
199
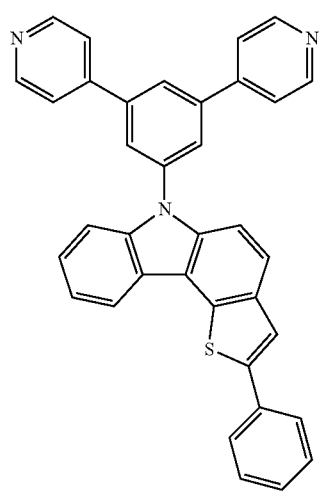
200
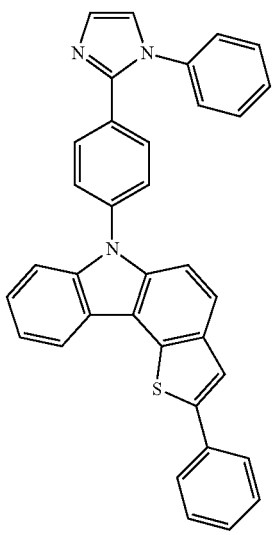
201
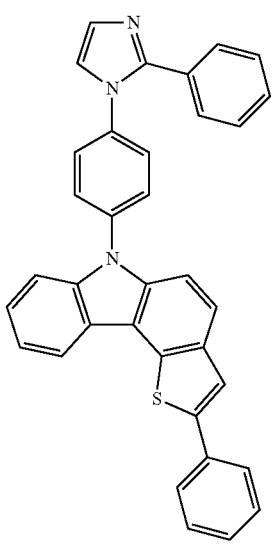
202
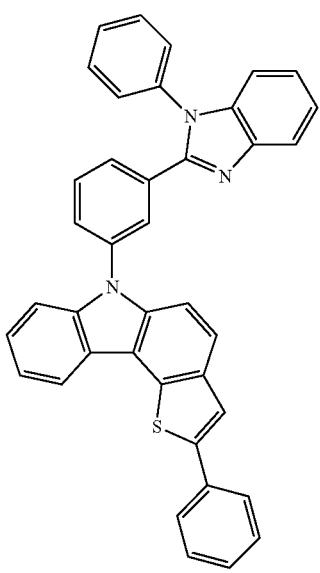

107
-continued
203
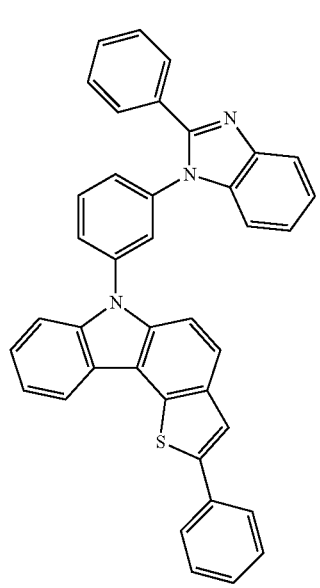
204
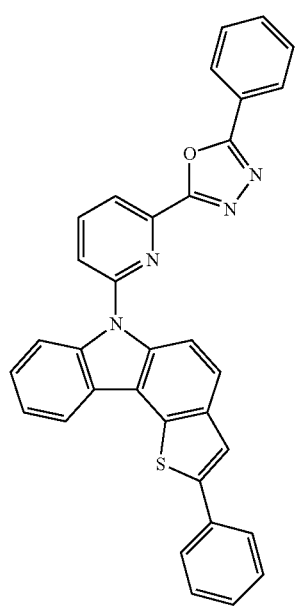
108
-continued
205
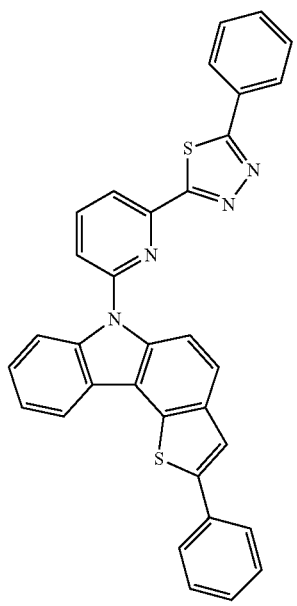
206
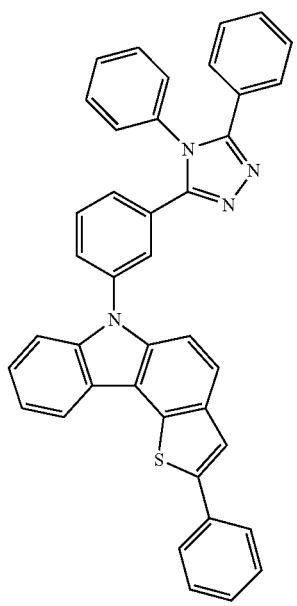

109
-continued
207
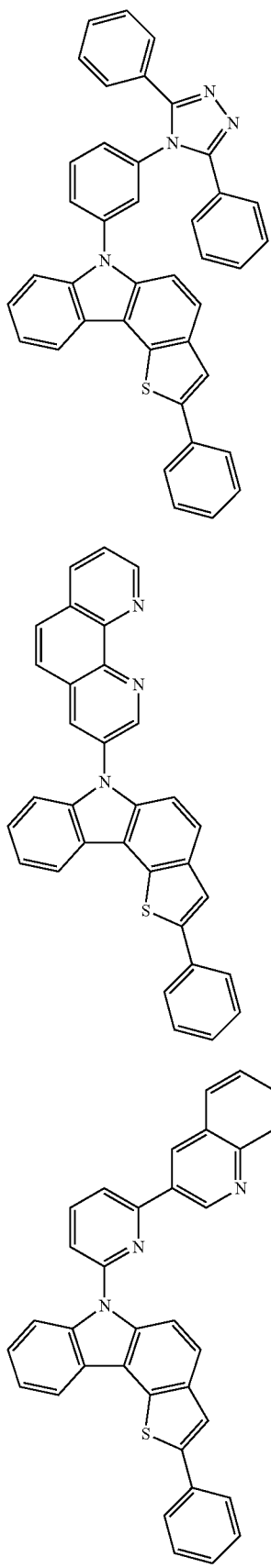
208
209
110
-continued
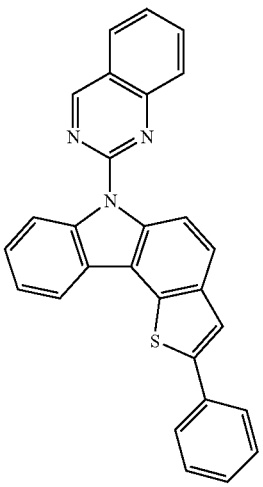
210
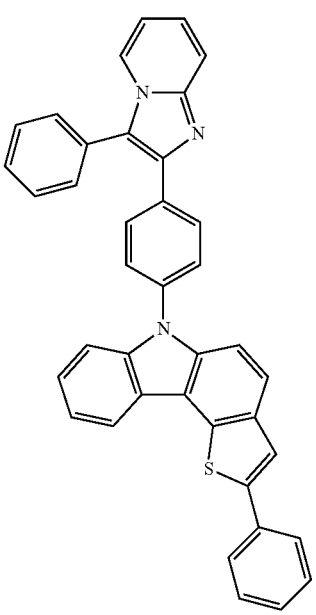
211
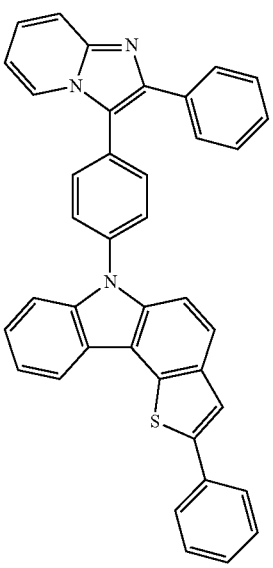
212

111
-continued
112
-continued
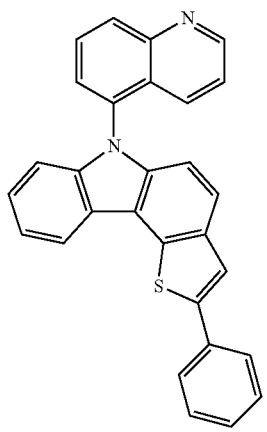
213
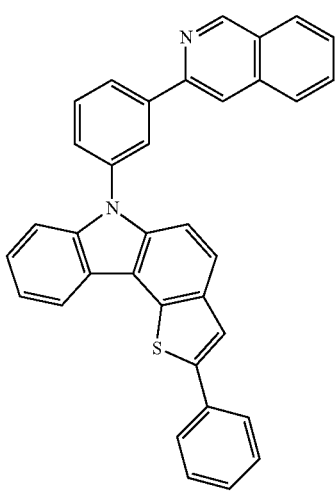
216
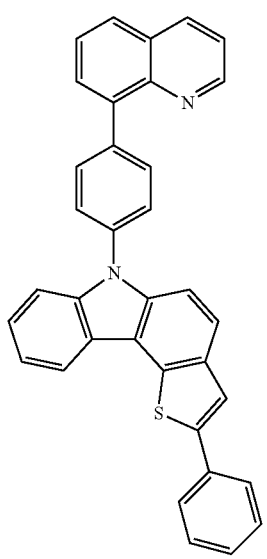
214
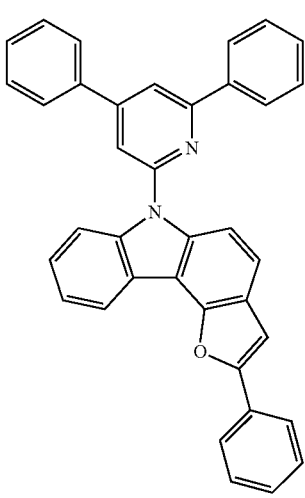
217
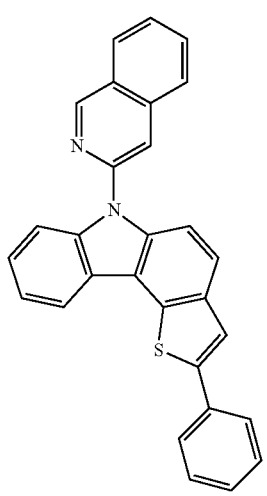
215
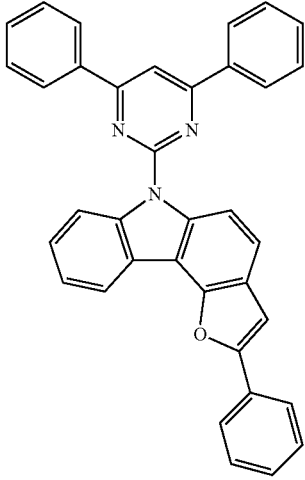
218

113
-continued
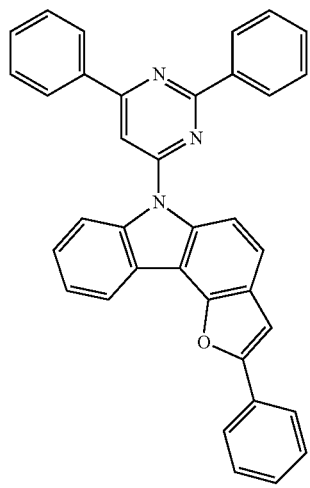
219
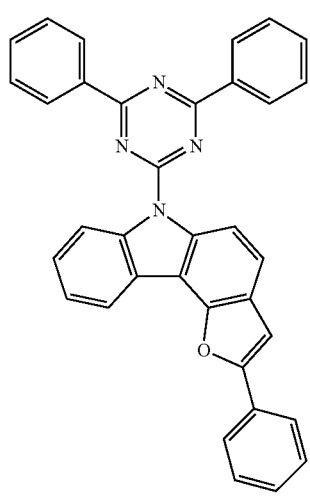
220
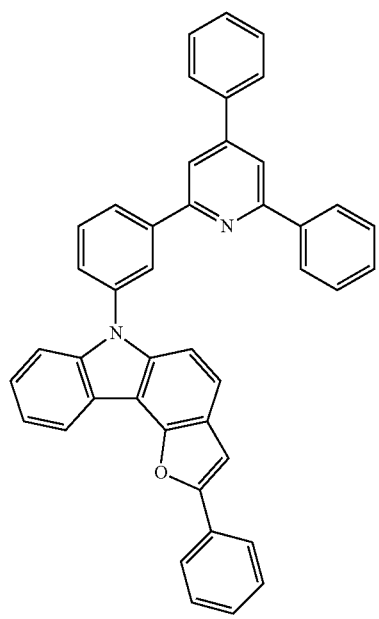
221
114
-continued
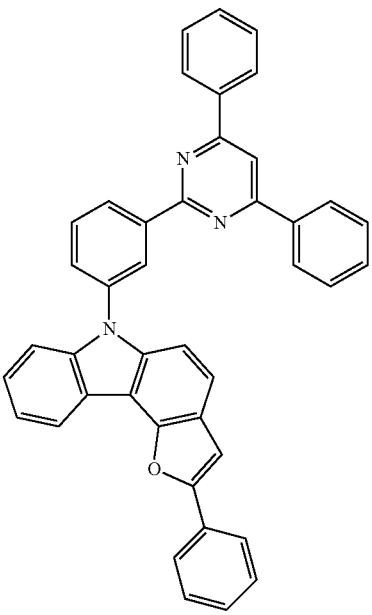
222
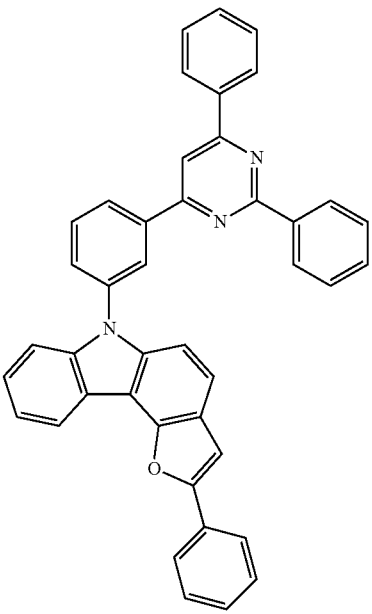
223

224 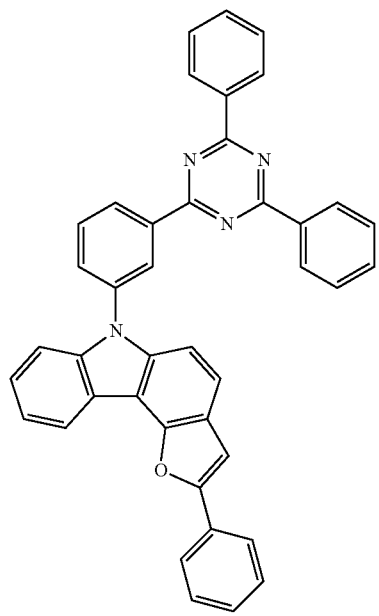
225 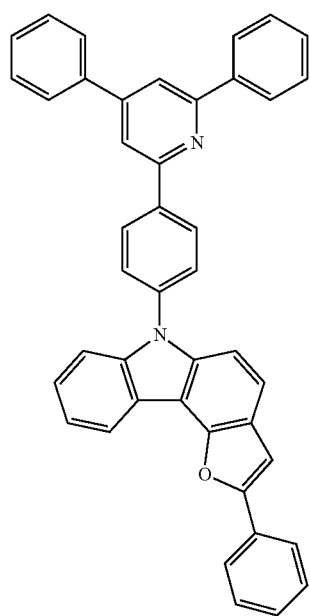
226 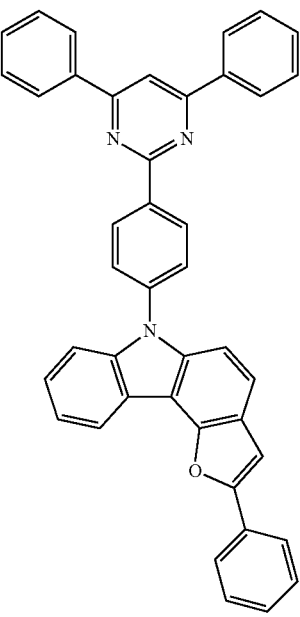
227 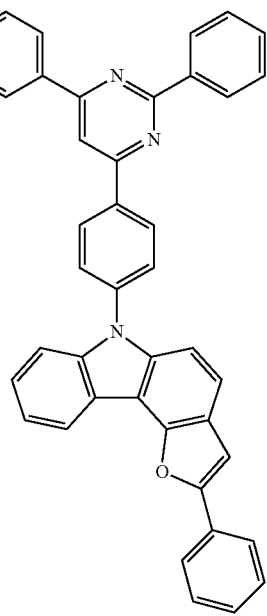

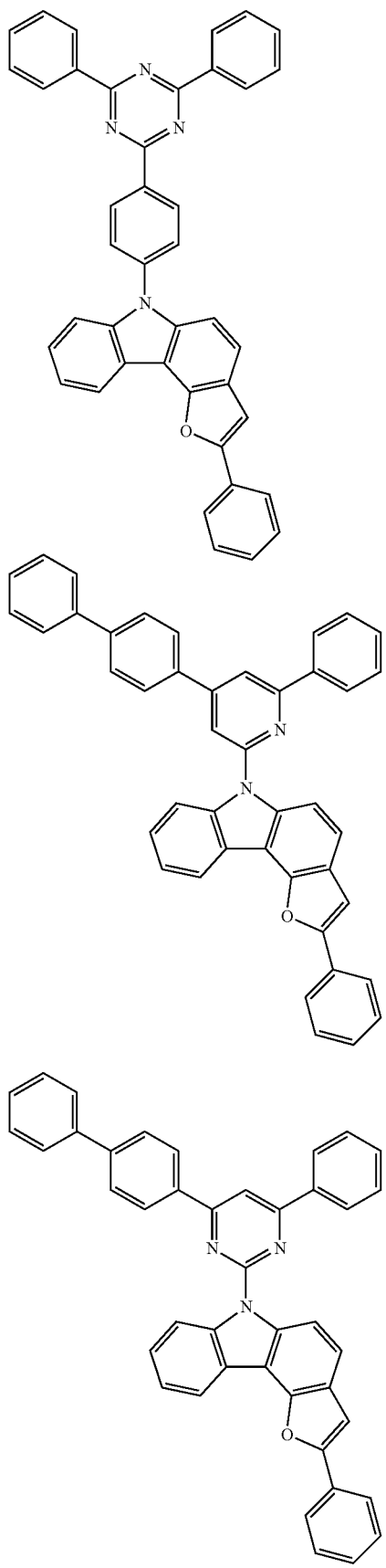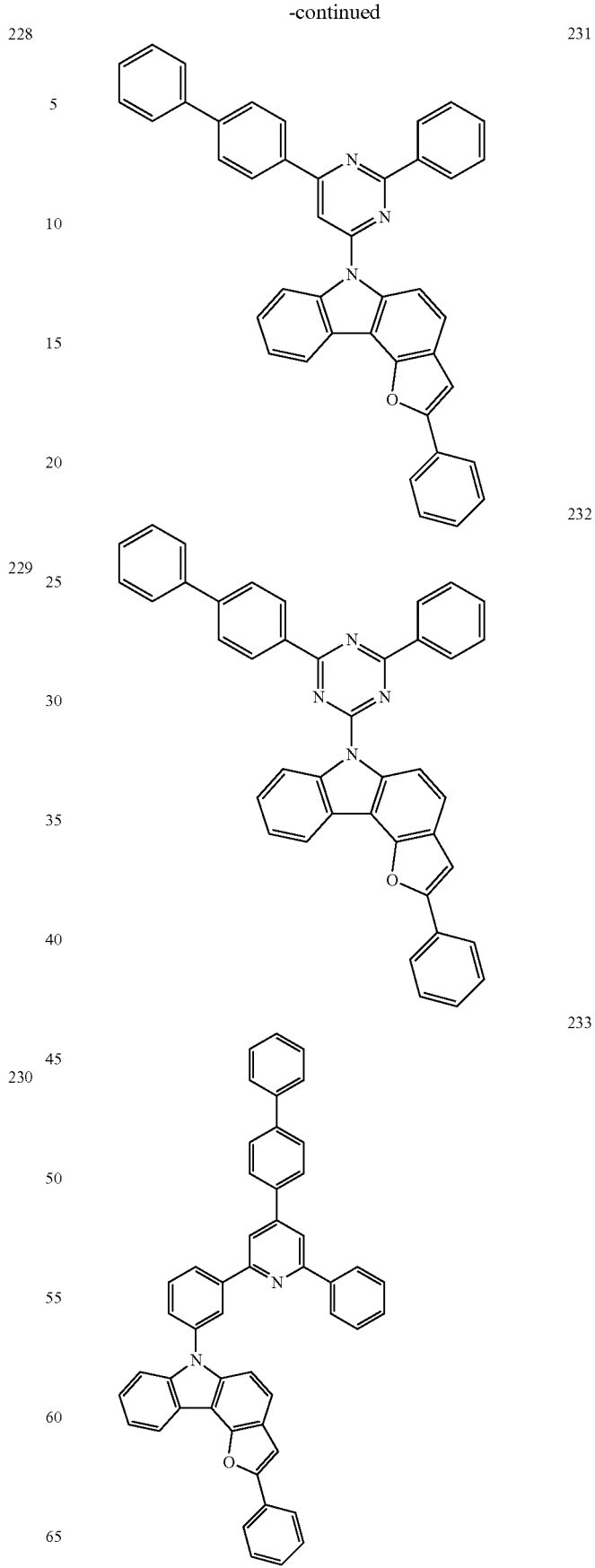

119
-continued
120
-continued
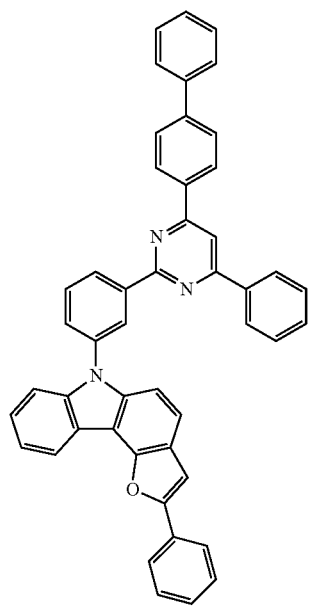
234
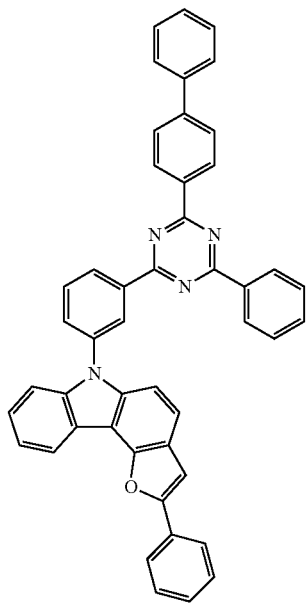
236
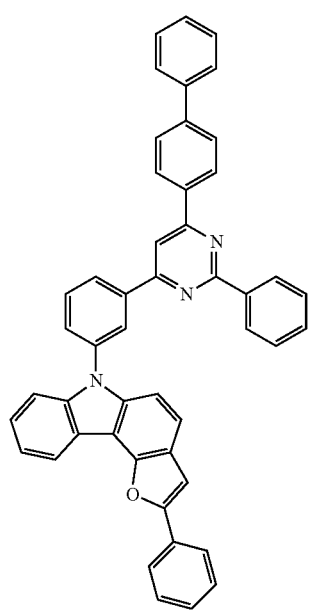
235
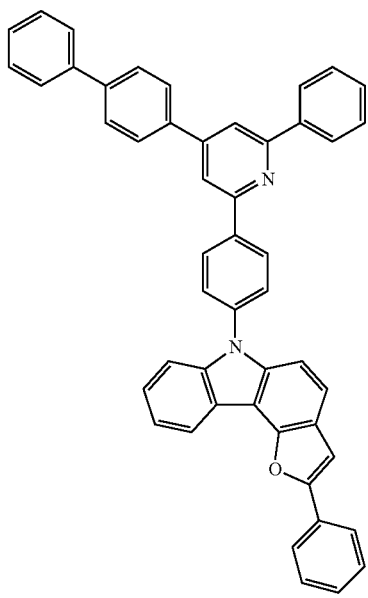
237

121
-continued
238
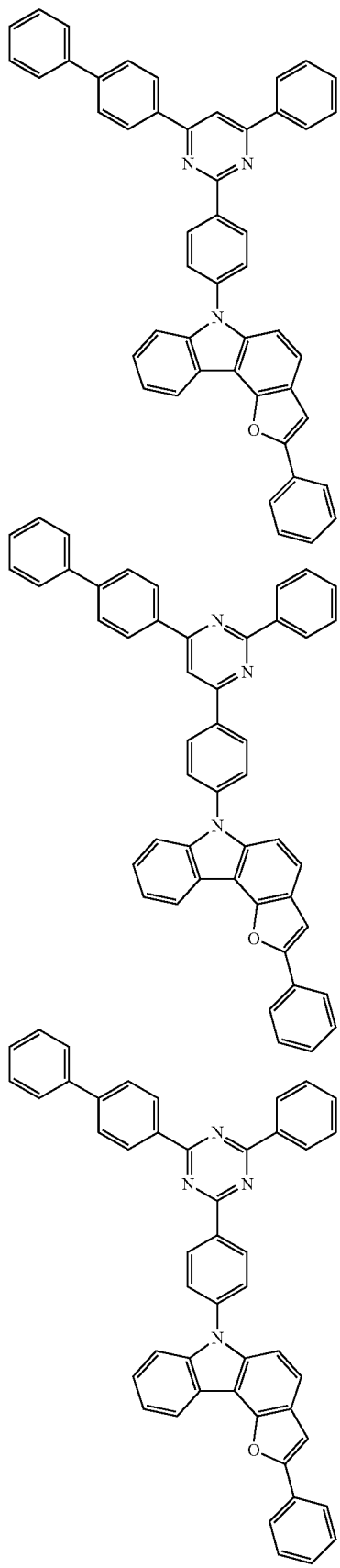
239
240
122
-continued
241
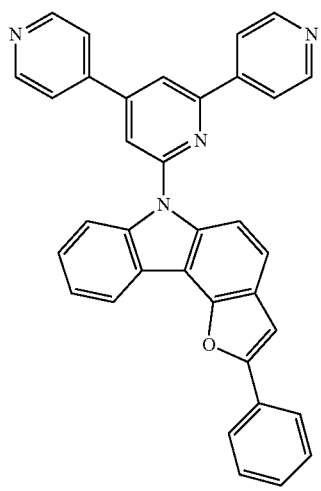
242
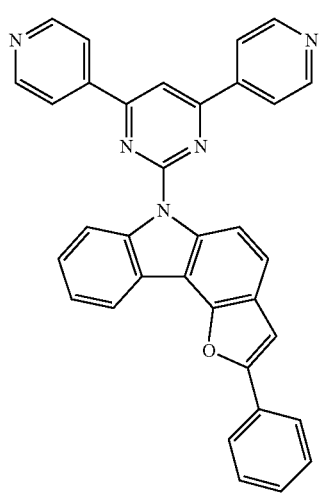
243
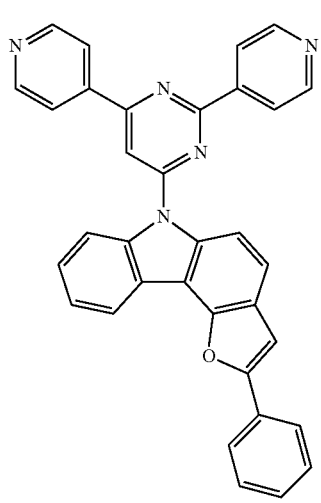

123
-continued
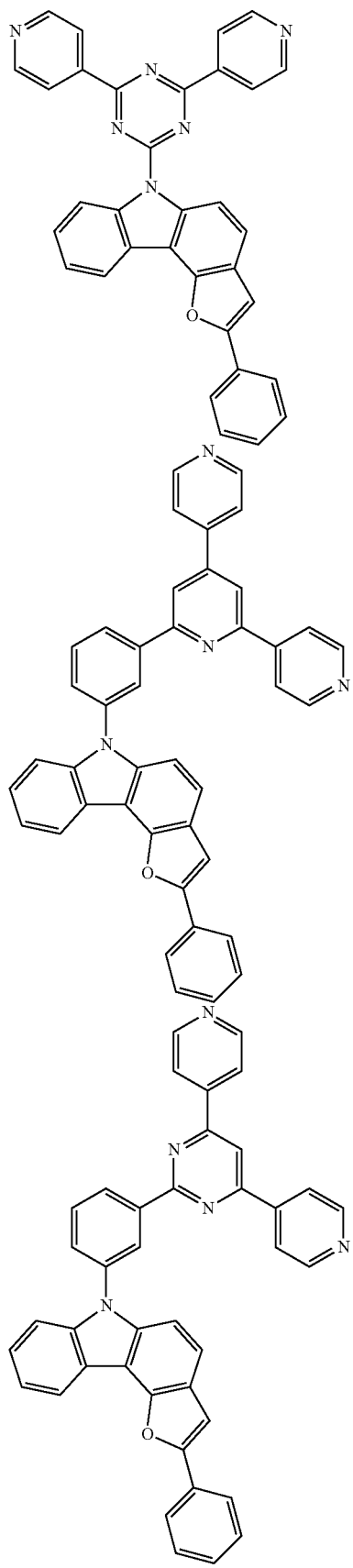
124
-continued
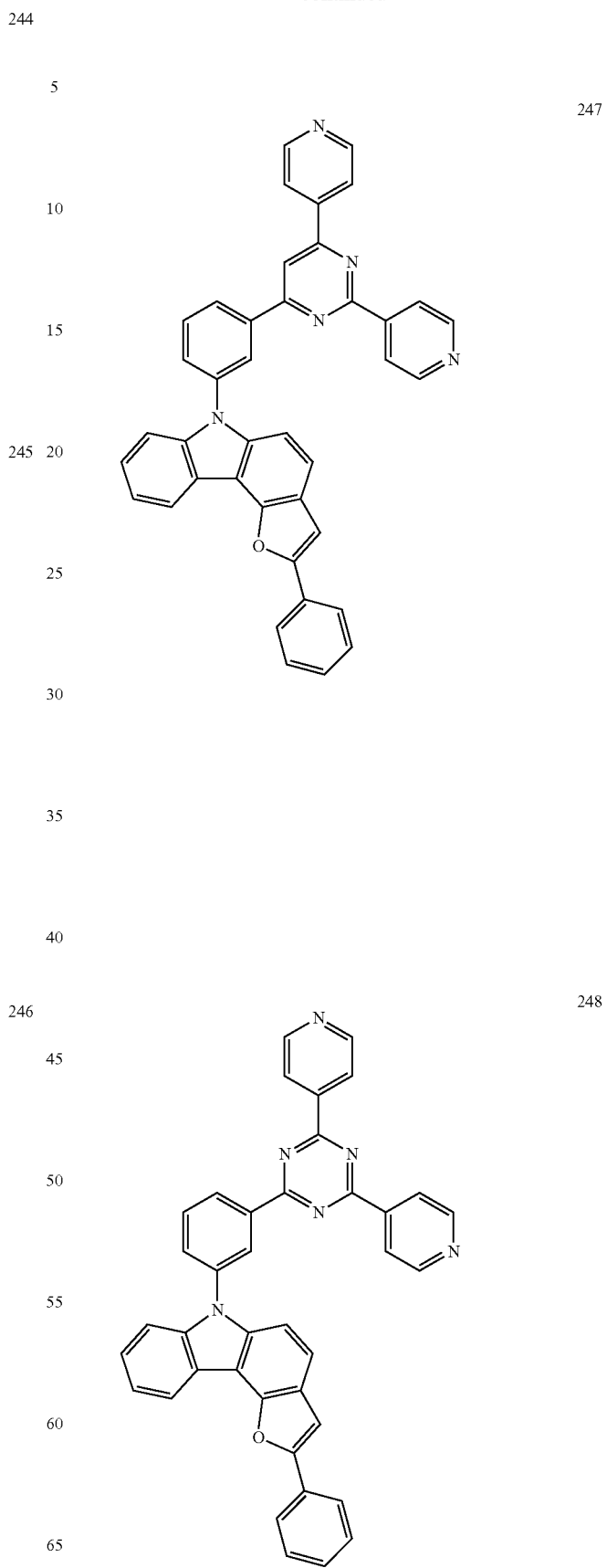

125
-continued
249
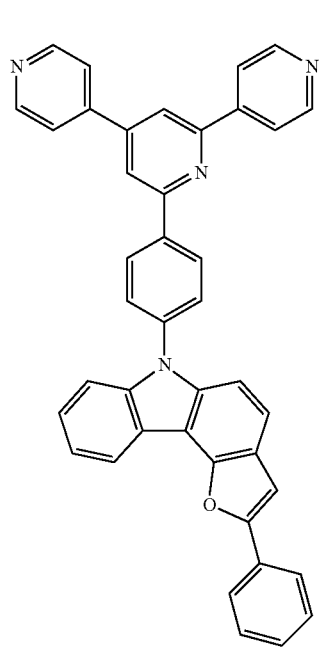
250
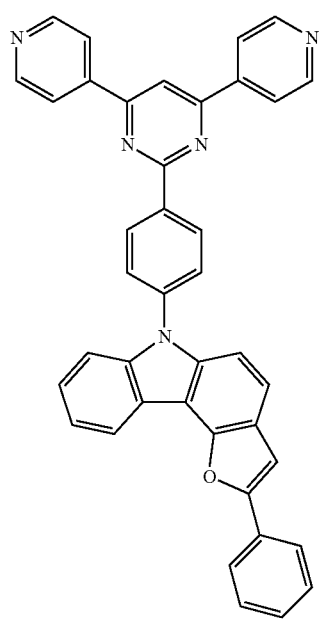
126
-continued
251
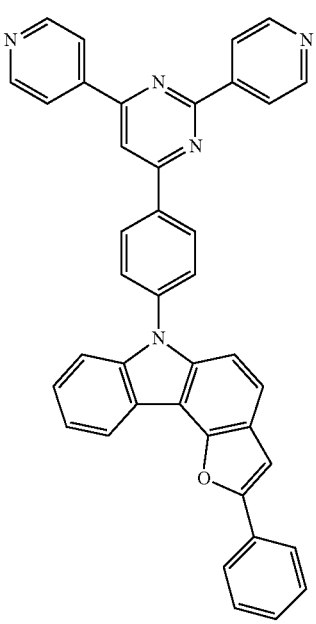
252
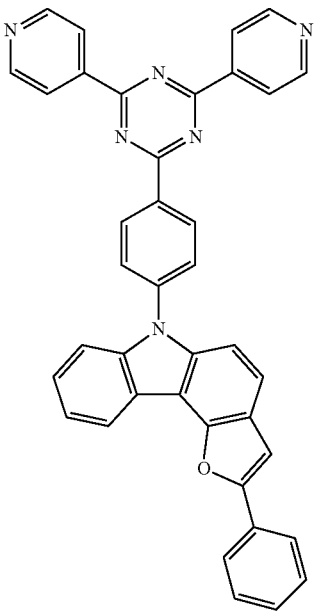

253
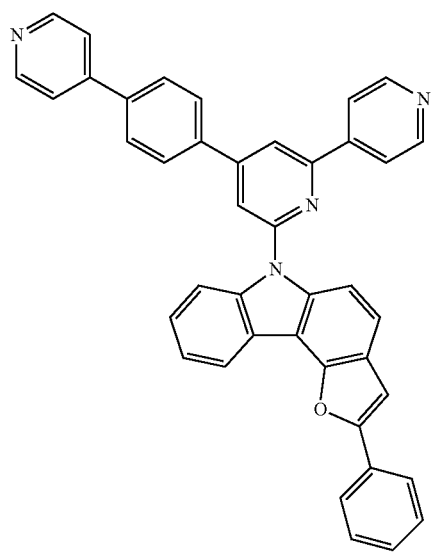
254
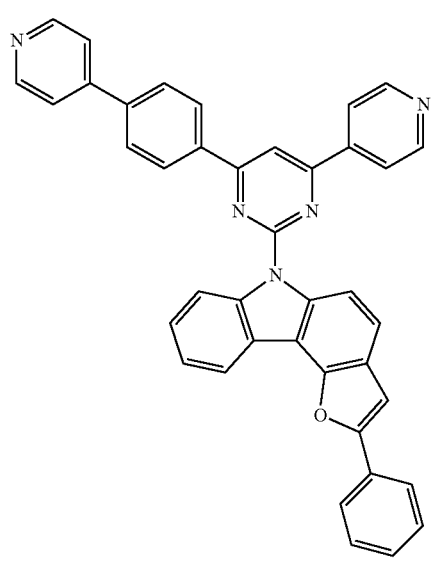
255
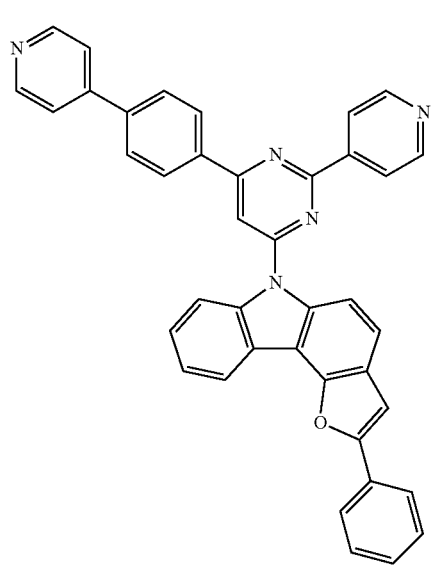
256
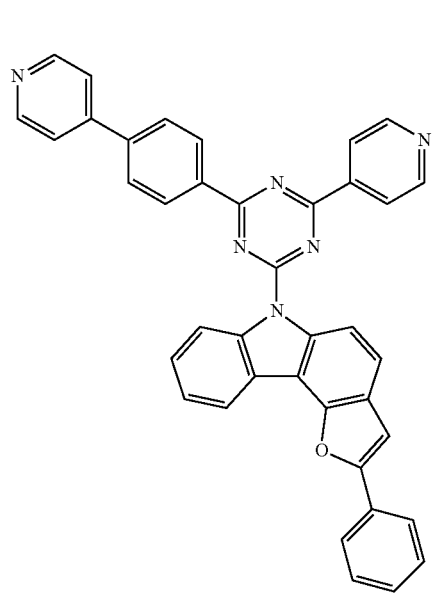
257
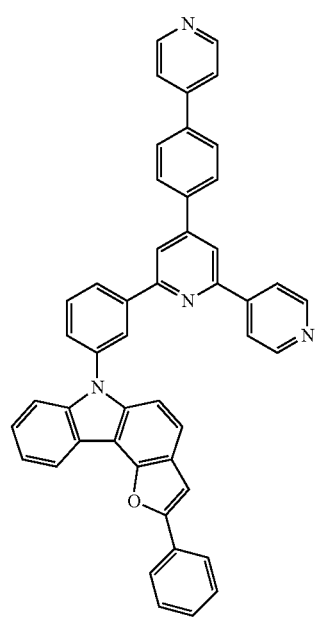

129
-continued
130
-continued
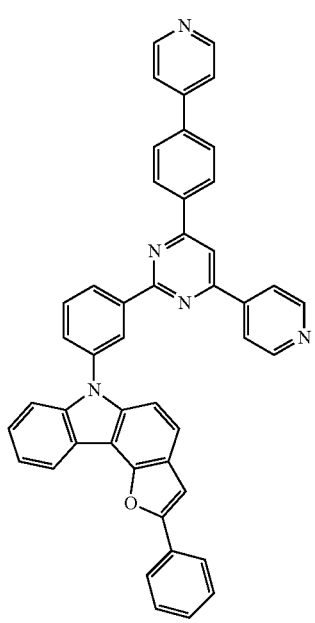
258
259
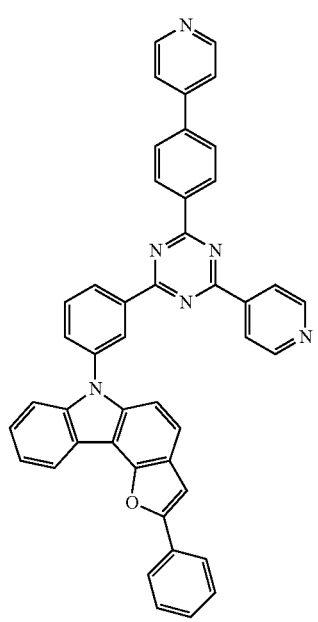
260
261

131
-continued
262
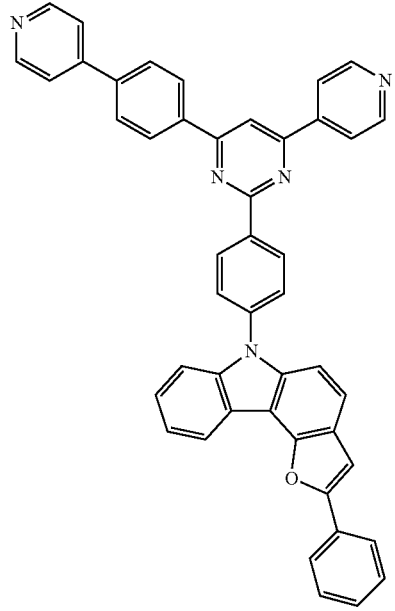
263
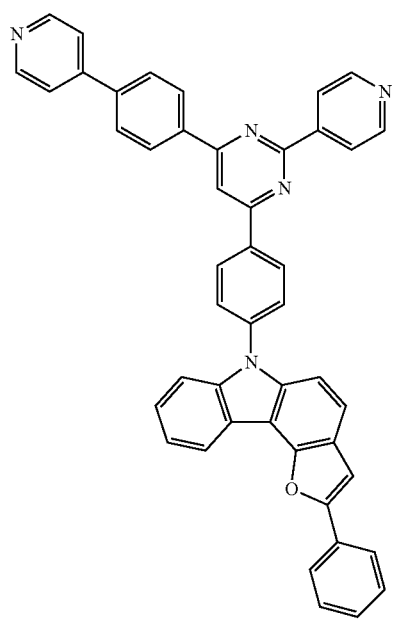
132
-continued
264
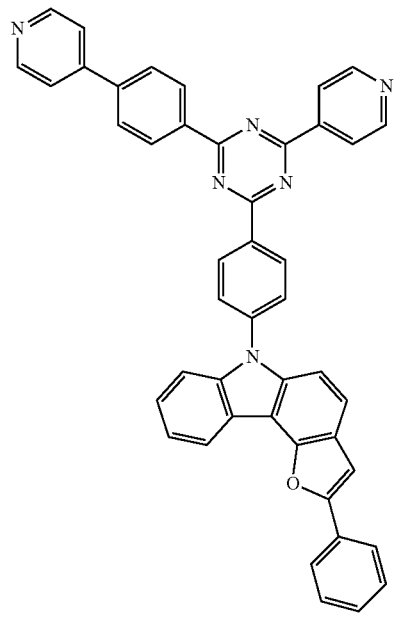
265
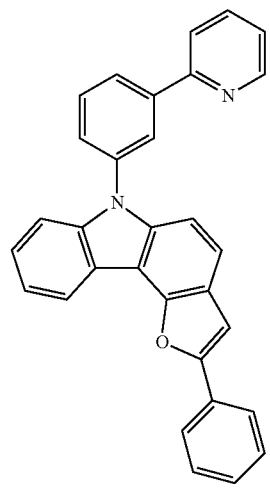
266
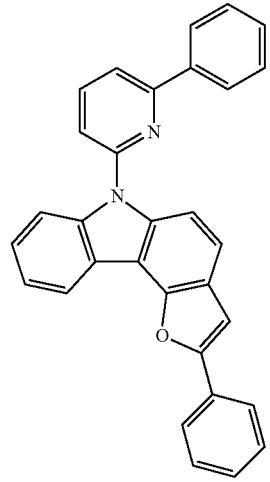

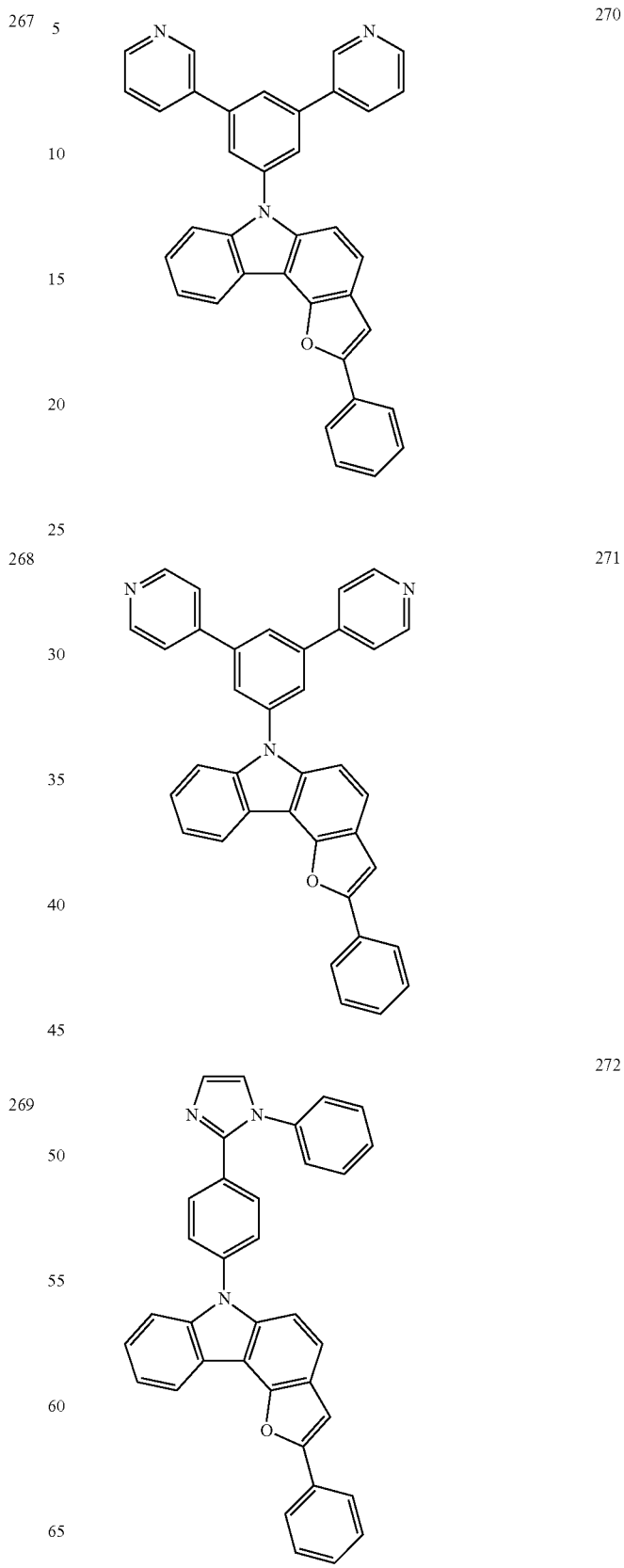

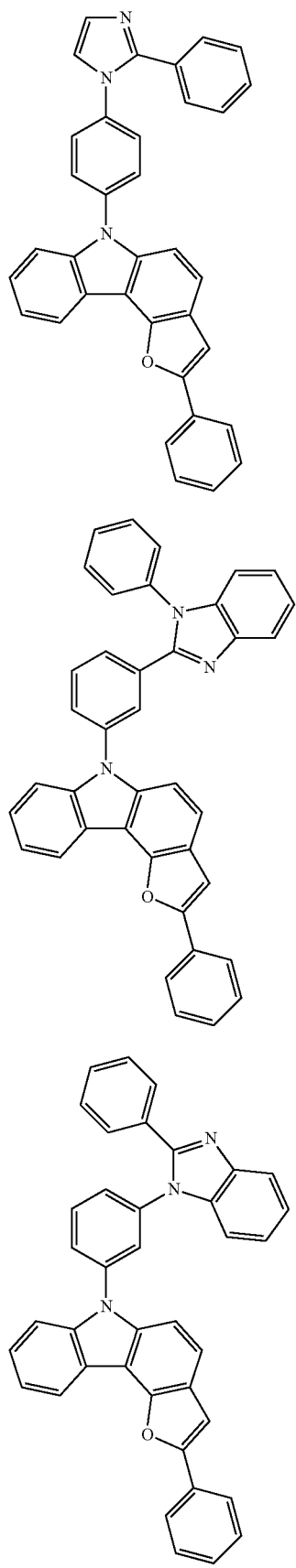

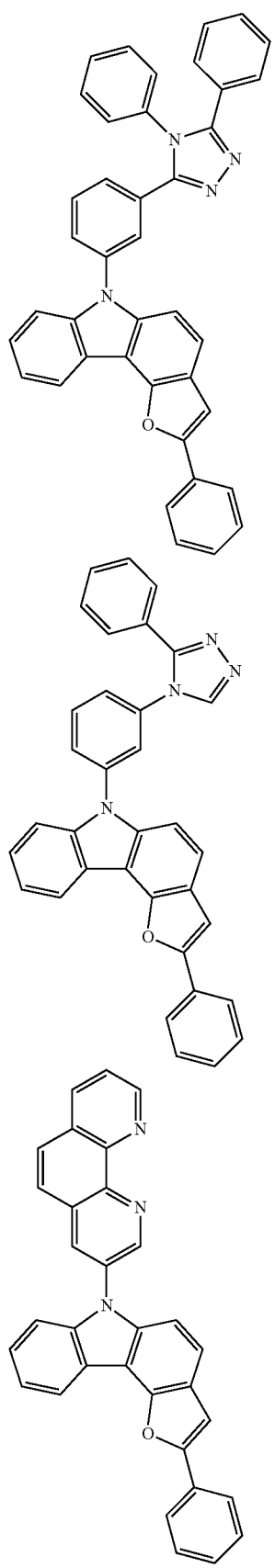
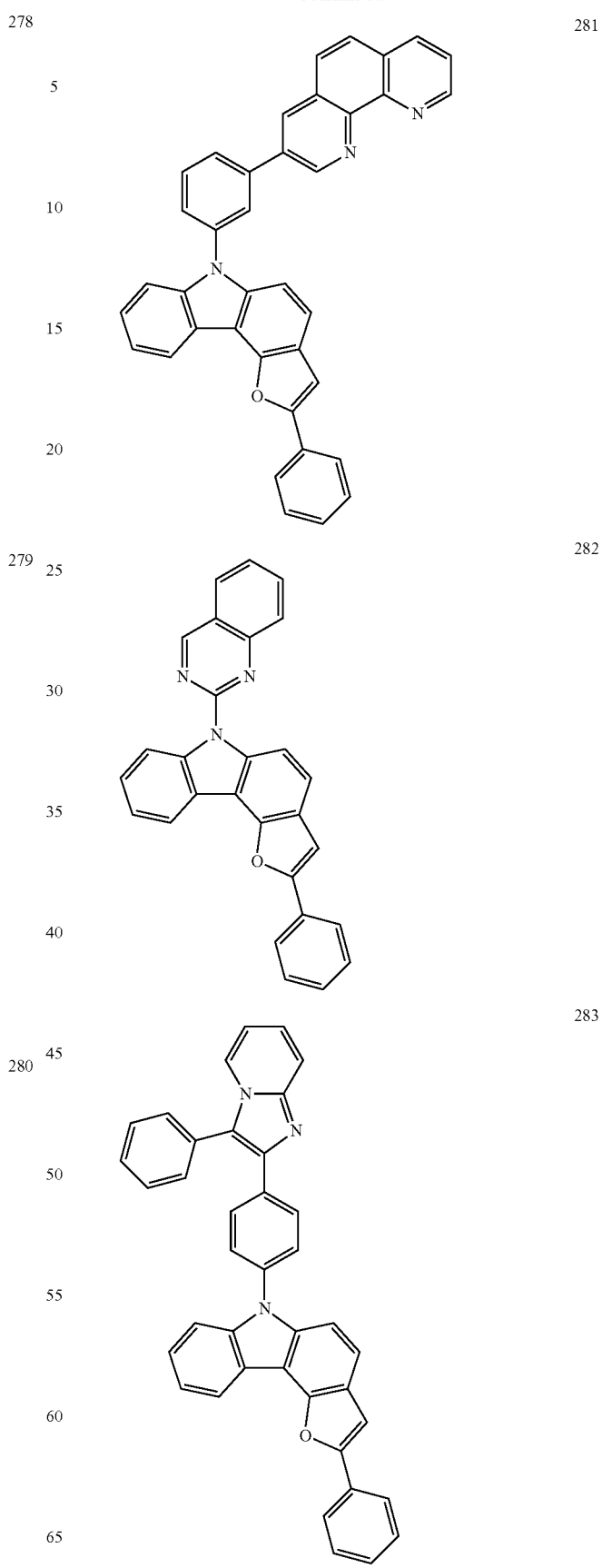

284
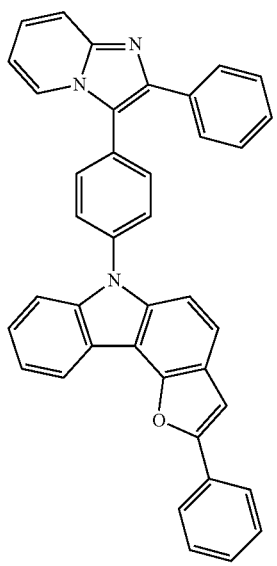
287
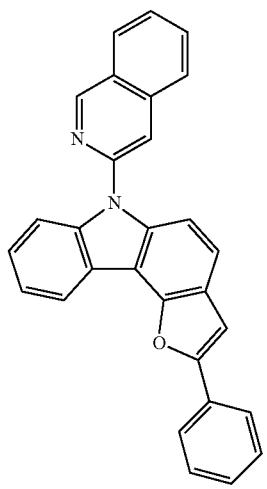
285
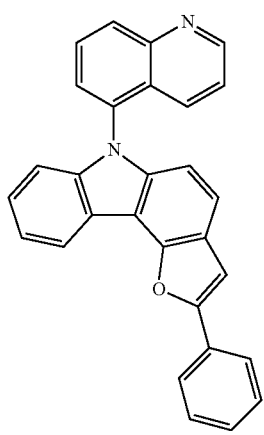
288
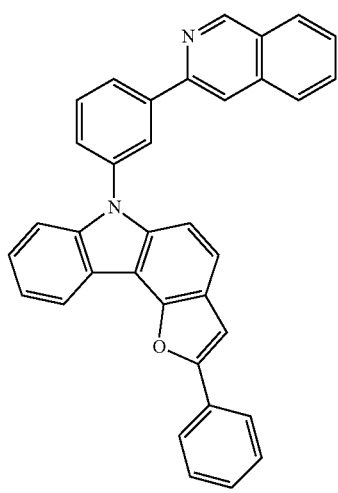
286
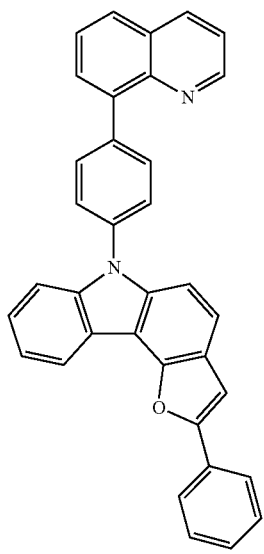
289
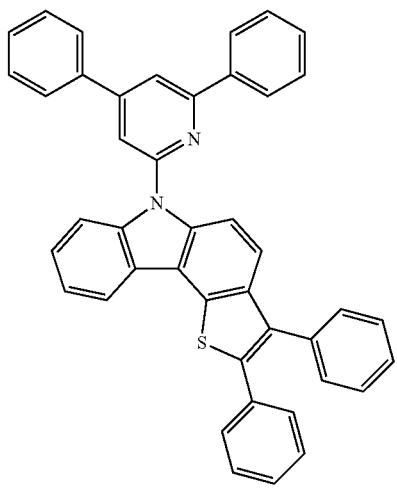

141
-continued
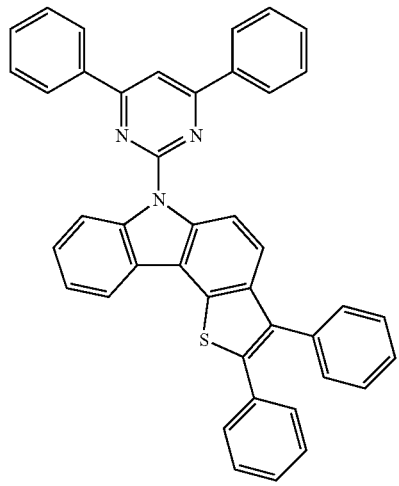
290
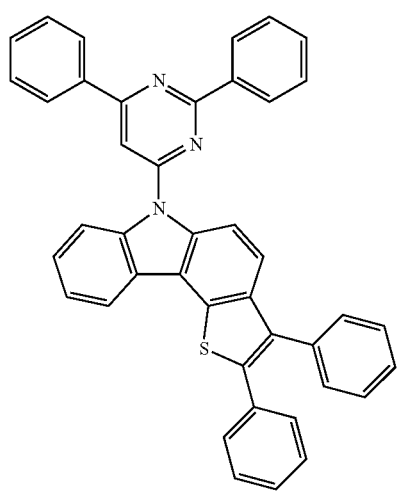
291
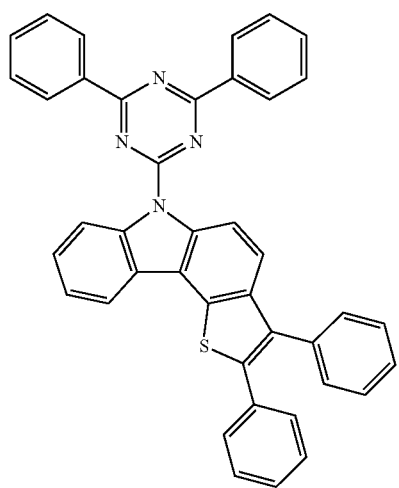
292
142
-continued
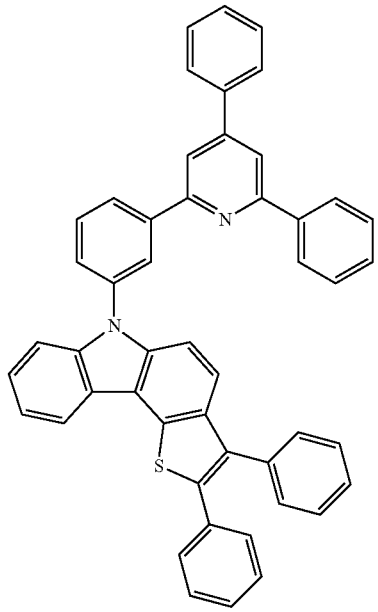
293
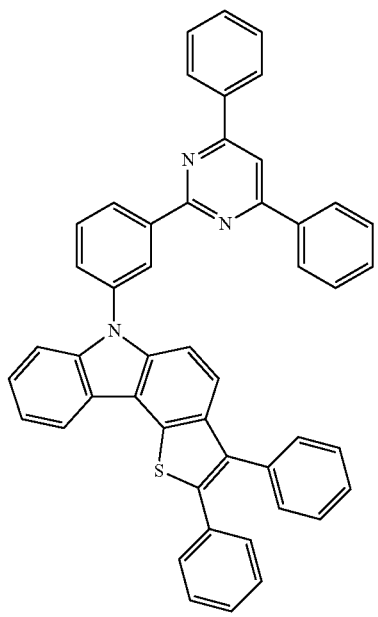
294

143
-continued
295
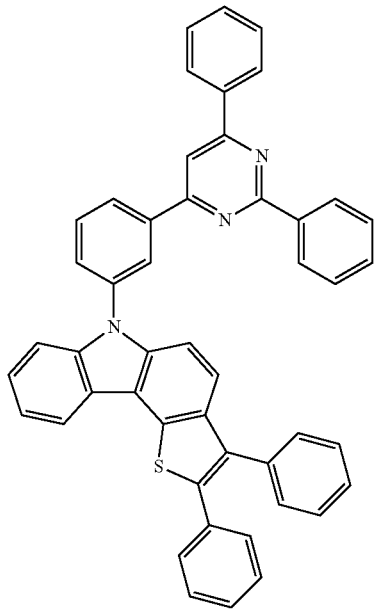
297
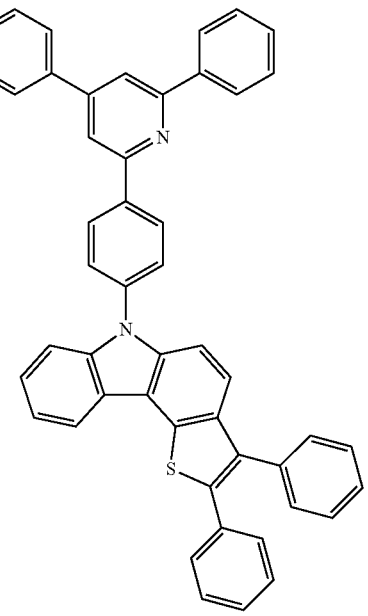
296
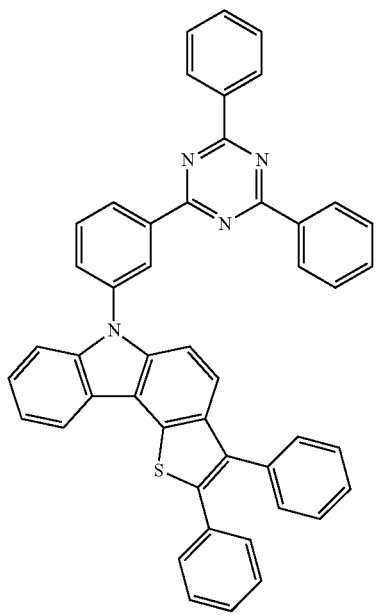
298
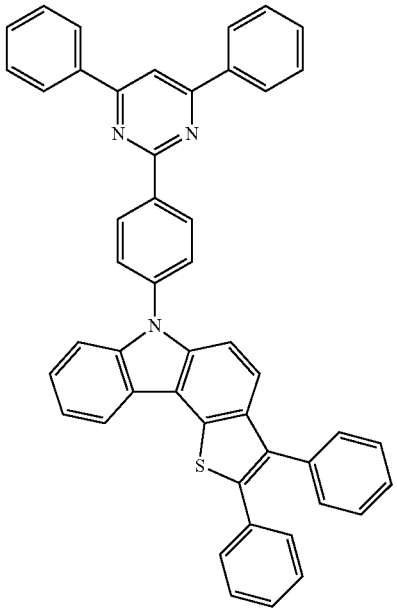

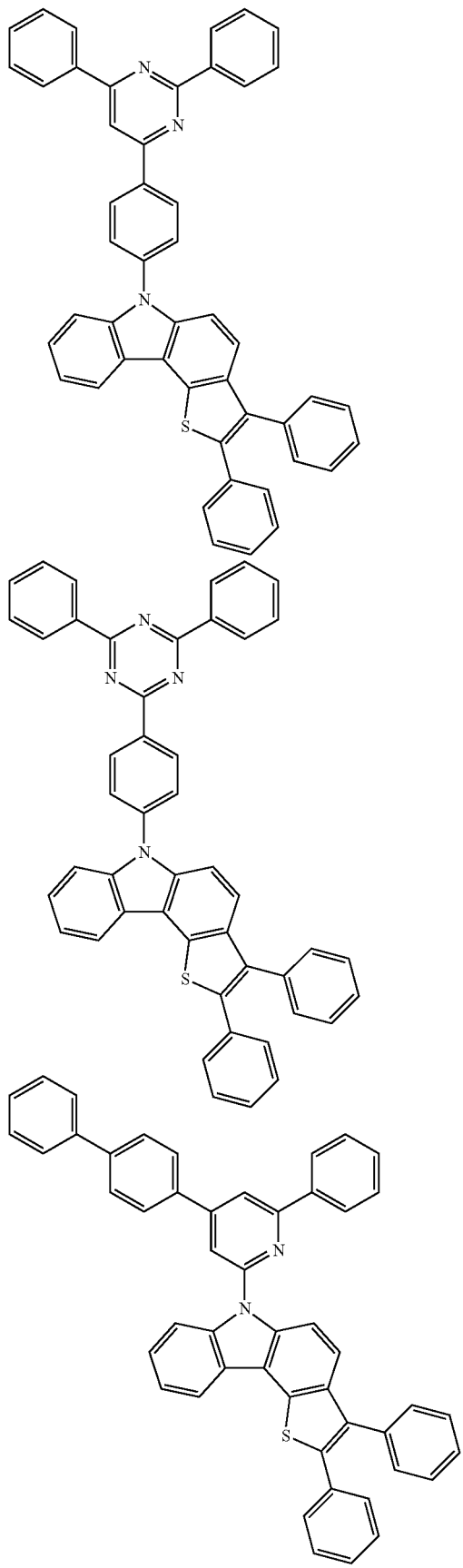
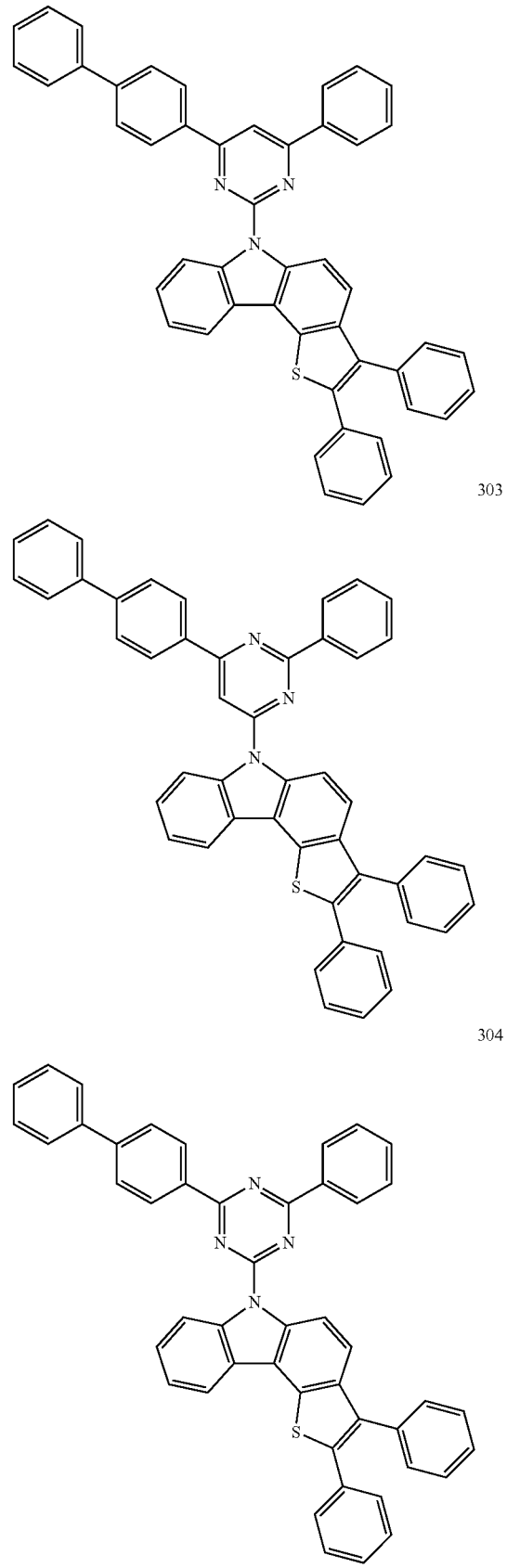

305
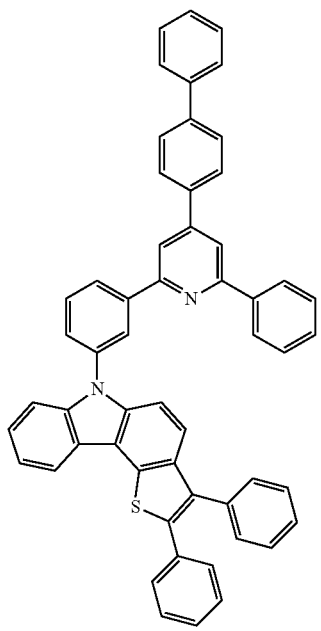
306
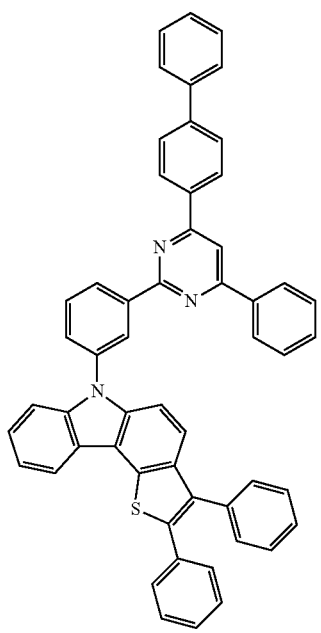
307
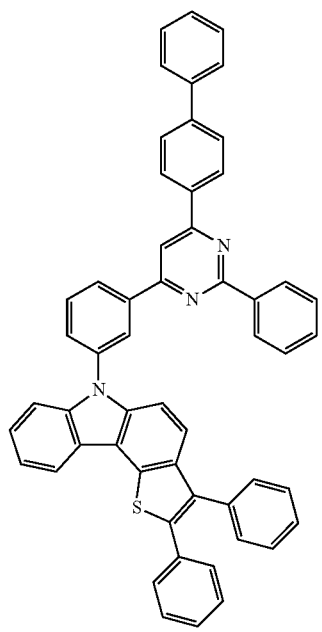
308
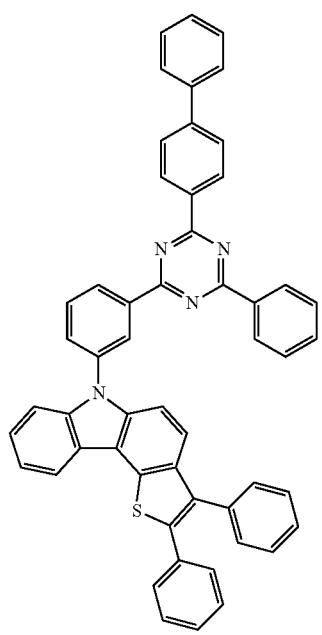

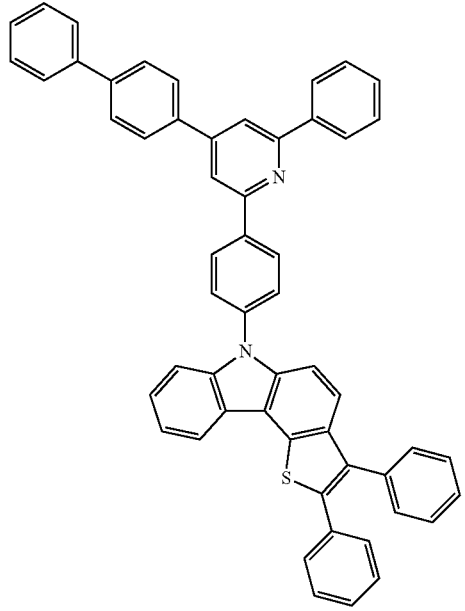
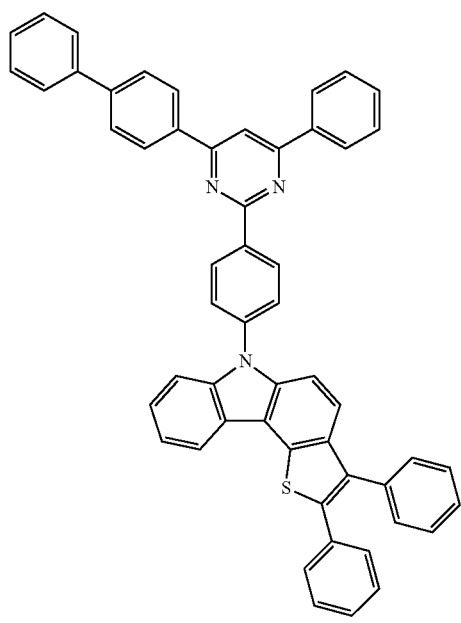
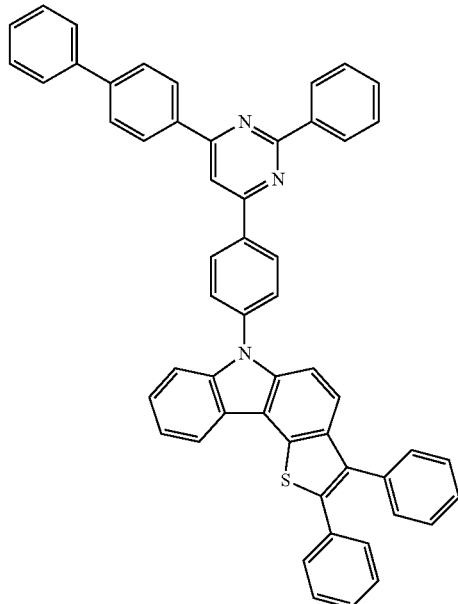
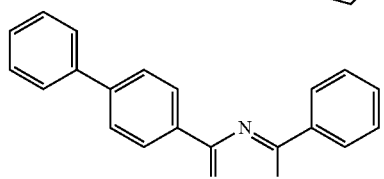
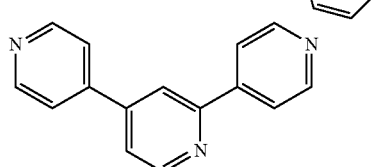
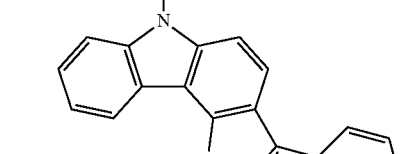

151
-continued
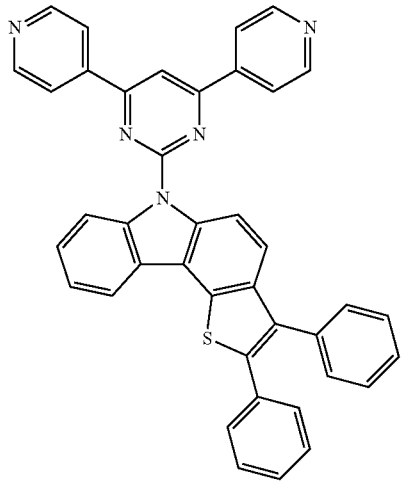
314
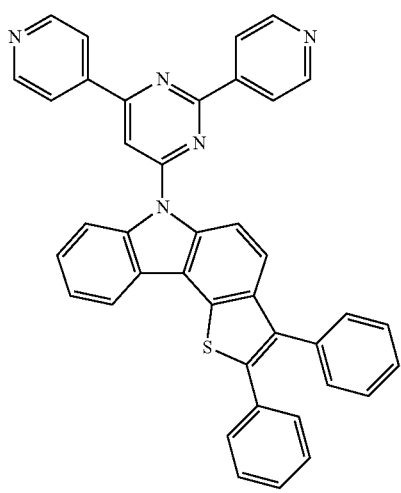
315
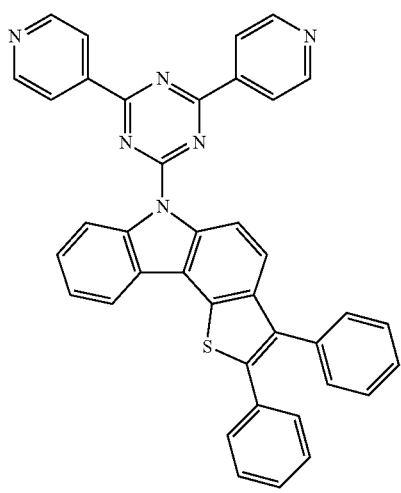
316
152
-continued
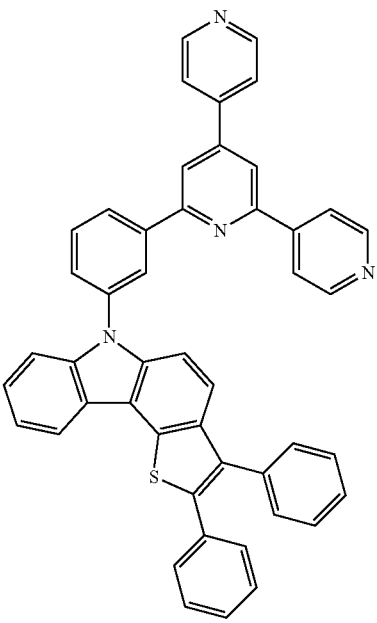
317
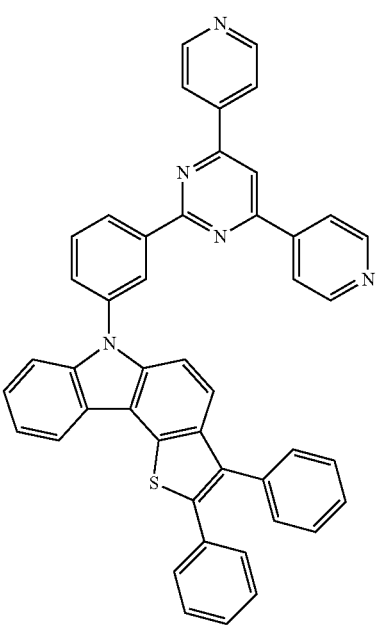
318

153
-continued
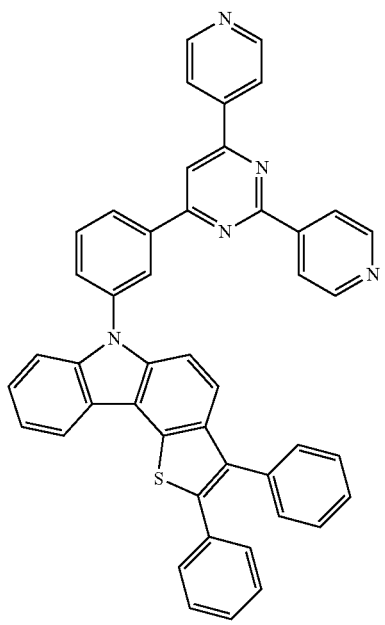
319
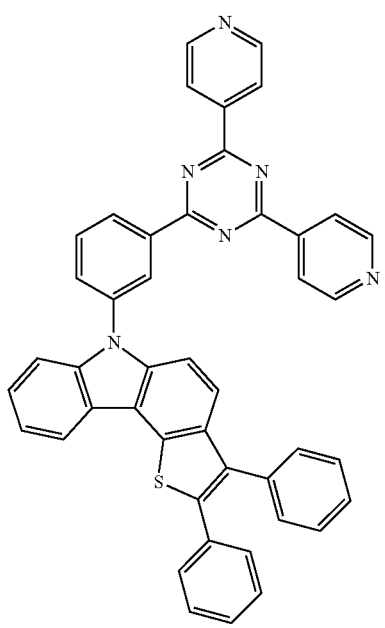
320
154
-continued
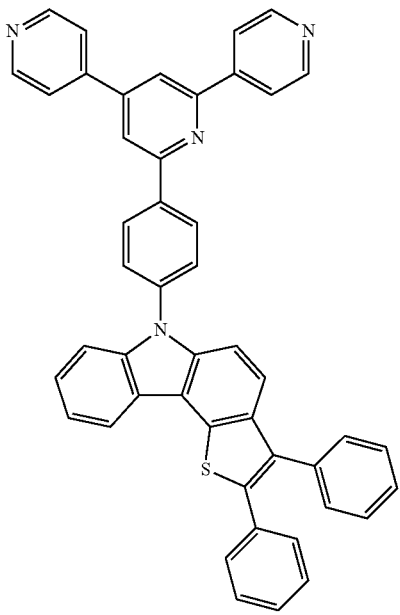
321
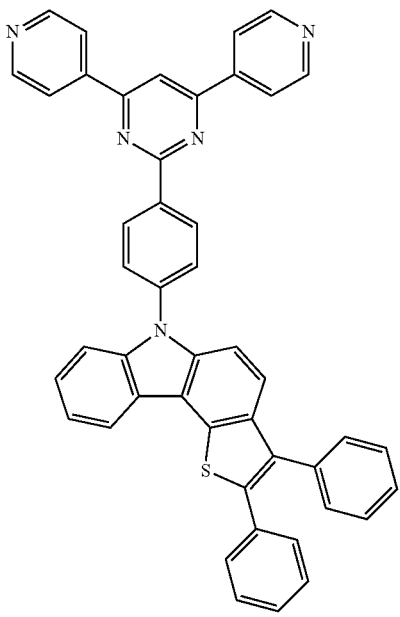
322

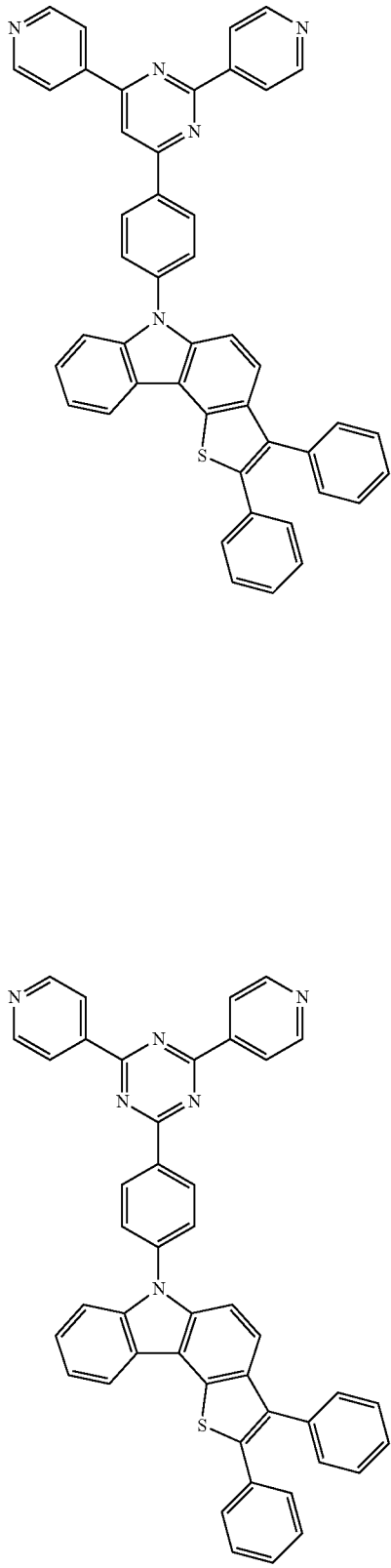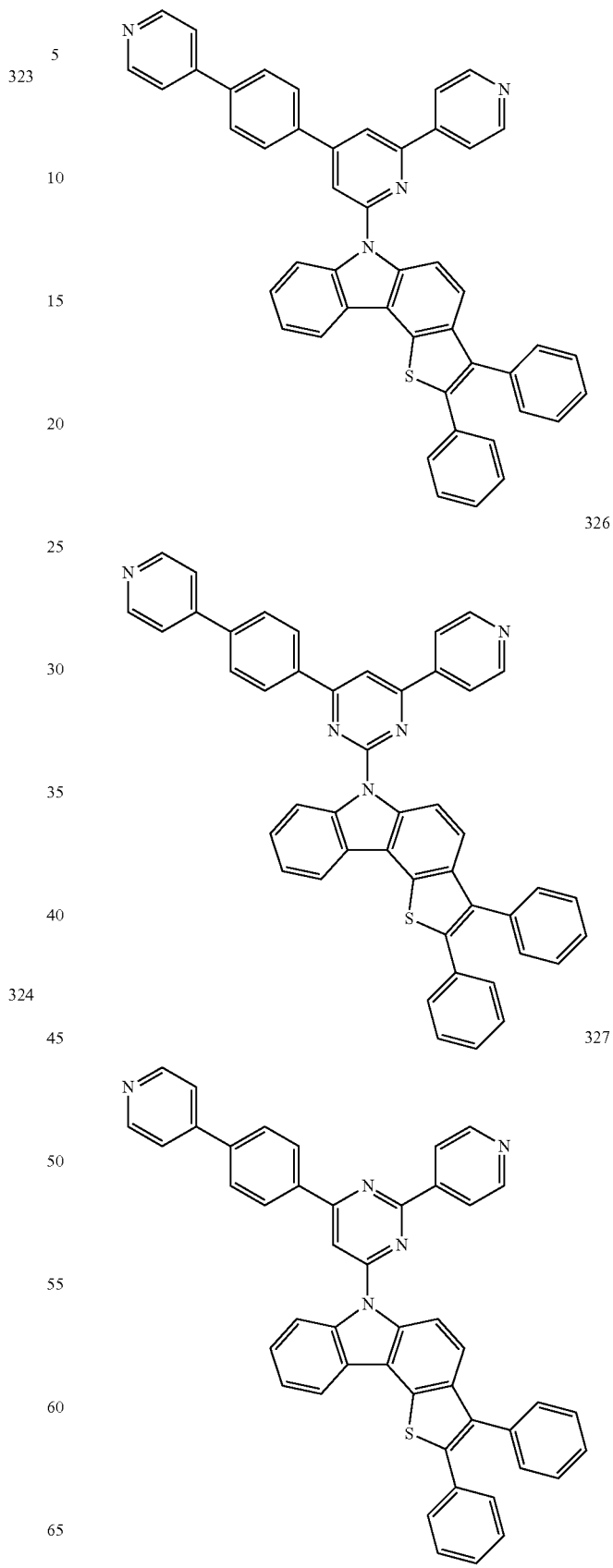

157
-continued
158
-continued
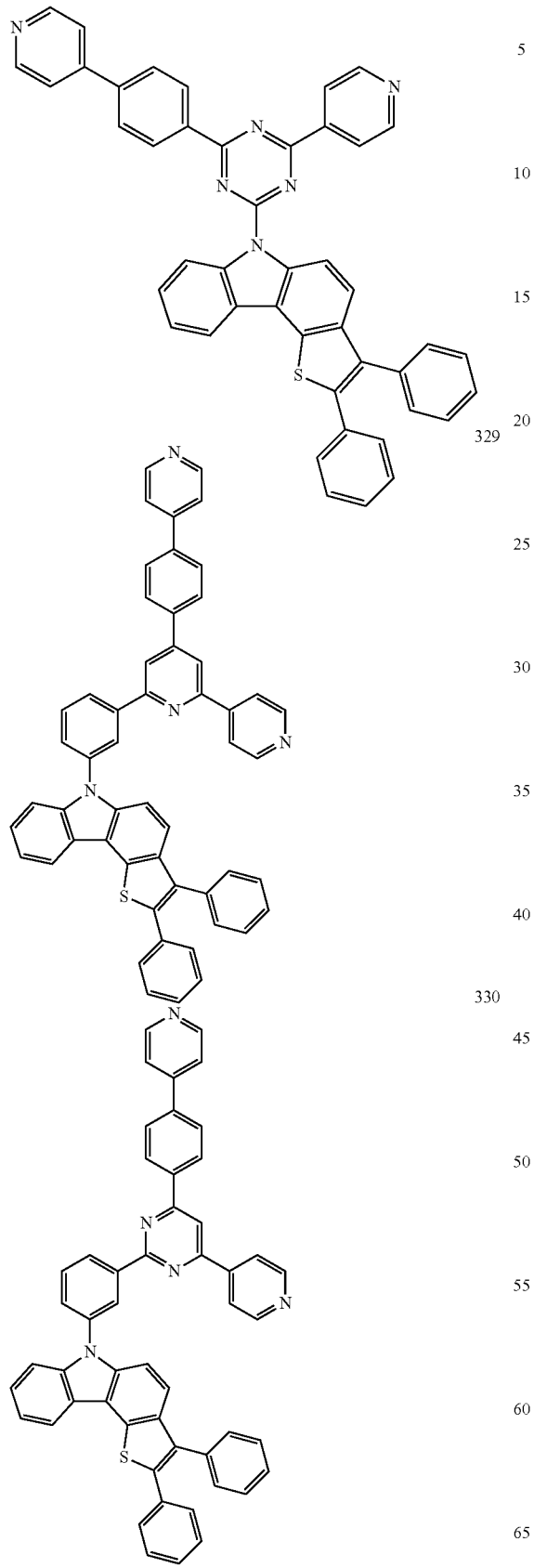

159
-continued
333
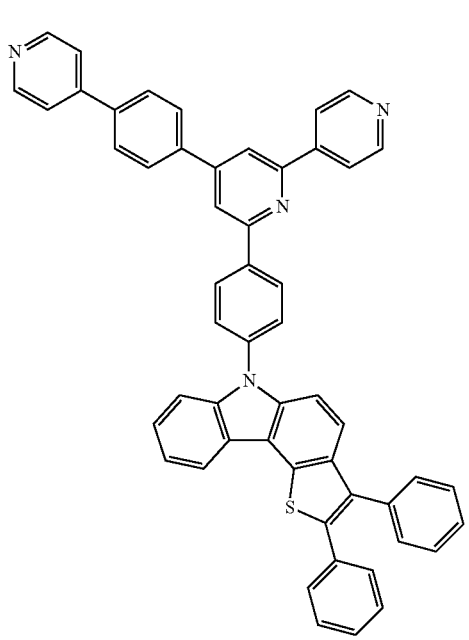
334
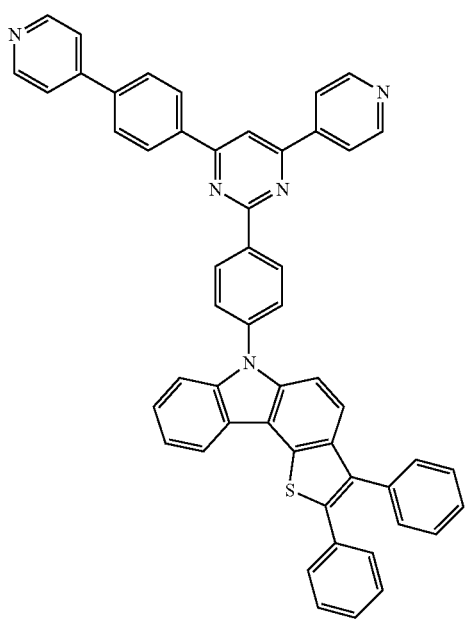
160
-continued
335
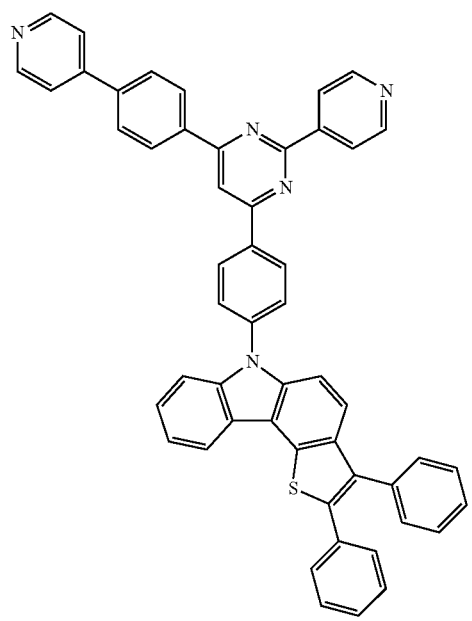
336
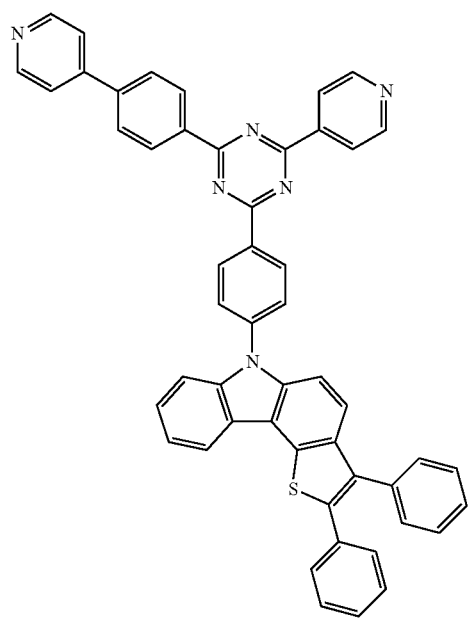

161
-continued
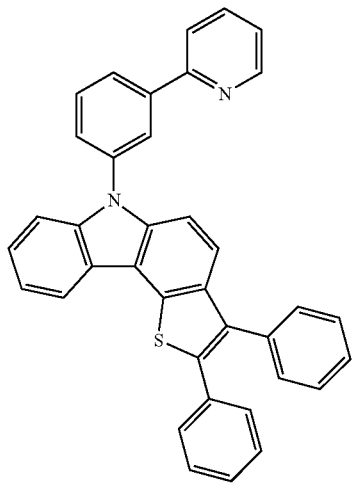
337
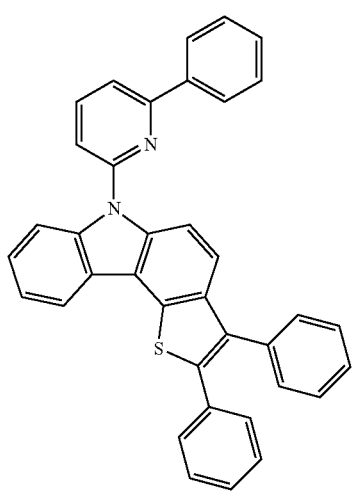
338
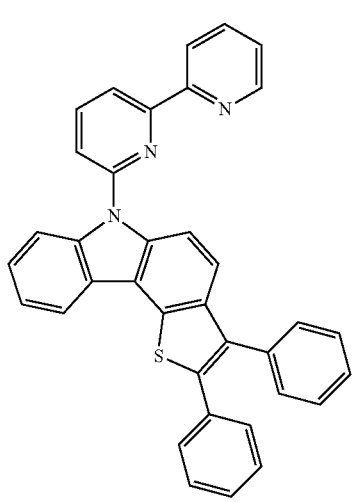
339
162
-continued
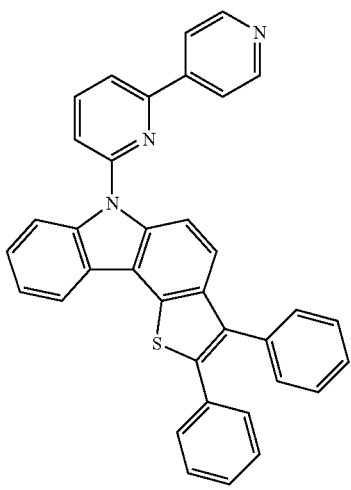
340
341
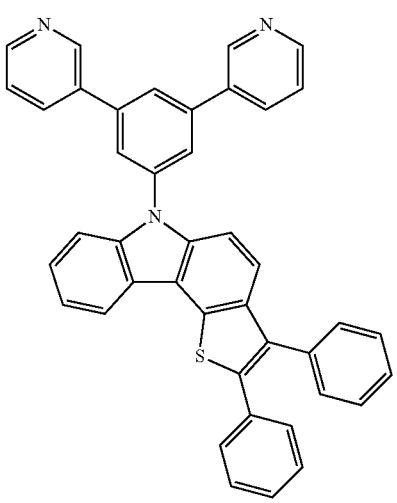
342

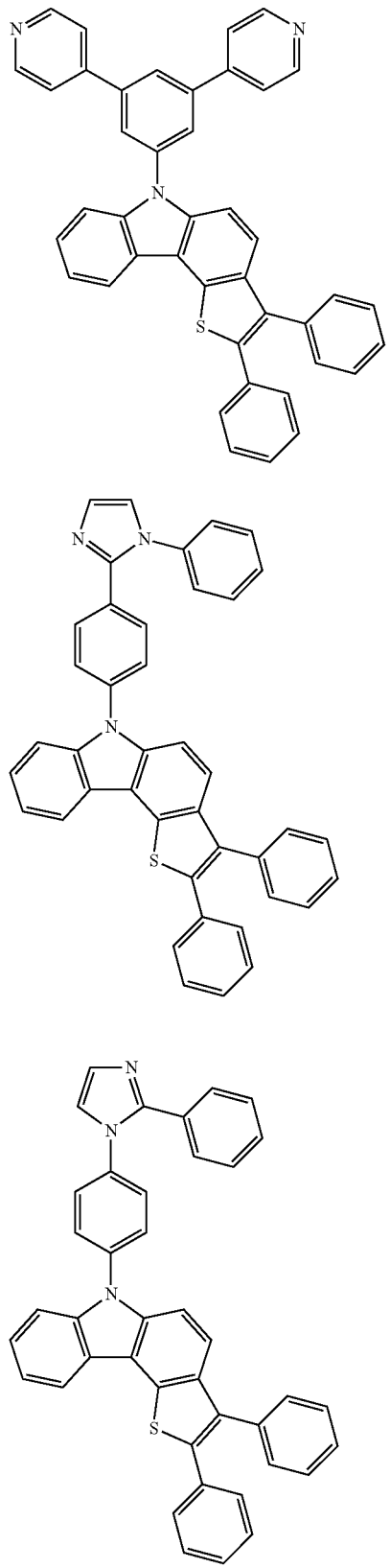
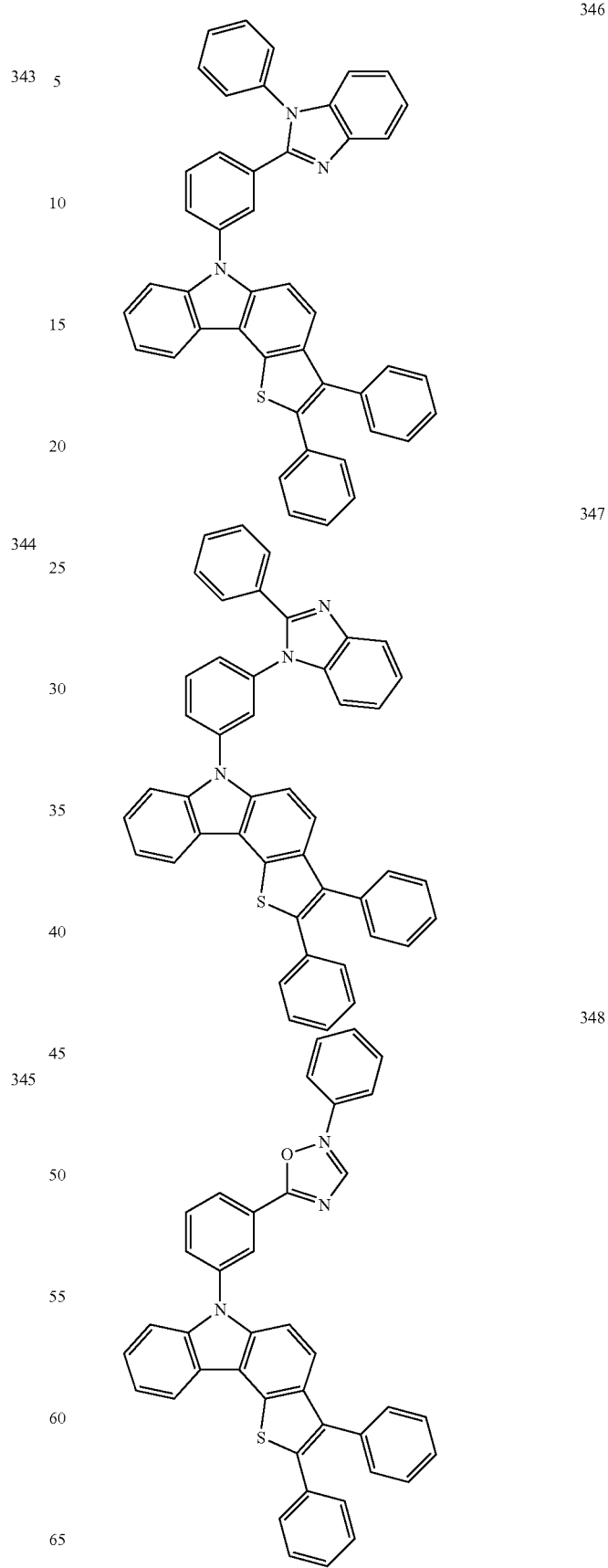

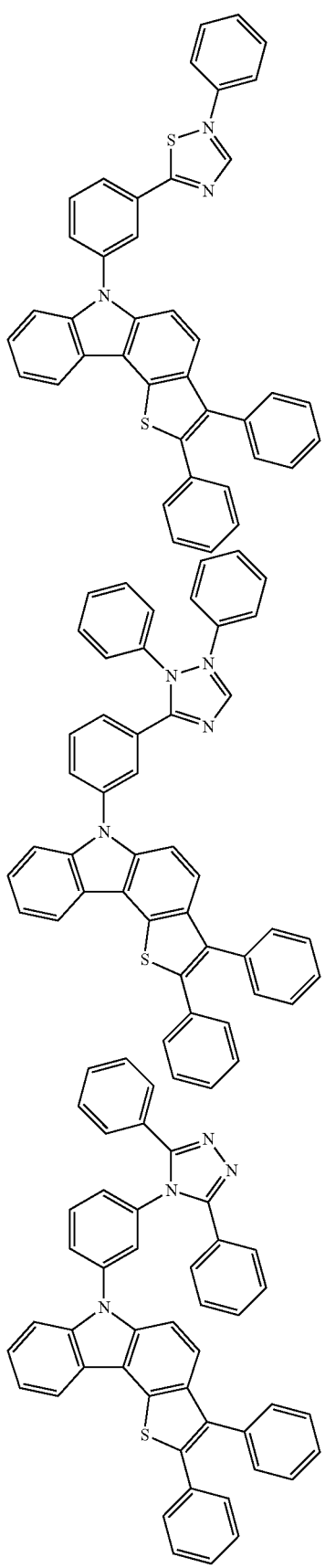
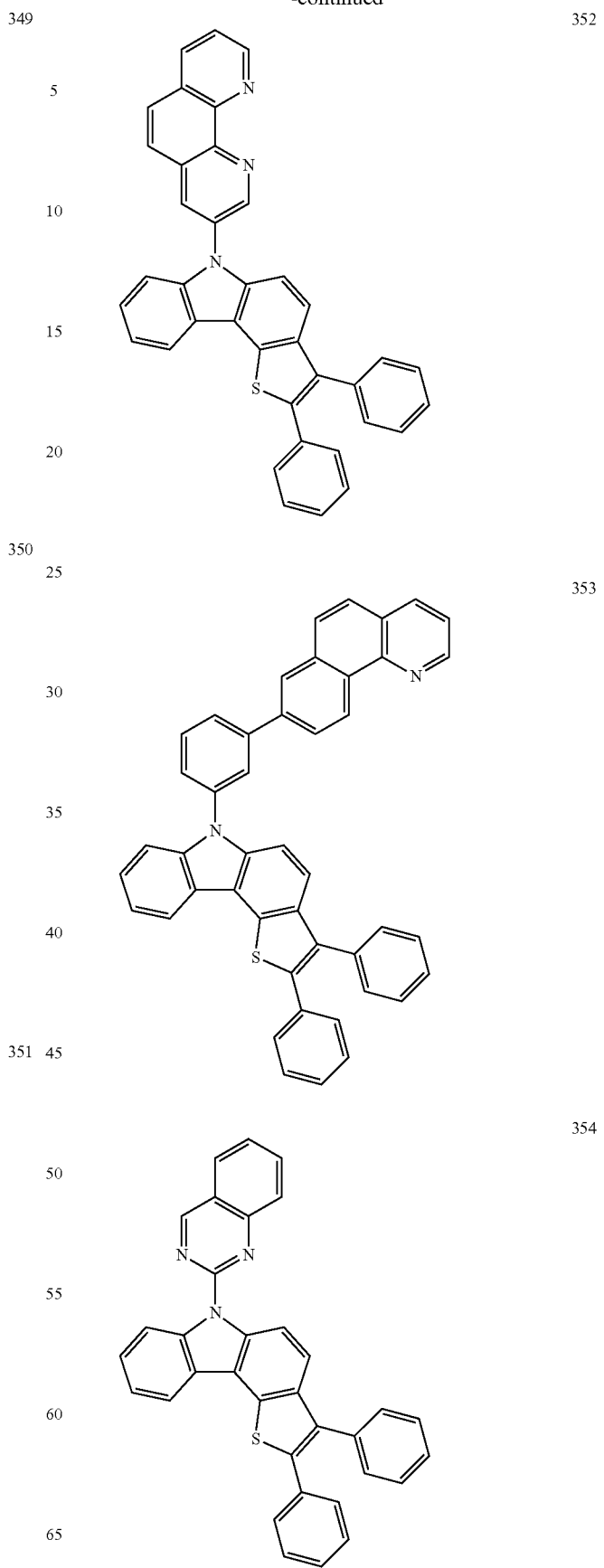

167
-continued
168
-continued
355
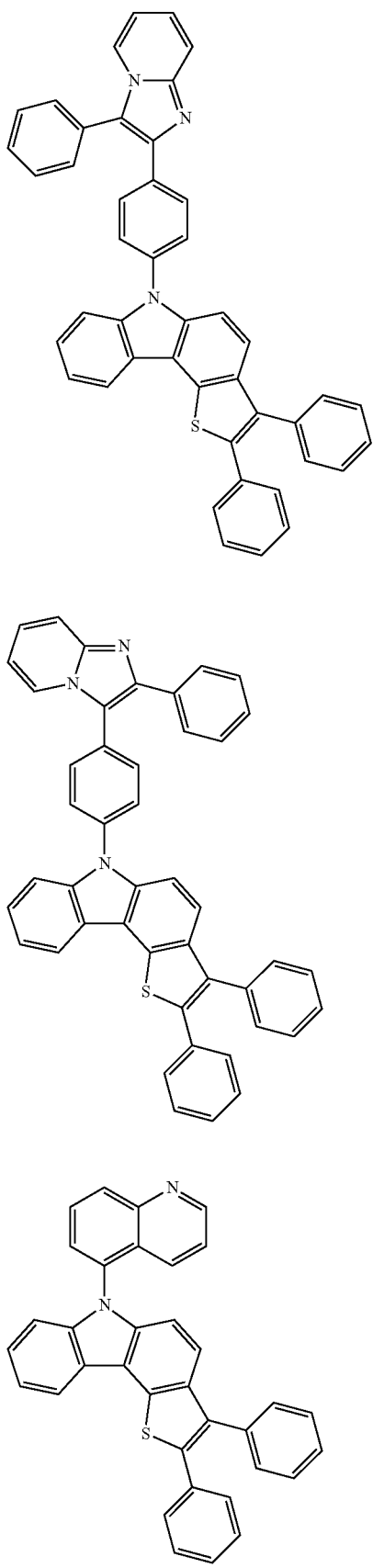
356
357
358
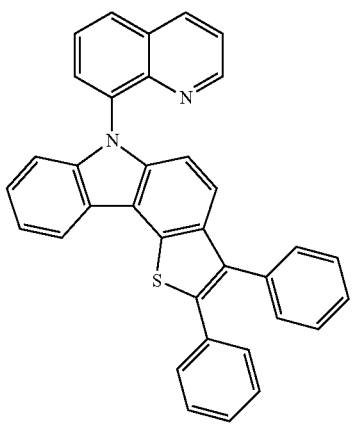
359
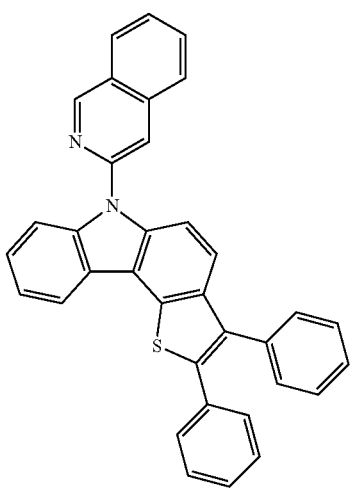
360
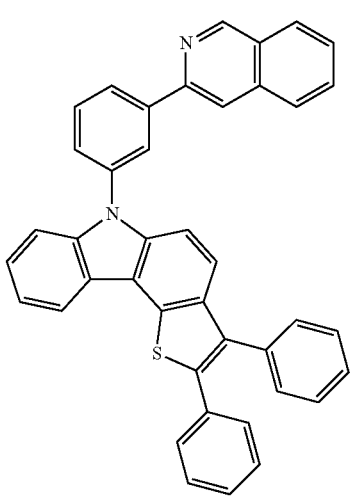

361 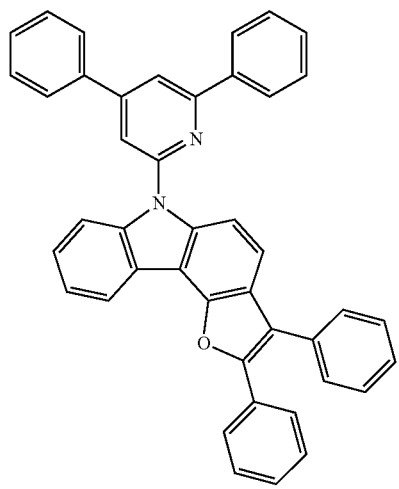
362 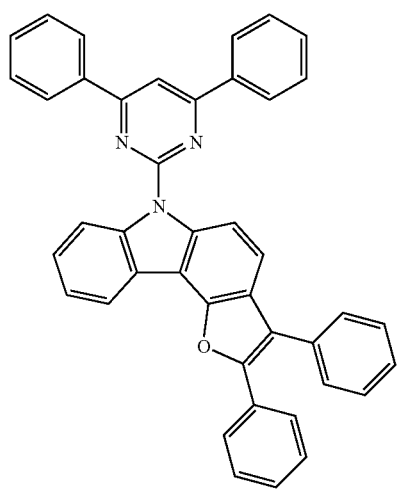
363 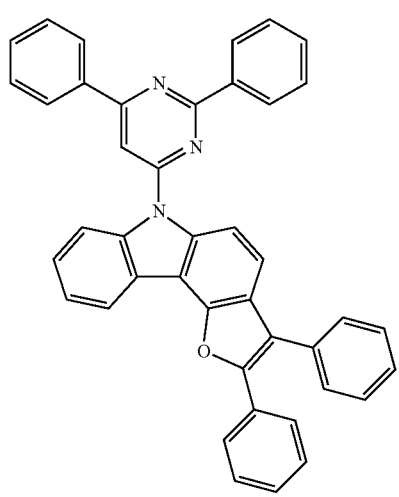
364 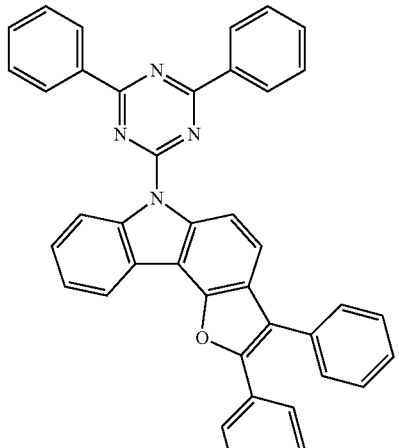
365 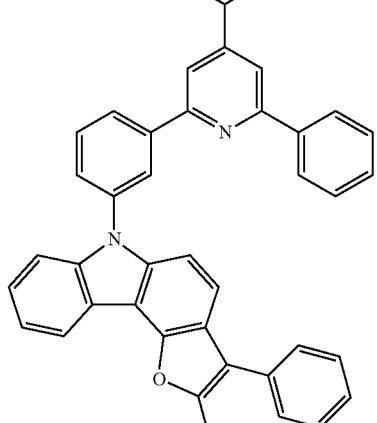
366 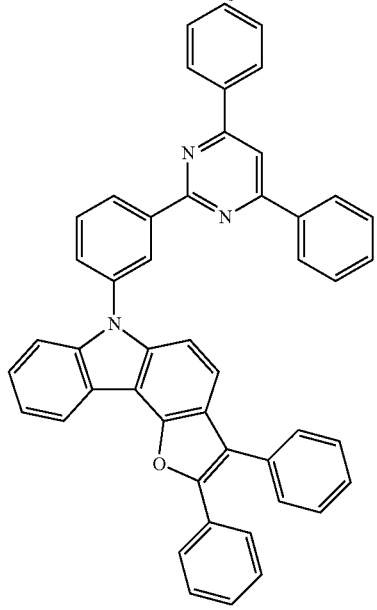

367 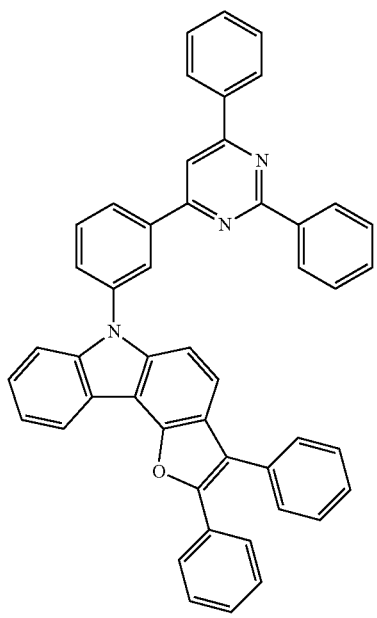
368 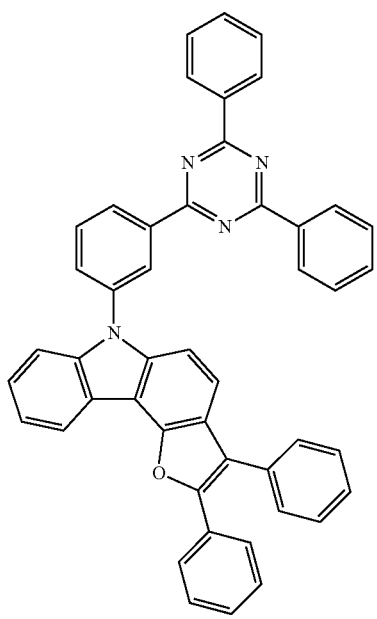
369 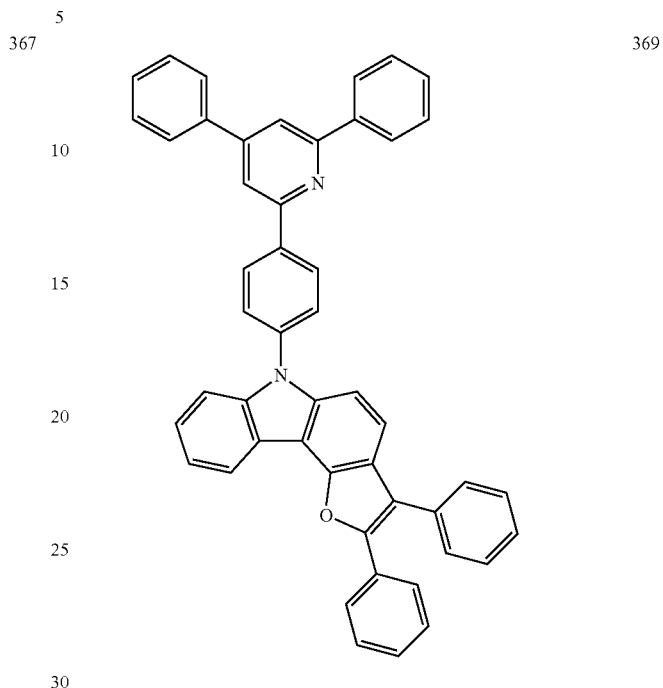
370 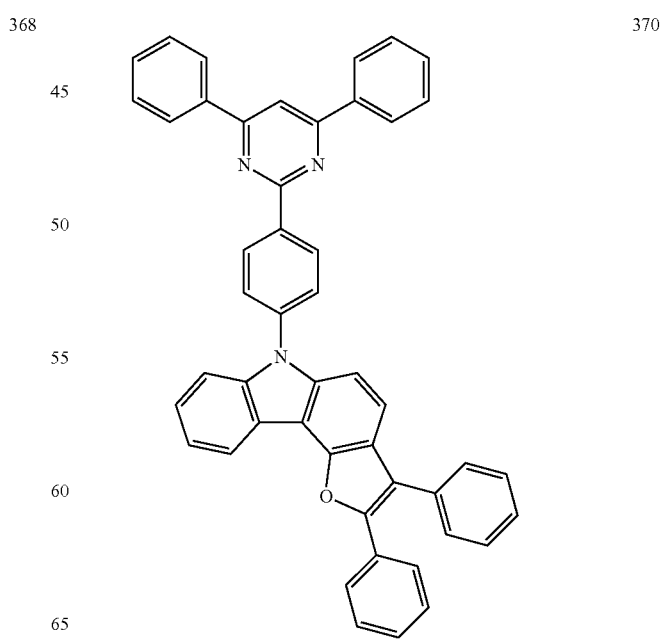

173
-continued
174
-continued
371
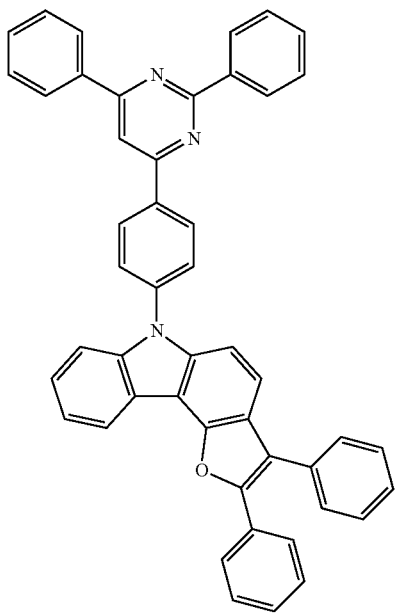
373
372
374
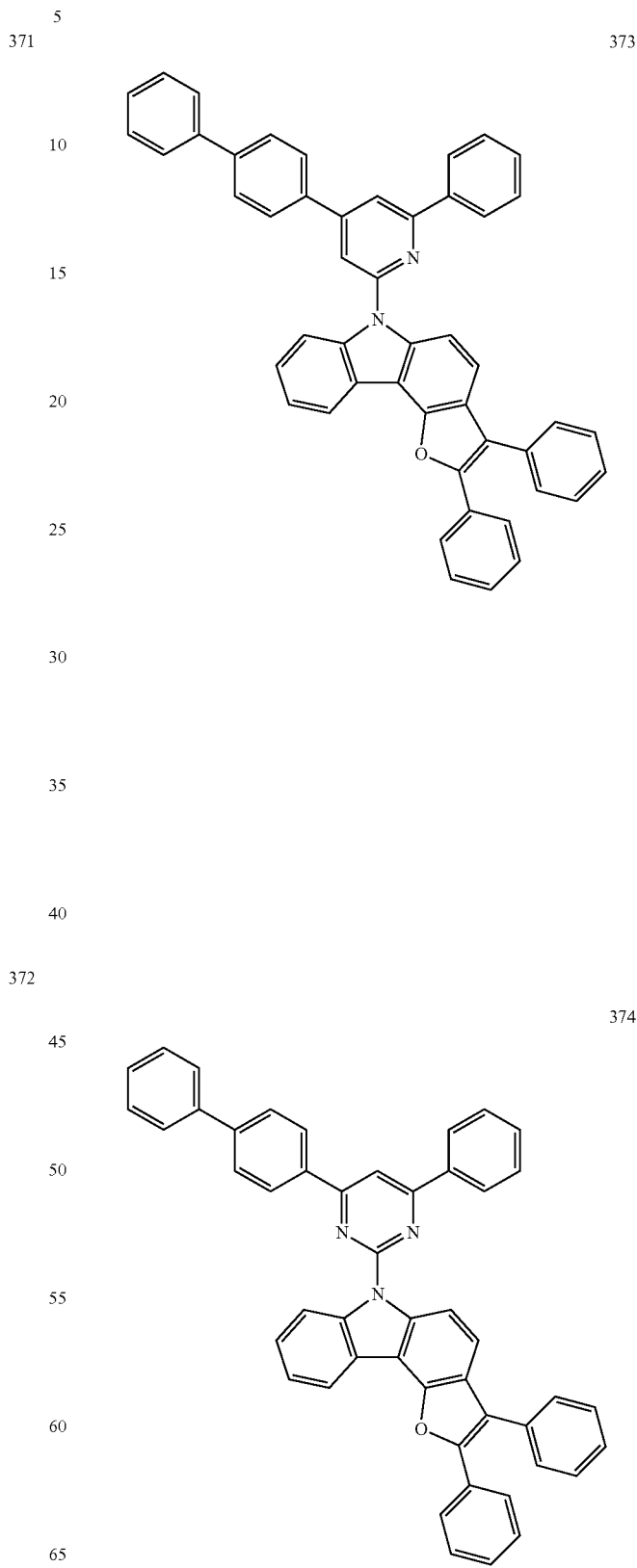

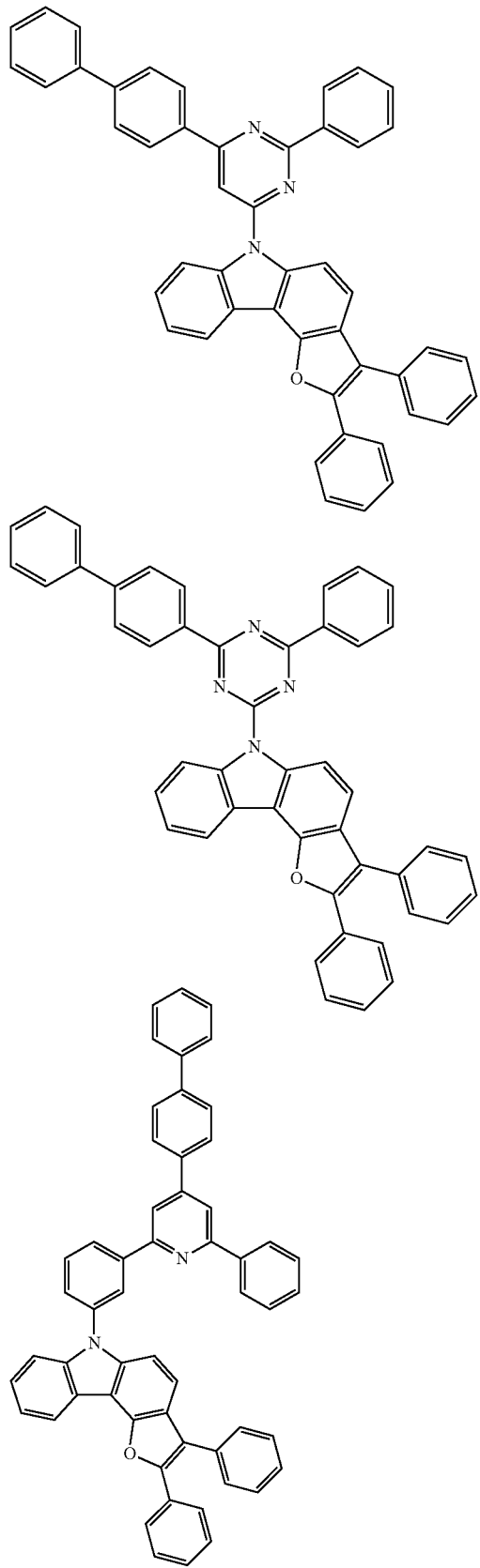

177
178
-continued
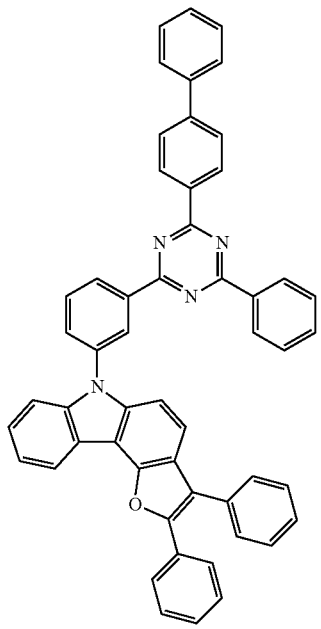
380
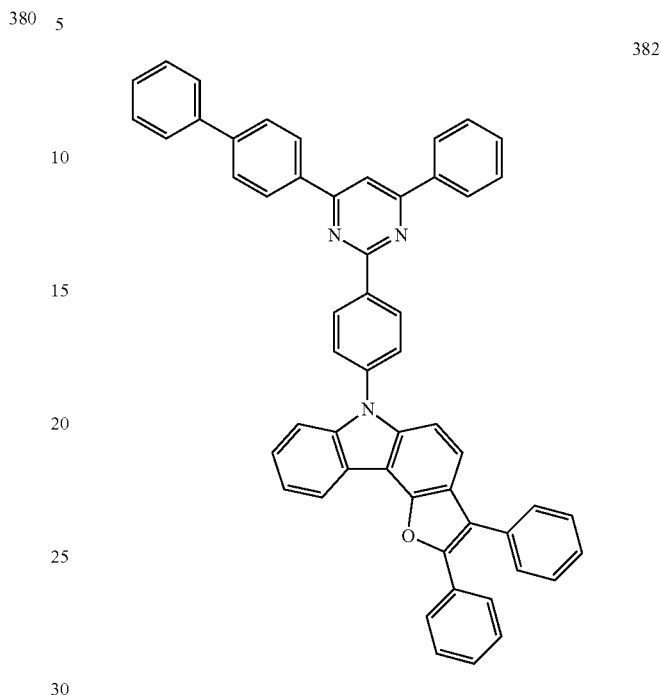
381
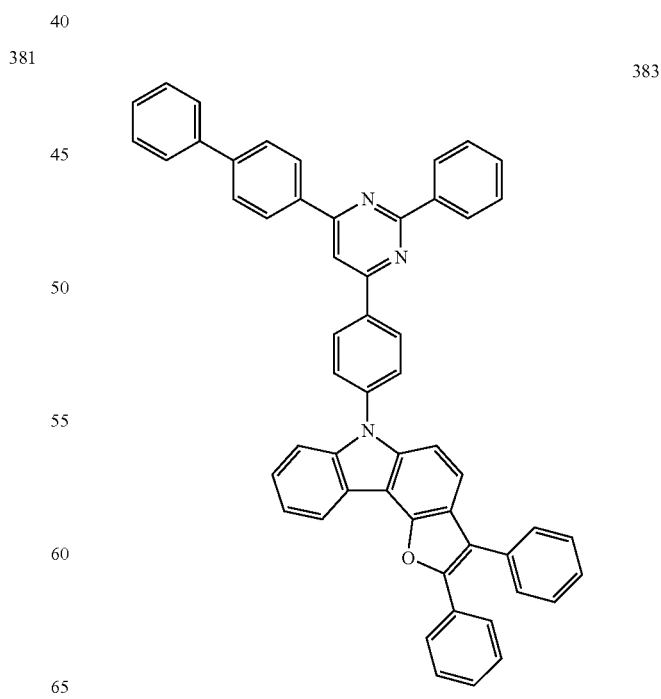

384
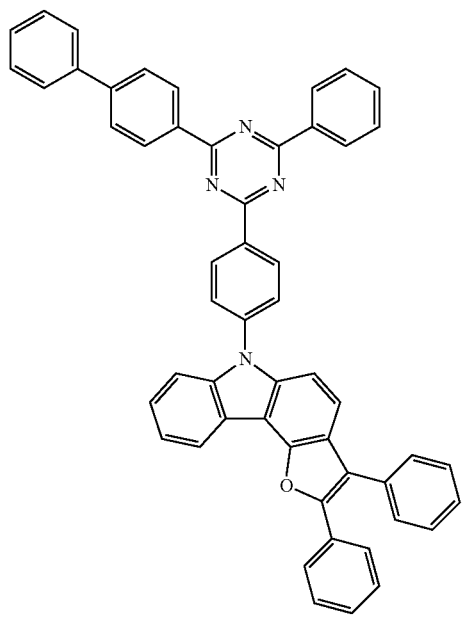
385
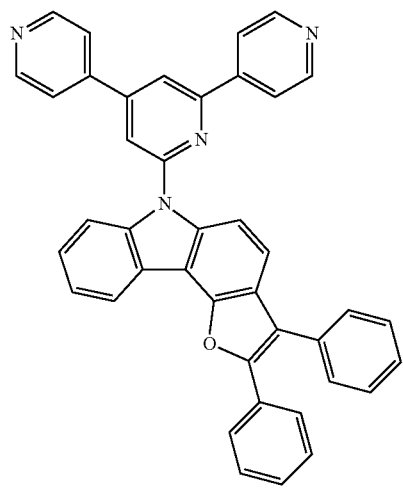
386
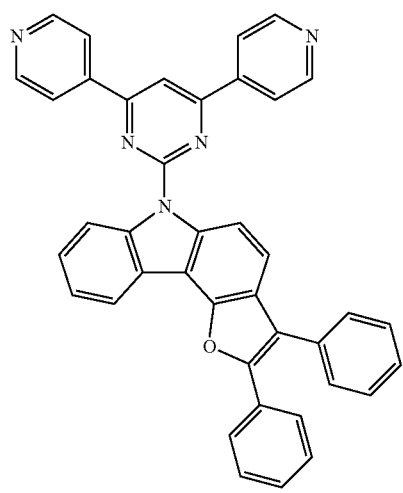
387
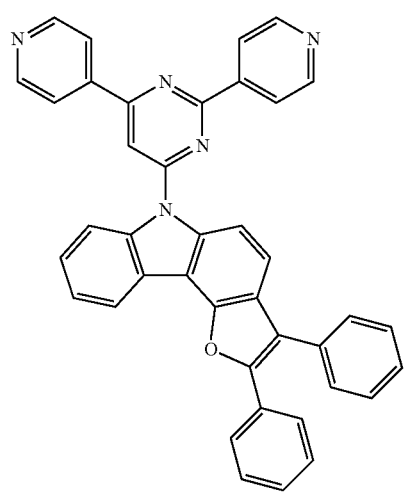
388
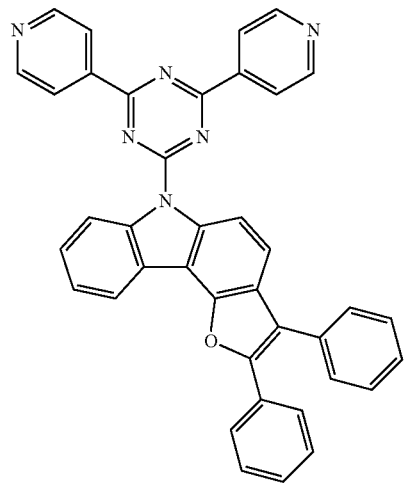
389
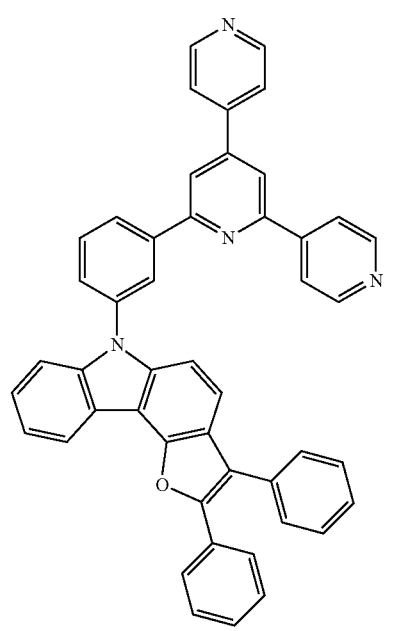

181
-continued
182
-continued
390
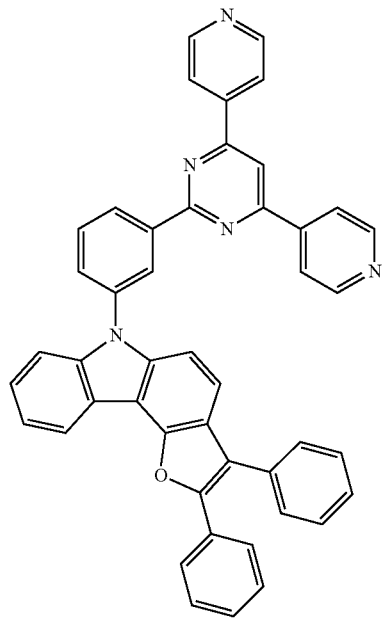
392
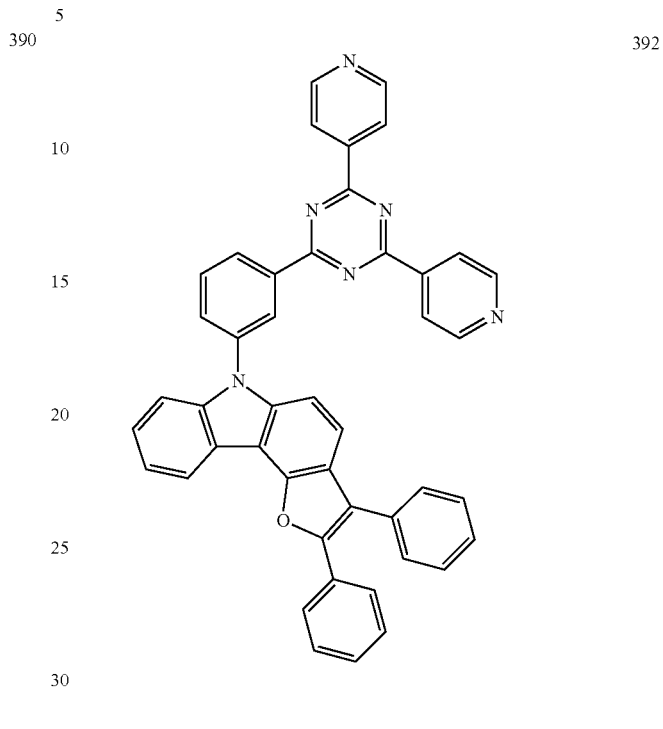
391
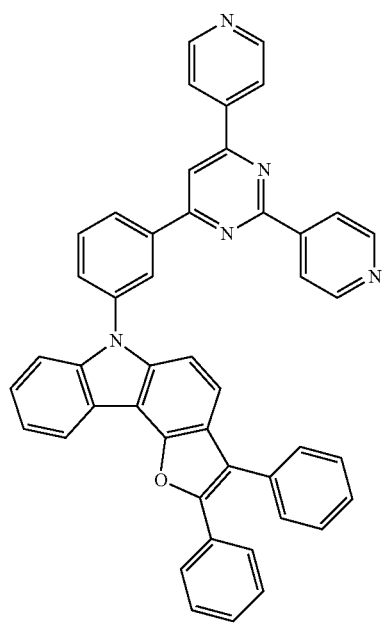
393
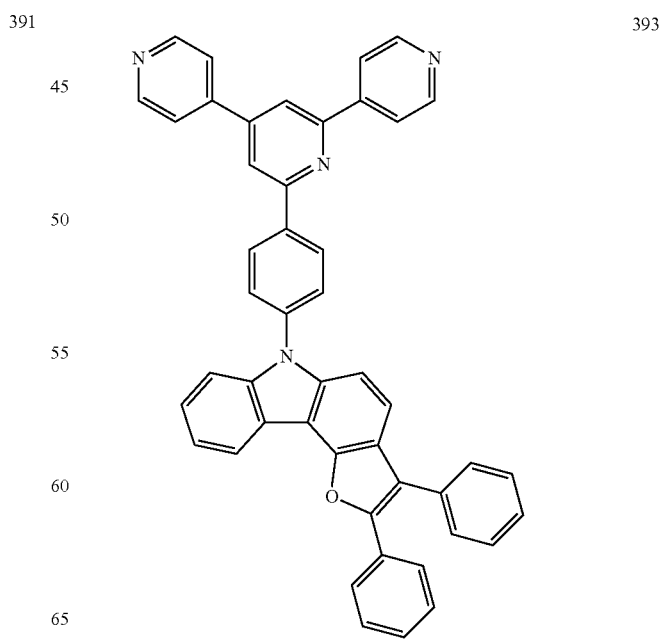

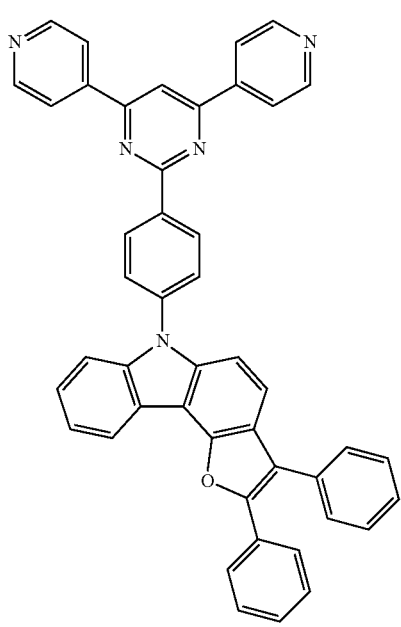
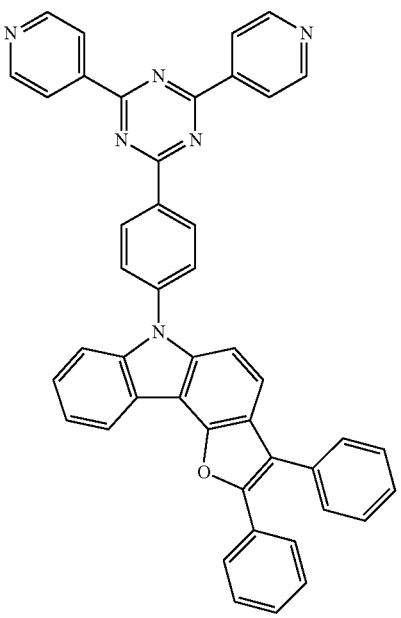

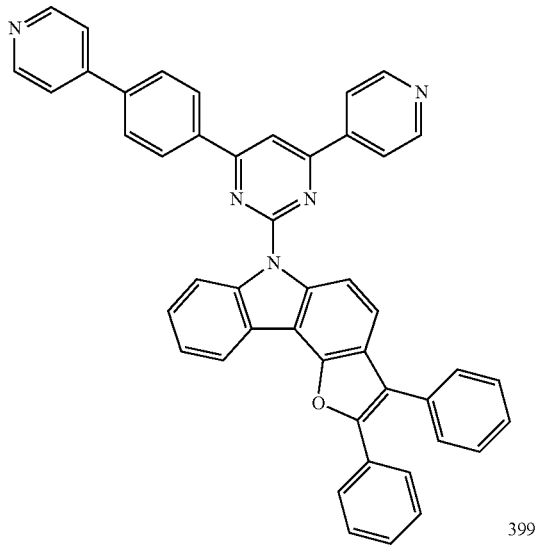
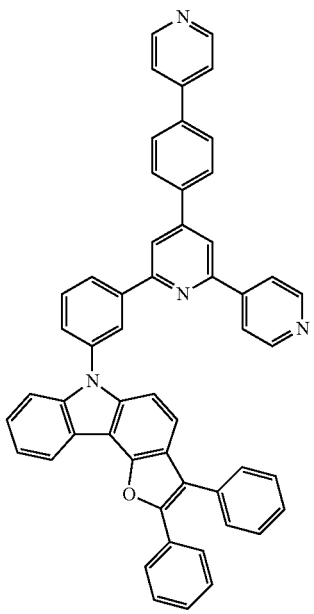

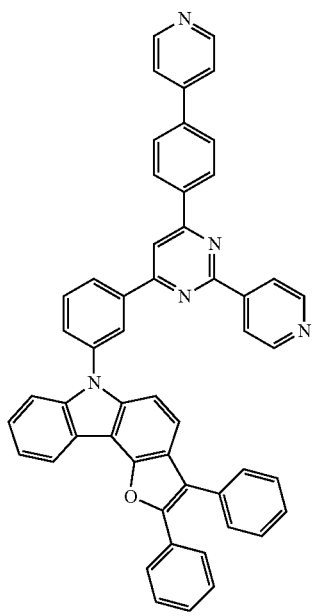
403
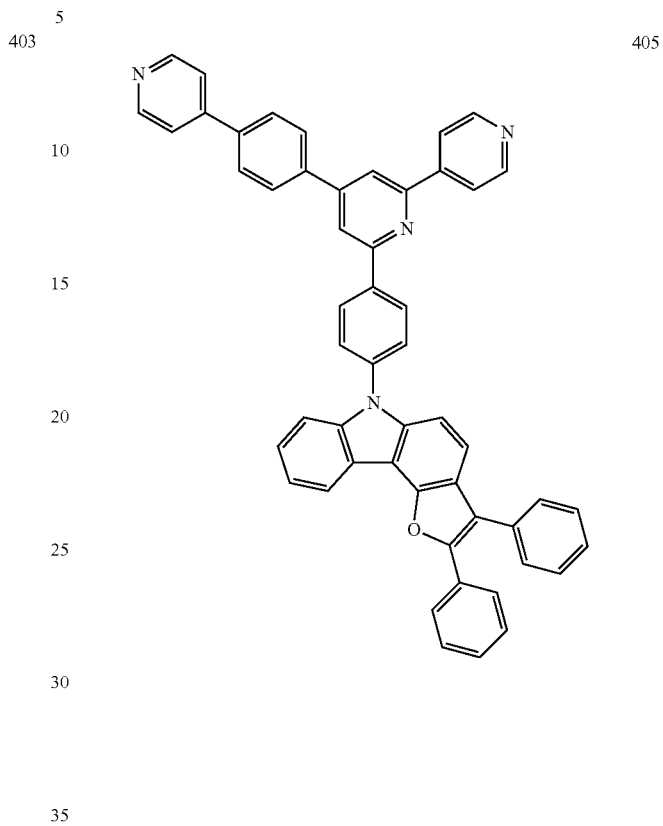
405
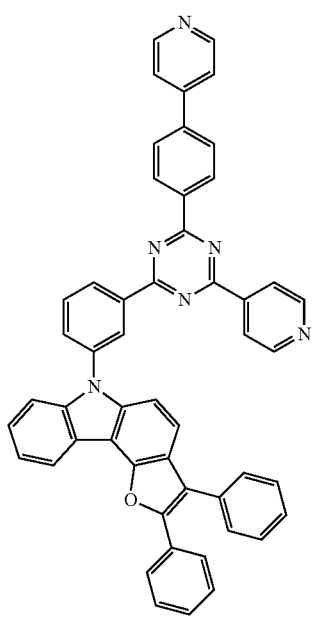
404
406

189
-continued
407
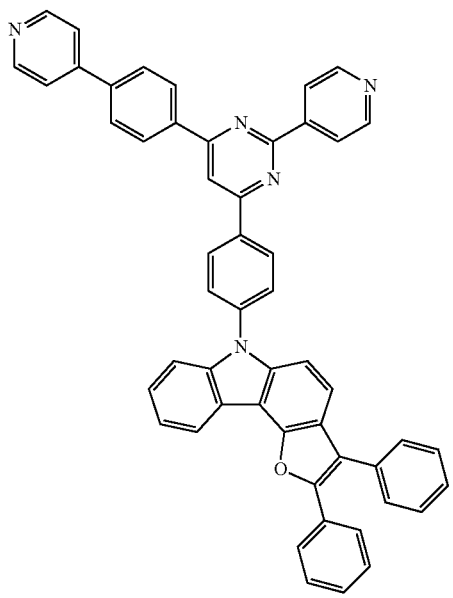
408
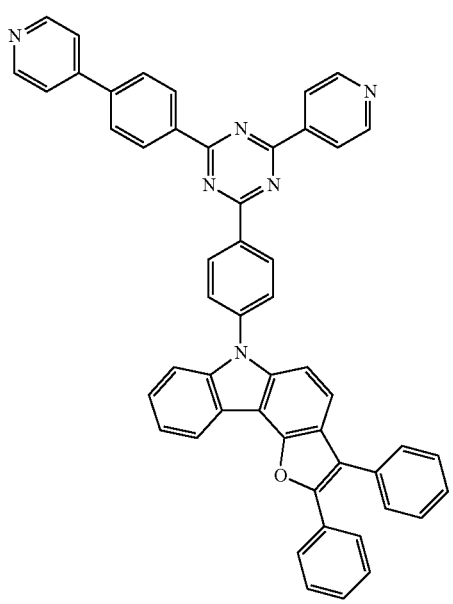
409
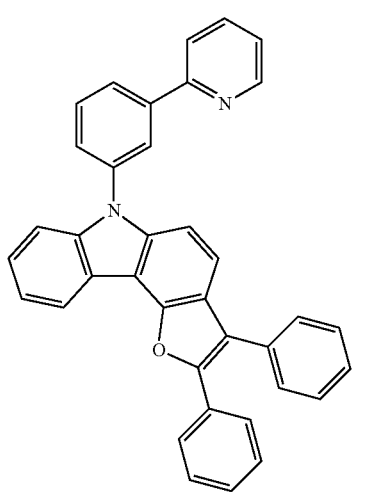
190
-continued
410
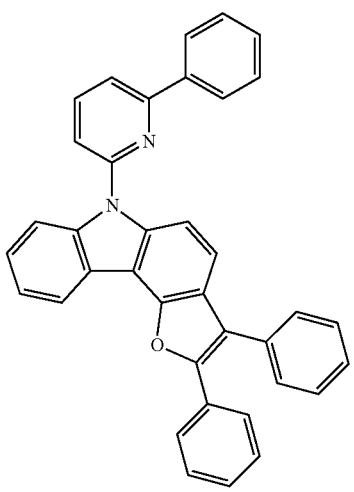
411
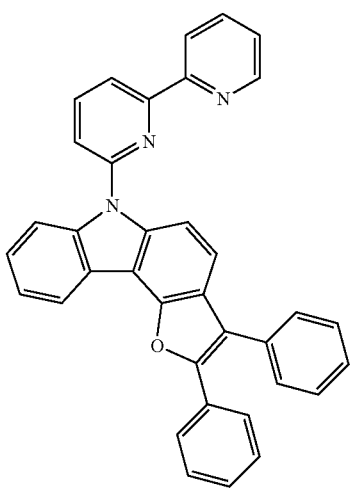
412
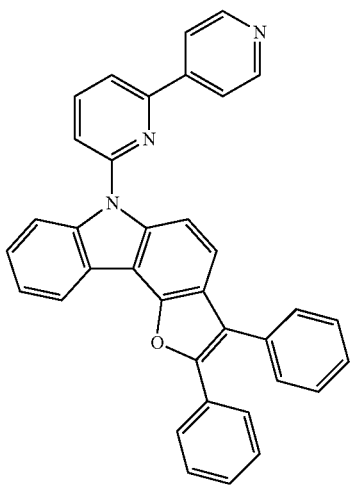

-continued
413
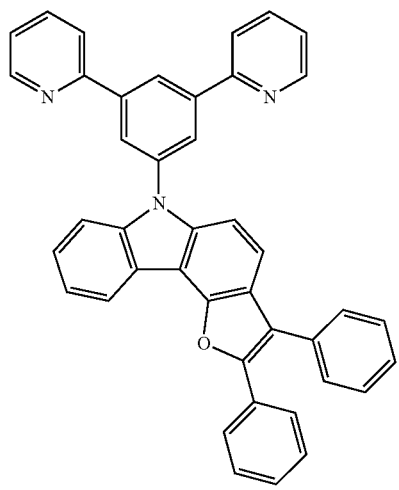
414
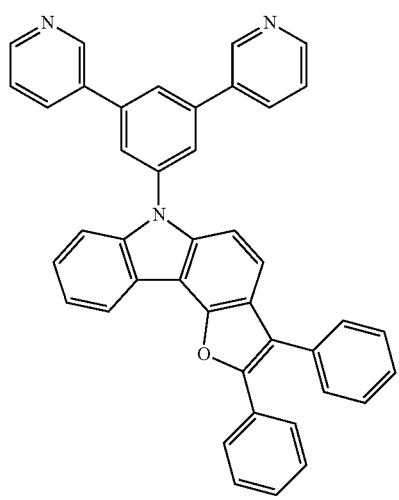
415
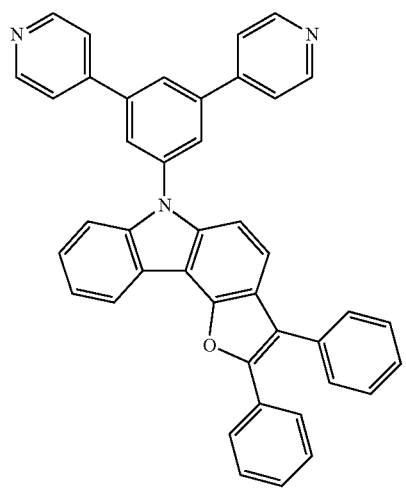
-continued
416
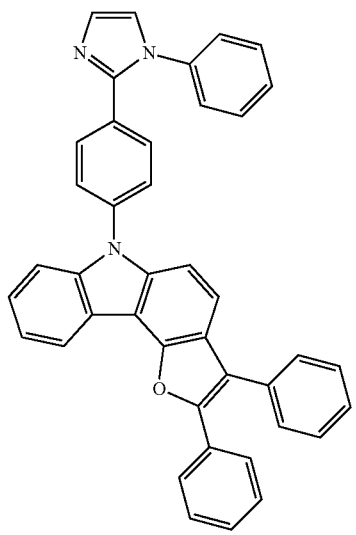
417
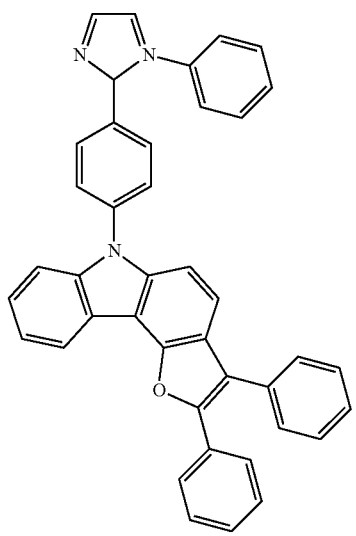
418
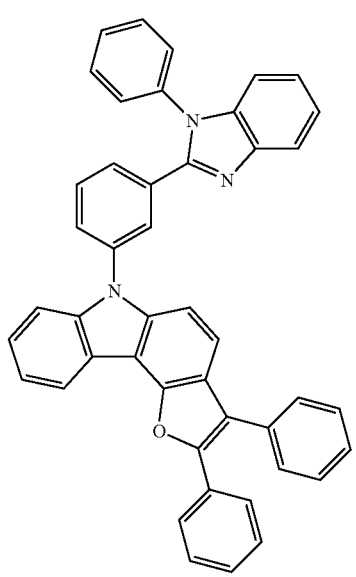

193
-continued
419
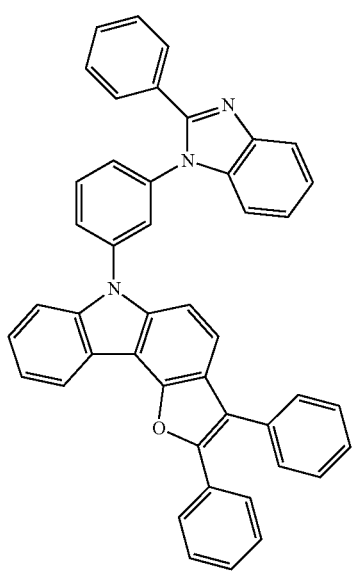
420
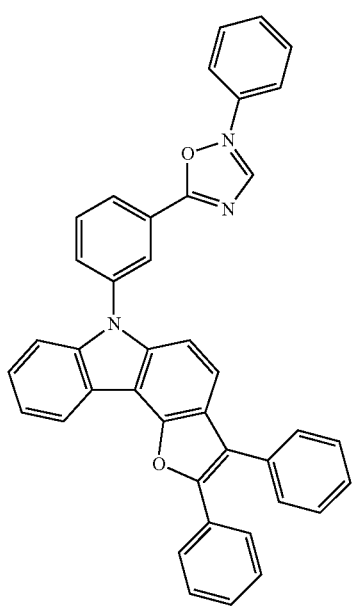
194
-continued
421
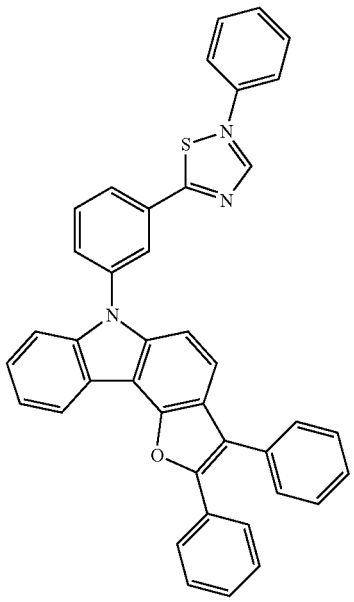
422
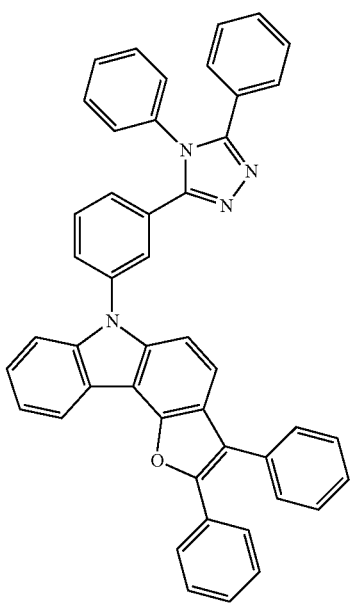

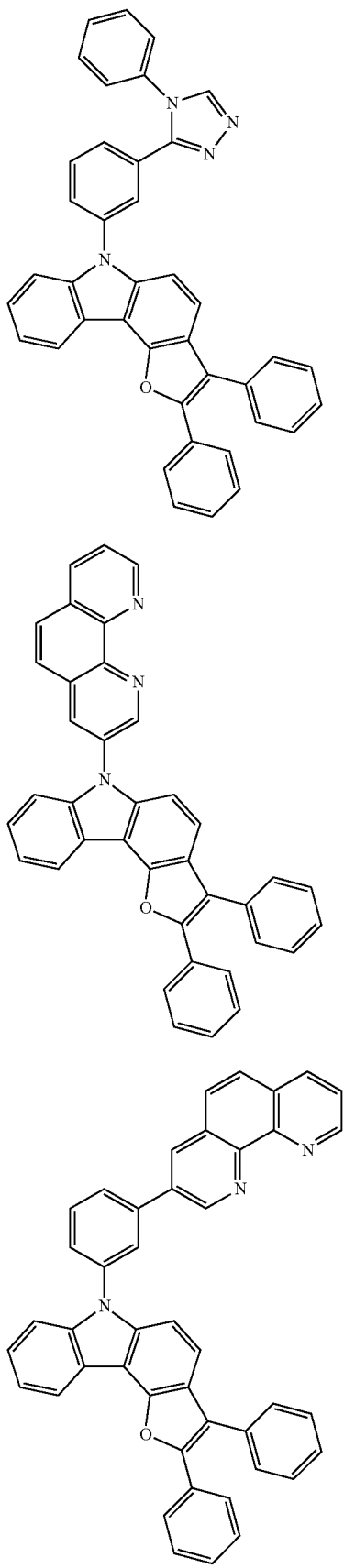
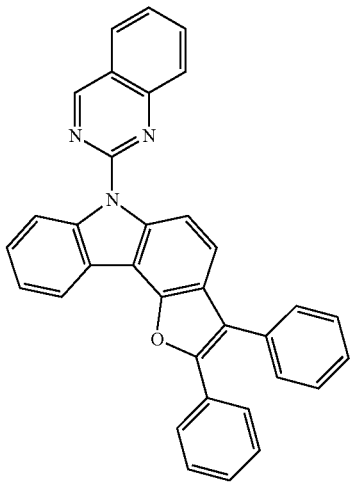
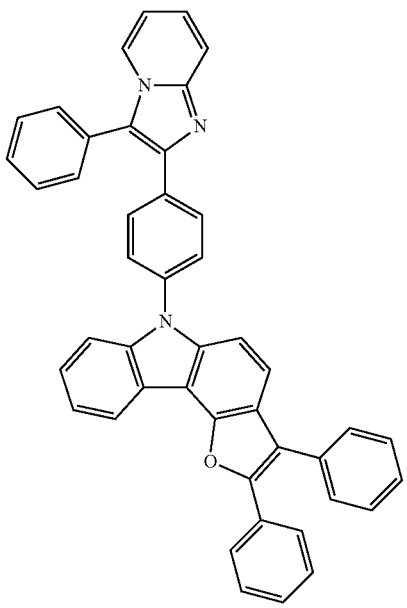
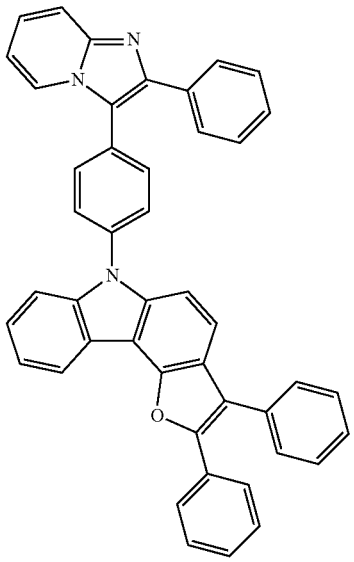

197
-continued
429
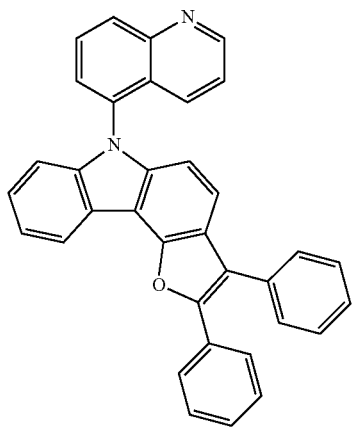
430
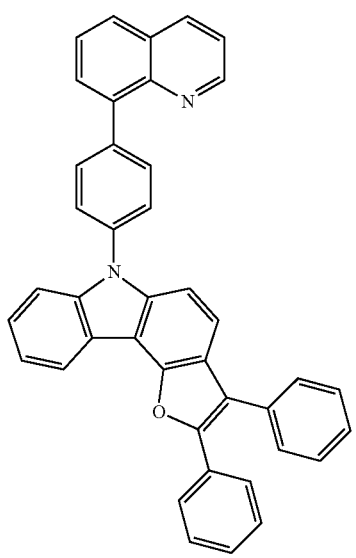
431
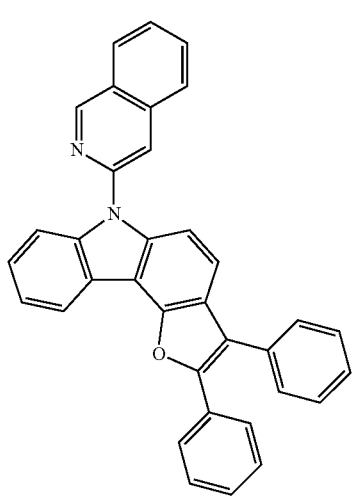
198
-continued
432
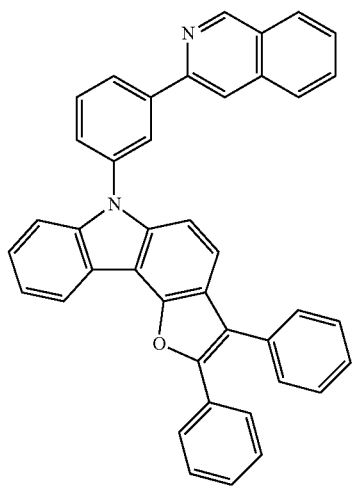
433
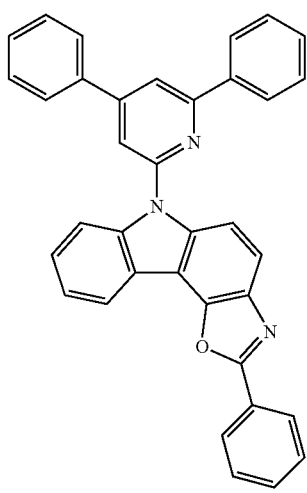
434
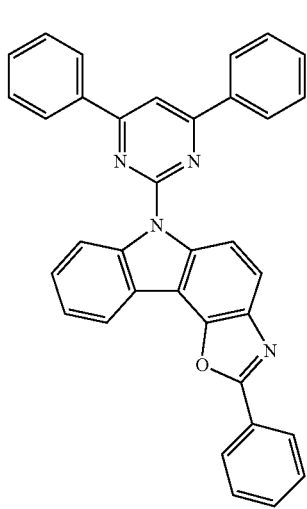

199
-continued
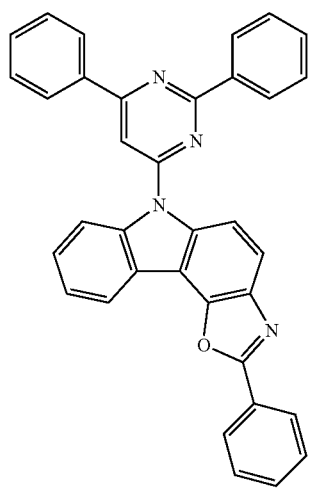
435
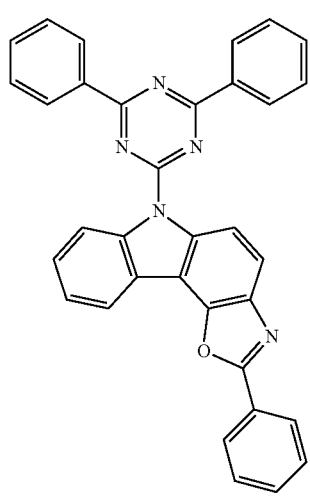
436
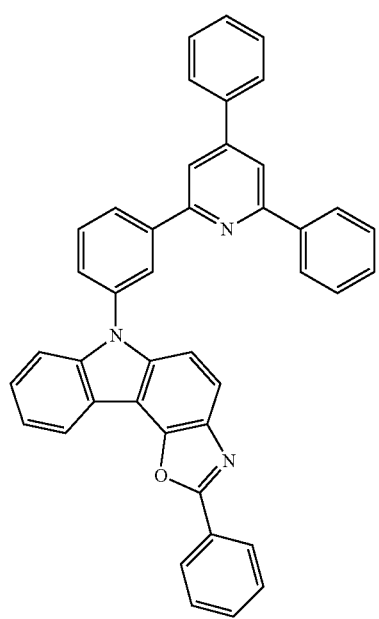
437
200
-continued
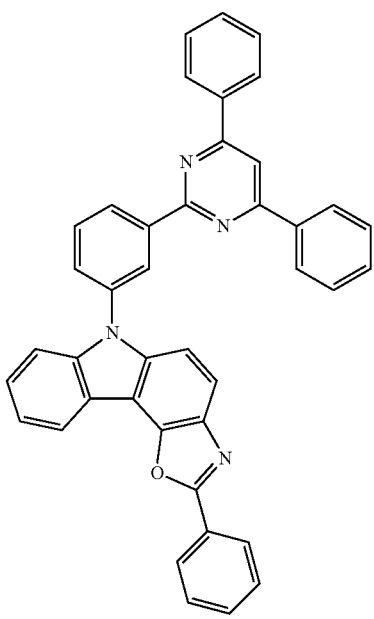
438
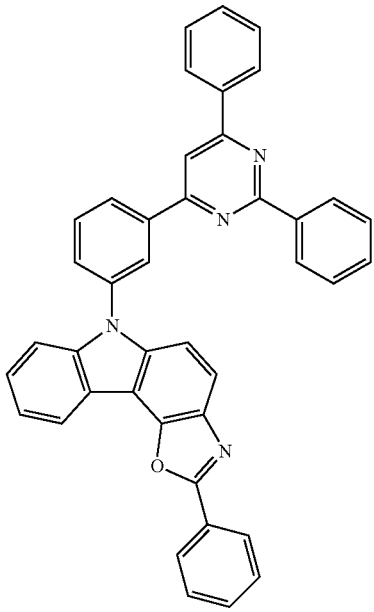
439

201
-continued
202
-continued
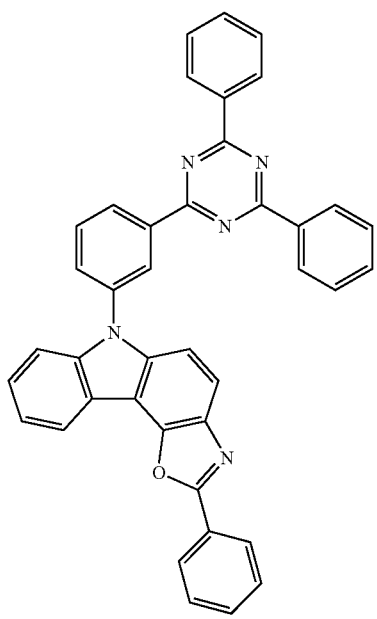
440
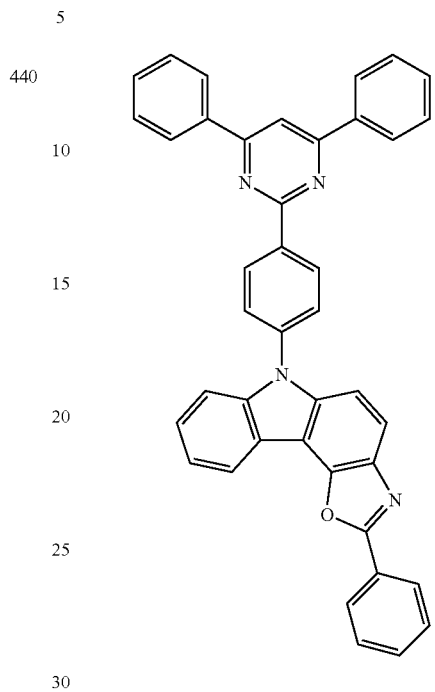
442
441
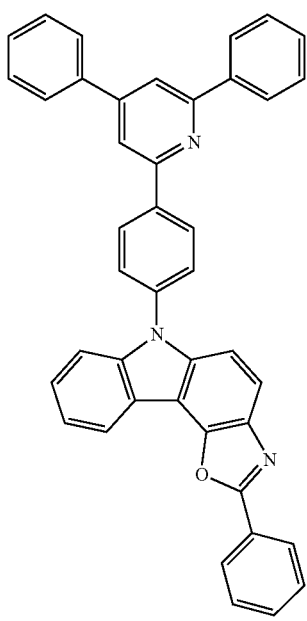
443
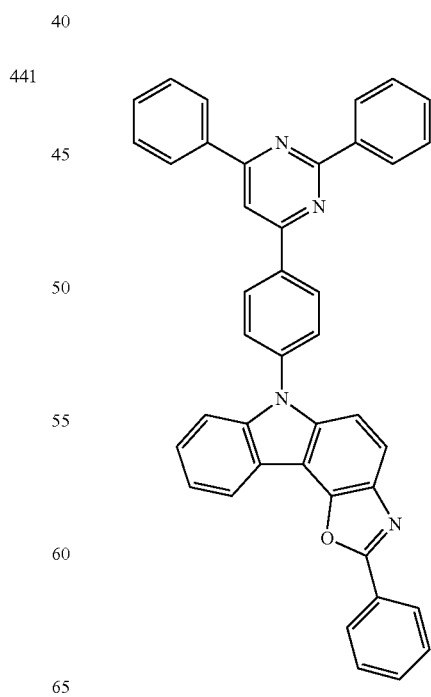

203
-continued
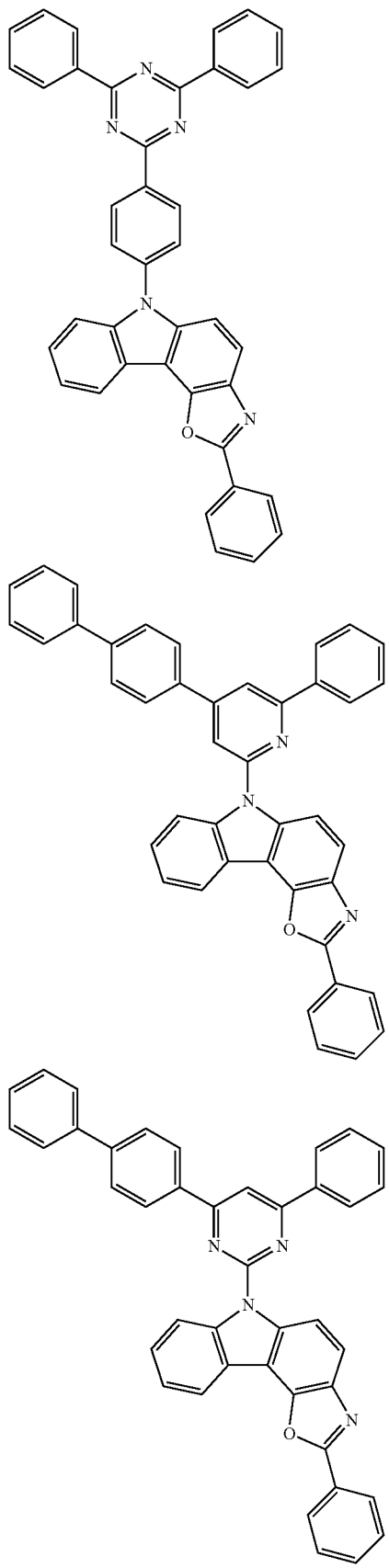
204
-continued
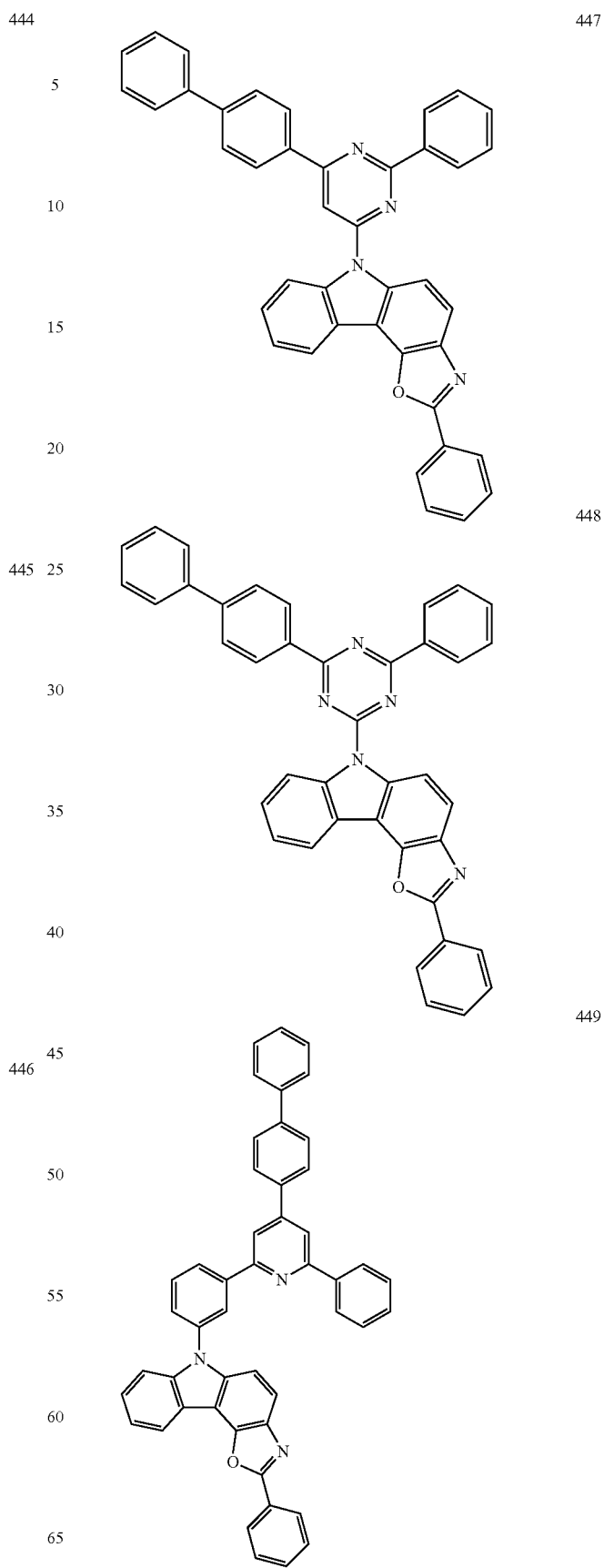

205
-continued
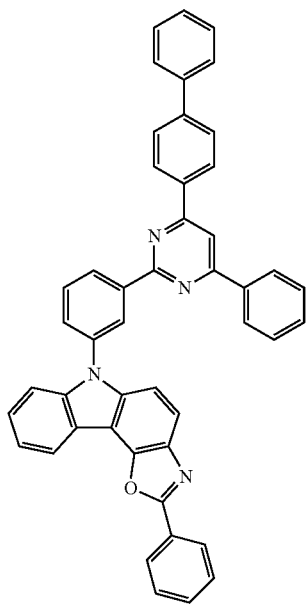
206
-continued
450
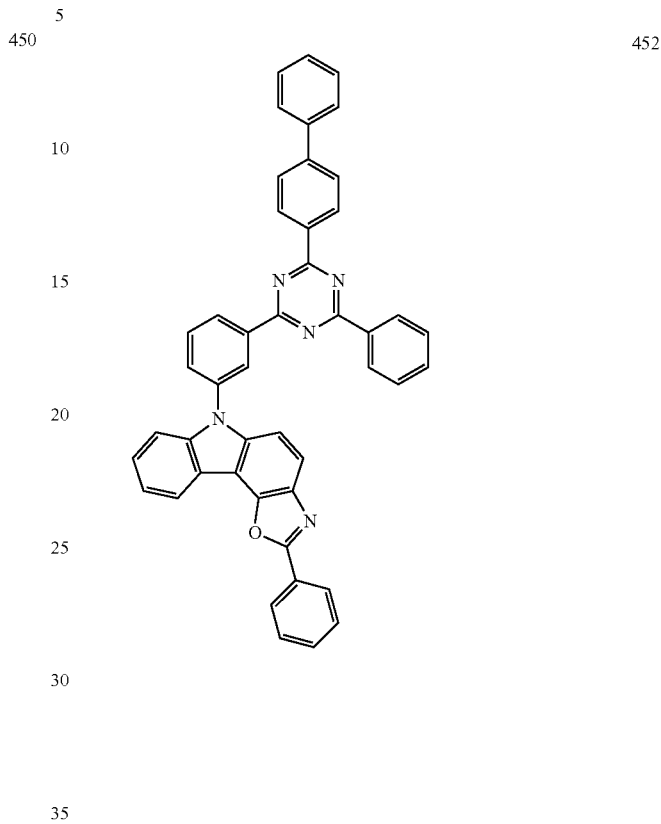
451
452
453
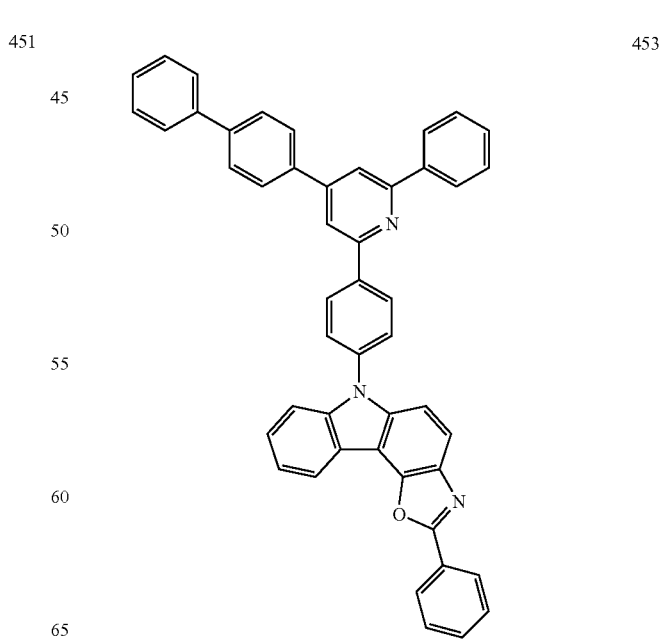

454
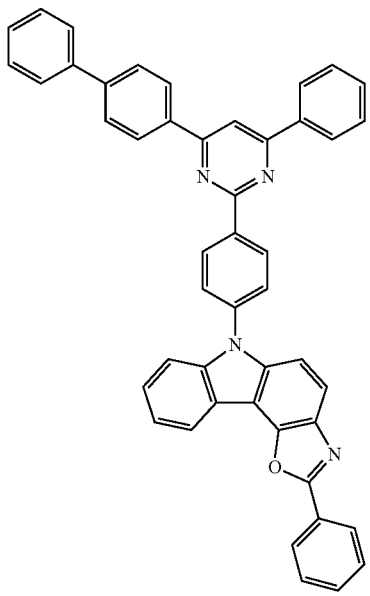
455
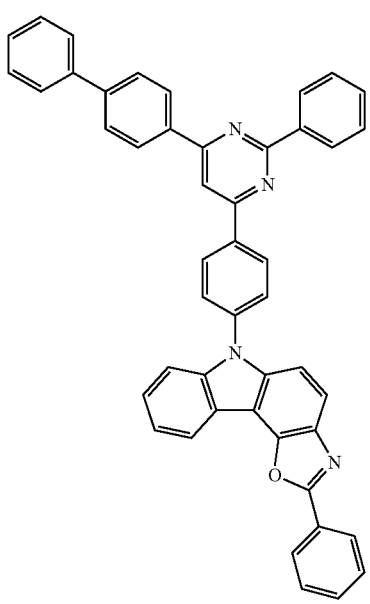
456
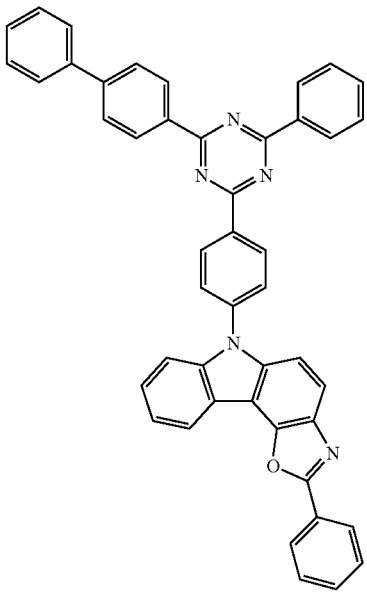
457
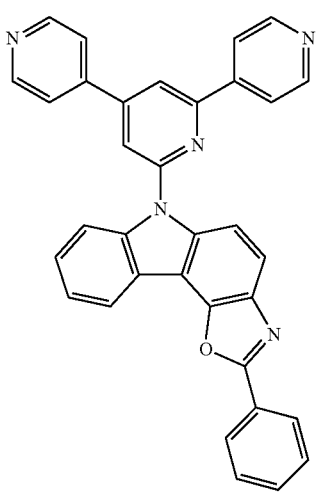
458

209
-continued
459
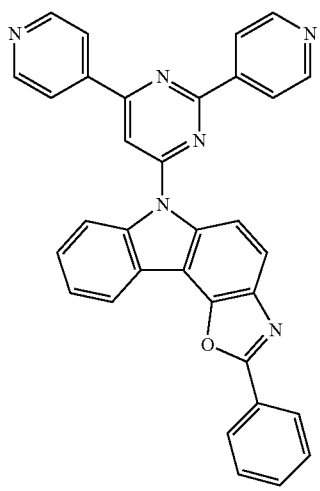
460
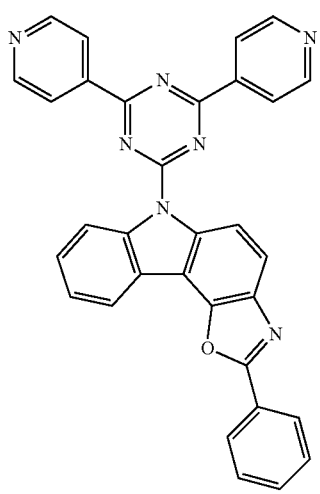
461
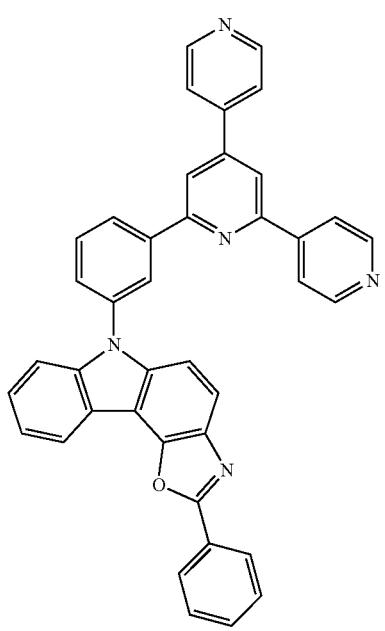
210
-continued
462
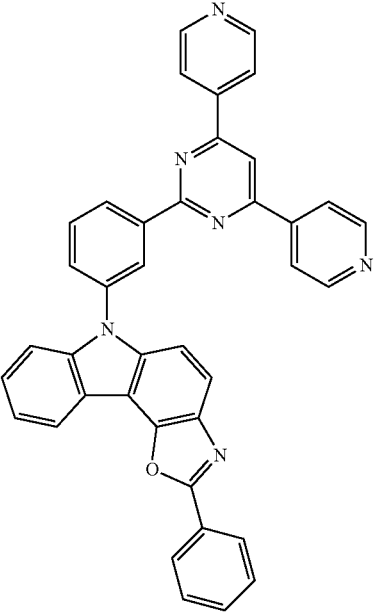
463
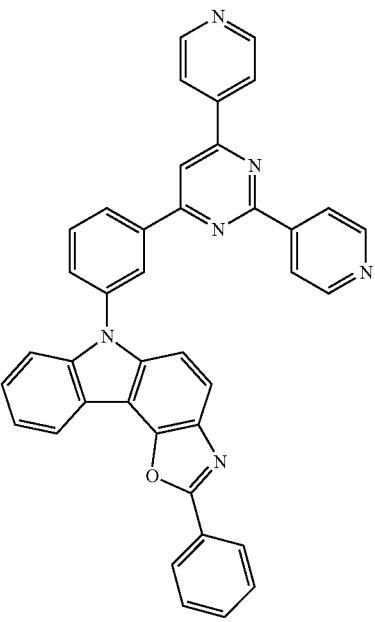

211
-continued
212
-continued
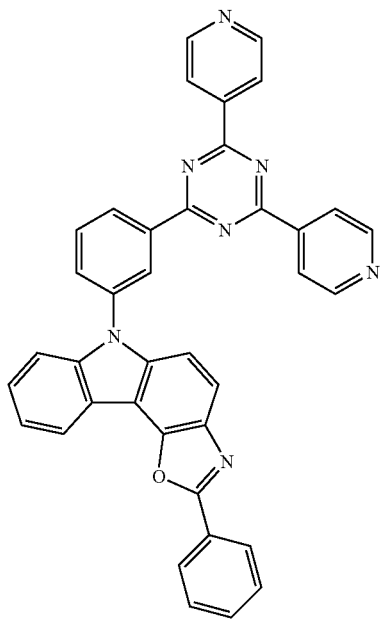
464
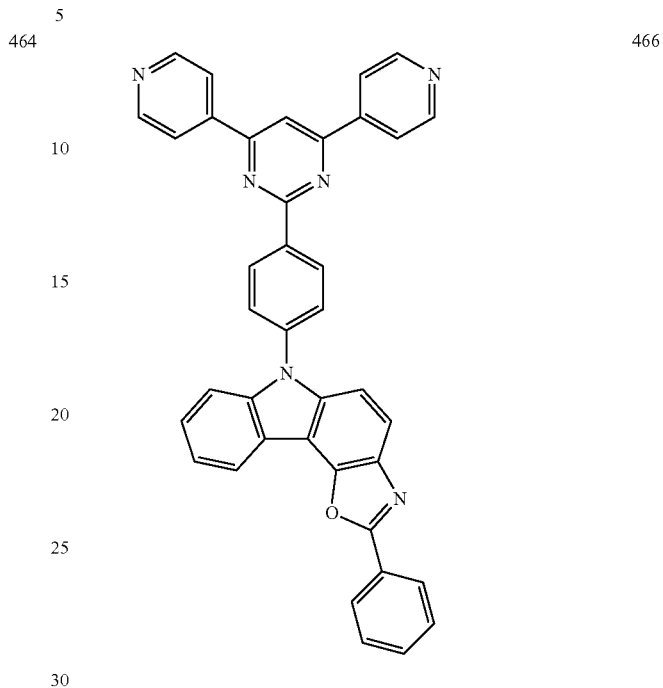
465
467
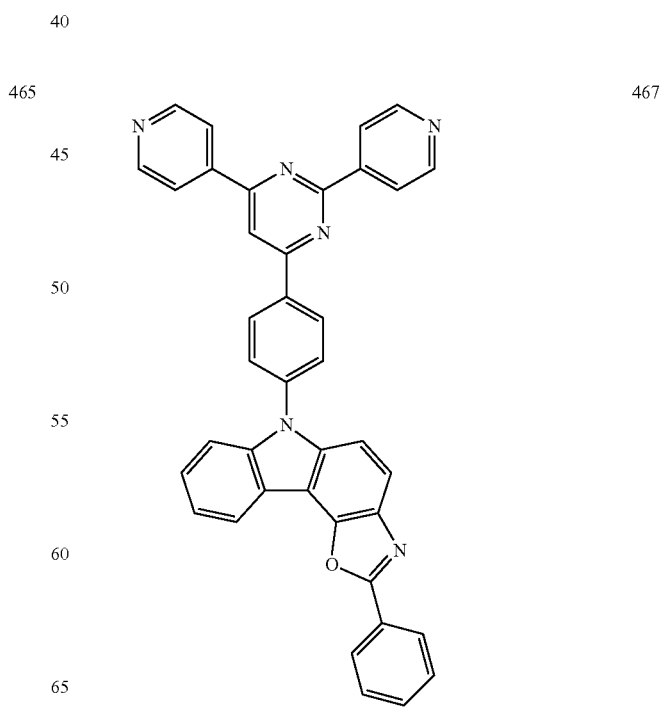

213
-continued
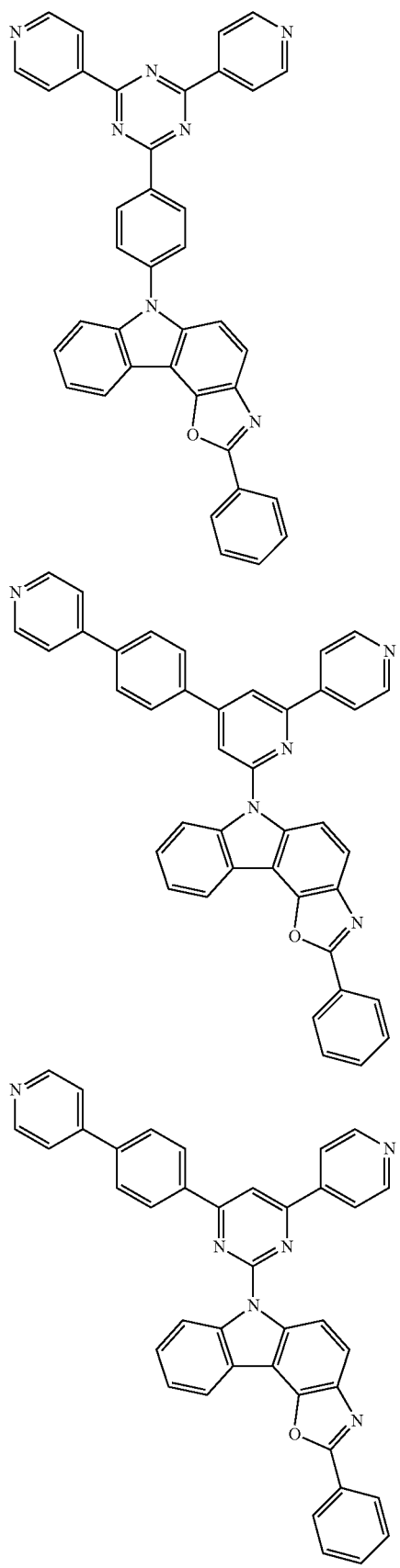
214
-continued
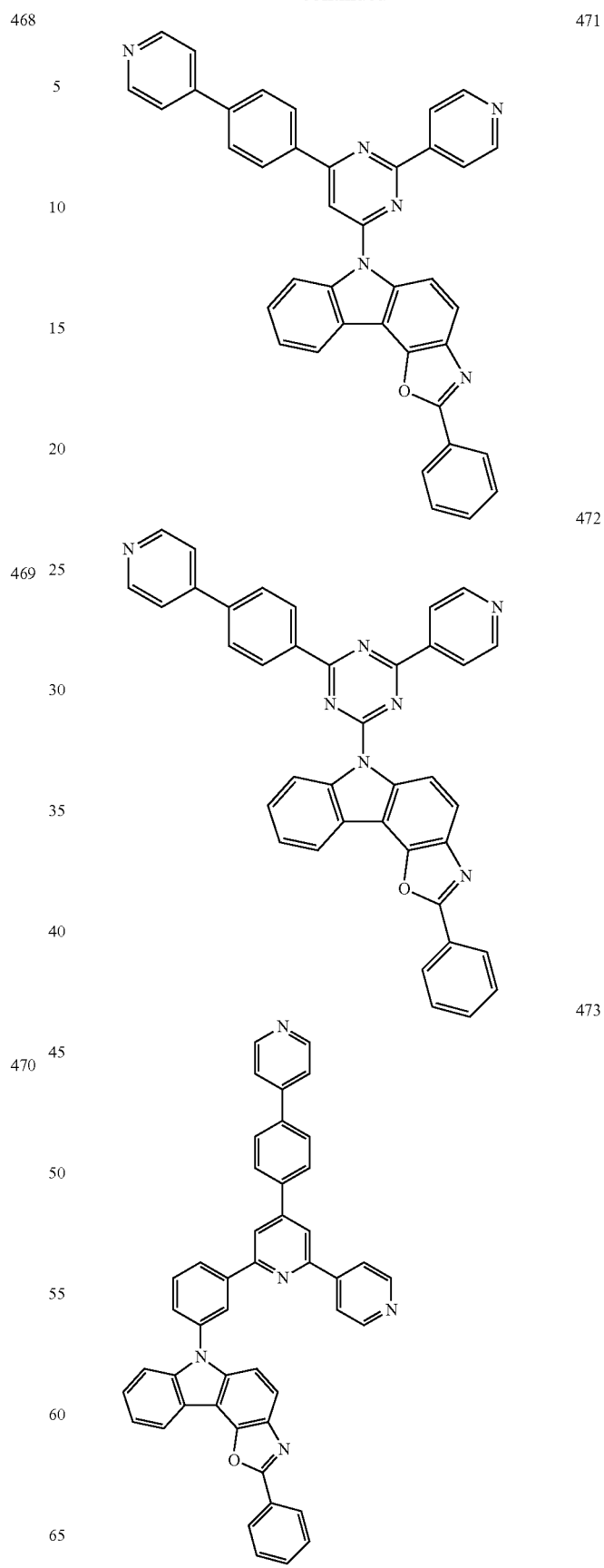

215
-continued
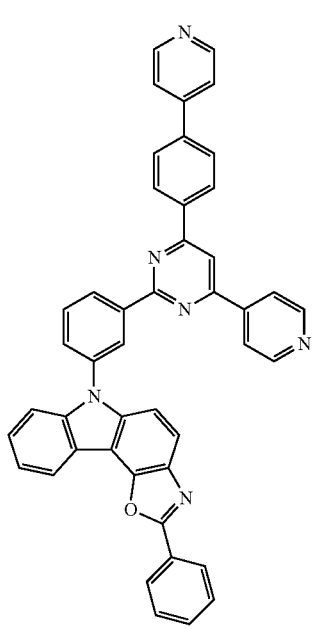
474
216
-continued
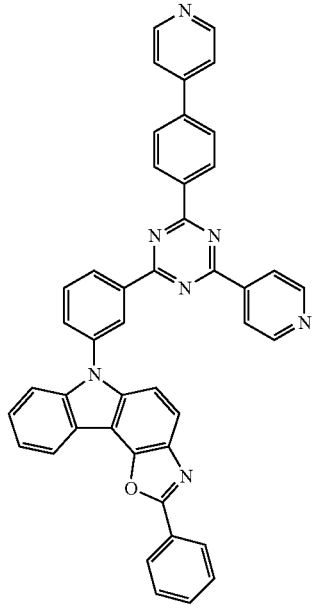
476
475
477
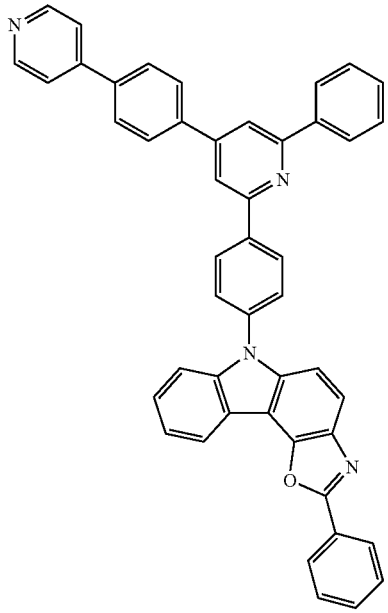

217
-continued
478
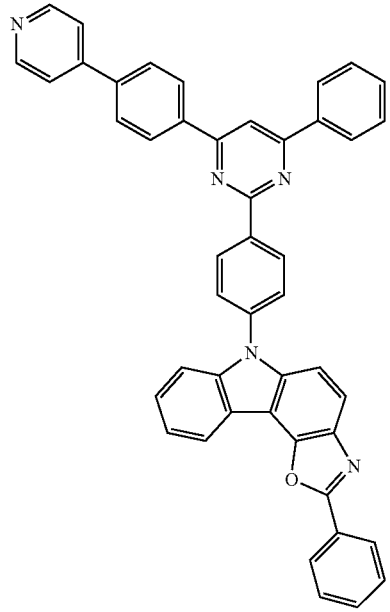
479
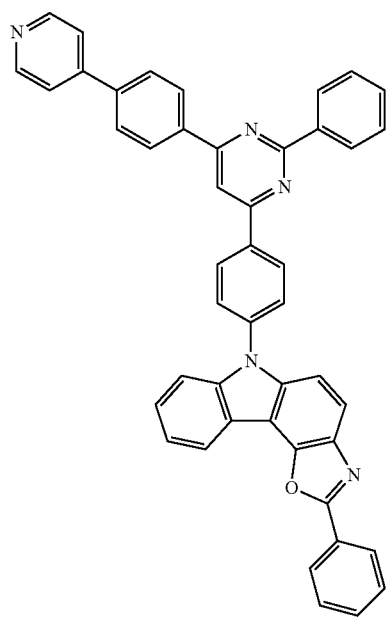
218
-continued
480
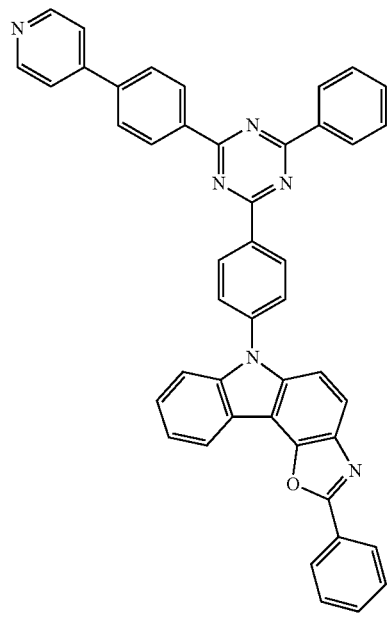
481
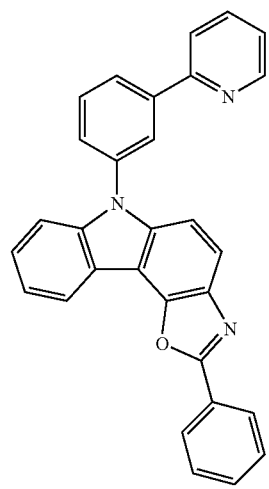
482
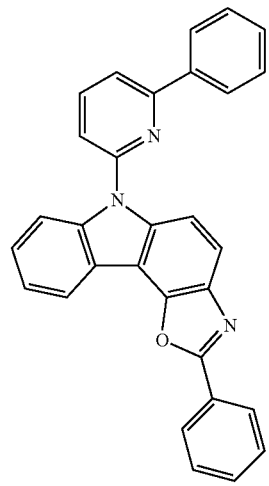

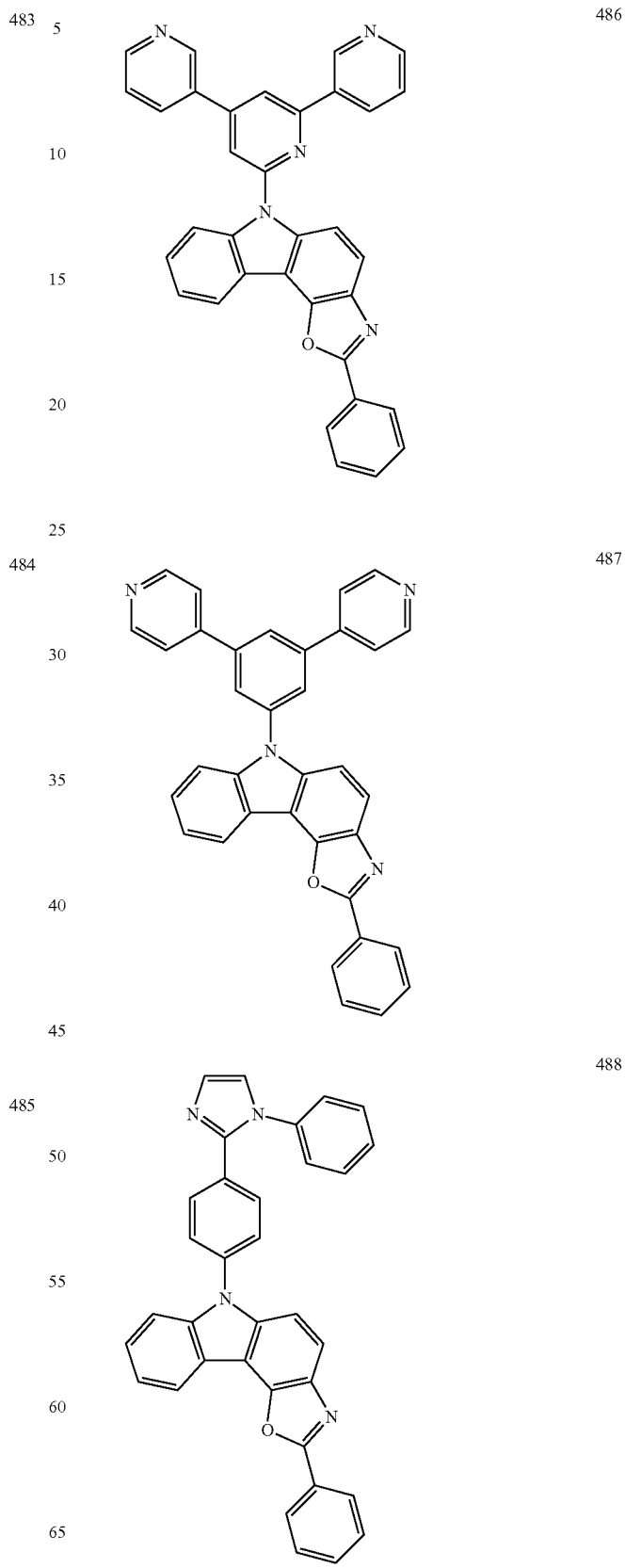

221
-continued
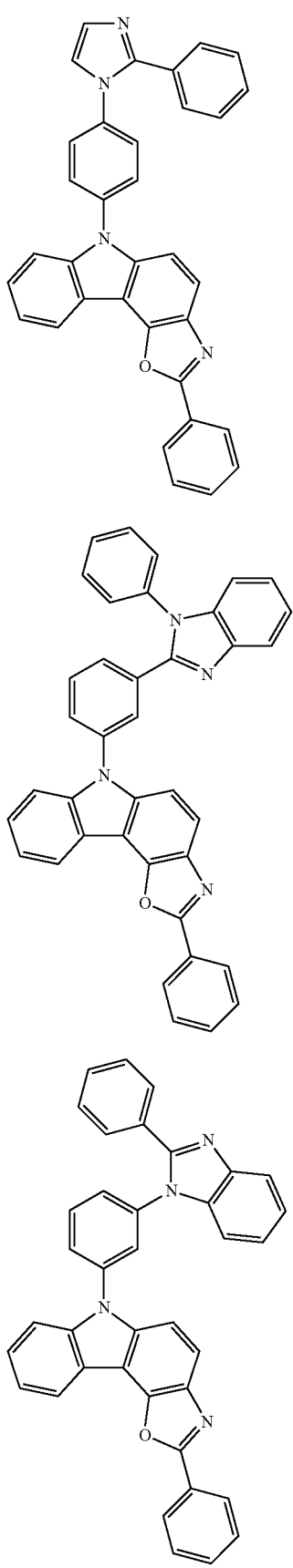
222
-continued
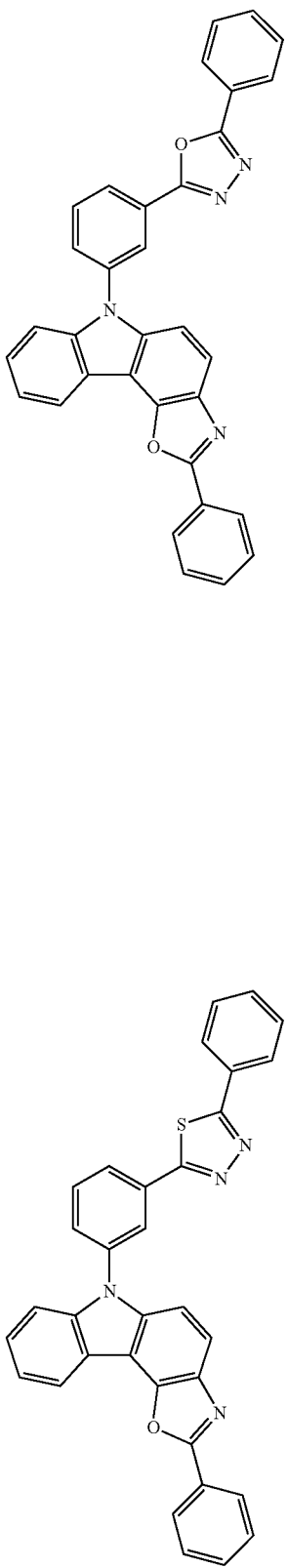

223
-continued
224
-continued
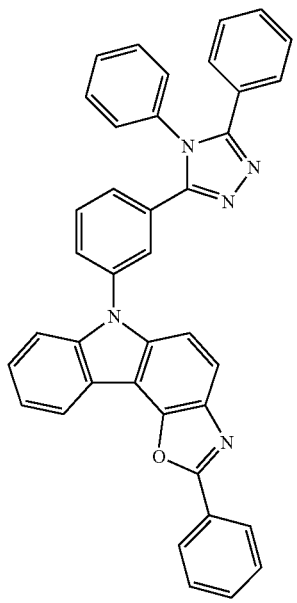
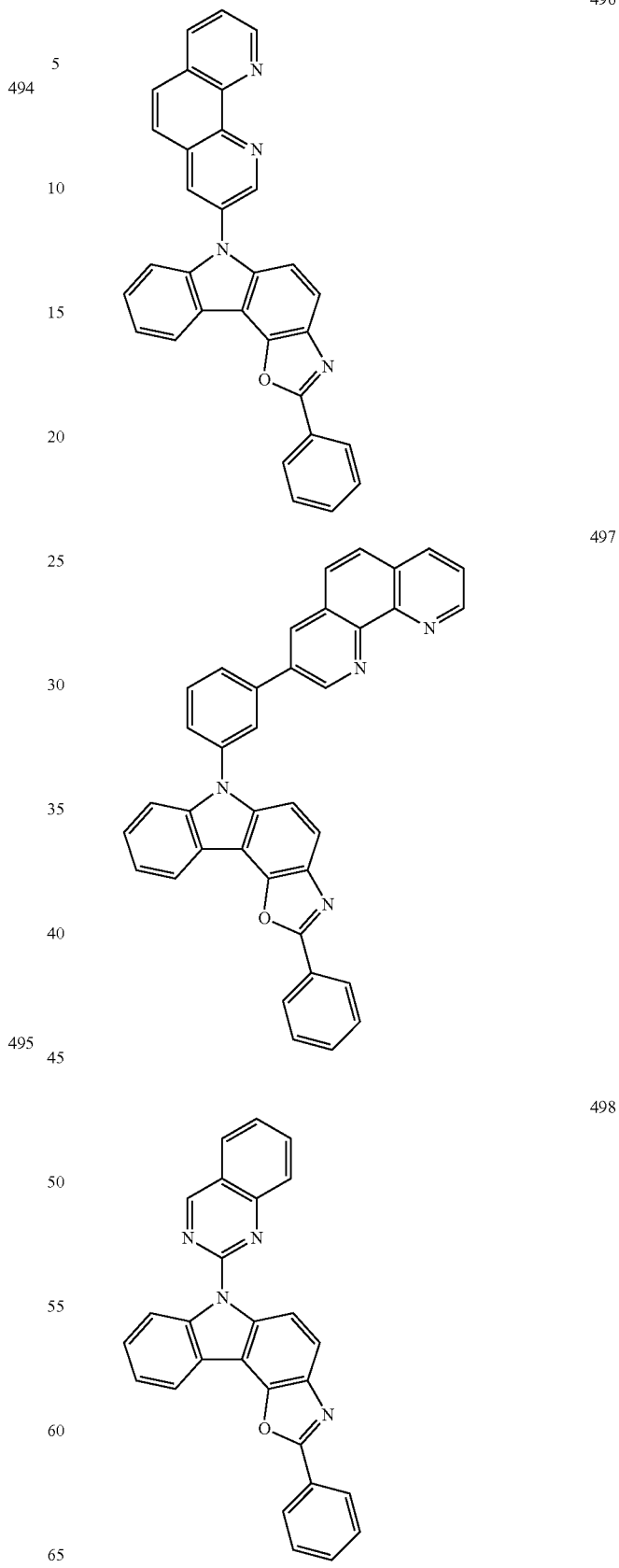

225
-continued
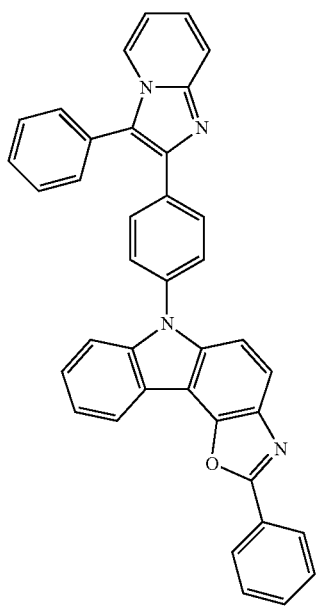
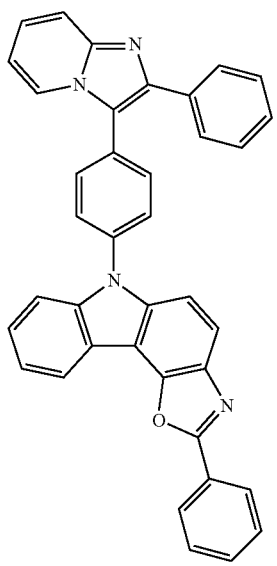
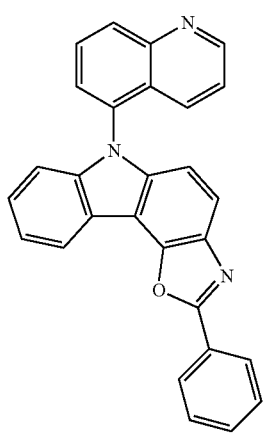
226
-continued
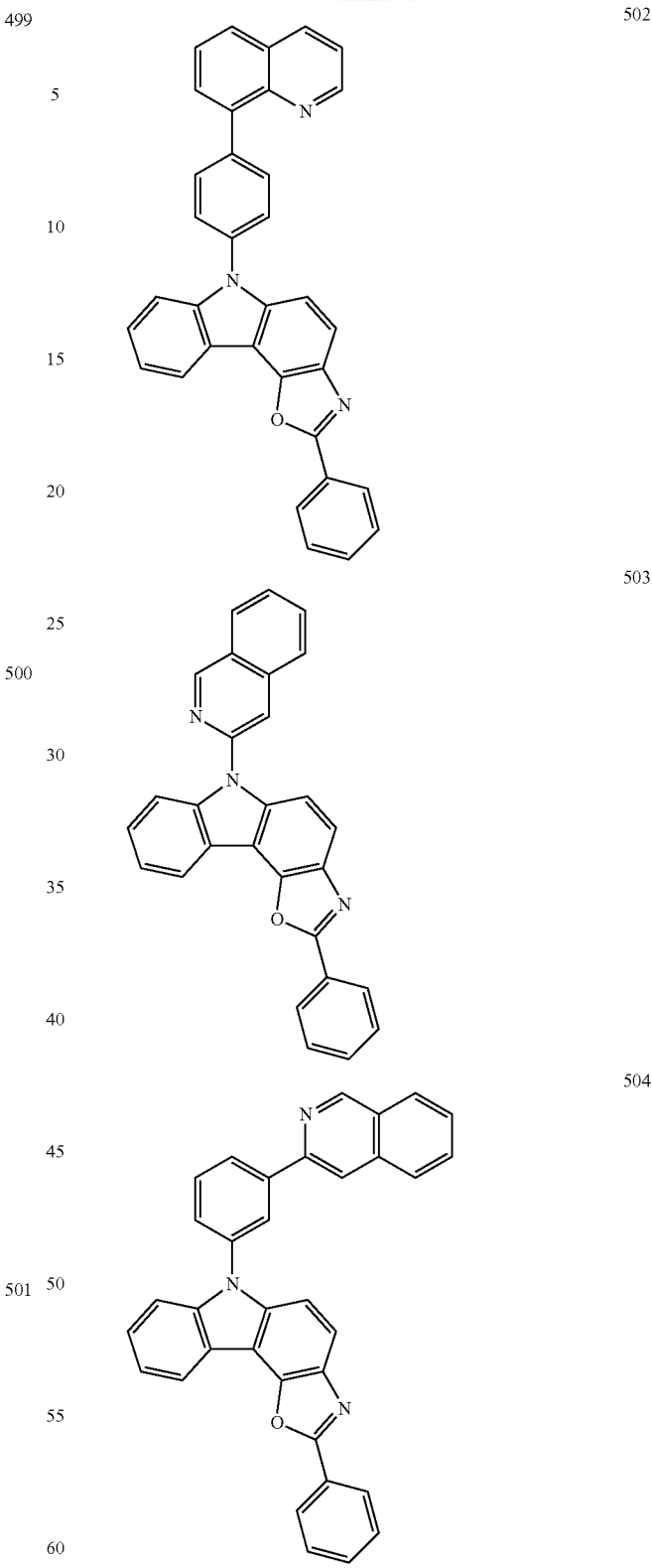
The condensed cyclic compound of Formula 1 above may have a core in which a 5-membered ring is fused to a carbazole-based ring (refer to Formula 1' below). Furthermore, the condensed cyclic compound of Formula 1 above has to include at least one of $E_1$, $E_{11}$ to $E_{13}$, and $E_{21}$ to $E_{26}$ that are substituted or unsubstituted nitrogen-containing electron transporting moieties. Accordingly, the condensed cyclic compound of Formula 1 above may have good bipolar characteristics, and highest occupied molecular orbital (HOMO) and lowest unoccupied molecular orbital (LUMO) energy levels may be effectively controlled. Accordingly, an organic light-emitting device including condensed cyclic compound of Formula 1 above may have improved efficiency.

Formula 1'

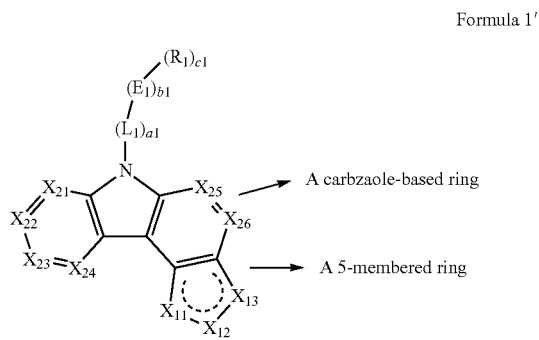

A carbzaole-based ring

A 5-membered ring

In an experimental example, HOMO, LUMO, and $T_1$ energy levels of Compounds A and B were simulated using Gaussian functions. The results are shown in Table 1 below:

TABLE 1

| Compound | HOMO | LUMO | $T_1$ |
|---|---|---|---|
| Compound A | −5.221 | −1.774 | 2.124 |
| Compound B | −4.834 | −0.642 | 2.904 |

Compound A

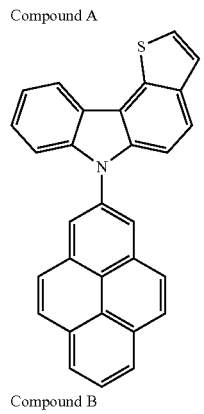

Compound B

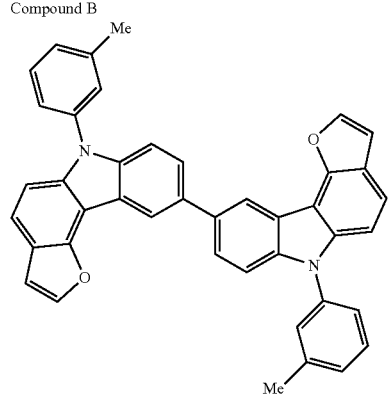

Referring to Table 1, Compound B had a high LUMO energy level of about −0.642 electron volts (eV), due to lack of an electron transporting moiety. This may inhibit injection of electrons. In other words, when the EML may use only Compound B as a host, a balance between holes and electrons may be not reached in the EML, so the emission efficiency of the organic light-emitting device may be reduced.

Referring to Table 1 above, Compound A was found to have a very low $T_1$ energy level of about 2.124 eV, and is not suitable for use as a material for organic light-emitting devices, for example, a green host or red host.

However, unlike Compounds A and B, the condensed cyclic compound of Formula 1 above includes a core in which a 5-membered ring is fused to a carbazole ring and at least one of $E_1$, $E_{11}$ to $E_{13}$, and $E_{21}$ to $E_{26}$ that are substituted or unsubstituted nitrogen-containing electron transporting moieties, as described above.

Thus the condensed cyclic compound of Formula 1 above may have a LUMO energy level and a T1 energy level that are both suitable for use as a material for organic light-emitting devices. This is apparent from Table 3 below.

A synthesis method of the condensed cyclic compound of Formula 1 above may be easily understood by one of ordinary skill in the art based on the synthesis examples described below.

As described above, the condensed cyclic compound of Formula 1 above may be appropriate for use as a material for the organic layer, for example, a host of the EML.

According to another embodiment of the present disclosure, an organic light-emitting device includes:
a first electrode,
a second electrode, and
an organic layer disposed between the first electrode and the second electrode, wherein the organic layer includes an EML and at least one condensed cyclic compound of Formula 1 above.

Due to the inclusion of the organic layer including the condensed cyclic compound of Formula 1 described above, the organic light-emitting device may have a low driving voltage, a high efficiency, and a long lifetime.

The condensed cyclic compound of Formula 1 above may be used between a pair of electrodes of an organic light-emitting device. For example, the condensed cyclic compound of Formula 1 above may be included in at least one of the EML, a hole transport region between the first electrode and the EML (for example, the hole transport region may include at least one of a hole injection layer (HIL), a hole transport layer (HTL), and an electron blocking layer (EBL)), and an electron transport region between the EML and the second electrode (for example, the electron transport region may include at least one of a hole blocking layer (HBL), an electron transport layer (ETL), and an electron injection layer (EIL)). For example, the condensed cyclic compound of Formula 1 above may be included in the EML, wherein the EML may further include a dopant, and the condensed cyclic compound of Formula 1 in the EML may serve as a host. For example, the EML may be a green EML, and the dopant may be a phosphorescent dopant.

As used herein, "(for example, the organic layer) including at least one condensed cyclic compound means that "(the organic layer) including one of the condensed cyclic compounds of Formula 1 above, or at least two different condensed cyclic compounds of Formula 1 above".

For example, the organic layer of the organic light-emitting device may include only Compound 1 as the condensed cyclic compound. For example, Compound 1 may be included in the EML of the organic light-emitting device. In some embodiments, the organic layer of the organic light-emitting device may include Compounds 1 and 2 as the condensed cyclic compound. For example, Compounds 1 and 2 may be included in the same layer (for example, in the EML) or in different layers.

The first electrode may be an anode as a hole injection electrode, and the second electrode may be a cathode as an electron injection electrode. In some embodiments, the first electrode may be a cathode as an electron injection electrode, and the second electrode may be a cathode as a hole injection electrode.

For example, the first electrode may be an anode, the second electrode may be a cathode, and the organic layer may include:

i) a hole transport region disposed between the first electrode and the emission layer, wherein the hole transport region includes at least one of a hole injection layer, a hole transport layer, and an electron blocking layer; and ii) an electron transport region disposed between the emission layer and the second electrode, wherein the electron transport region includes at least one of a hole blocking layer, an electron transport layer, and an electron injection layer.

The term "organic layer" as used herein refers to a single layer and/or a plurality of layers disposed between the first and second electrodes of the organic light-emitting device. The "organic layer" may include, for example, an organic compound or an organometallic complex including a metal.

The FIGURE a schematic view of an organic light-emitting device 10 according to an embodiment of the present disclosure. Hereinafter, a structure of an organic light-emitting device according to an embodiment of the present disclosure and a method of manufacturing the same will now be described with reference to the FIGURE. Referring to the FIGURE, the organic light-emitting device 10 has a structure in which a first electrode 11, an organic layer 15, and a second electrode 19 are sequentially stacked in this order.

A substrate (not shown) may be disposed under the first electrode 11 or on the second electrode 190 in the FIGURE. The substrate may be any substrate that is used in conventional organic light emitting devices. In some embodiments, the substrate may be a glass substrate or a transparent plastic substrate with strong mechanical strength, thermal stability, transparency, surface smoothness, ease of handling, and water resistance.

The first electrode 11 may be formed by depositing or sputtering a first electrode-forming material on the substrate. The first electrode 11 may be an anode. A material having a high work function may be selected as a material for the first electrode to facilitate hole injection. The first electrode 11 may be a reflective electrode, a semi-transmissive electrode, or a transmissive electrode. For example, the material for the first electrode 11 may be indium tin oxide (ITO), indium zinc oxide (IZO), tin oxide ($SnO_2$), or zinc oxide (ZnO). In some embodiments, the material for the first electrode 11 may be metals, for example, magnesium (Mg), aluminum (Al), aluminum-lithium (Al—Li), calcium (Ca), magnesium-indium (Mg—In), magnesium-silver (Mg—Ag), or the like.

The first electrode 11 may have a single-layer structure or a multi-layer structure including at least two layers. For example, the first electrode 11 may have, but not limited to, a three-layered structure including ITO, Ag, and ITO layers.

The organic layer 15 may be disposed on the first electrode 11.

The organic layer 15 may include at least one a hole transport region; an EML, and an electron transport region.

The hole transport region may be disposed between the first electrode 11 and the EML.

The hole transport region may include at least one of a hole injection layer (HIL), a hole transport layer (HTL), an electron blocking layer (EBL), and a buffer layer.

The hole transport region may include exclusively the HIL or the HTL. In some embodiments, the hole transport region may have a structure including a HIL/HTL or a HIL/HTL/EBL, wherein the layers forming the structure of the hole transport region may be sequentially stacked on the first electrode 11 in the stated order.

When the hole transport region includes the HIL, the HIL may be formed on the first electrode 11 by any of a variety of methods, for example, vacuum deposition, spin coating, casting, Langmuir-Blodgett (LB) deposition, or the like.

When the HIL is formed using vacuum deposition, vacuum deposition conditions may vary depending on the material that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Angstroms per second (Å/sec). However, the deposition conditions are not limited thereto.

When the HIL is formed using spin coating, the coating conditions may vary depending on the material that is used to form the HIL, and the desired structure and thermal properties of the HIL to be formed. For example, the coating rate may be in the range of about 2,000 revolutions per minute (rpm) to about 5,000 rpm, and a temperature at which heat treatment is performed to remove a solvent after coating may be in a range of about 80° C. to about 200° C. However, the coating conditions are not limited thereto.

Conditions for forming the HTL and the EBL may be the same as those for the HIL described above.

In some embodiments, the hole transport region may include at least one of m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly (4-styrenesulfonate)(PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below.

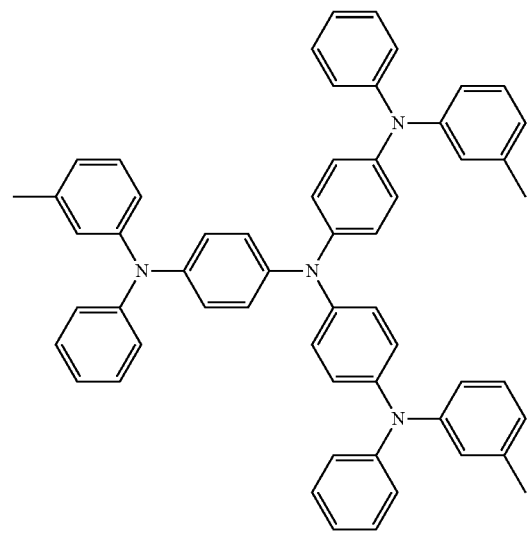

m-MTDATA

-continued
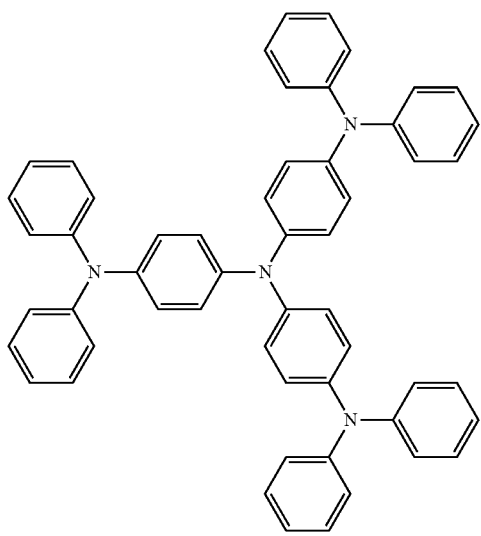
TDATA
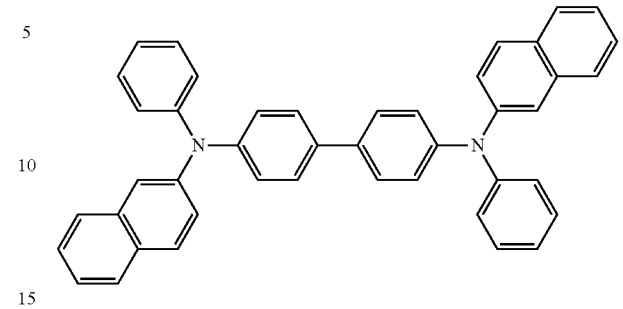
β-NPB
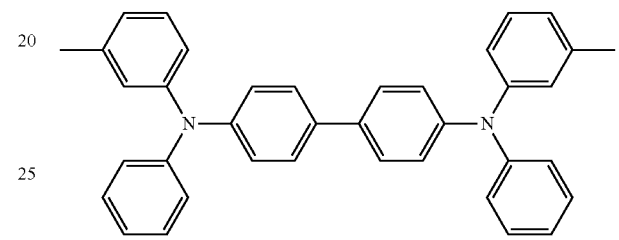
TPD
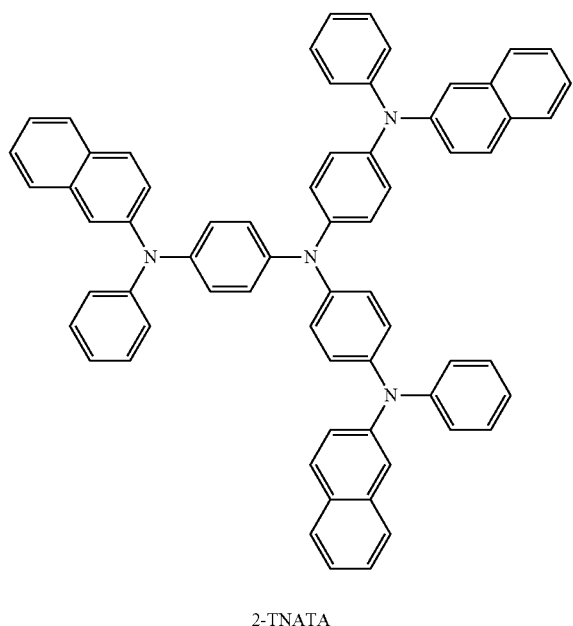
2-TNATA
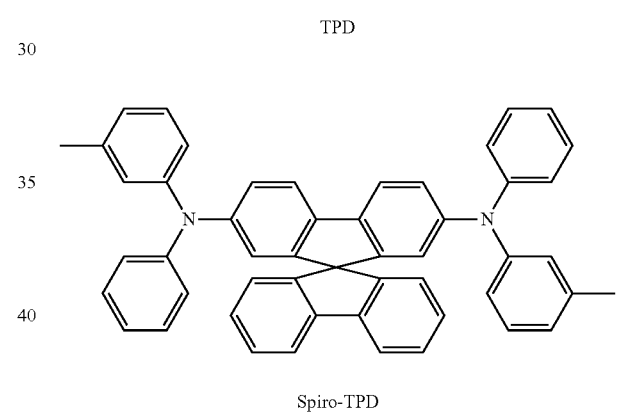
Spiro-TPD
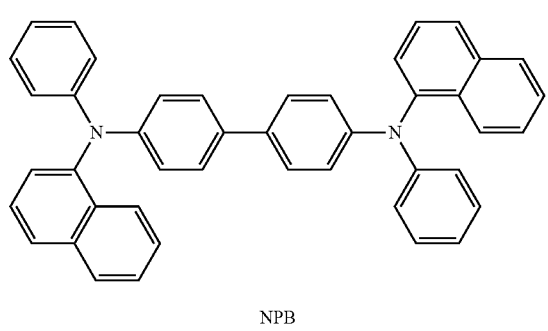
NPB
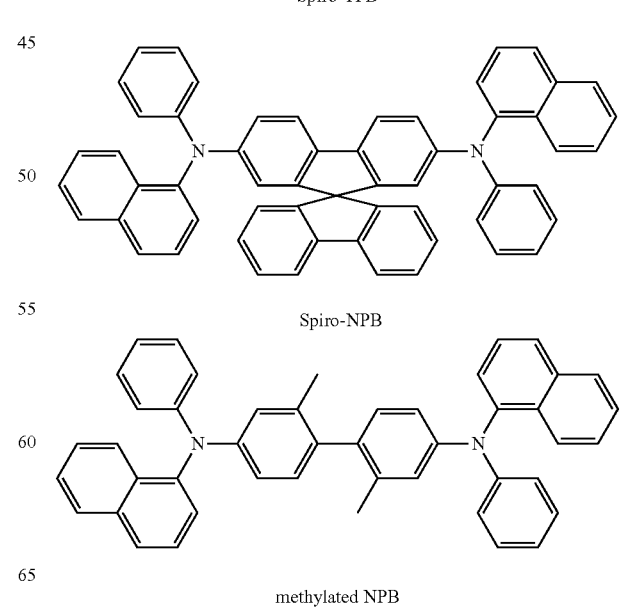
Spiro-NPB
methylated NPB

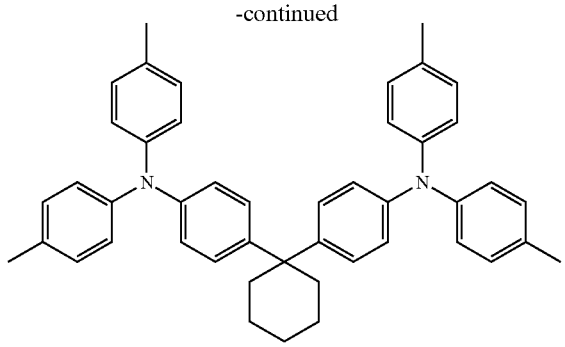

TAPC

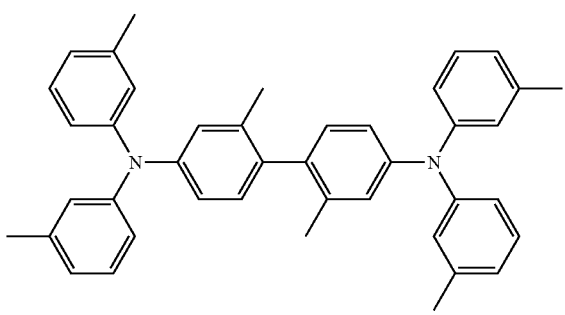

HMTPD

Formula 201

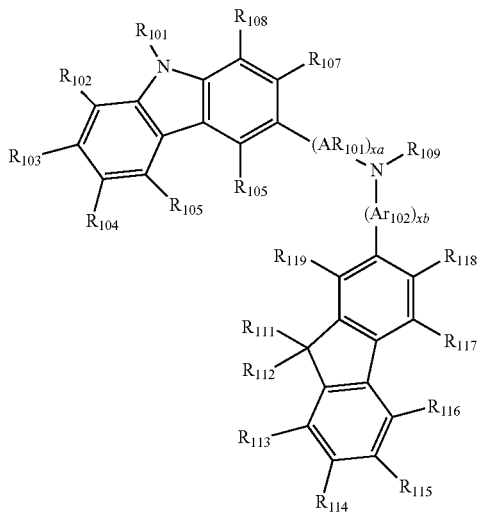

Formula 202

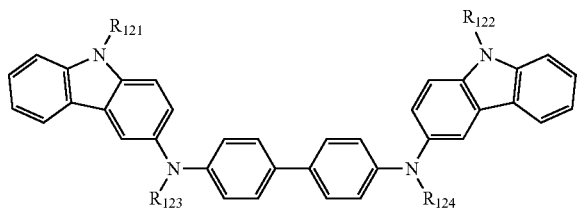

In Formula 201 above, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer from 0 to 5, for example, may be 0, 1, or 2. For example, xa may be 1, and xb may be 0, but are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, or the like), and a $C_1$-$C_{10}$ alkoxy group (for example, a methoxy group, an ethoxy group, a propoxy group, a butoxy group, a pentoxy group, or the like), a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthracenyl group, a fluorenyl group, and a pyrenyl group, and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group. However, embodiments of the present disclosure are not limited thereto.

In Formula 201 above, $R_{109}$ may be selected from a phenyl group, a naphthyl group, an anthracenyl group, and a pyridinyl group, and a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In some embodiments, the compound of Formula 201 may be a compound represented by Formula 201A, but is not limited thereto:

Formula 201A

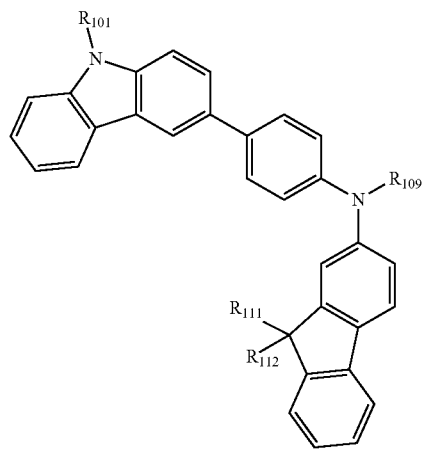

In Formula 201A, $R_{101}$, $R_{111}$, $R_{112}$, and $R_{109}$ may be the same as those defined above.

For example, the compound of Formula 201 and the compound of Formula 202 may be Compounds HT1 to HT20 below, but are not limited thereto:

HT1

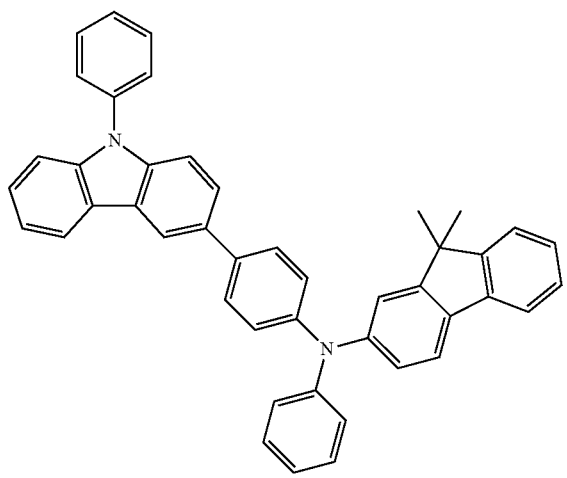

HT2

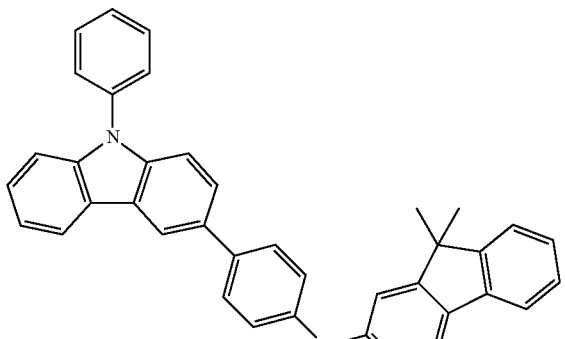

HT3

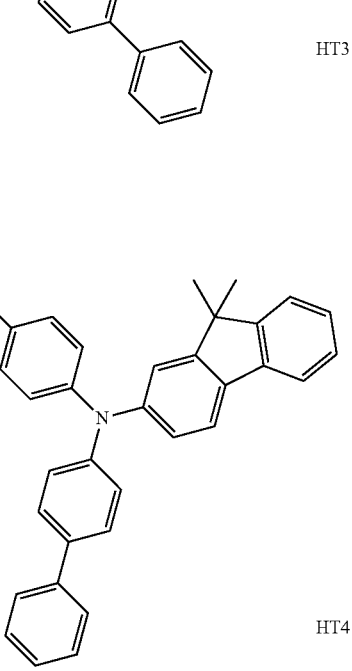

HT4

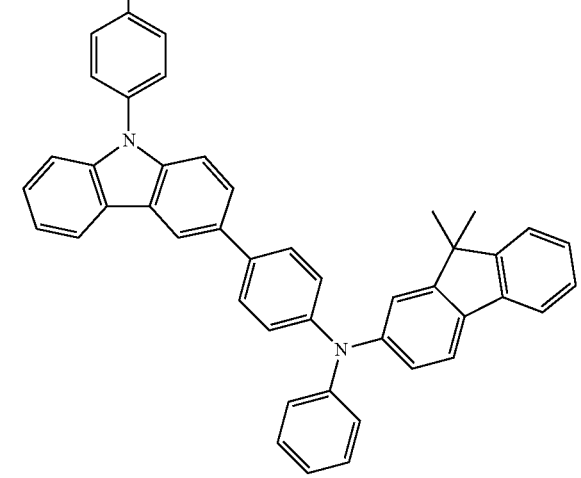

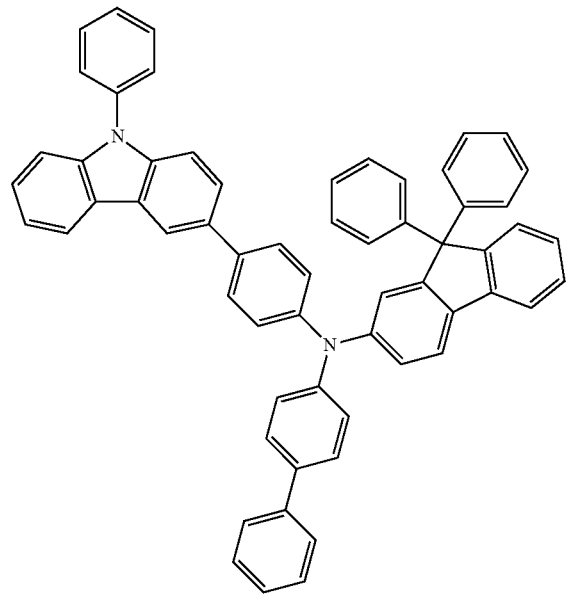
HT5
HT6
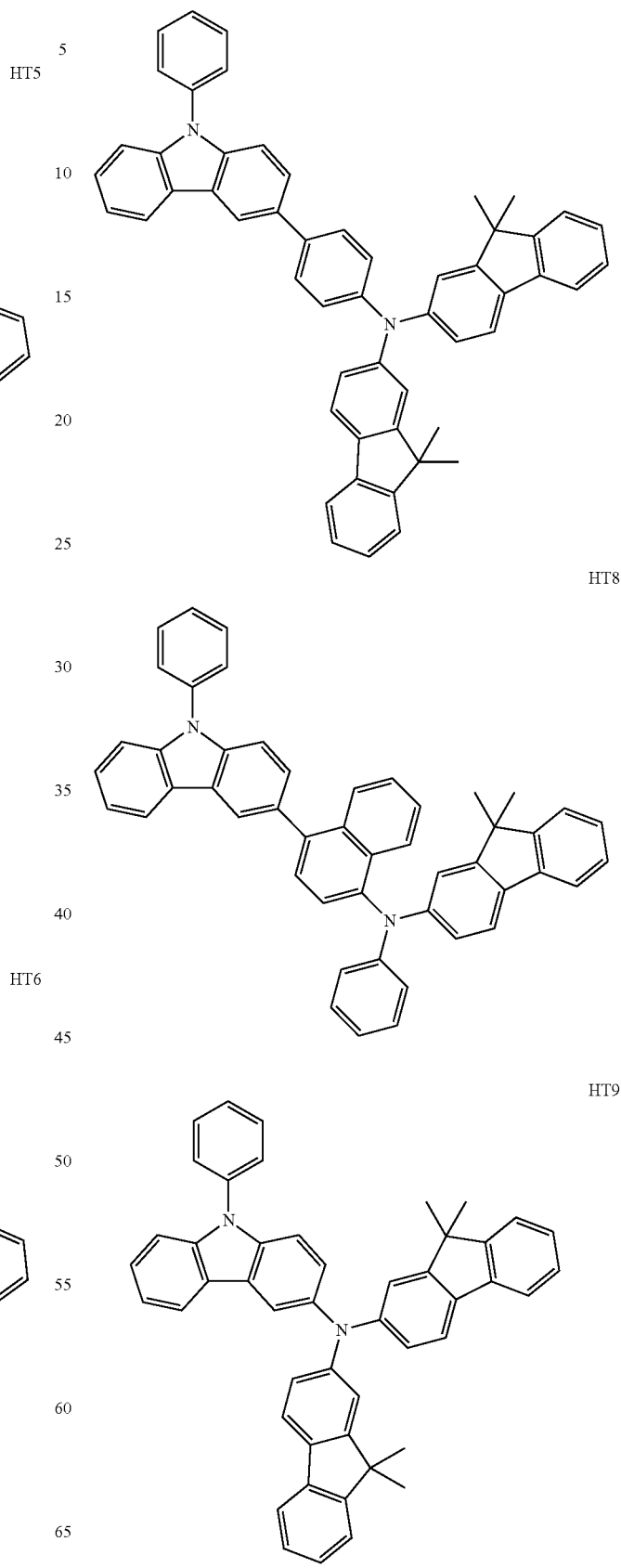
HT7
HT8
HT9

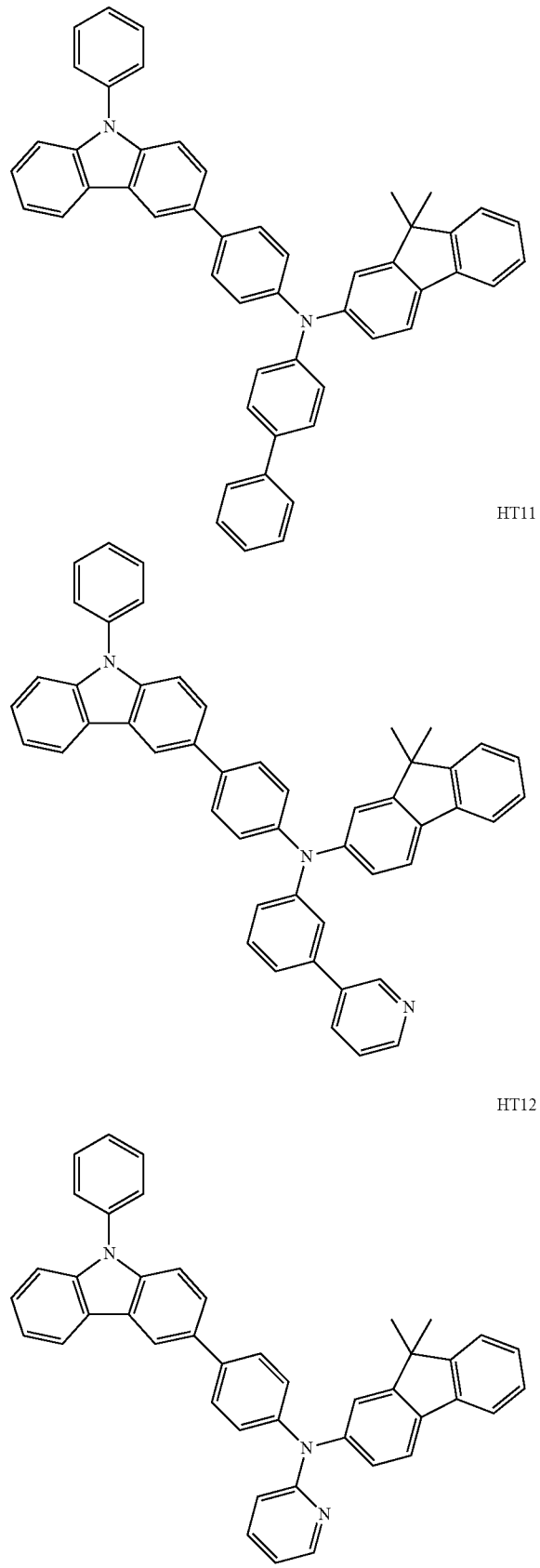
HT10
HT11
HT12
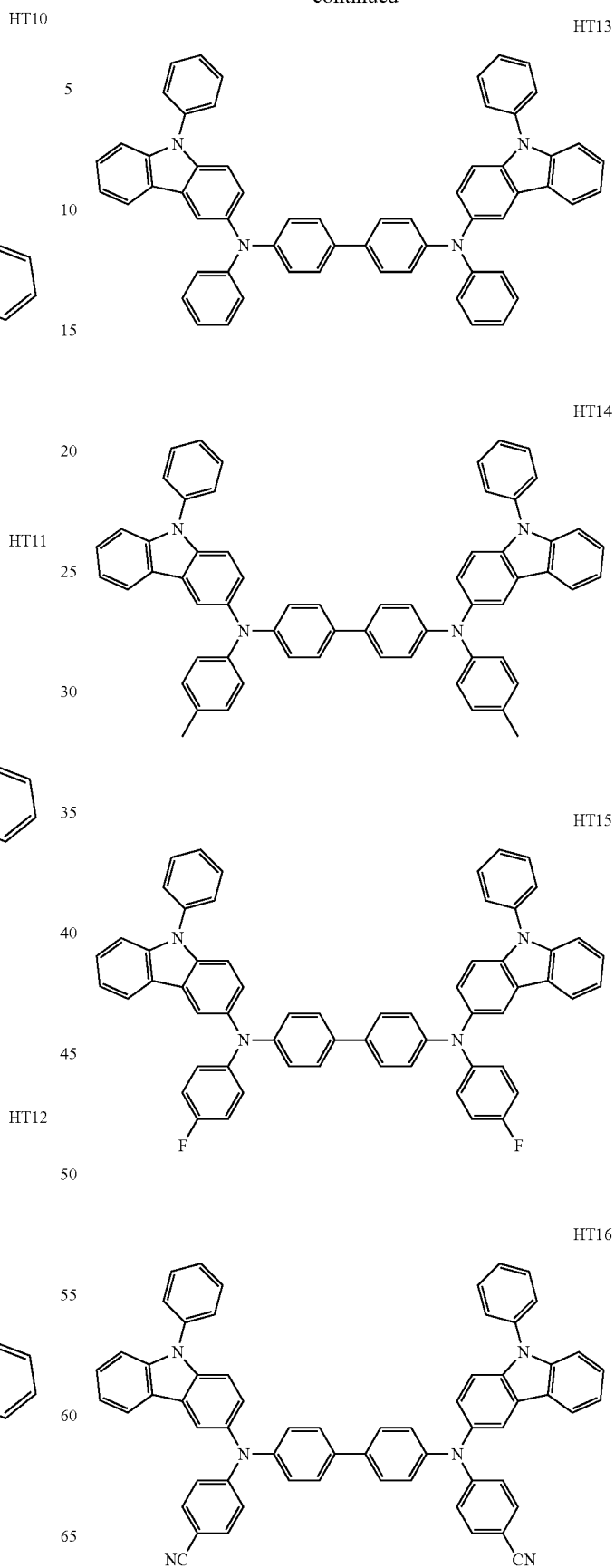
HT13
HT14
HT15
HT16

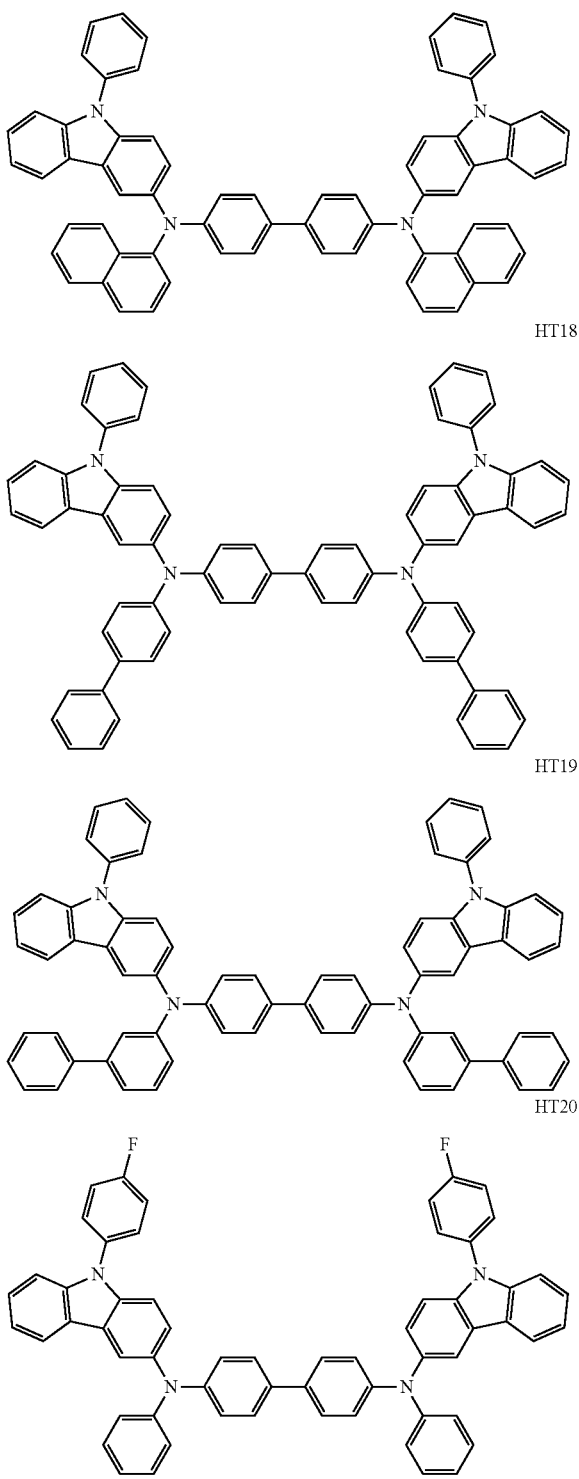

A thickness of the hole transport region may be from about 100 Angstroms (Å) to about 10,000 Å, and in some embodiments, from about 100 Å to about 1,000 Å. When the hole transport region includes a HIL and a HTL, a thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinone derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

The hole transport region may further include a buffer layer.

The buffer layer may compensate for an optical resonance distance of light according to a wavelength of the light emitted from the EML, and thus may increase efficiency.

The EML may be formed on the hole transport region by using vacuum deposition, spin coating, casting, LB deposition, or the like. When the EML is formed using vacuum deposition or spin coating, the conditions for deposition and coating may be similar to those for the formation of the HIL, though the conditions for the deposition and coating may vary depending on the material that is used to form the EML.

When the organic light-emitting device is a full color organic light-emitting device, the emission layer may be patterned into a red emission layer, a green emission layer, and a blue emission layer. In some embodiments, the EML may have a stack structure including a red emission layer, a green emission layer, and/or a blue emission layer that are stacked upon one another to emit white light, but is not limited thereto.

The EML may include at least one condensed cyclic compound of Formula 1 above. The EML may further include a dopant. The dopant may include at least one of a phosphorescent dopant and a fluorescent dopant.

The EML may include a host and a dopant. The host may include at least one condensed cyclic compound of Formula 1 above.

In some embodiments, the EML may include a first host, a second host, and a dopant. The first host and the second host may be different from each other. For example, the first host may include a condensed cyclic compound of Formula 1 above, and the second host may include at least one of a first compound represented by Formula 41 below, a second compound represented by Formula 61 below, and a third compound represented by Formula 31 below.

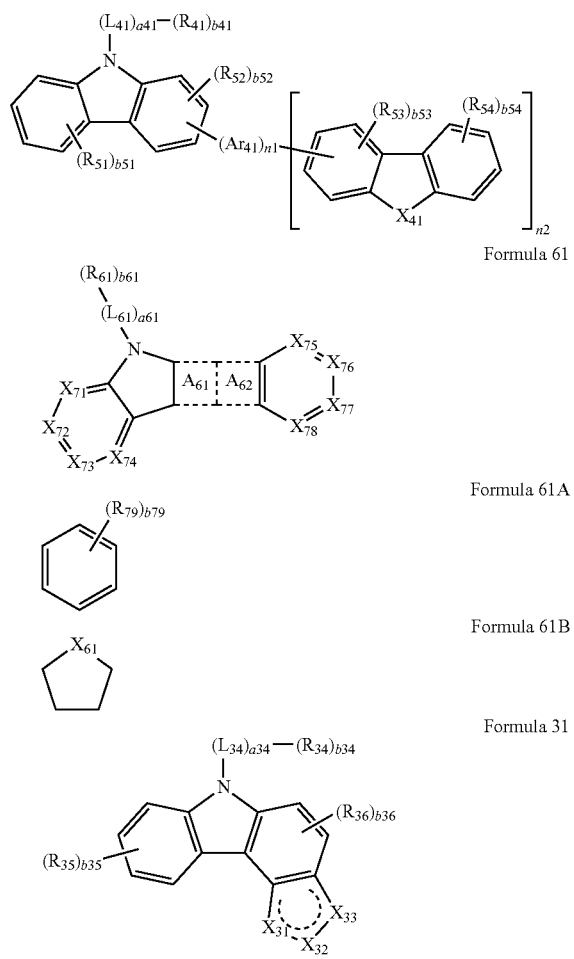

Formula 41

Formula 61

Formula 61A

Formula 61B

Formula 31

In Formulae 41, 61, 61A, 61B, and 31 above, $X_{41}$ may be N-$[(L_{42})_{a42}$-$(R_{42})_{b42}]$, S, O, S(=O), S(=O)$_2$, C(=O), C($R_{43}$)($R_{44}$), Si($R_{43}$)($R_{44}$), P($R_{43}$), P(=O)($R_{43}$), or C=N($R_{43}$);

ring $A_{61}$ in Formula 61 may be represented by Formula 61A;

ring $A_{62}$ in Formula 61 may be represented by Formula 61B;

$X_{61}$ may be N-$[(L_{62})_{a62}$-$(R_{62})_{b62}]$, S, O, S(=O), S(=O)$_2$, C(=O), C($R_{63}$)($R_{64}$), Si($R_{63}$)($R_{64}$), P($R_{63}$), P(=O)($R_{63}$), or C=N($R_{63}$);

$X_{71}$ may be C($R_{71}$) or N;
$X_{72}$ may be C($R_{72}$) or N;
$X_{73}$ may be C($R_{73}$) or N;
$X_{74}$ may be C($R_{74}$) or N;
$X_{75}$ may be C($R_{75}$) or N;
$X_{76}$ may be C($R_{76}$) or N;
$X_{77}$ may be C($R_{77}$) or N;
$X_{78}$ may be C($R_{78}$) or N;
$X_{31}$ may be S, O, N, C-$[(L_{31})_{a31}$-$(R_{31})_{b31}]$, or Si-$[(L_{31})_{a31}$-$(R_{31})_{b31}]$;
$X_{32}$ may be S, O, N, C-$[(L_{32})_{a32}$-$(R_{32})_{c32}]$, or Si-$[(L_{32})_{a32}$-$(R_{32})_{b32}]$;
$X_{33}$ may be S, O, N, C-$[(L_{33})_{a33}$-$(R_{33})_{b33}]$, or Si-$[(L_{33})_{a33}$-$(R_{33})_{c33}]$;

$Ar_{41}$, $L_{41}$, $L_{42}$, $L_{61}$, and $L_{62}$ may be the same as $L_1$ described above;

$L_{31}$ to $L_{34}$ may be each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent nonaromatic condensed polycyclic group;

n1 and n2 may be each independently an integer selected from 0 to 3;

a41, a42, a61, a62, and a31 to a34 may be each independently an integer selected from 0 to 3;

$R_{41}$ to $R_{44}$, $R_{51}$ to $R_{54}$, $R_{61}$ to $R_{64}$, and $R_{71}$ to $R_{79}$ may be each independently selected from a hydrogen, a deuterium, a fluoro group (—F), a chloro group (—Cl), a bromo group (—Br), an iodo group (—I), a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent nonaromatic condensed polycyclic group, a substituted or unsubstituted monovalent nonaromatic condensed heteropolycyclic group, —N($Q_1$)($Q_2$), —Si($Q_3$)($Q_4$)($Q_5$), and —B($Q_6$)($Q_7$);

$R_{31}$ to $R_{36}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group, and a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group;

b41, b42, b51 to b54, b61, b62, b79, and b31 to b34 may be each independently an integer selected from 1 to 3;

b35 may be an integer selected from 1 to 3; and b36 may be 1 or 2,

In some embodiments, $R_{41}$ to $R_{44}$, $R_{51}$ to $R_{54}$, $R_{61}$ to $R_{64}$, and $R_{71}$ to $R_{79}$ in Formulae 41, 61, 61A, 61B, and 31 above may be each independently, but are not limited to, selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —Si($Q_{33}$)($Q_{34}$)($Q_{35}$), phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group, and —Si($Q_3$)($Q_4$)($Q_5$); and $Q_3$ to $Q_5$, and $Q_{33}$ to $Q_{35}$ may be each independently selected from a hydrogen, $C_1$-$C_{20}$ alkyl group, a $C_1$-$C_{20}$ alkoxy group, phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

For example, the first compound may be represented by one of Formulae 41-1 to 41-12 below, and the second compound may be represented by one of Formulae 61-1 to 61-6:

Formula 41-1

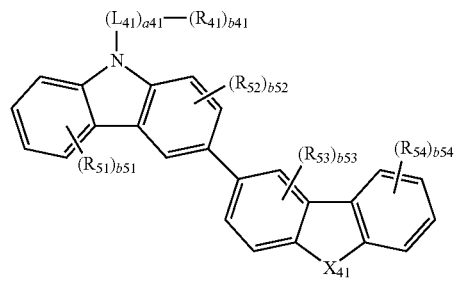

Formula 41-2

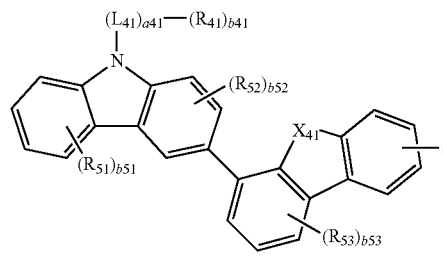

Formula 41-3

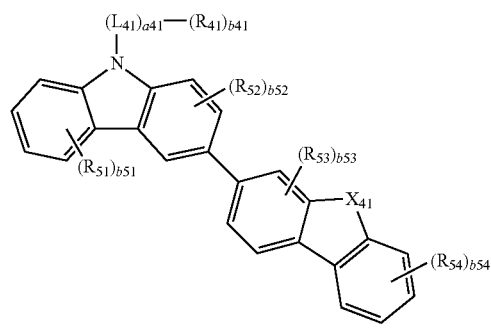

Formula 41-4

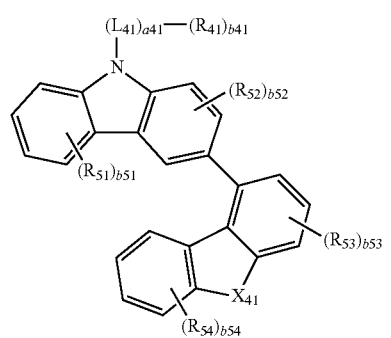

Formula 41-5

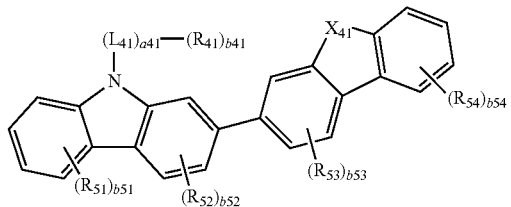

Formula 41-6

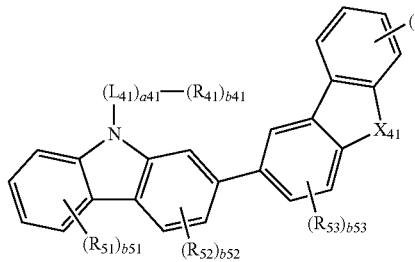

Formula 41-7

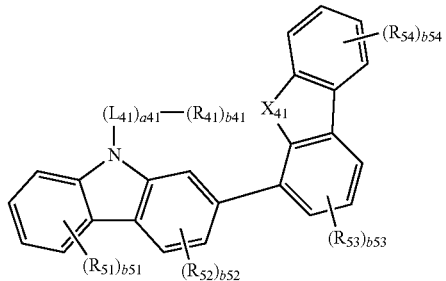

Formula 41-8

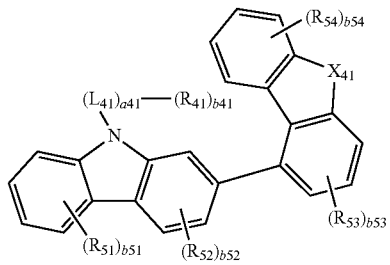

Formula 41-9

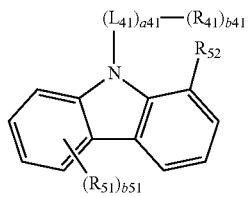

Formula 41-10

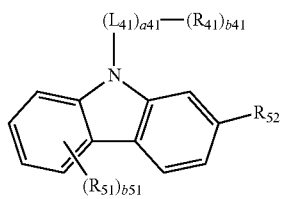

-continued

Formula 41-11
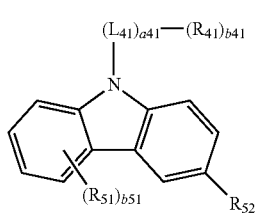

Formula 41-12
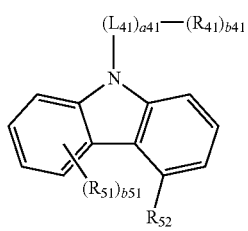

Formula 61-1
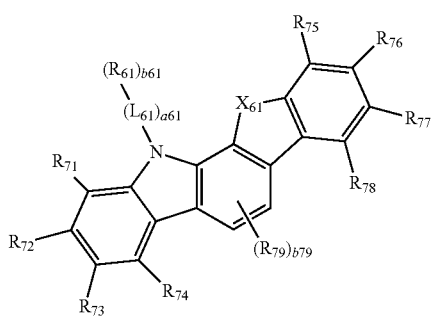

Formula 61-2
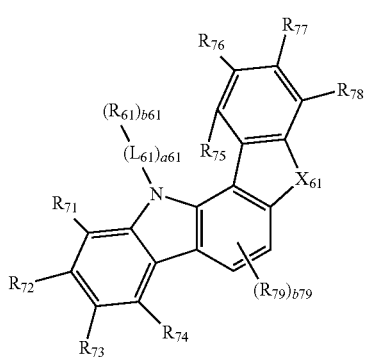

Formula 61-3
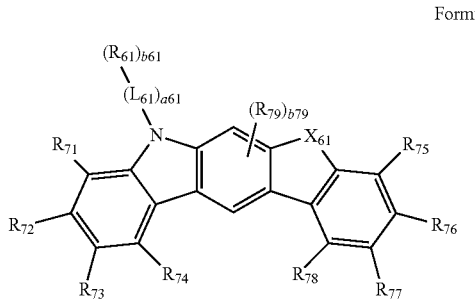

-continued

Formula 61-4
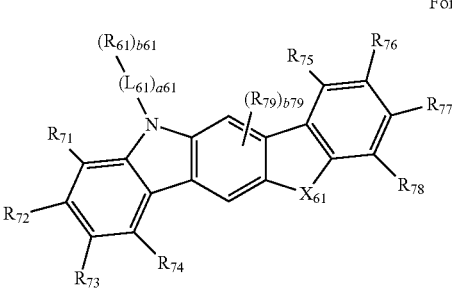

Formula 61-5
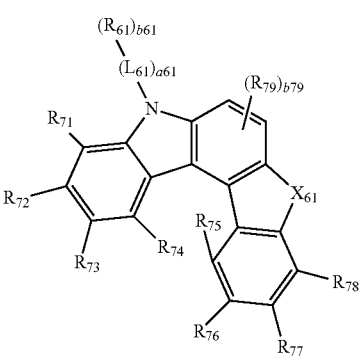

Formula 61-6
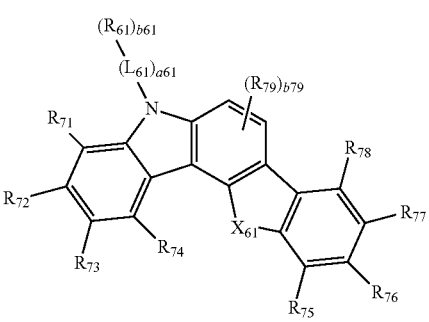

In Formulae 41-1 to 41-12, and Formulae 61-1 to 61-6, $X_{41}$, $X_{61}$, $L_{41}$, $L_{42}$, a41, a42, $L_{61}$, $L_{62}$, a61, a62, $R_{41}$ to $R_{44}$, b41, b42, $R_{61}$ to $R_{64}$, b61, b62, $R_{71}$ to $R_{79}$, and b79 may be the same as those defined above.

In Formula 31 above, $R_{35}$ and $R_{36}$ may be each independently, but is not limited to, selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, phenyl group, a naphthyl group, a phenanthrenyl group, and a triphenylenyl group.

In some embodiments, the first compound of Formula 41 above may include one of Compounds A1 to A83, the second compound of Formula 61 above may include one of Compounds B1 to B20, and the third compound of Formula 31 above may include one of Compounds 601 to 656 below. However, embodiments of the present disclosure are not limited thereto.

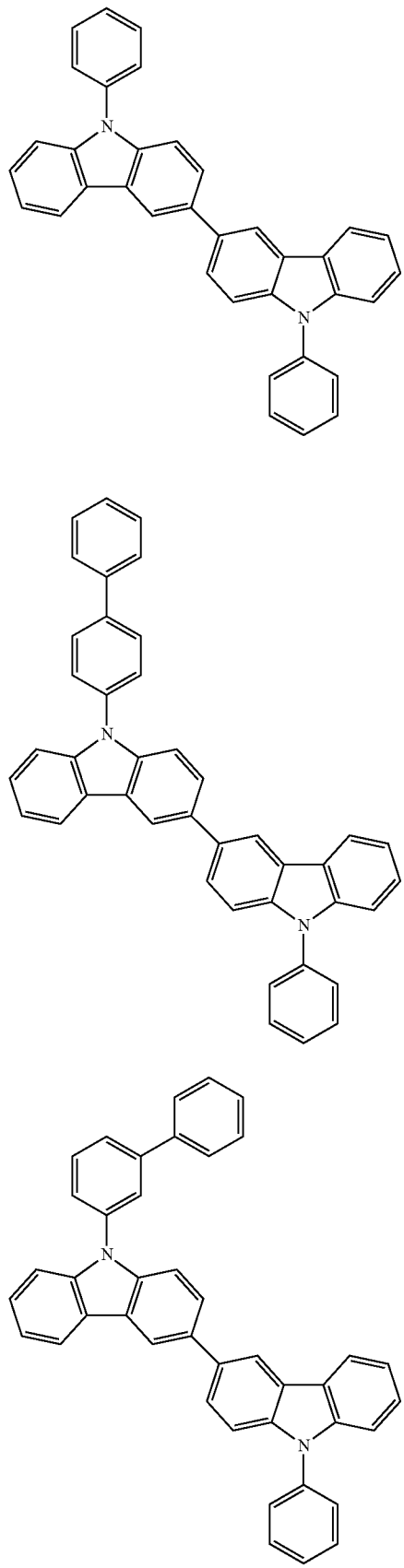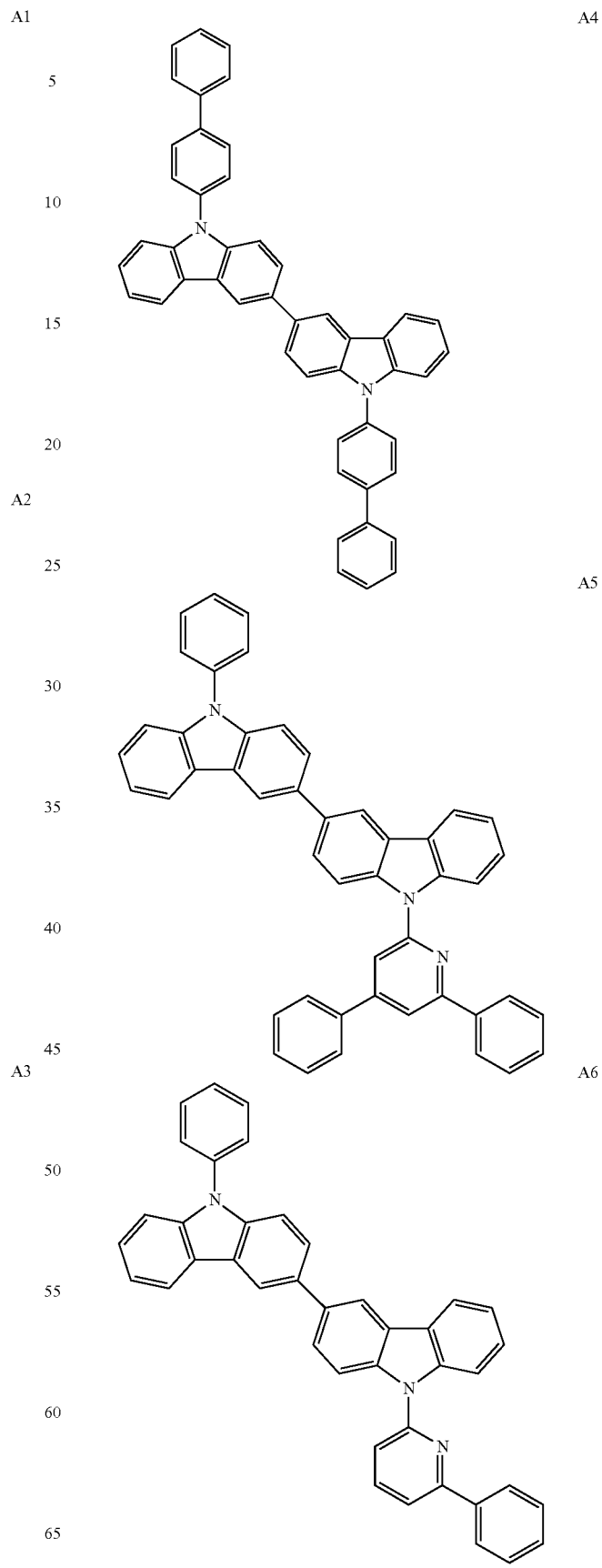

253
-continued
A7
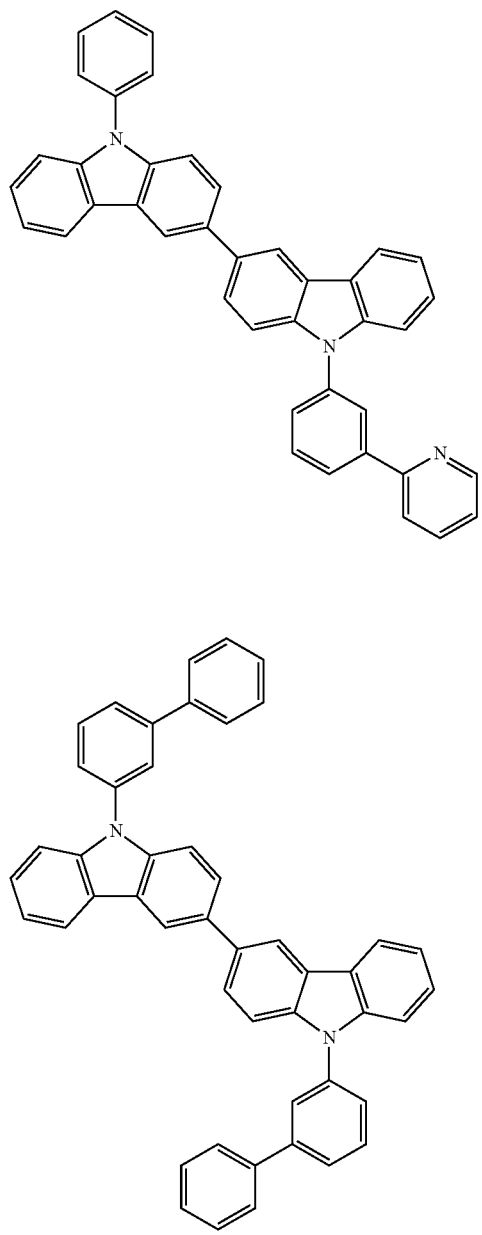
A8
A9
254
-continued
A10
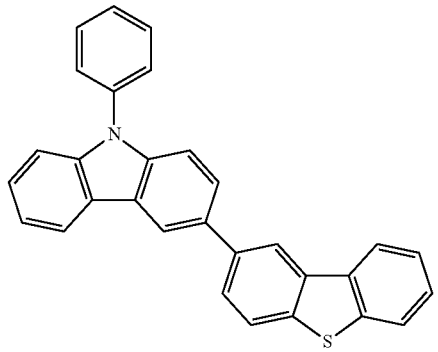
A11
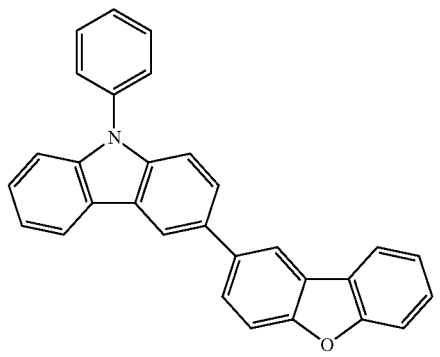
A12
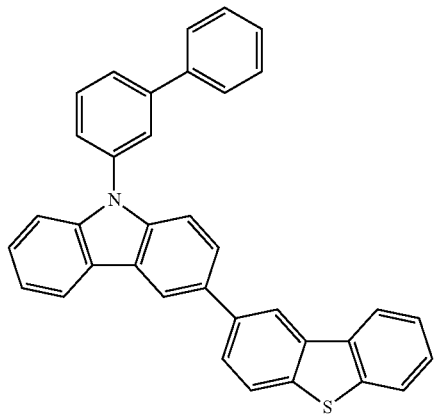
A13
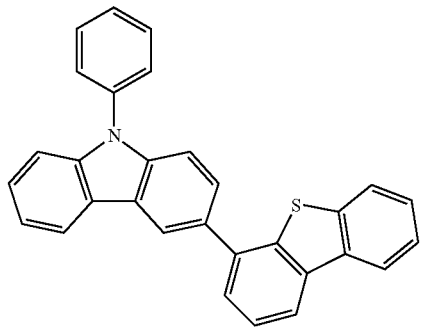

A14
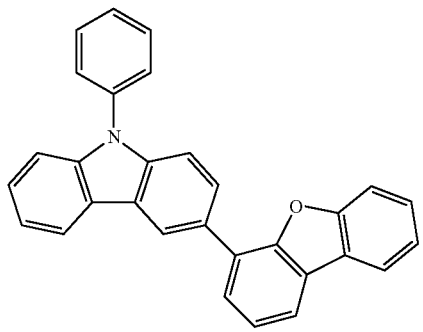
A15
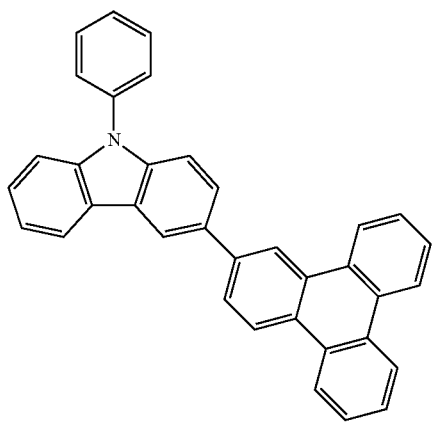
A16
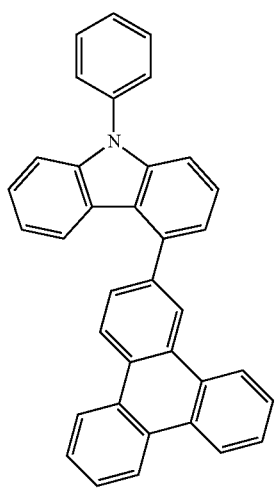
A17
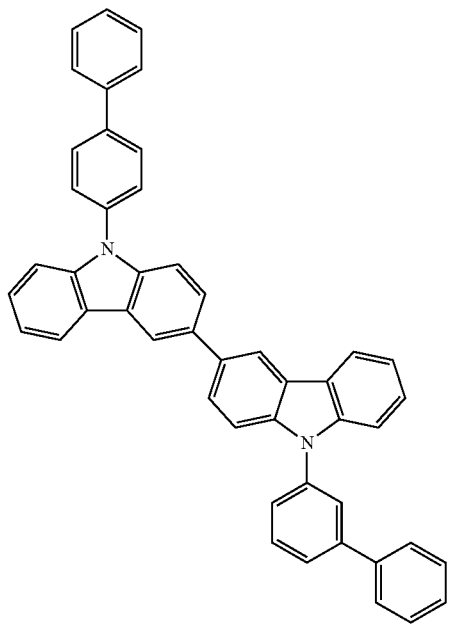
A18
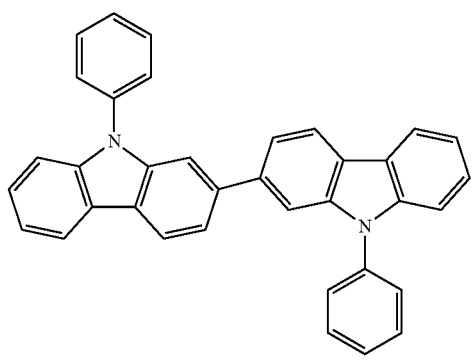
A19
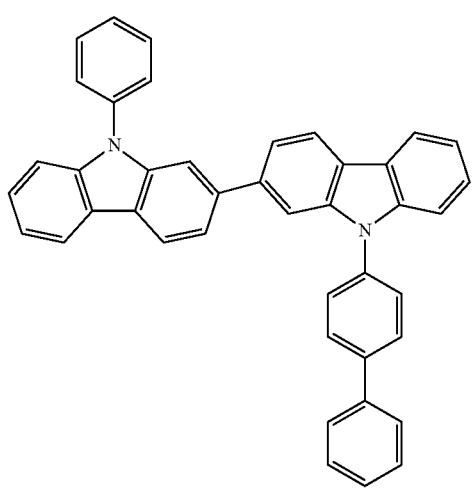

A20
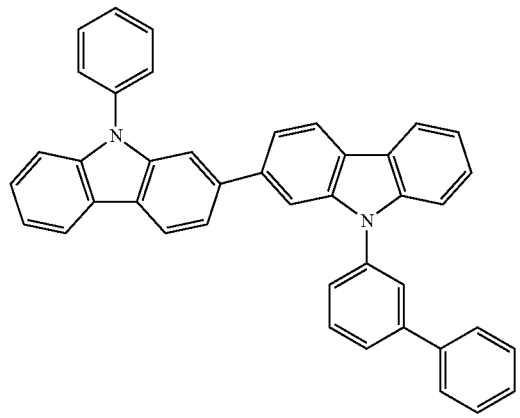
A21
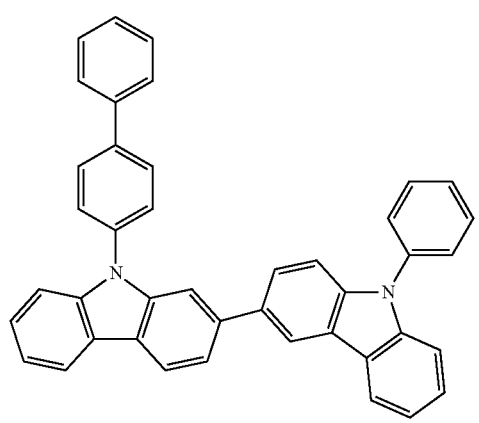
A22
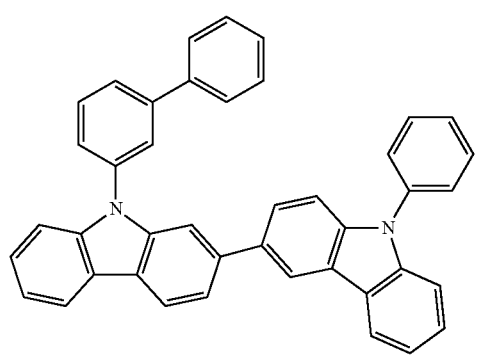
A23
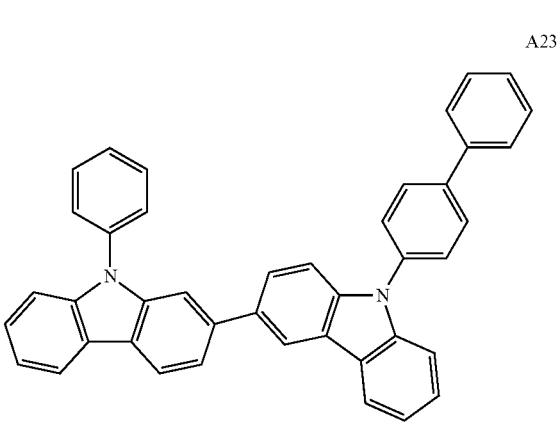
A24
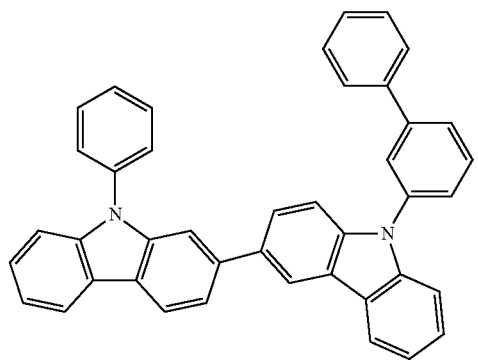
A25
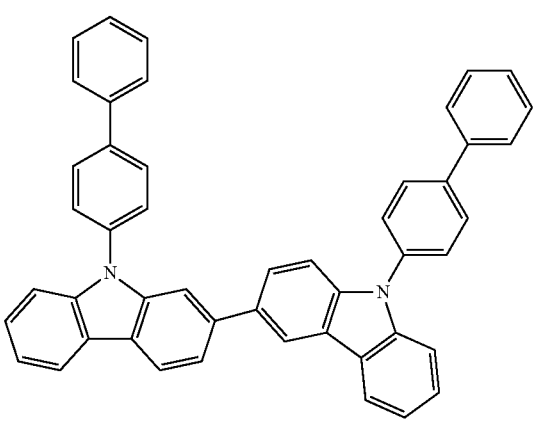
A26
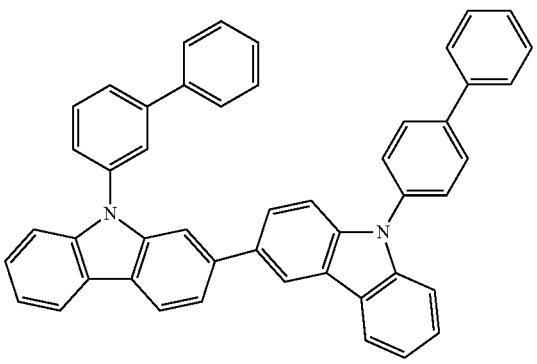
A27
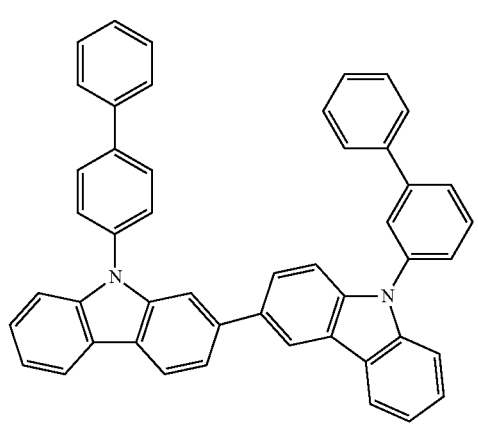

-continued
A28
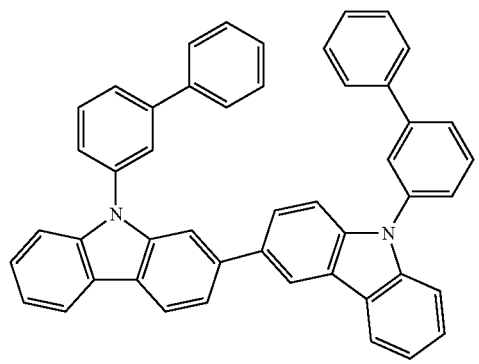
A29
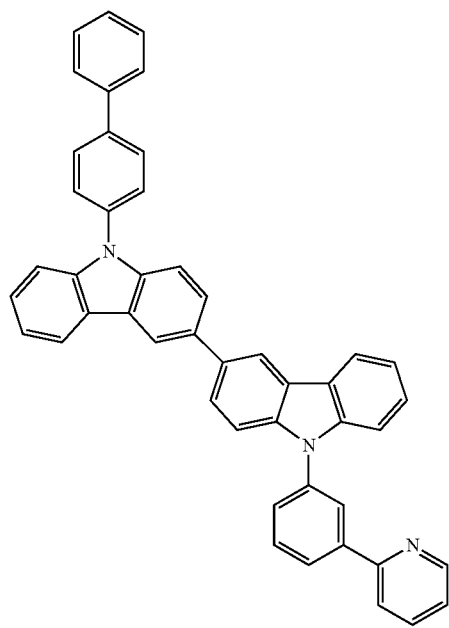
A30
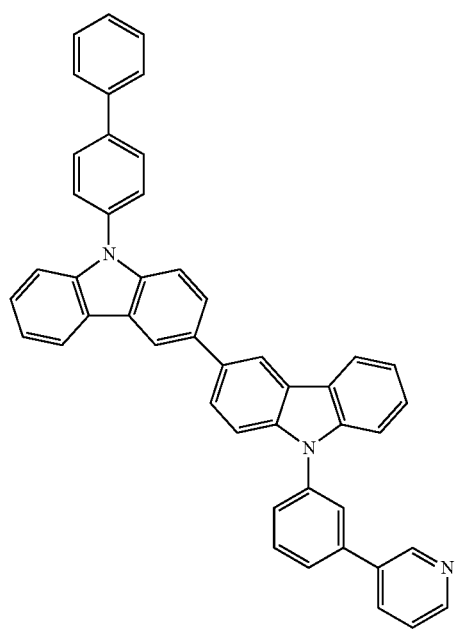
-continued
A31
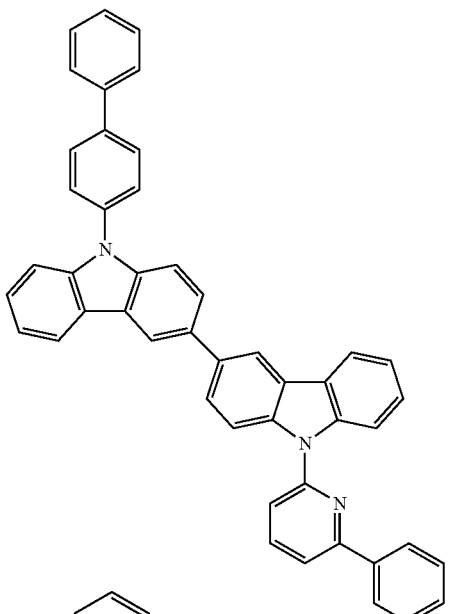
A32
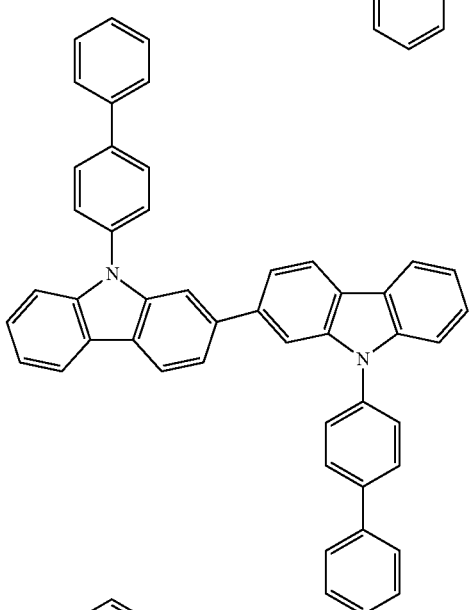
A33
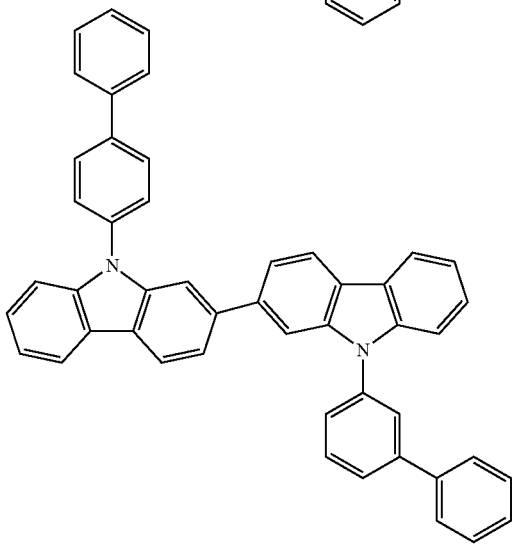

A34
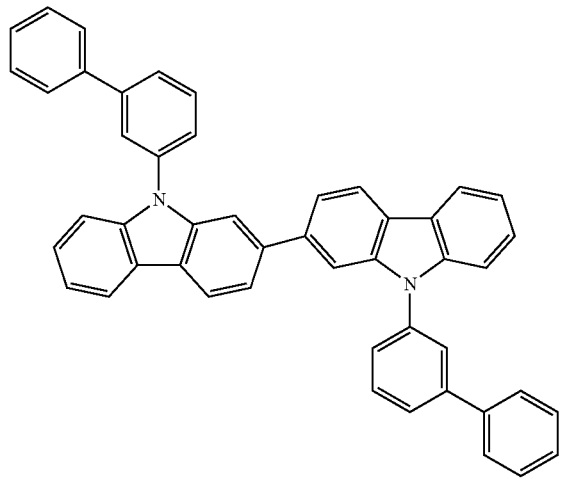
A35
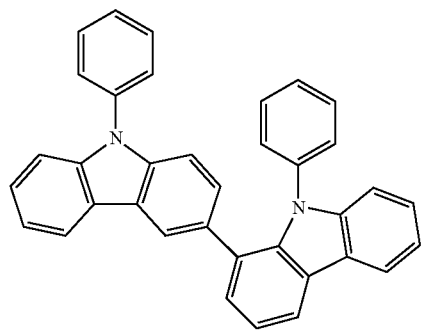
A36
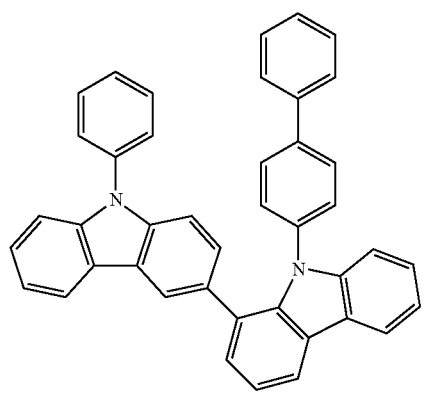
A37
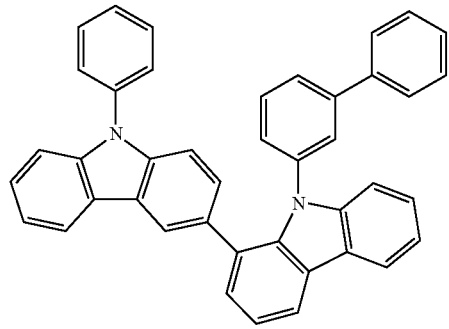
A38
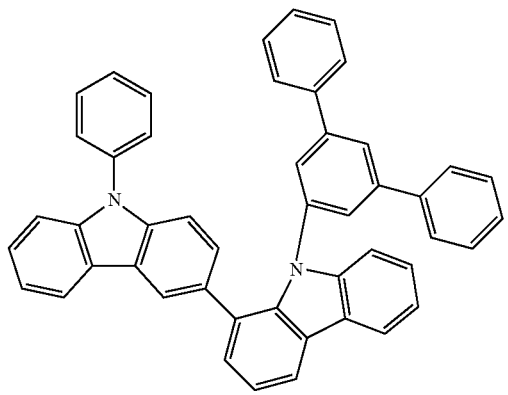
A39
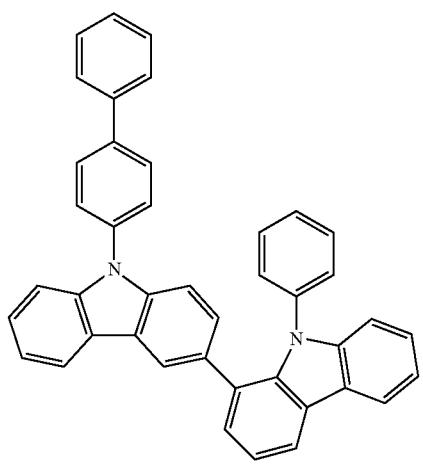
A40
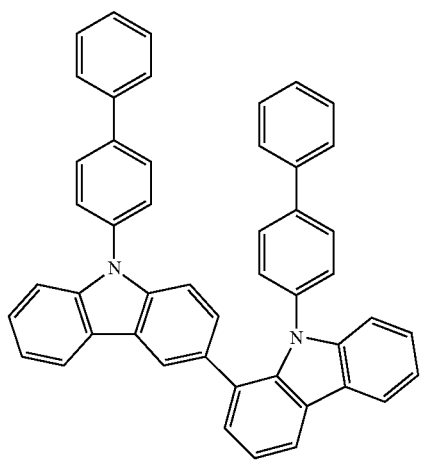

A41
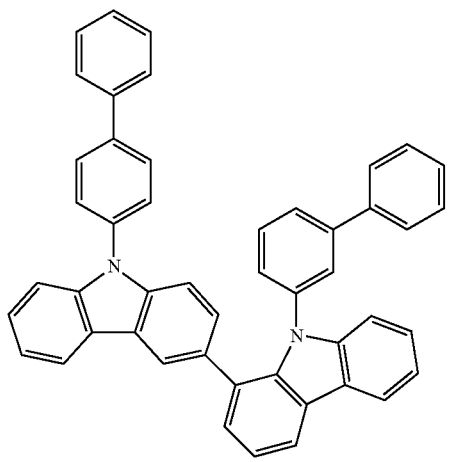
A42
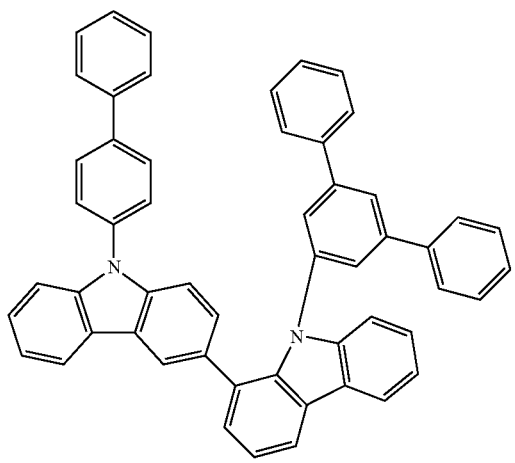
A43
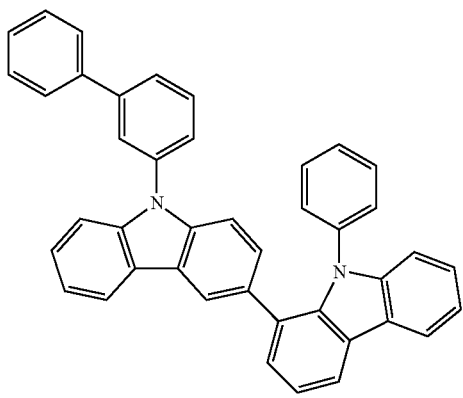
A44
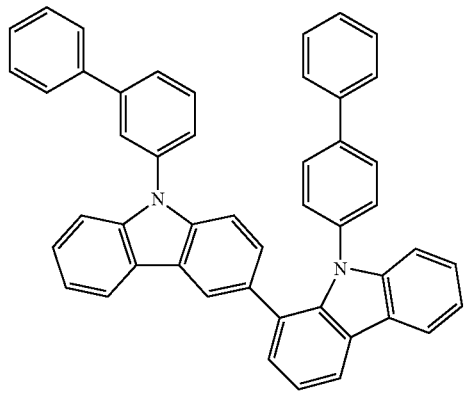
A45
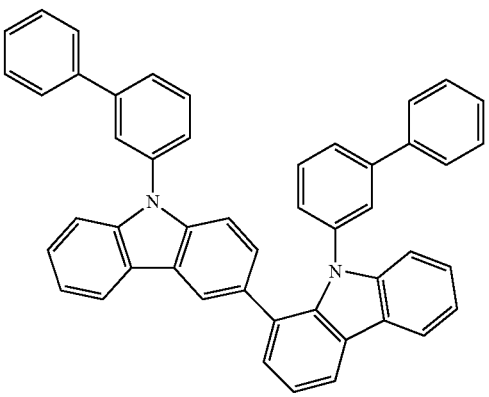
A46
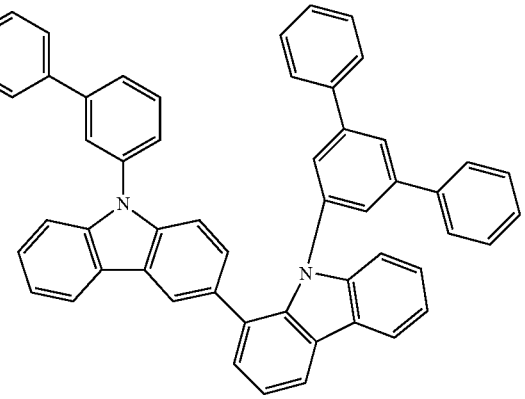
A47
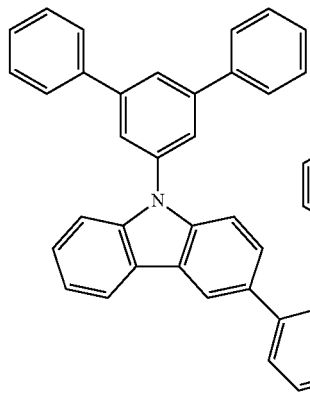

A48
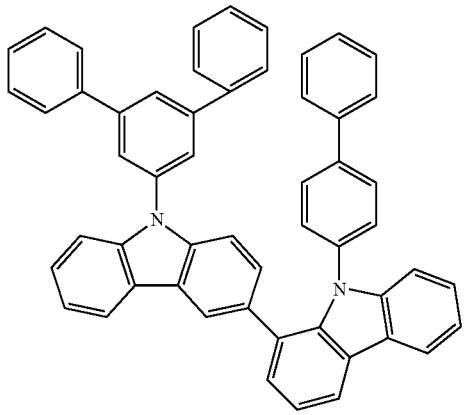
A49
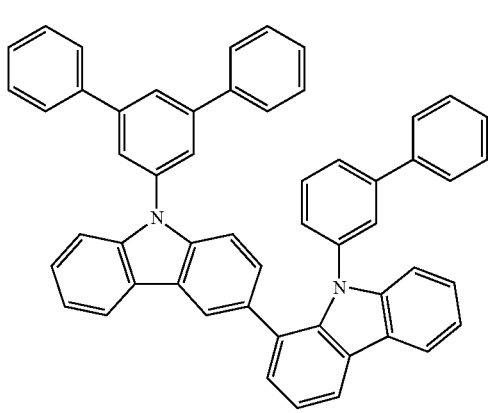
A50
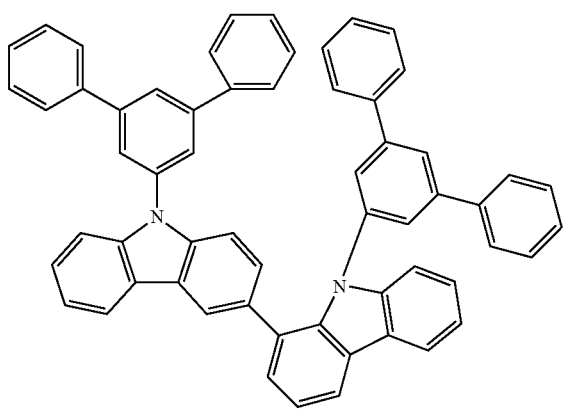
A51
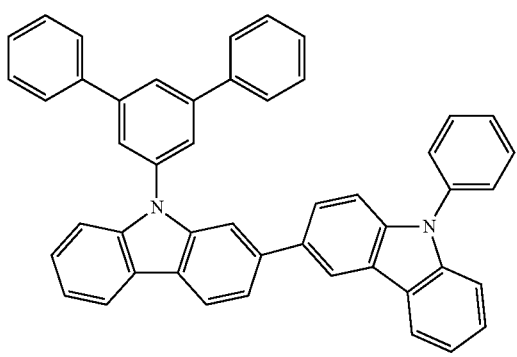
A52
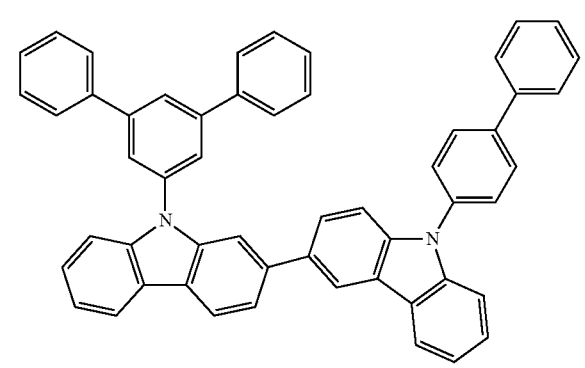
A53
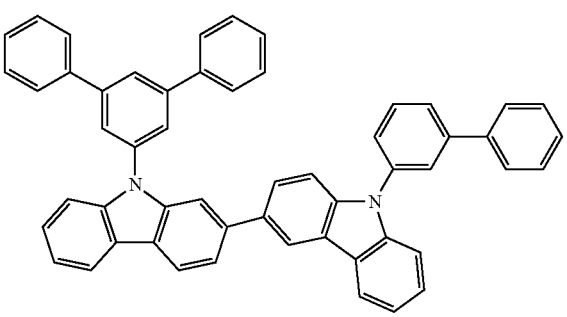
A54
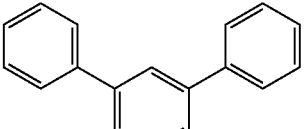
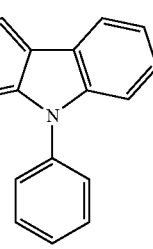

-continued
A55
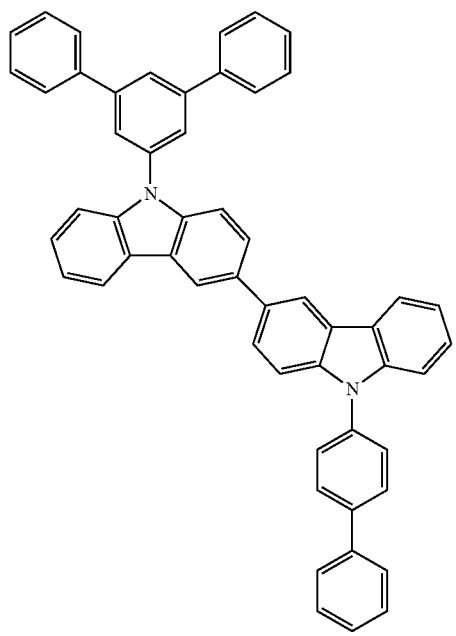
A56
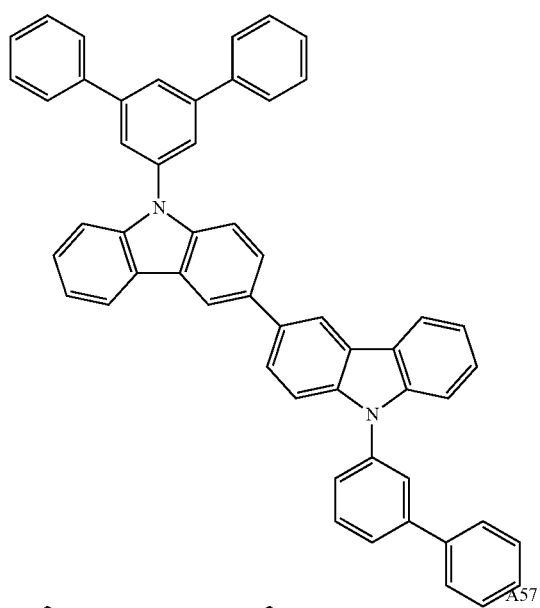
A57
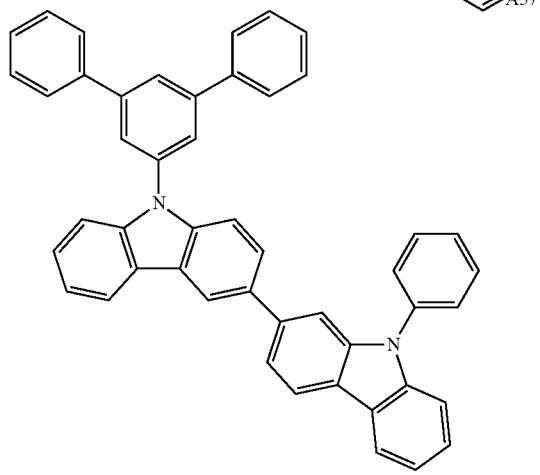
-continued
A58
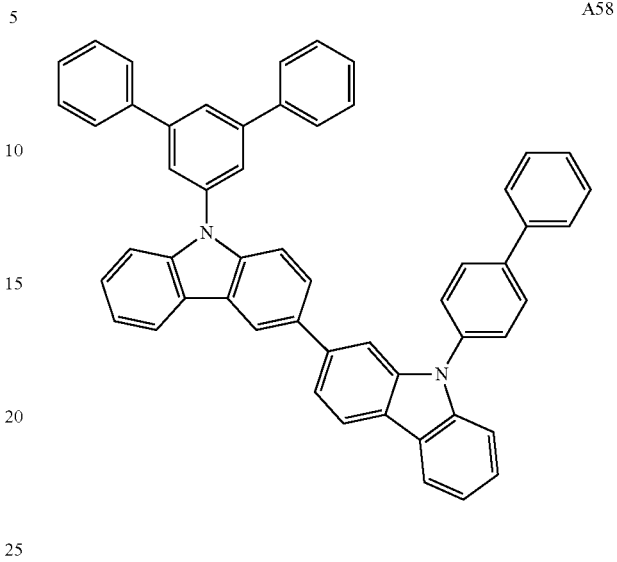
A59
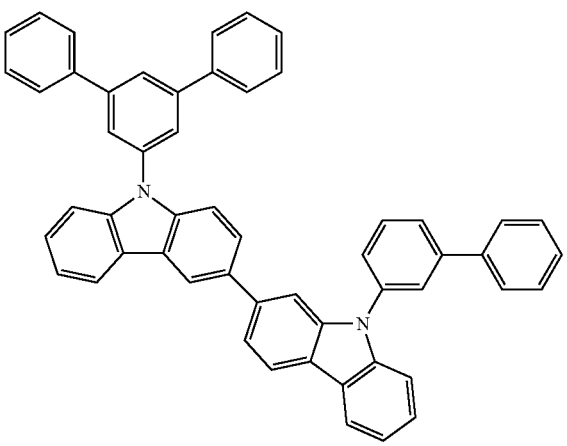
A60
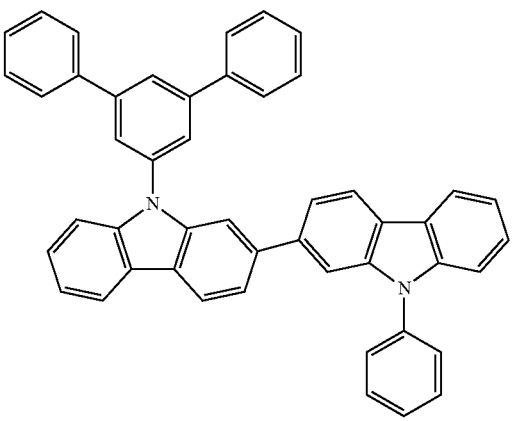

A61
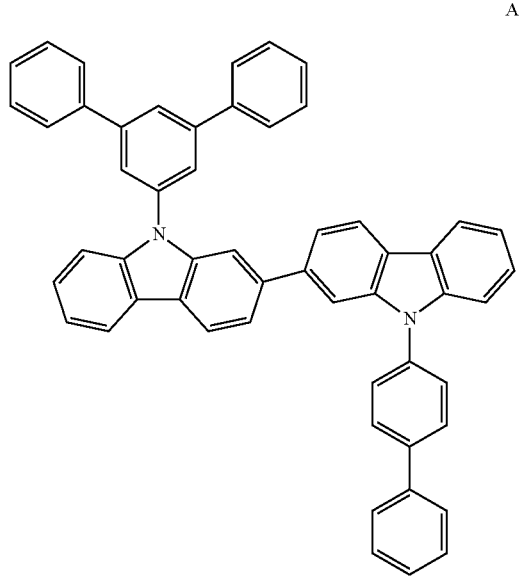
A62
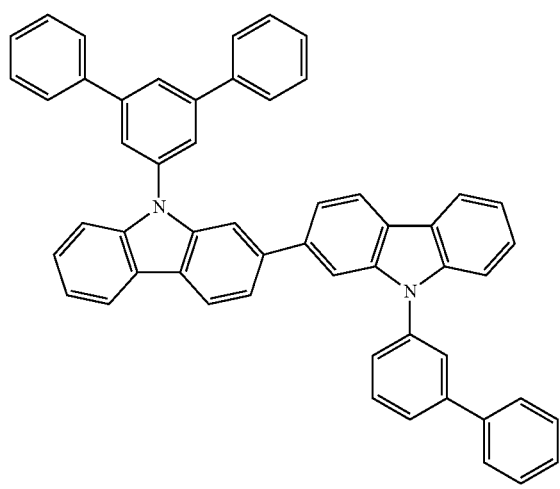
A63
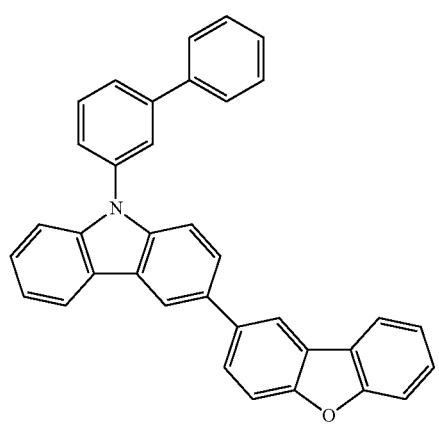
A64
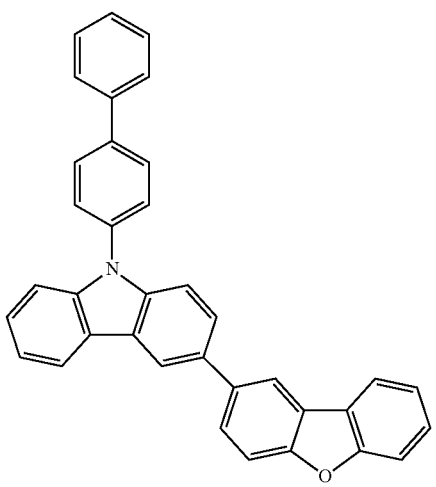
A65
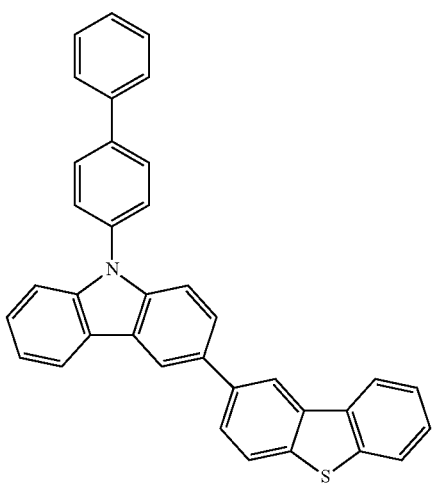
A66
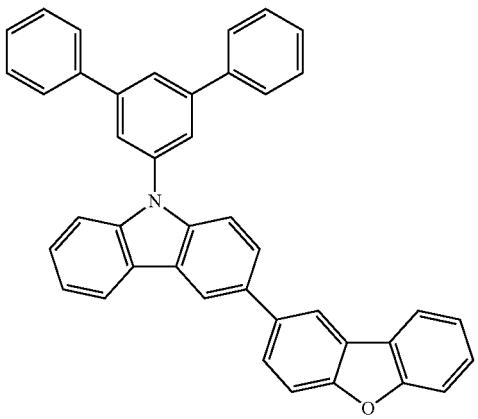

-continued
A67
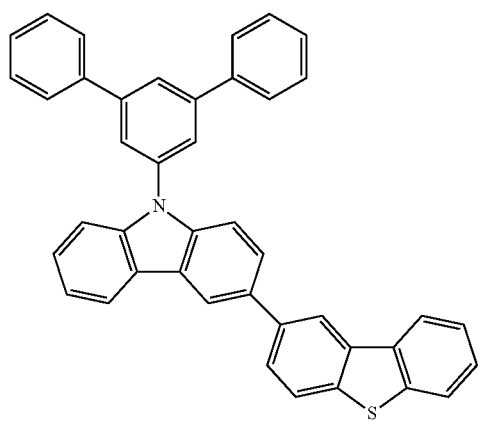
A68
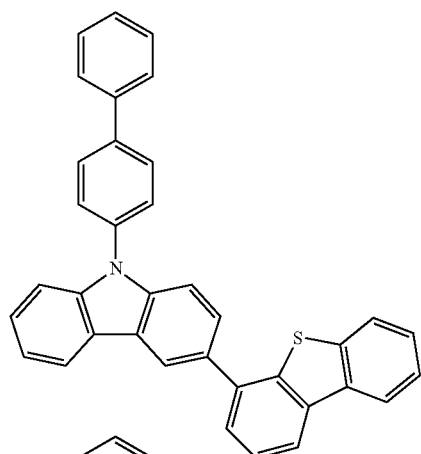
A69
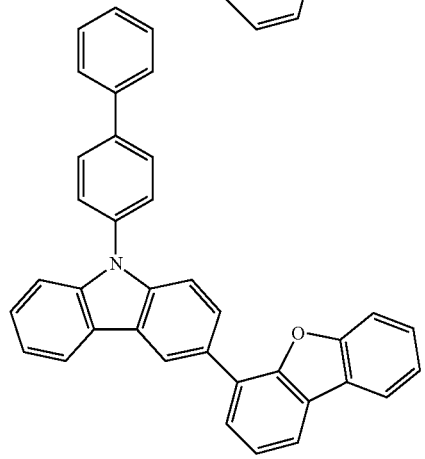
A70
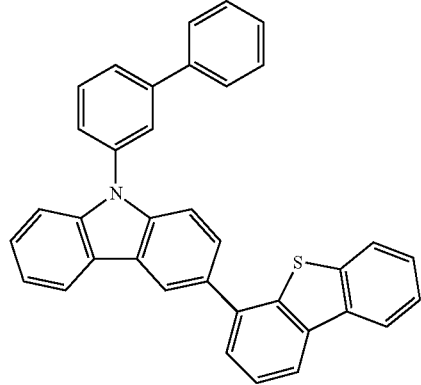
-continued
A71
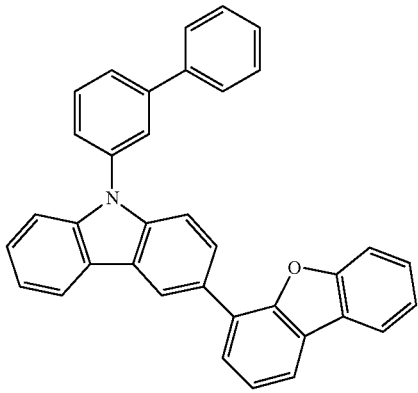
A72
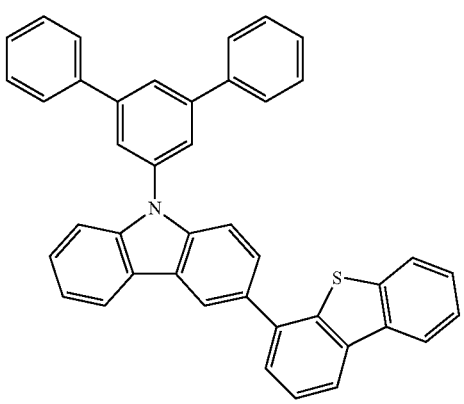
A73
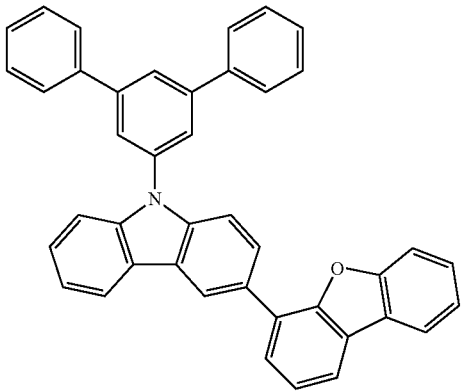
A74
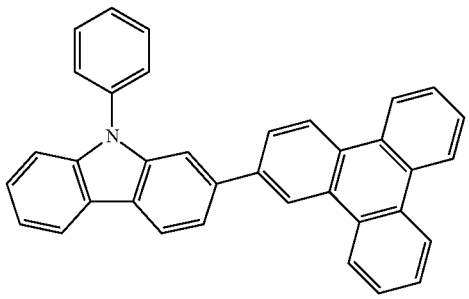

A75
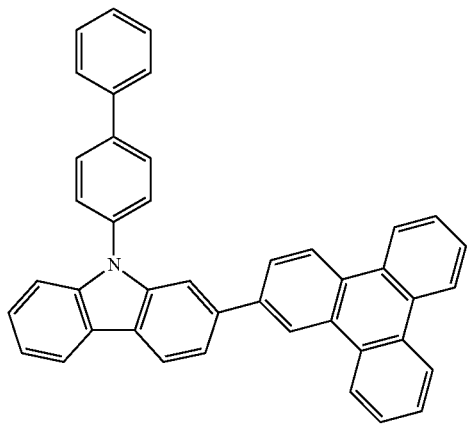
A76
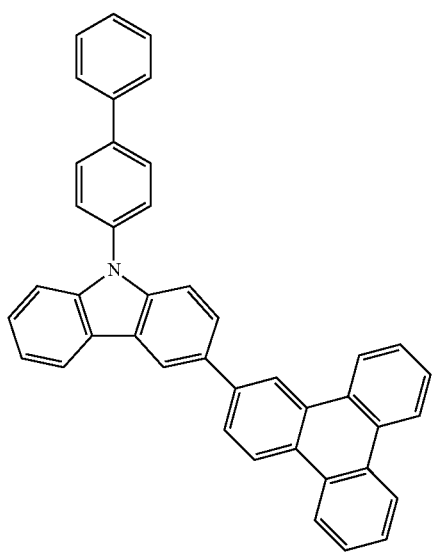
A77
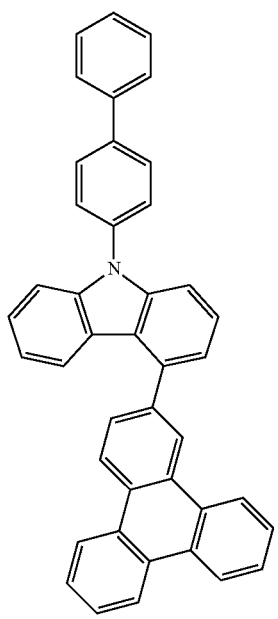
A78
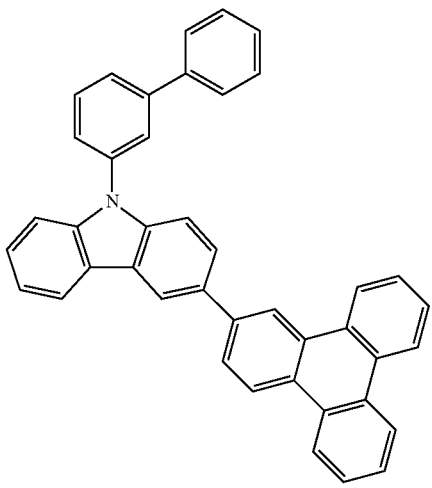
A79
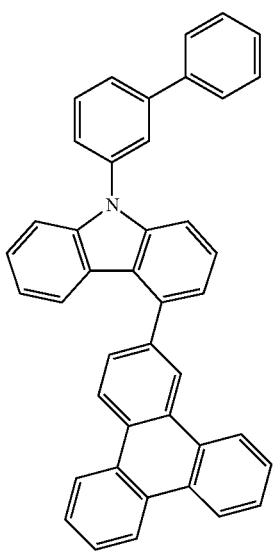
A80
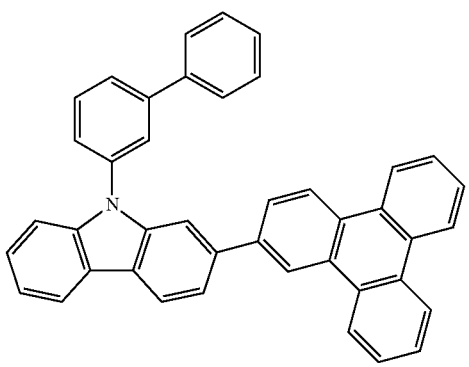

A81 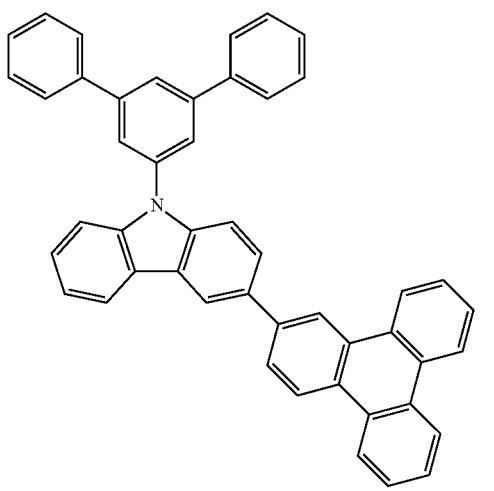
A82 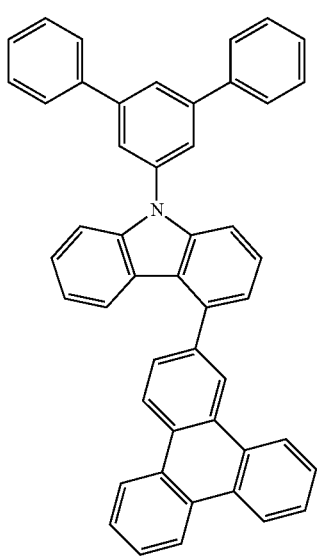
A83 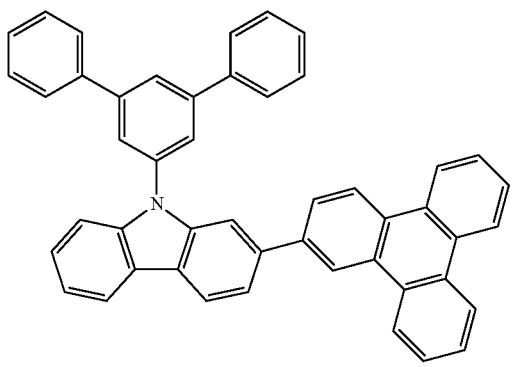
B1 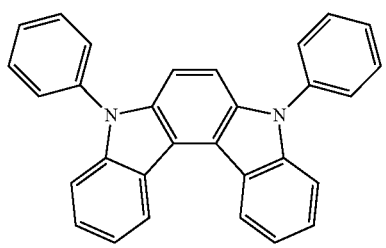
B2 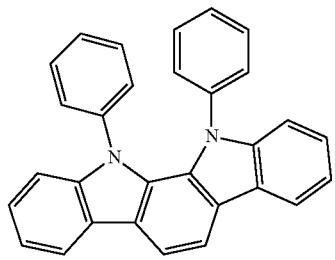
B3 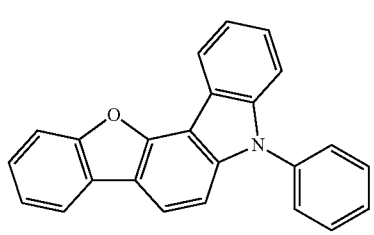
B4 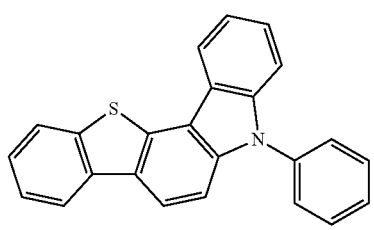
B5 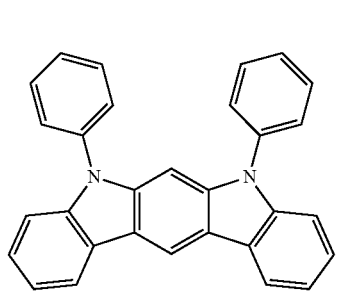
B6 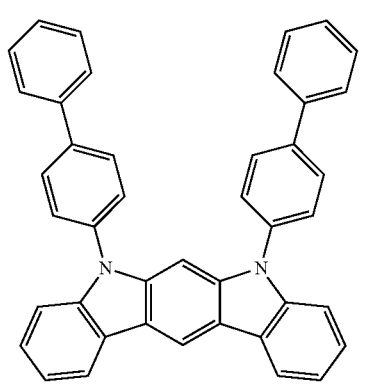

B7
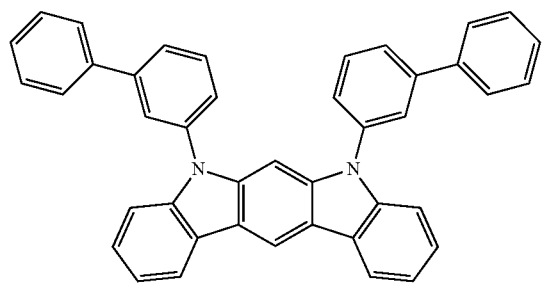
B8
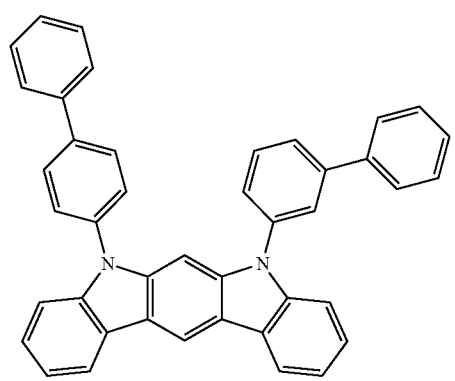
B9
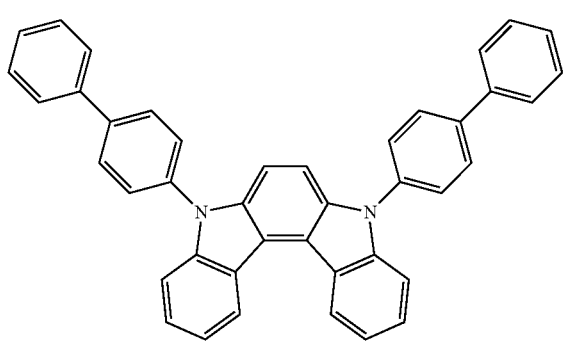
B10
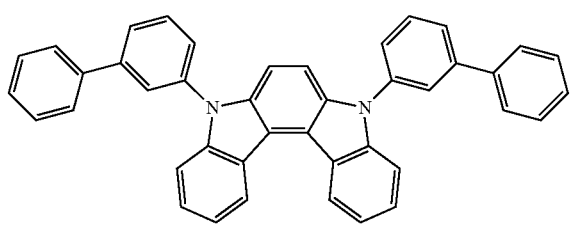
B11
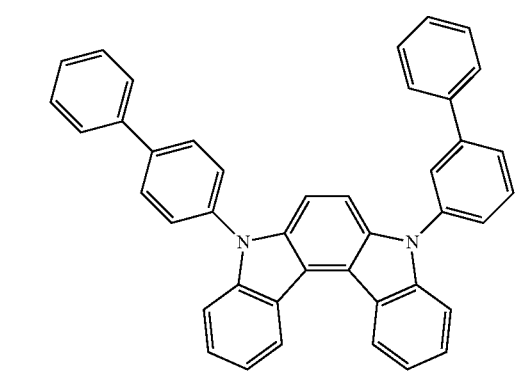
B12
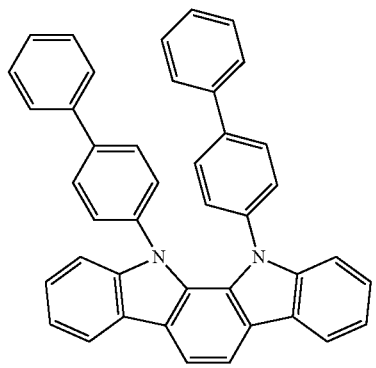
B13
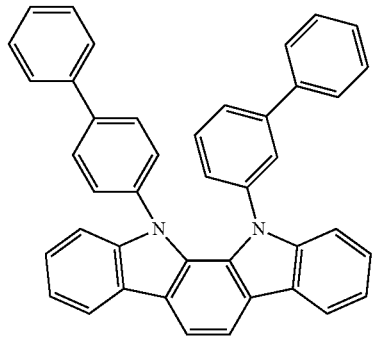
B14
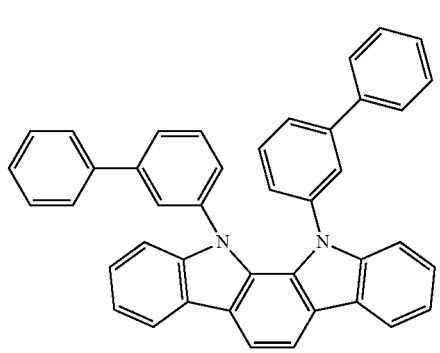
B15
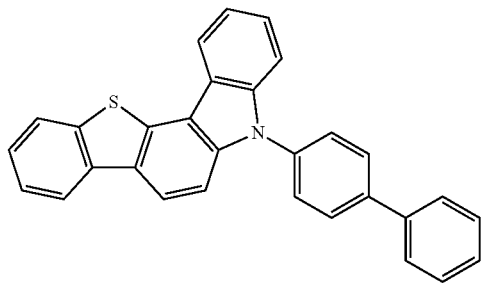
B16
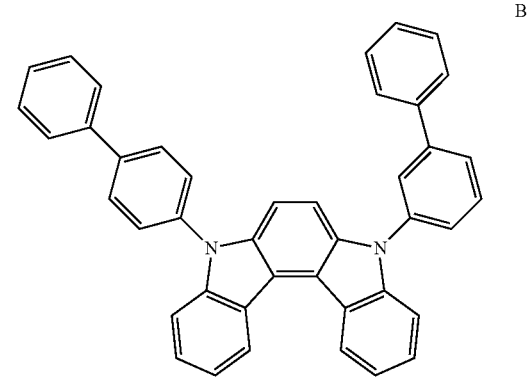

-continued
B17
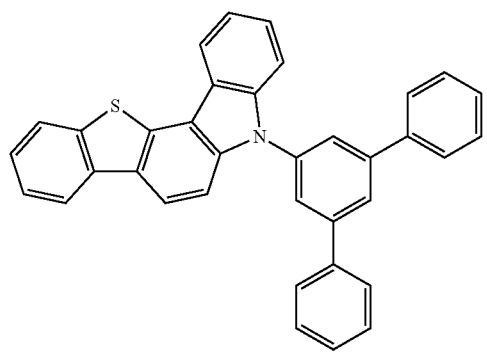
B18
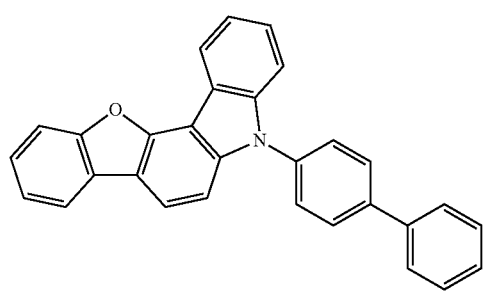
B19
B20
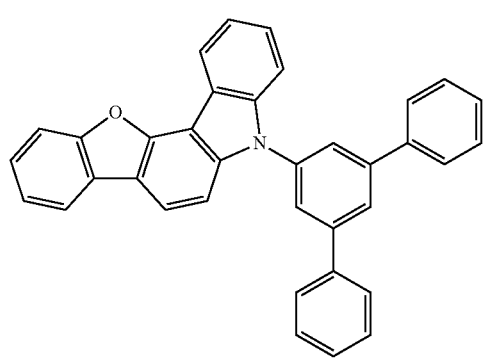
601
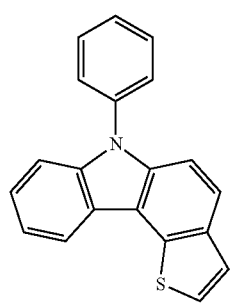
-continued
602
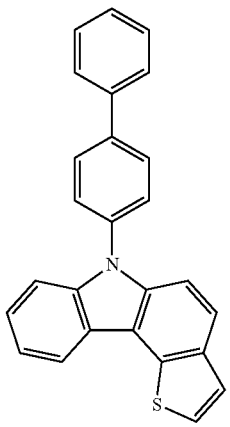
603
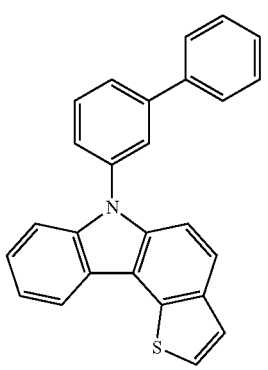
604
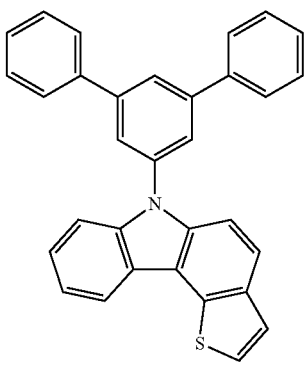
605
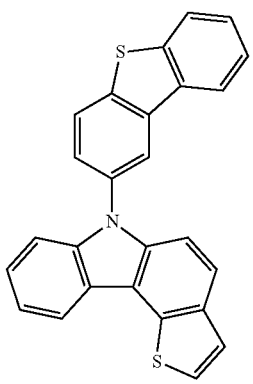

606
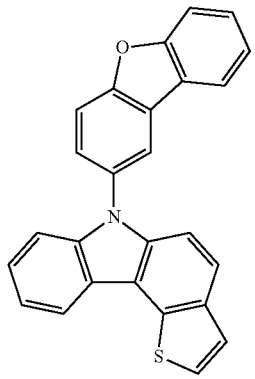
607
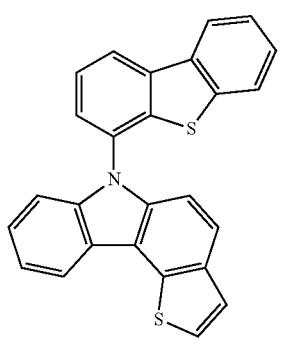
608
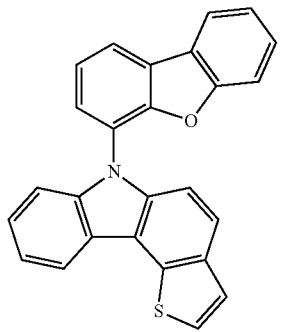
609
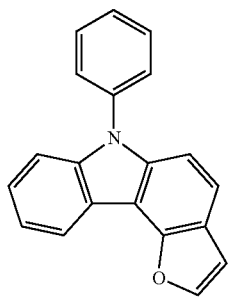
610
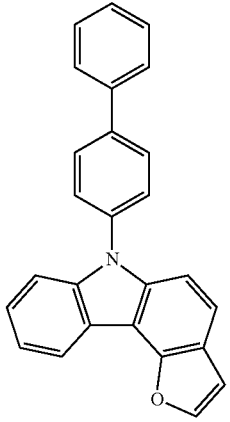
611
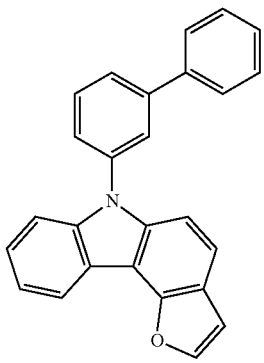
612
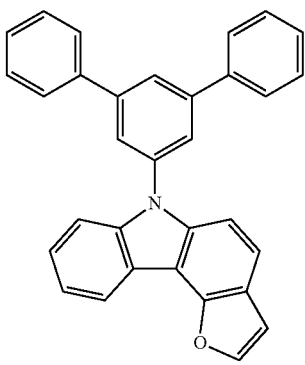
613
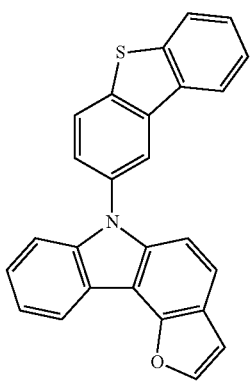

-continued
614
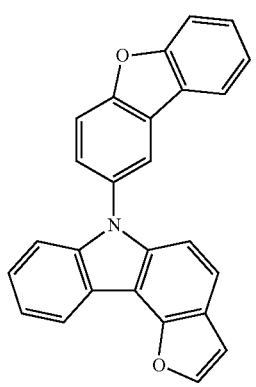
615
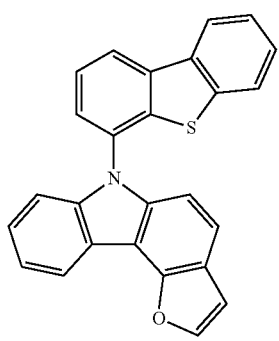
616
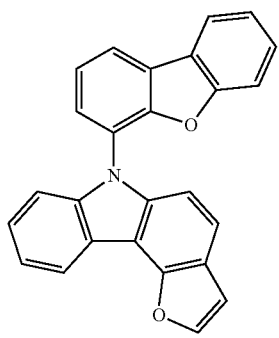
617
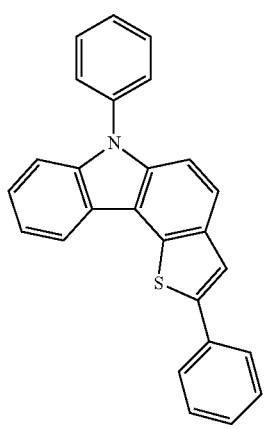
-continued
618
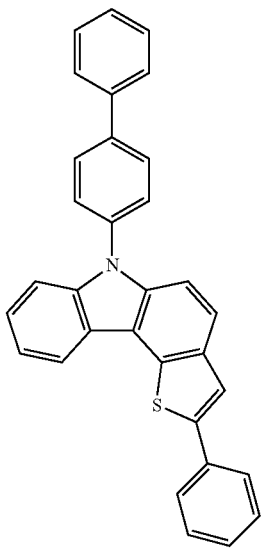
619
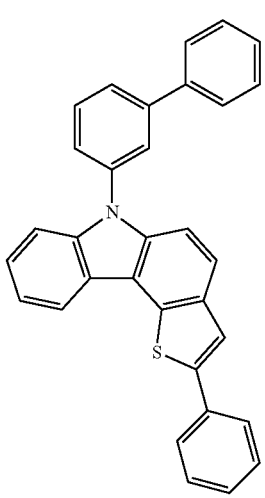
620
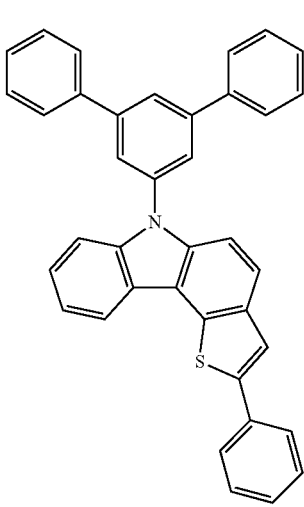

285
-continued
621
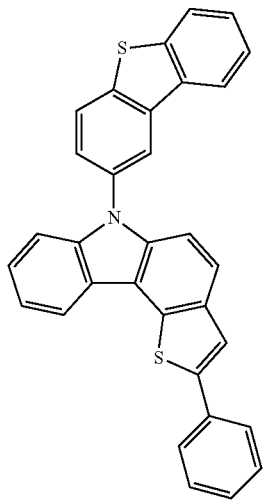
622
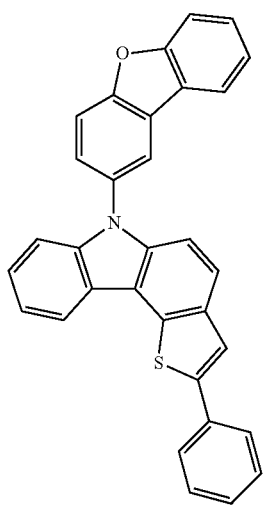
623
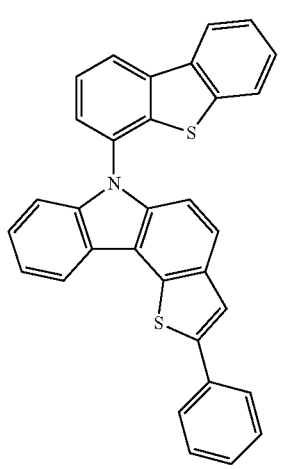
286
-continued
624
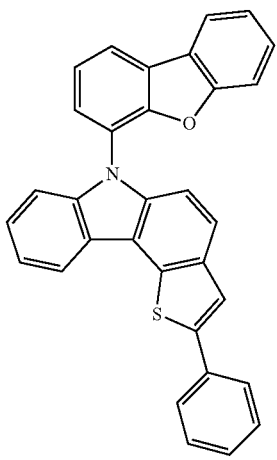
625
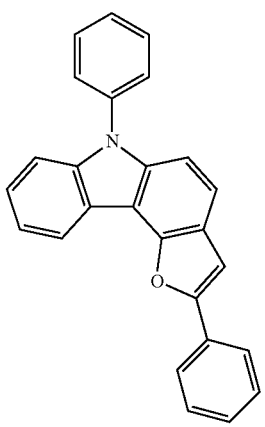
626
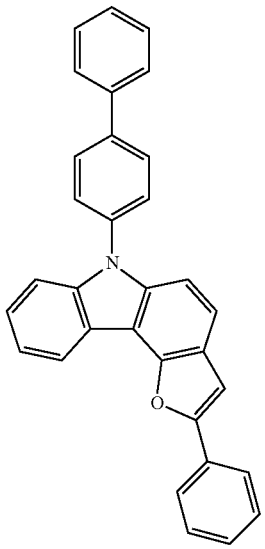

287
-continued
288
-continued
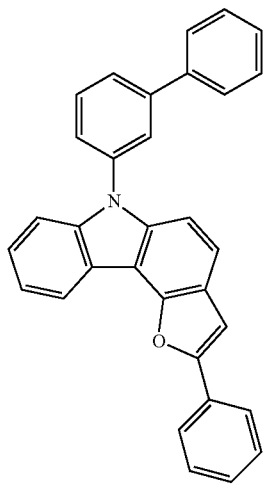
627
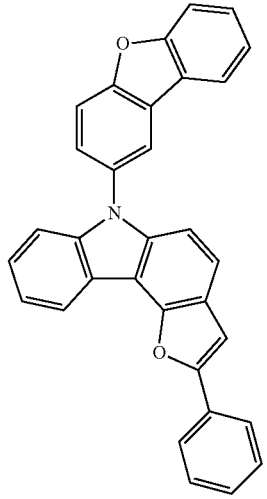
630
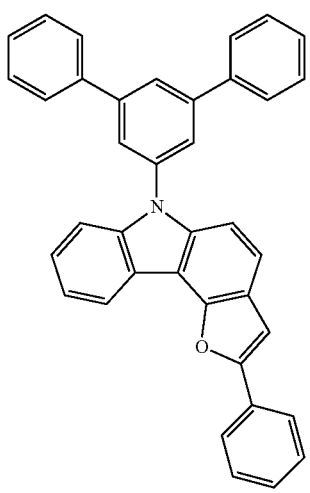
628
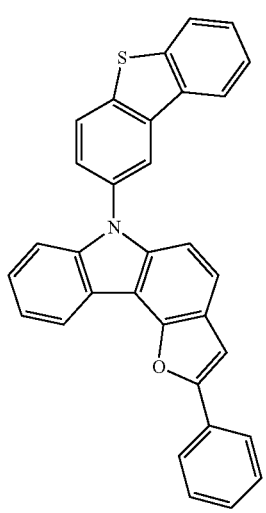
631
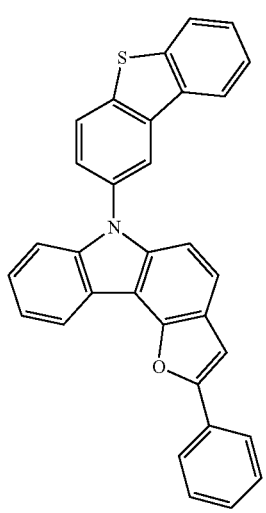
629
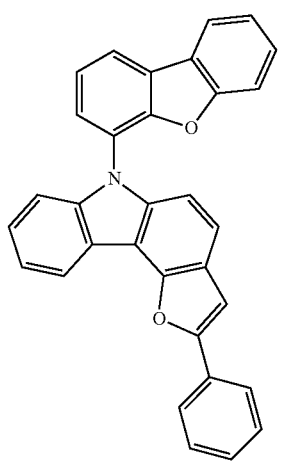
632

289
-continued
290
-continued
633
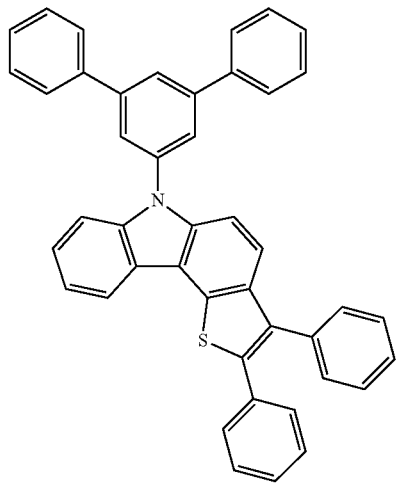
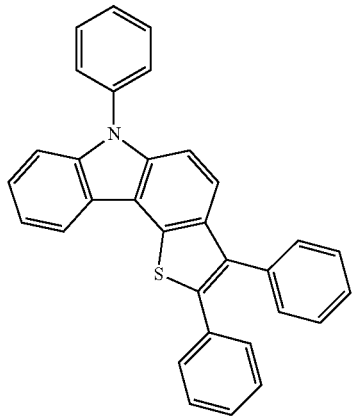
634
637
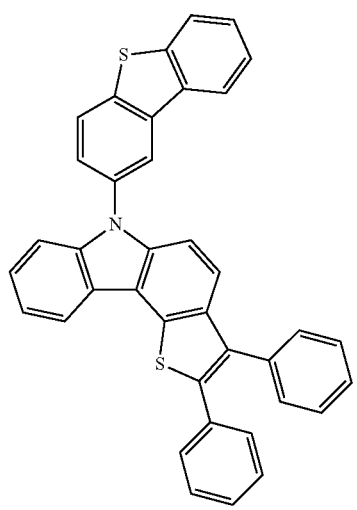
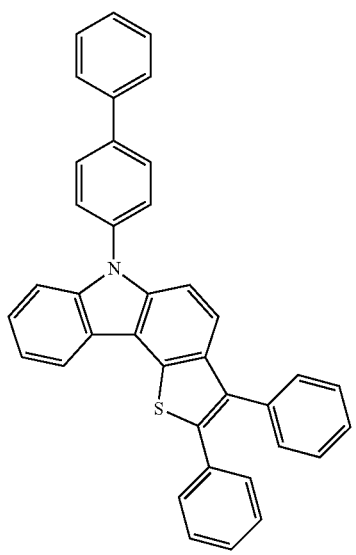
635
638
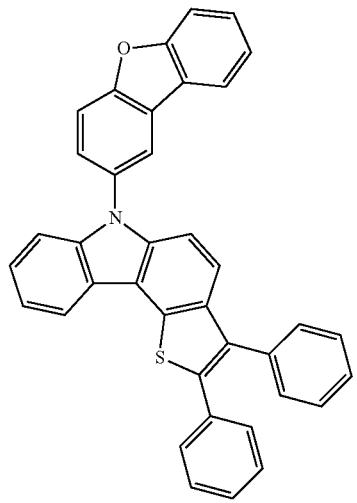
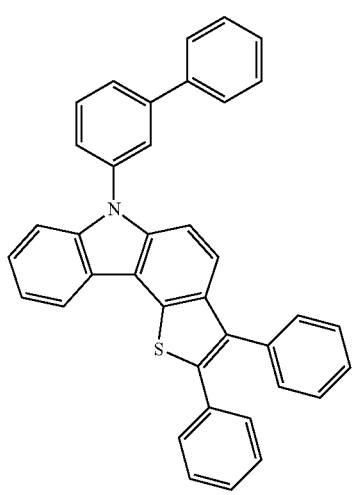

291
-continued
292
-continued
639
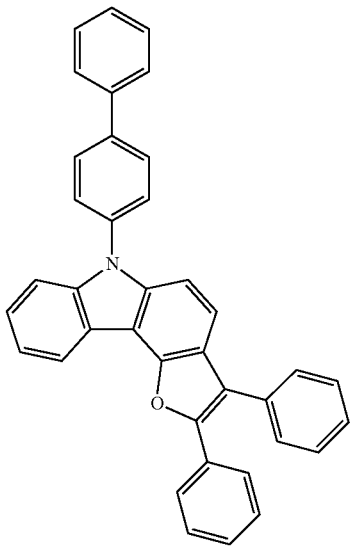
642
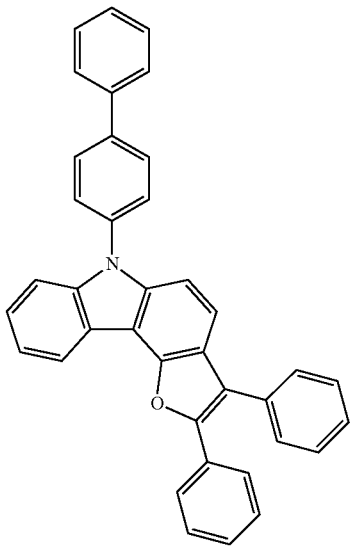
640
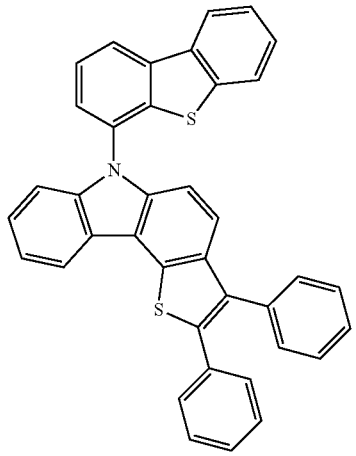
643
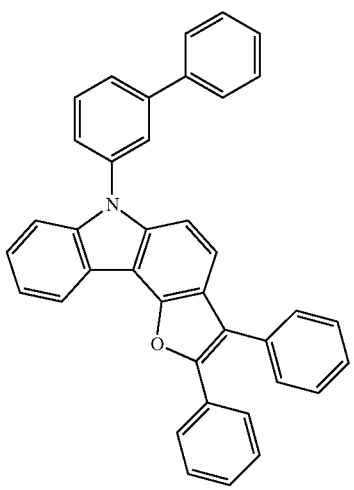
641
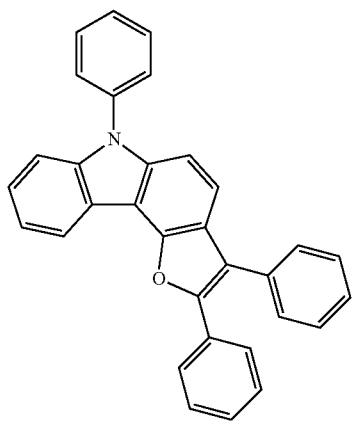
644
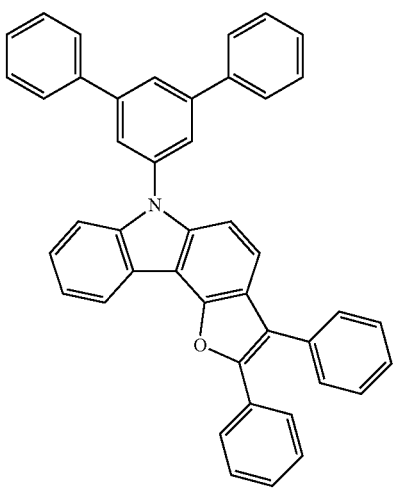

293
-continued
294
-continued
645
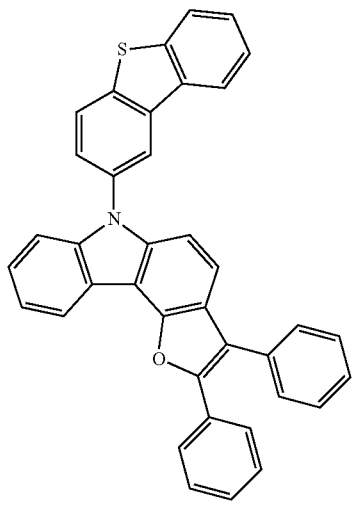
648
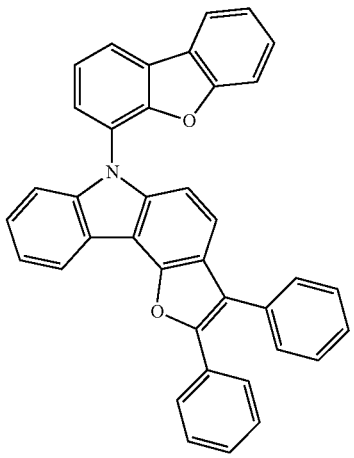
646
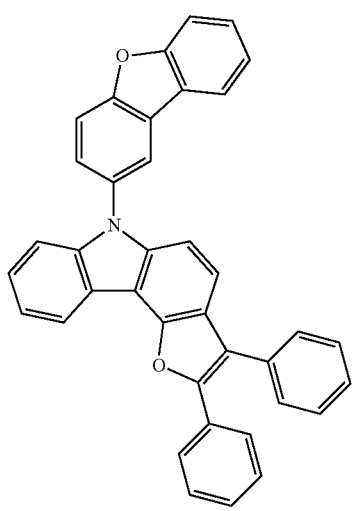
649
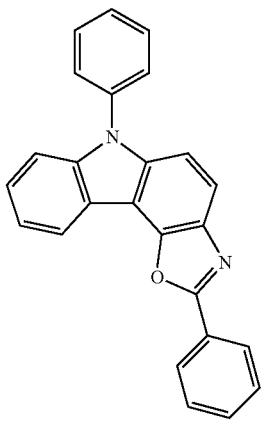
647
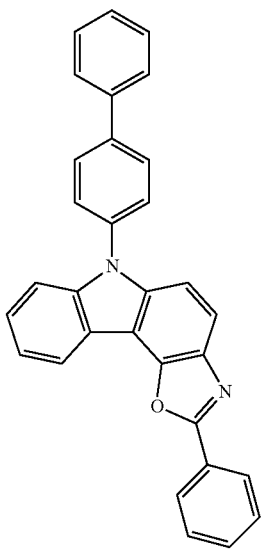
650

651

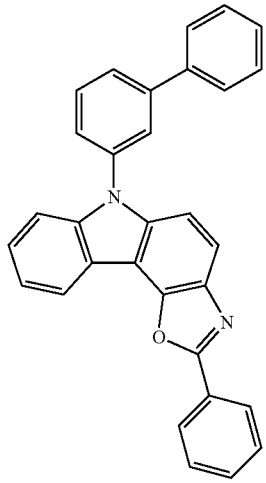

652

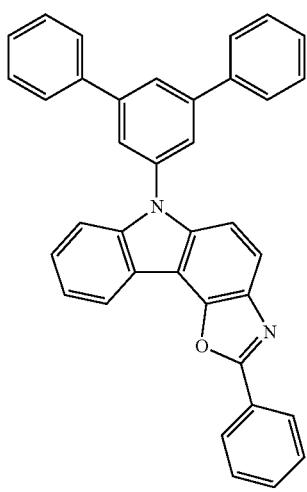

653

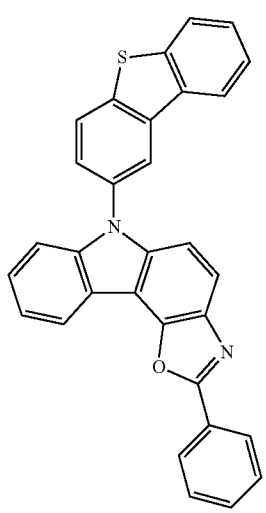

654

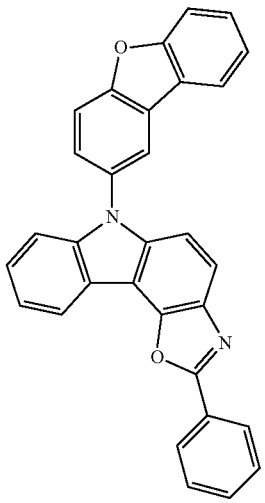

655

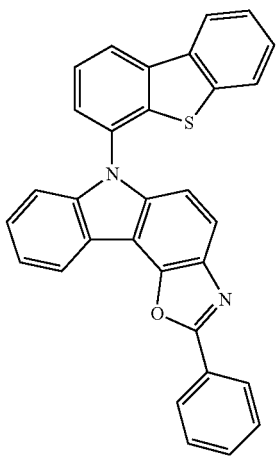

656

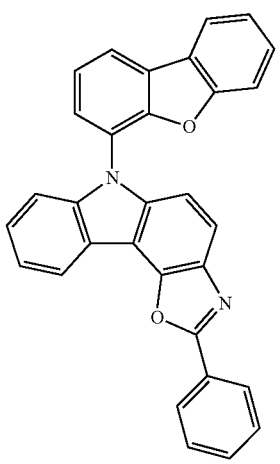

The second host (including at least one of the first compound of Formula 41 above, the second compound of Formula 61, and the third compound of Formula 31) used along with the first host (including the condensed cyclic compound of Formula 1 above) in the EML may control a balance of holes and electrons injected into the EML, and thus may contribute to implementing an organic light-emitting device having improved emission efficiency and improved lifetime.

For example, a weight ratio of the first host to the second host may be in a range of about 1:99 to about 99:1, and in some embodiments, about 10:90 to about 90:10. When the weight ratio of the first host to the second host is within these ranges, the balance of holes and electrons injected into the EML may be effectively controlled.

The dopant in the EML may include a fluorescent dopant emitting light based on fluorescence mechanism, or a phosphorescent dopant emitting light based on phosphorescent mechanism.

In some embodiments, the dopant of the EML may be a phosphorescent dopant. The phosphorescent dopant may include an organometallic compound represented by Formula 81 below:

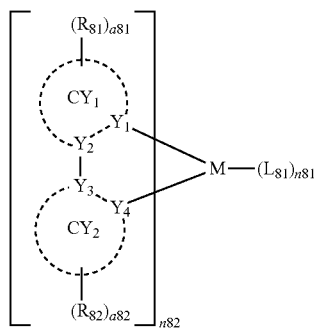

Formula 81

In Formula 81,

M may be iridium (Ir), platinum (Pt), osmium (Os), titanium (Ti), zirconium (Zr), hafnium (Hf), europium (Eu), terbium (Tb), or thulium (Tm);

$Y_1$ to $Y_4$ may be each independently a carbon (C) or a nitrogen (N);

$Y_1$ and $Y_2$ may be linked to each other via a single bond or a double bond, and $Y_3$ and $Y_4$ may be linked to each other via a single bond or a double bond;

$CY_1$ and $CY_2$ may be each independently benzene, naphthalene, fluorene, spiro-fluorene, indene, pyrrole, thiophene, furan, imidazole, pyrazole, thiazole, isothiazole, oxazole, isooxazole, pyridine, pyrazine, pyrimidine, pyridazine, quinoline, isoquinoline, benzoquinoline, quinoxaline, quinazoline, carbazole, benzoimidazole, benzofuran, benzothiophene, isobenzothiophene, benzooxazole, isobenzooxazole, triazole, tetrazole, oxadiazole, triazine, dibenzofuran, or dibenzothiophene, wherein $CY_1$ and $CY_2$ may be optionally linked to each other via a single bond or an organic linking group;

$R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent nonaromatic condensed polycyclic group, a substituted or unsubstituted monovalent nonaromatic condensed heteropolycyclic group, —N(Q$_1$)(Q$_2$), —Si(Q$_3$)(Q$_4$)(Q$_5$), and —B(Q$_6$)(Q$_7$);

a81 and a82 may be each independently an integer selected from 1 to 5;

n81 may be an integer selected from 0 to 4;

n82 may be 1, 2, or 3;

$L_{81}$ may be a monovalent organic ligand, a divalent organic ligand, or a trivalent organic ligand.

$R_{81}$ and $R_{82}$ in Formula 81 may be defined to be the same as described above with reference to $R_{41}$ above, and detailed descriptions of $R_{81}$ and $R_{82}$ are not provided herein.

The phosphorescent dopant may include at least one of Compounds PD1 to PD78, but is not limited thereto:

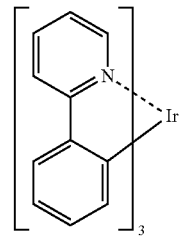

PD1

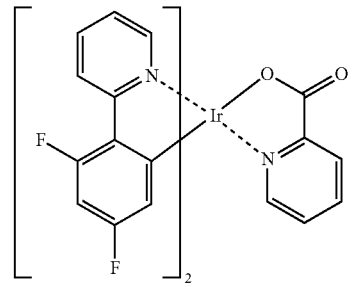

PD2

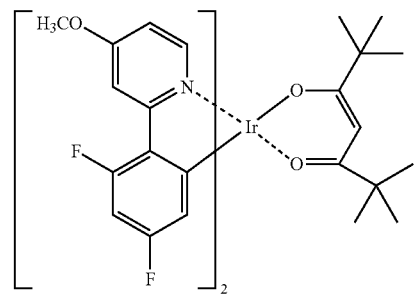

PD3

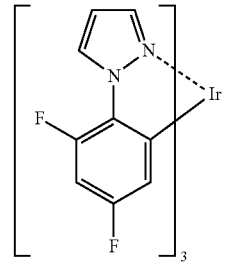

PD4

-continued
PD5 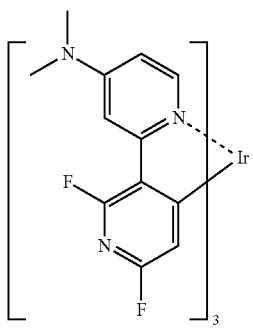
PD10 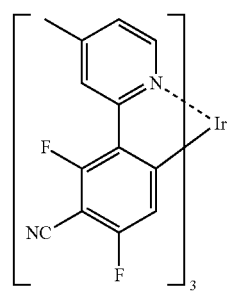
PD6 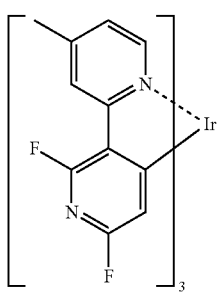
PD11 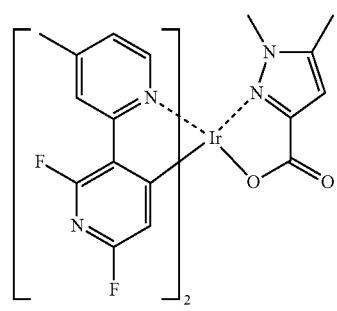
PD7 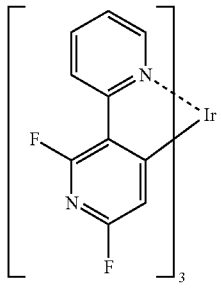
PD12 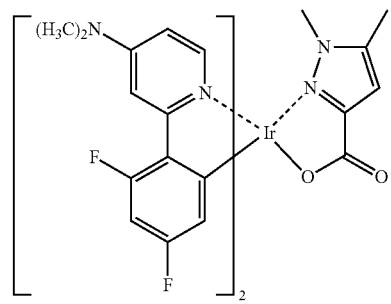
PD8 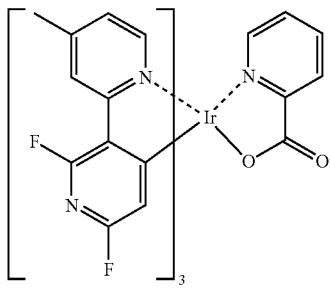
PD13 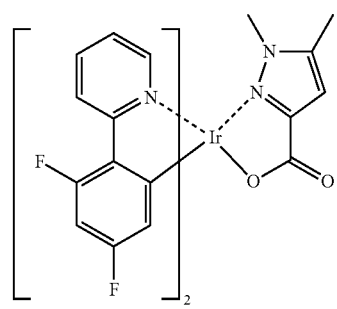
PD9 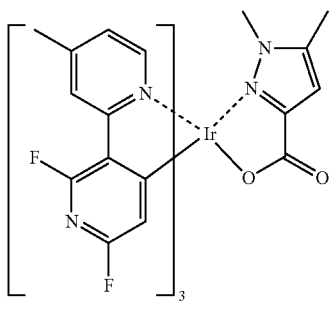
PD14 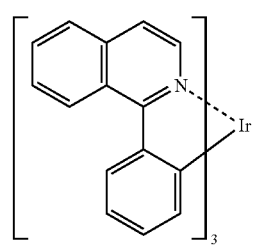

-continued
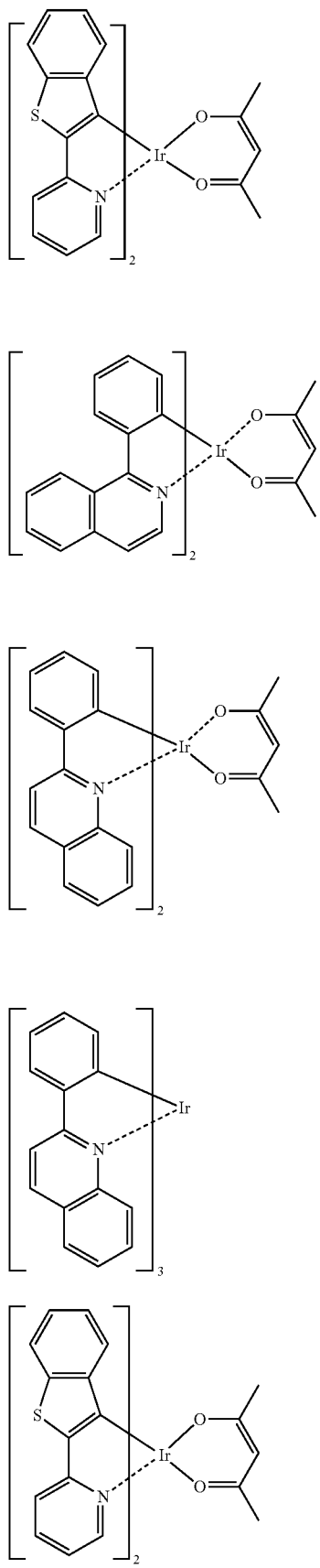
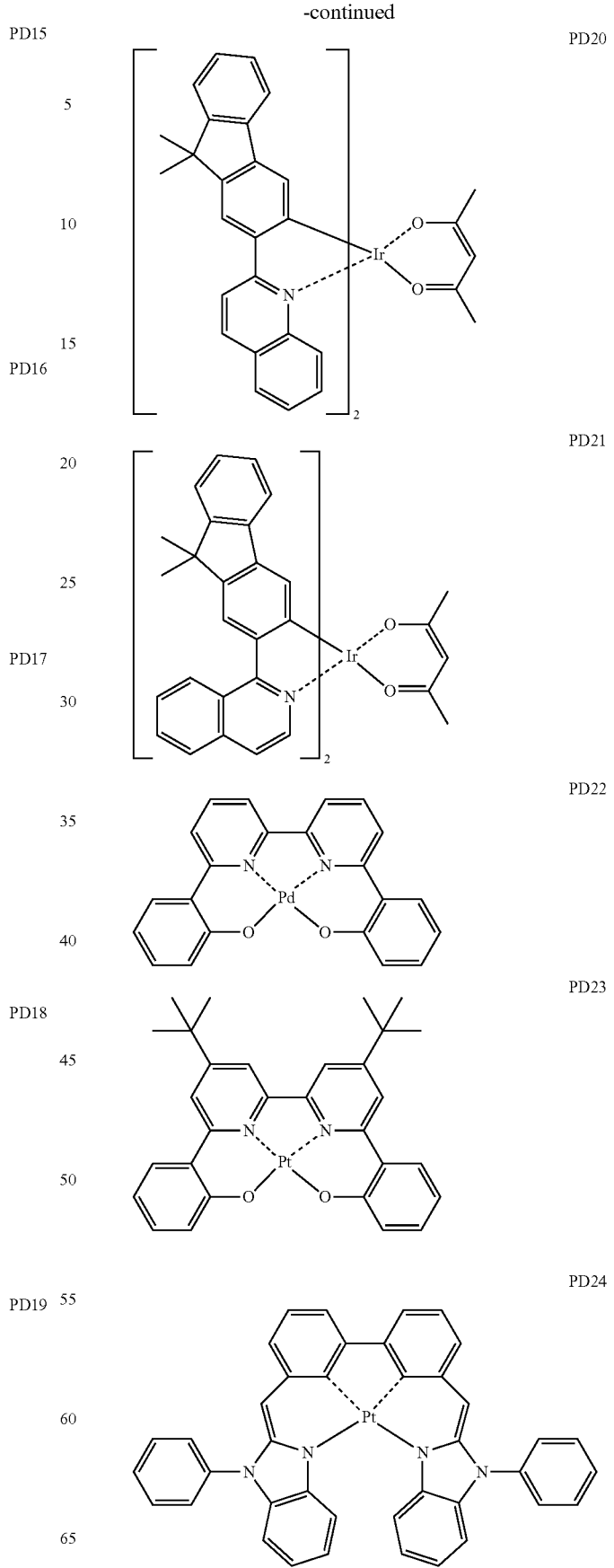

-continued
PD25
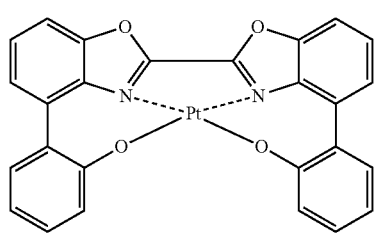
PD26
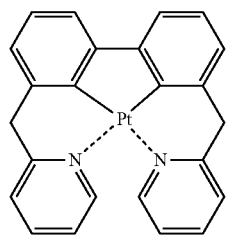
PD27
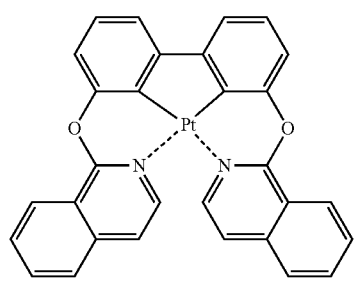
PD28
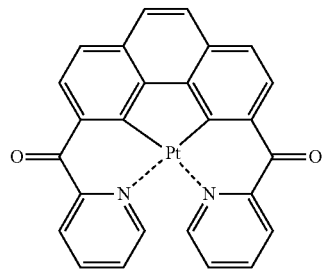
PD29
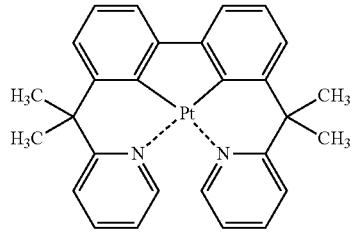
PD30
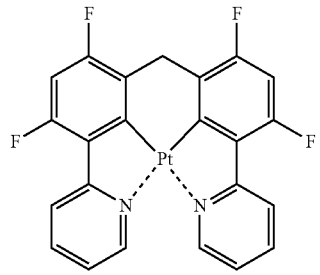
-continued
PD31
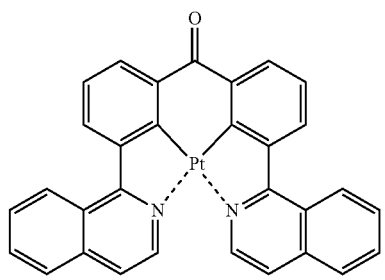
PD32
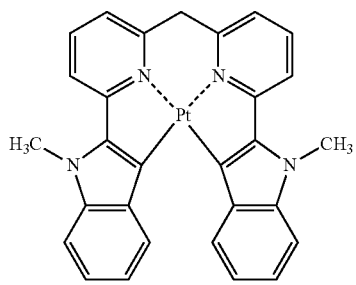
PD33
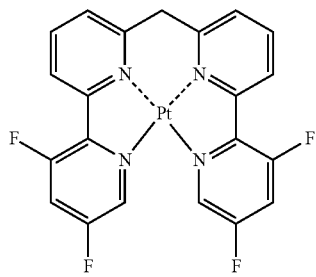
PD34
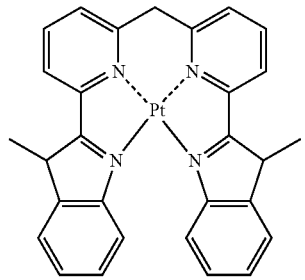
PD35
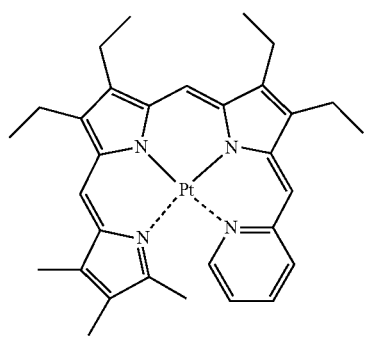

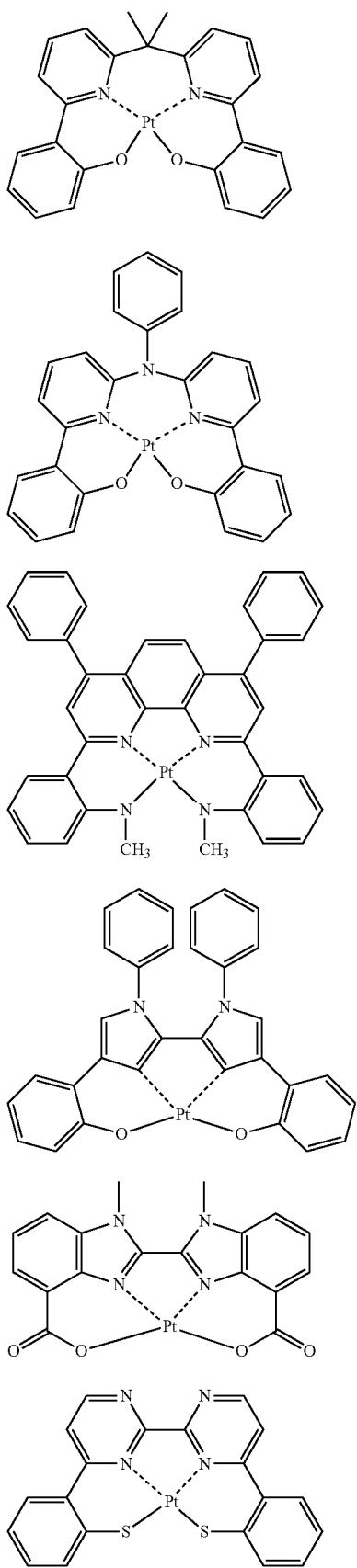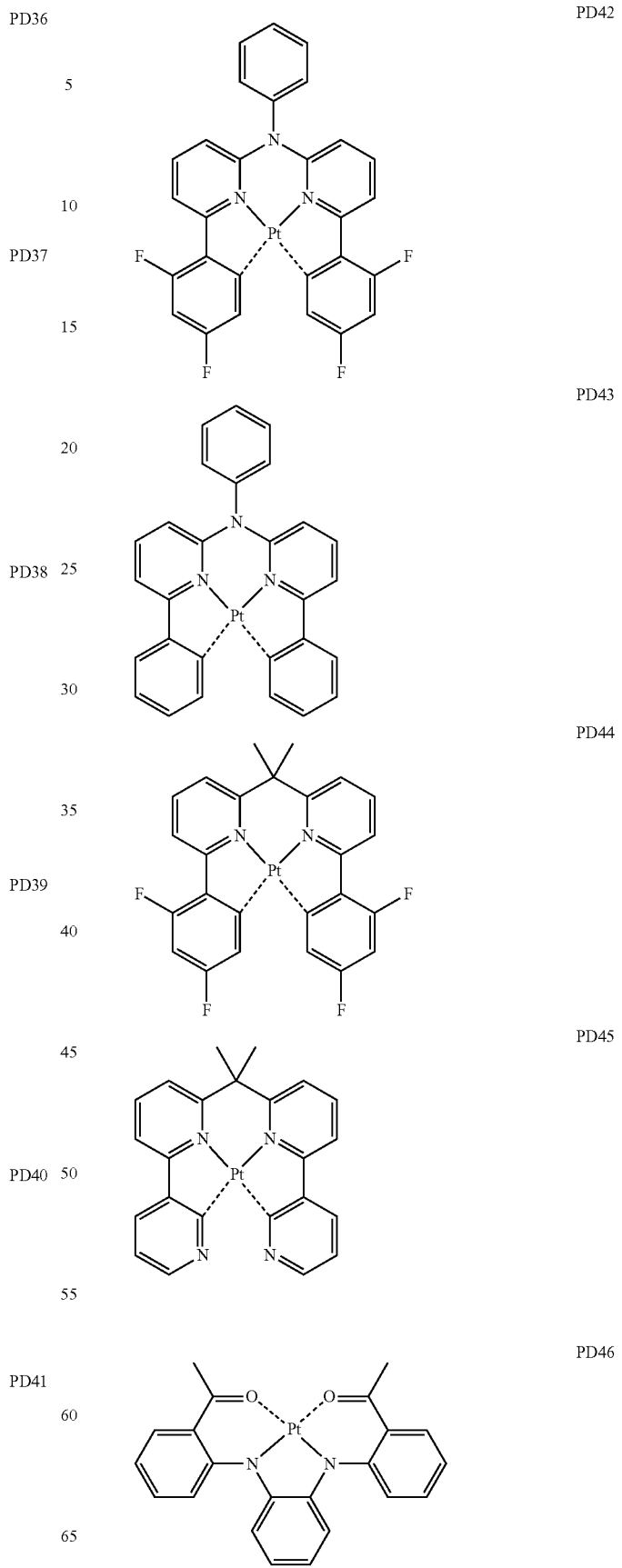

307
-continued
PD47
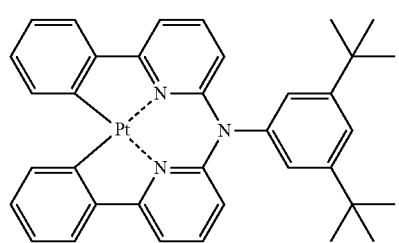
PD48
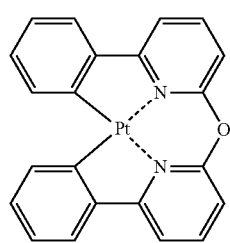
PD49
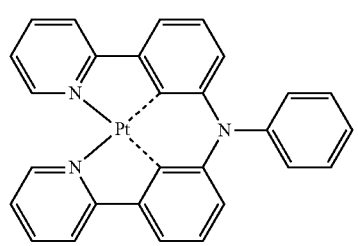
PD50
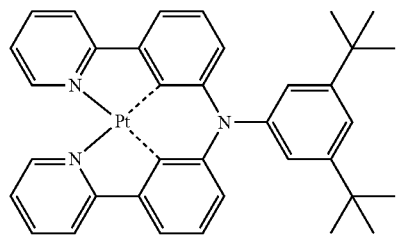
PD51
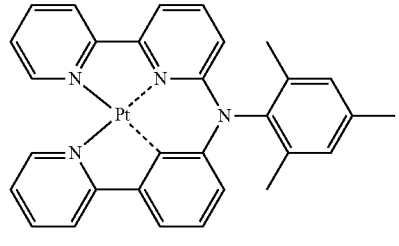
PD52
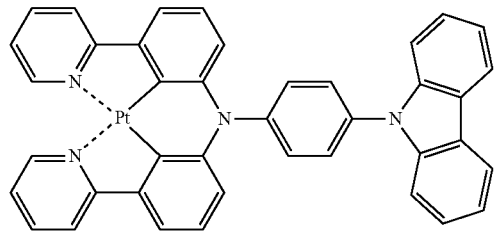
308
-continued
PD53
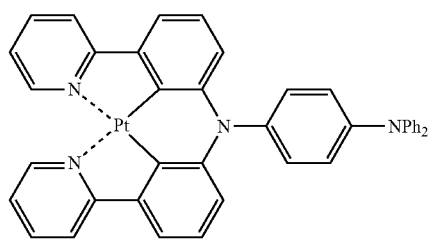
PD54
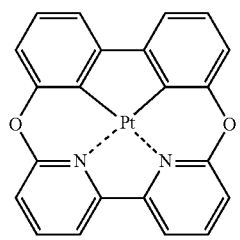
PD55
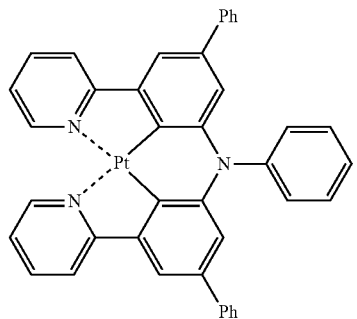
PD56
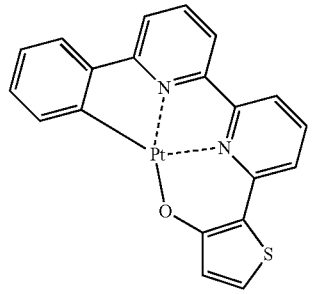
PD57
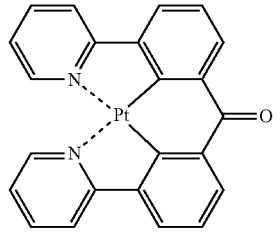

-continued
PD58
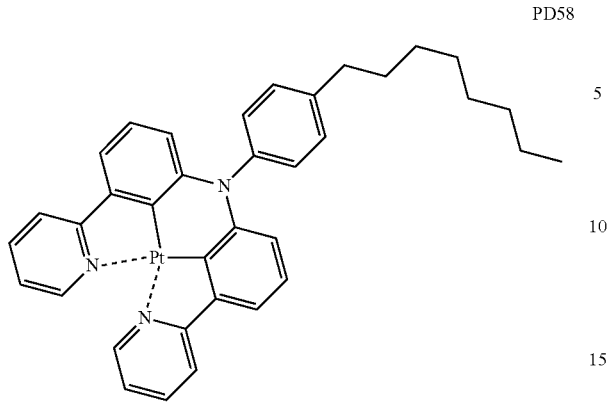
PD59
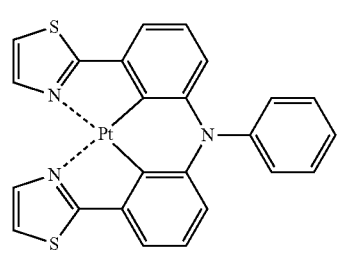
PD60
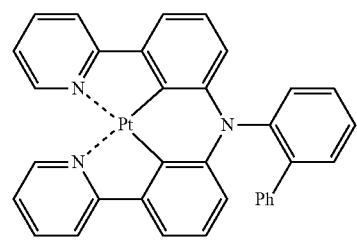
PD61
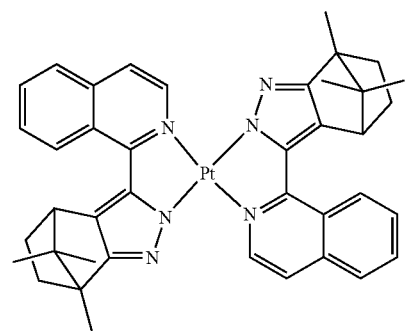
PD62
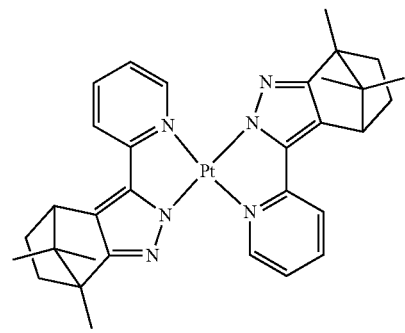
-continued
PD63
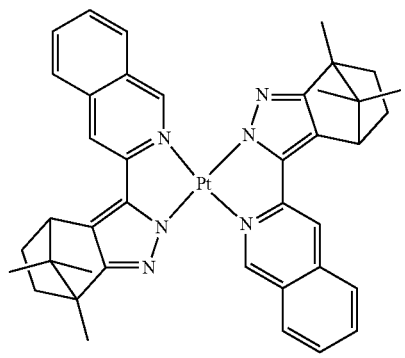
PD64
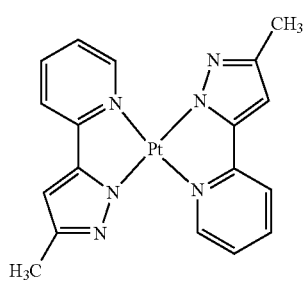
PD65
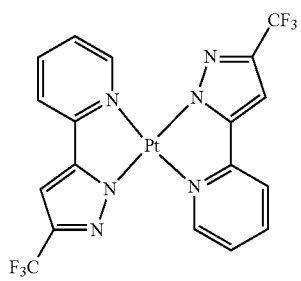
PD66
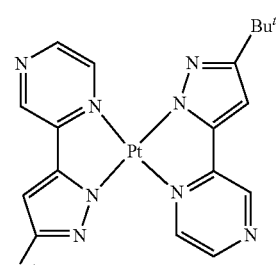
PD67
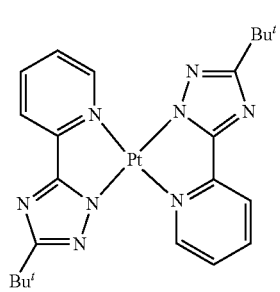

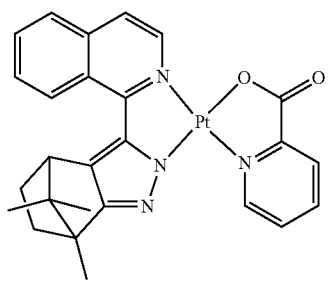
PD68
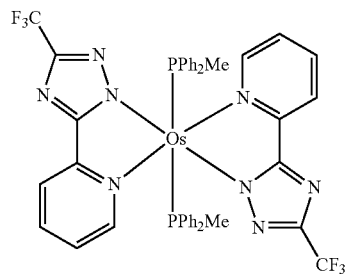
PD73
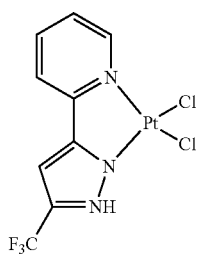
PD69
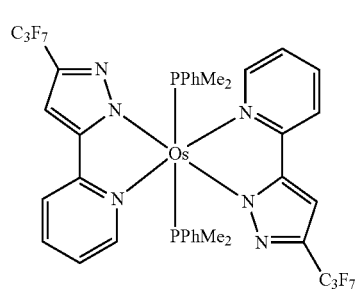
PD74
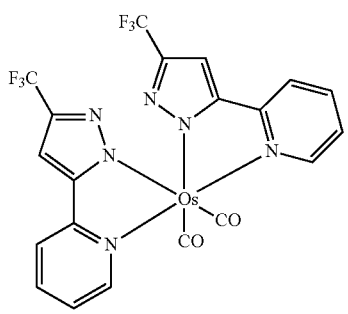
PD70
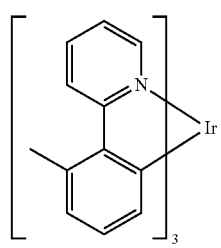
PD75
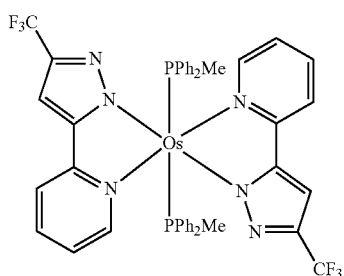
PD71
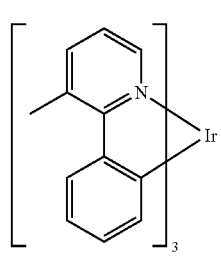
PD76
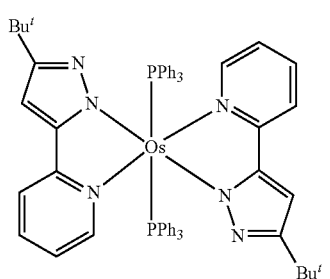
PD72
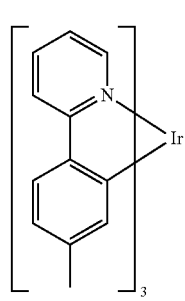
PD77

PD78
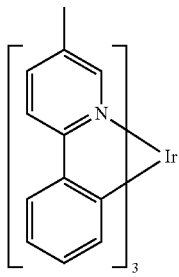
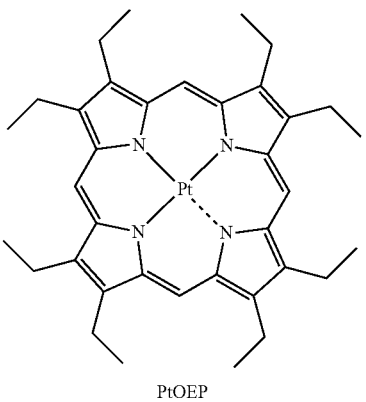
PtOEP
For example, the phosphorescent dopant may include PtOEP below:
The fluorescent dopant may include at least one of DPAVBi, BDAVBi, TBPe, DCM, DCJTB, Coumarin 6, and C545T below.
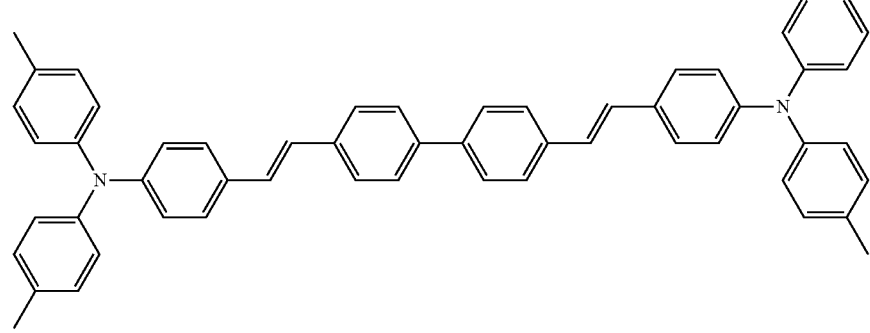
DPAVBi
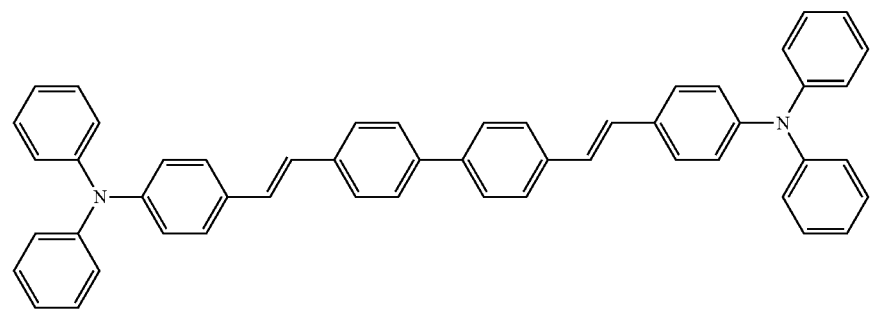
BDAVBi
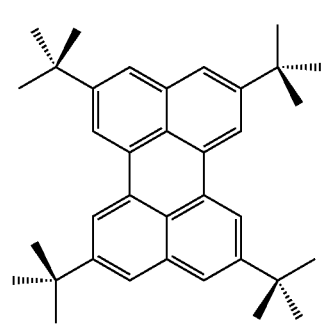
TBPe
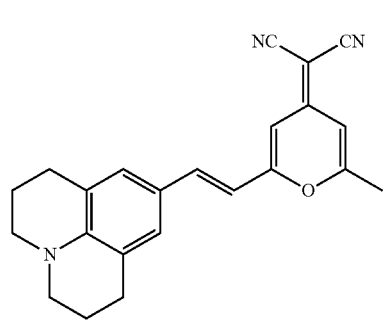
DCM
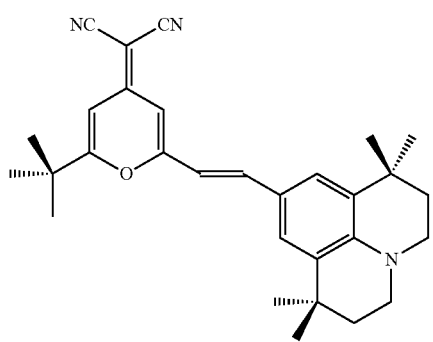
DCJTB Coumarin 6

C545T

When the EML includes both a host and a dopant, the amount of the dopant may be from about 0.01 to about 20 parts by weight based on 100 parts by weight of the host. However, the amount of the dopant is not limited to this range.

The thickness of the EML may be about 100 Å to about 1,000 Å, and in some embodiments, may be from about 200 Å to about 600 Å. When the thickness of the EML is within these ranges, the EML may have improved light emitting ability without a substantial increase in driving voltage.

Next, the electron transport region may be formed on the EML.

The electron transport region may include at least one of a HBL, an ETL, and an EIL.

In some embodiments, the electron transport region may have a structure including a HBL/ETL/EIL, or an ETL/EIL, wherein the layers forming the structure of the electron transport region may be sequentially stacked on the EML in the stated order. However, embodiments of the present disclosure are not limited thereto. The ETL may have a single-layer structure or a multi-layer structure including at least two different materials.

Conditions for forming the HBL, ETL, and EIL of the electron transport region may be the same as those for the HIL described above.

When the electron transport region includes the HBL, the HBL may include at least one of BCP below and Bphen below. However, embodiments of the present disclosure are not limited thereto.

BCP

Bphen

The thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The ETL may further include at least one of $Alq_3$, Balq, TAZ, and NTAZ below, in addition to BCP and Bphen described above.

$Alq_3$

BAlq

TAZ

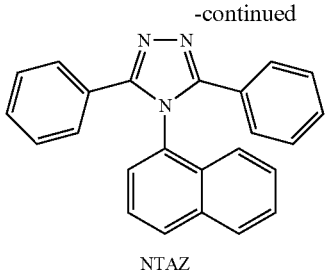

NTAZ

In some embodiments, the ETL may include at least one of Compounds ET1 and ET2 represented below, but is not limited thereto.

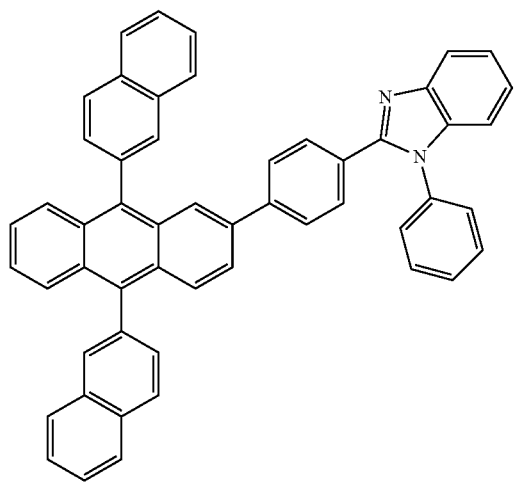

ET1

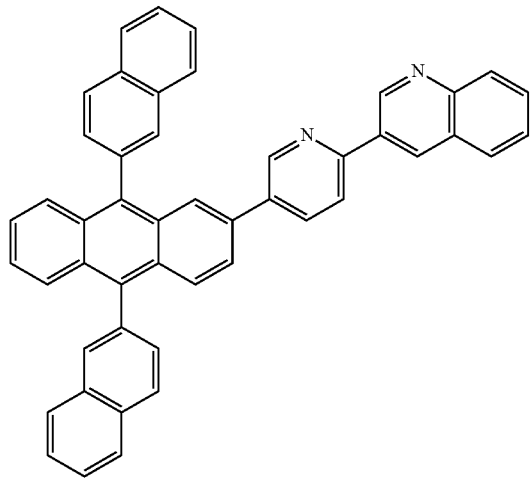

ET2

A thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex are compound ET-D1 below (lithium quinolate (LiQ)), or compound ET-D2 below.

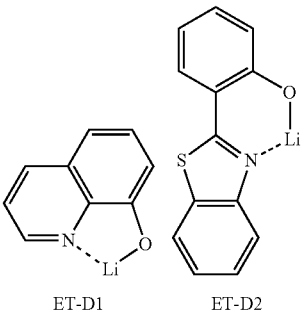

ET-D1        ET-D2

The electron transport region may include an EIL that may facilitate injection of electrons from the second electrode 19. The EIL may include at least one selected from LiF, NaCl, CsF, $Li_2O$, and BaO. The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 19 is disposed on the organic layer 15. The second electrode 19 may be a cathode. A material for the second electrode 19 may be a metal, an alloy, or an electrically conductive compound that have a low work function, or a combination thereof. Non-limiting examples of the material for the second electrode 19 are lithium (Li), magnesium (Mg), aluminum (Al), aluminum (Al)-lithium (Li), calcium (Ca), magnesium (Mg)-indium (In), and magnesium (Mg)-silver (Ag), or the like. In some embodiments, to manufacture a top-emission light-emitting device, the second electrode 19 may be formed as a transmissive electrode from, for example, indium tin oxide (ITO) or indium zinc oxide (IZO).

Although the organic light-emitting device of the FIGURE described above, embodiments of the present disclosure are not limited thereto.

As used herein, a $C_1$-$C_{60}$ alkyl group refers to a saturated linear or branched aliphatic hydrocarbon monovalent group having 1 to 60 carbon atoms. Non-limiting examples of the $C_1$-$C_{60}$ alkyl group are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above. Non-limiting examples of the $C_1$-$C_{60}$ alkoxy group are a methoxy group, an ethoxy group, and an isopropyloxy group.

As used herein, a $C_2$-$C_{60}$ alkenyl group refers to a structure including at least one carbon-carbon double bond in the middle or at the terminal of the $C_2$-$C_{60}$ alkyl group. Non-limiting examples of the $C_2$-$C_{60}$ alkenyl group are an ethenyl group, a propenyl group, and a butenyl group. A $C_2$-$C_{60}$ alkenylene group refers to a divalent group having the same structure as the $C_2$-$C_{60}$ alkenyl group.

As used herein, a $C_2$-$C_{60}$ alkynyl group refers to a structure including at least one carbon-carbon triple bond in the middle or at the terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, saturated monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_1$-$C_{10}$ heterocycloalkyl group refers to a monovalent, saturated monocyclic group having 1 to 10 carbon atoms in which at least one hetero atom selected from N, O, P, and S is included as a ring-forming atom. Non-limiting examples of the $C_1$-$C_{10}$ heterocycloalkyl group are a tetrahydrofuranyl group and a tetrahydrothiophenyl group. A $C_1$-$C_{10}$ heterocycloalkylene group refers to a divalent group having the same structure as the $C_1$-$C_{10}$ heterocycloalkyl group.

As used herein, a $C_3$-$C_{10}$ cycloalkenyl group refers to a monovalent monocyclic hydrocarbon group having 3 to 10 carbon atoms that includes at least one double bond in the ring thereof, which is not aromatic. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_1$-$C_{10}$ heterocycloalkenyl group used herein refers to a monovalent monocyclic group having 1 to 10 carbon atoms that includes at least one double bond in the ring and in which at least one hetero atom selected from N, O, P, and S is included as a ring-forming atom. Non-limiting examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group used herein refers to a divalent group having the same structure as the $C_1$-$C_{10}$ heterocycloalkenyl group.

As used herein, a $C_6$-$C_{60}$ aryl group refers to a monovalent, aromatic carbocyclic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other.

As used herein, a $C_1$-$C_{60}$ heteroaryl group refers to a monovalent, aromatic group having 1 to 60 carbon atoms in which at least one hetero atom selected from N, O, P, and S is included as a ring-forming atom. A $C_1$-$C_{60}$ heteroarylene group refers to a divalent, aromatic group having 1 to 60 carbon atoms in which at least one hetero atom selected from N, O, P, and S is included as a ring-forming atom. Non-limiting examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl and the $C_1$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group as described above), and a $C_6$-$C_{60}$ arylthio group indicates —$SA_{103}$ (where $A_{103}$ is a $C_6$-$C_{60}$ aryl group as described above).

As used herein, a monovalent non-aromatic condensed polycyclic group refers to a monovalent group having at least two rings condensed to each other, in which only carbon atoms (for example, 8 to 60 carbon atoms) are exclusively included as ring-forming atoms and the entire molecule is non-aromatic. A non-limiting example of the monovalent non-aromatic condensed polycyclic group is a fluorenyl group. A divalent non-aromatic condensed polycyclic group refers to a divalent group having the same structure as the monovalent non-aromatic condensed polycyclic group.

As used herein, a monovalent non-aromatic condensed heteropolycyclic group refers to a monovalent group having at least two rings condensed to each other, in which carbon atoms (for example, 1 to 60 carbon atoms) and a hetero atom selected from N, O, P, and S are as ring-forming atoms and the entire molecule is non-aromatic. A non-limiting example of the monovalent non-aromatic condensed heteropolycyclic group is a carbazolyl group. A divalent non-aromatic condensed heteropolycyclic group refers to a divalent group having the same structure as the monovalent non-aromatic condensed heteropolycyclic group.

As used herein, at least one of substituents of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent nonaromatic condensed polycyclic group, and the substituted monovalent nonaromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —$N(Q_{21})(Q_{22})$, —$Si(Q_{23})(Q_{24})(Q_{25})$, and —$B(Q_{26})(Q_{27})$, and —$N(Q_{31})(Q_{32})$, —$Si(Q_{33})(Q_{34})(Q_{35})$, and —$B(Q_{36})(Q_{37})$.

As used herein, $Q_1$ to $Q_7$, $Q_{11}$ to $Q_{17}$, $Q_{21}$ to $Q_{27}$, and $Q_{31}$ to $Q_{37}$ may be each independently selected from a hydrogen, $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent nonaromatic condensed polycyclic group, and a monovalent nonaromatic condensed heteropolycyclic group.

For example, at least one of substituents of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent nonaromatic condensed polycyclic group, and the substituted monovalent nonaromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —$N(Q_{11})(Q_{12})$, —$Si(Q_{13})(Q_{14})(Q_{15})$, and —$B(Q_{16})(Q_{17})$, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group 및 $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently, but is not limited to, selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group.

As used herein, the "biphenyl group" refers to a "phenyl group substituted with a phenyl group".

One or more embodiments of the present disclosure, which include condensed cyclic compounds, and organic light-emitting devices including the same, will now be described in detail with reference to the following examples. However, these examples are only for illustrative purposes and are not intended to limit the scope of one or more embodiments of the present disclosure. In the following synthesis example, the expression that "'B' instead of 'A' was used" means that 'B' was used in the same equivalent amounts as 'A'.

EXAMPLES

Synthesis Example 1: Synthesis of Compound 290

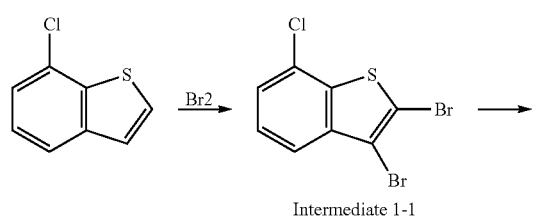

Intermediate 1-1

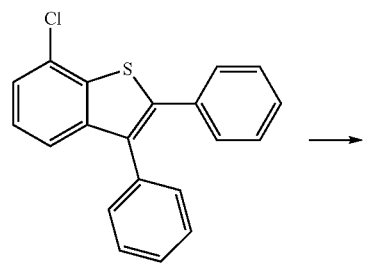

Intermediate 1-2

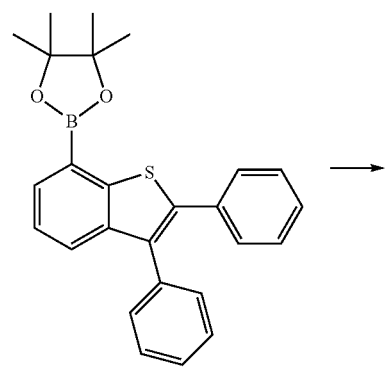

Intermediate 1-3

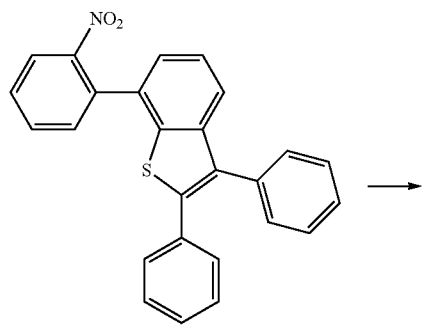

Intermediate 1-4

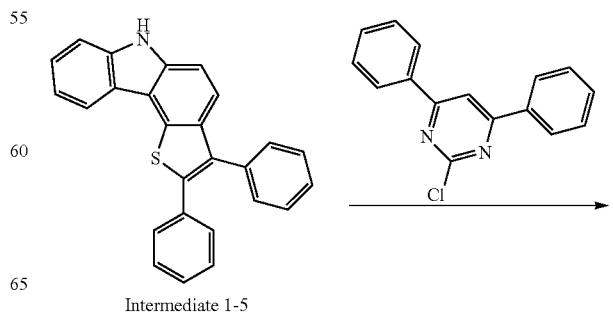

Intermediate 1-5

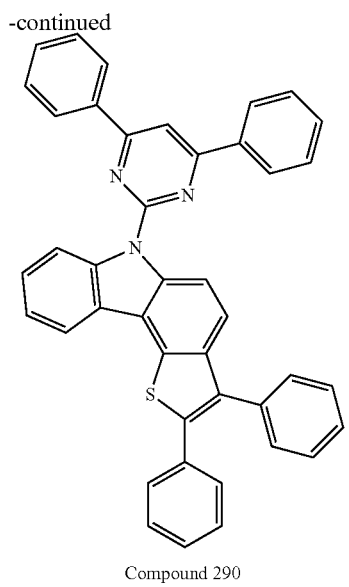

Compound 290

Synthesis of Intermediate 1-1

After 34.4 g (204.22 mmol) of 7-chlorobenzothiophene was dissolved in 680 mL of dichloromethane to obtain a solution, 81.6 g (510.56 mmol) of bromine was slowly dropwise added to the solution and stirred for about 20 hours. The resulting reaction product was poured into a sodium thiosulfate solution to terminate the reaction. An organic layer was collected from the resulting reaction product and distilled at a reduced pressure to evaporate the solvent. The residue was subjected to column chromatography to obtain 45 g of Intermediate 1-1 (Yield: 68%).

Synthesis of Intermediate 1-2

42.4 g (129.87 mmol) of 2,3-dibromo-7-chlorobenzothiophene (Intermediate 1-1), 39.6 g (324.67 mmol) of phenyl boronic acid, 53.8 g (389.60 mmol) of potassium carbonate, 7.5 g (6.49 mmol) of tetrakis(triphenylphosphine) palladium, 500 mL of tetrahydrofuran, and 200 mL of distilled water were put into a reaction vessel, and heated at about 80° C. for about 10 hours. After completion of the reaction, an organic layer was collected from the resulting reaction product and distilled at a reduced pressure to evaporate the solvent. The residue was subjected to column chromatography to obtain 30 g of Intermediate 1-2 (Yield: 72%).

Synthesis of Intermediate 1-3

25.9 g (80.84 mmol) of 2,3-diphenyl-7-chlorobenzothiophene (Intermediate 1-2), 28.74 g (113.17 mmol) of bispinacolato diboron, 15.87 g (161.67 mmol) of potassium acetate, 1.98 g (2.43 mmol) of (diphenylphosphino)ferrocene-palladium(II) dichloride, and 320 mL of toluene were put into a reaction vessel and heated at about 100° C. for about 12 hours. The resulting reaction product was filtered and distilled at a reduced pressure to evaporate the solvent. The residue was separated by column chromatography to obtain 26.4 g of Intermediate 1-3 (Yield: 79%).

Synthesis of Intermediate 1-4

101.2 g (245.41 mmol) of Intermediate 1-3, 59.5 g (294.49 mmol) of 2-bromonitrobenzene, 67.8 g (490.82 mmol) of potassium carbonate, 14.2 g (12.27 mmol) of tetrakis(triphenylphosphine) palladium, 245 mL of distilled water, and 1 L of toluene were put into a reaction vessel, and heated at about 100° C. for about 8 hours. An organic layer was collected from the resulting reaction product and distilled at a reduced pressure to evaporate the solvent. The residue was subjected to column chromatography to obtain 78.4 g of Intermediate 1-4 (Yield: 78%).

Synthesis of Intermediate 1-5

72.3 g (177.55 mmol) of Intermediate 1-4, 139.7 g (532.65 mmol) of triphenylphosphine, and 710 mL of dichlorobenzene were heated at about 180° C. for about 12 hours. The resulting reaction product was distilled at a reduced pressure to evaporate the solvent. The residue was subjected to column chromatography to obtain 46.7 g of Intermediate 1-5 (Yield: 70%).

Synthesis of Compound 290

After 13.3 g (35.38 mmol) of Intermediate 1-5 and 2.83 g (70.75 mmol) of sodium hydride were added to 100 mL of dimethylformamide and stirred for about 30 minutes, a solution of 11.3 g (42.45 mmol) of 2-chloro-4,6-diphenylpyrimidine dissolved in 150 mL of dimethylformamide was dropwise added thereto and stirred for about 8 hours. The resulting reaction product was poured into water to obtain a solid, which was filtered, and then recrystallized using chlorobenzene to obtain 15.8 g of Compound 290 (Yield: 74%).

calcd. $C_{42}H_{27}N_3S$: C, 83.28; H, 4.49; N, 6.94; S, 5.29. found: C, 83.54; H, 4.52; N, 6.90.

1H-NMR (300 MHz, CDCl$_3$) (ppm) δ=7.25~7.30 (3H, m), 7.42~7.47 (7H, m), 7.59~7.67 (8H, m), 7.72~7.75 (1H, d), 8.88 (1H, s), 8.29~8.32 (5H, m), 9.01~9.07 (2H, m)

Synthesis Example 2: Synthesis of Compound 292

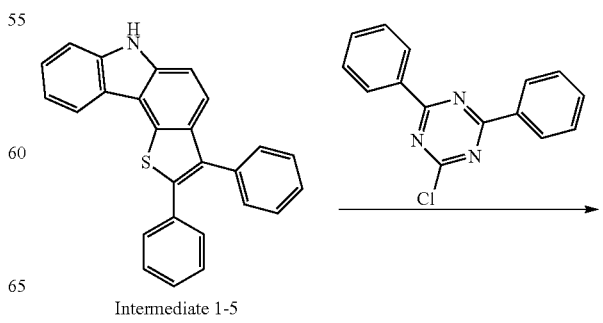

Intermediate 1-5

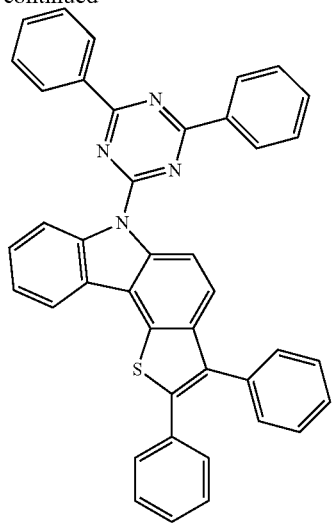

Compound 292

After 13.26 g (35.32 mmol) of Intermediate 1-5 and 2.825 g (70.64 mmol) of sodium hydride were added to 100 mL of dimethylformamide and stirred for about 30 minutes, a solution of 11.35 g (42.38 mmol) of 2-chloro-4,6-diphenyl-triazine dissolved in 150 mL of dimethylformamide was dropwise added thereto and stirred for about 8 hours. The resulting reaction product was poured into water to obtain a solid, which was filtered, and then recrystallized using chlorobenzene to obtain 17.4 g of Compound 292 (Yield: 81%).

calcd. $C_{41}H_{26}N_4S$: C, 81.16; H, 4.32; N, 9.23; S, 5.28. found: C, 81.32; H, 4.25; N, 9.33.

1H-NMR (300 MHz, $CDCl_3$) (ppm) δ=7.29~7.33 (3H, m), 7.43~7.64 (15H, m), 7.72~7.75 (1H, d), 8.20~8.23 (1H, d), 8.68~8.71 (4H, d), 9.13~9.18 (2H, m)

Synthesis Example 3: Synthesis of Compound 434

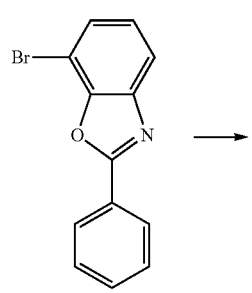

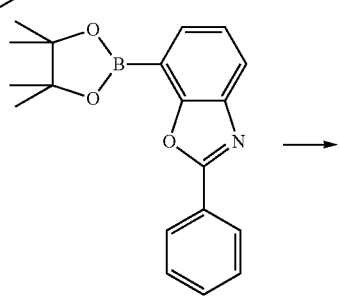

Intermediate 2-1

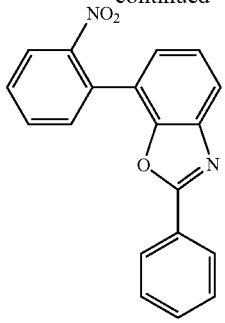

Intermediate 2-2

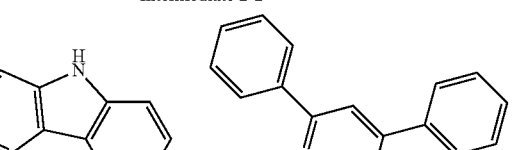

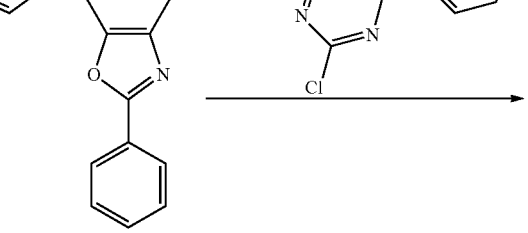

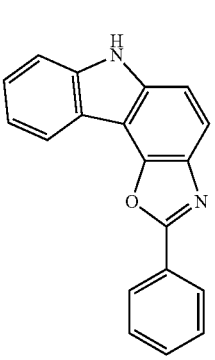

Intermediate 2-3

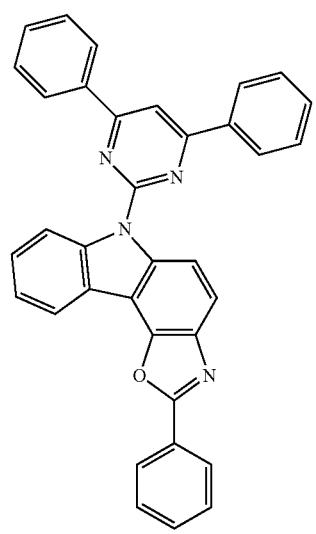

Compound 434

Synthesis of Intermediate 2-1

56.9 g (207.57 mmol) of 1-bromo-5-phenylbenzoxazole, 73.8 g (290.60 mmol) of bispinacolato diboron, 40.75 g (415.14 mmol) of potassium acetate, 5.085 g (6.23 mmol) of (diphenylphosphino)ferrocene-palladium(II) dichloride, and 320 mL of toluene were put into a reaction vessel and heated at about 100° C. for about 12 hours. The resulting reaction product was filtered and distilled at a reduced pressure to evaporate the solvent. The residue was subjected to column chromatography to obtain 45.2 g of Intermediate 2-1 (Yield: 68%).

Synthesis of Intermediate 2-2

42.3 g (131.73 mmol) of Intermediate 2-1, 31.9 g (158.07 mmol) of 2-bromonitrobenzene, 36.4 g (263.45 mmol) of potassium carbonate, 7.6 g (6.6 mmol) of tetrakis(triphenylphosphine) palladium, 130 mL of distilled water, and 530 mL of toluene were put into a reaction vessel, and heated at about 100° C. for about 8 hours. An organic layer was collected from the resulting reaction product and distilled at a reduced pressure to evaporate the solvent. The residue was subjected to column chromatography to obtain 28.9 g of Intermediate 2-2 (Yield: 69%).

Synthesis of Intermediate 2-3

25.87 g (81.8 mmol) of Intermediate 2-2, 64.37 g (245.41 mmol) of triphenylphosphine, and 330 mL of dichlorobenzene were heated at about 180° C. for about 12 hours. The resulting reaction product was distilled at a reduced pressure to evaporate the solvent. The residue was subjected to column chromatography to obtain 28.2 g of Intermediate 2-3 (Yield: 85%).

Synthesis of Compound 434

After 11.84 g (41.64 mmol) of Intermediate 2-3 and 2.5 g (62.46 mmol) of sodium hydride were added to 100 mL of dimethylformamide and stirred for about 30 minutes, a solution of 13.3 g (49.97 mmol) of 2-chloro-4,6-diphenylpyrimidine dissolved in 150 mL of dimethylformamide was dropwise added thereto and stirred for about 8 hours. The resulting reaction product was poured into water to obtain a solid, which was filtered, and then recrystallized using chlorobenzene to obtain 16.4 g of Compound 434 (Yield: 77%).

calcd. $C_{35}H_{22}N_4O$: C, 81.69; H, 4.31; N, 10.89; O, 3.11. found: C, 81.82; H, 4.29; N, 10.76.

1H-NMR (300 MHz, CDCl$_3$) (ppm) δ=7.54~7.56 (10H, m), 7.84~7.87 (1H, d), 7.94 (1H, s), 8.24~8.28 (4H, m), 8.36~8.42 (3H, m), 8.93~8.99 (2H, m)

Synthesis Example 4: Synthesis of Compound 436

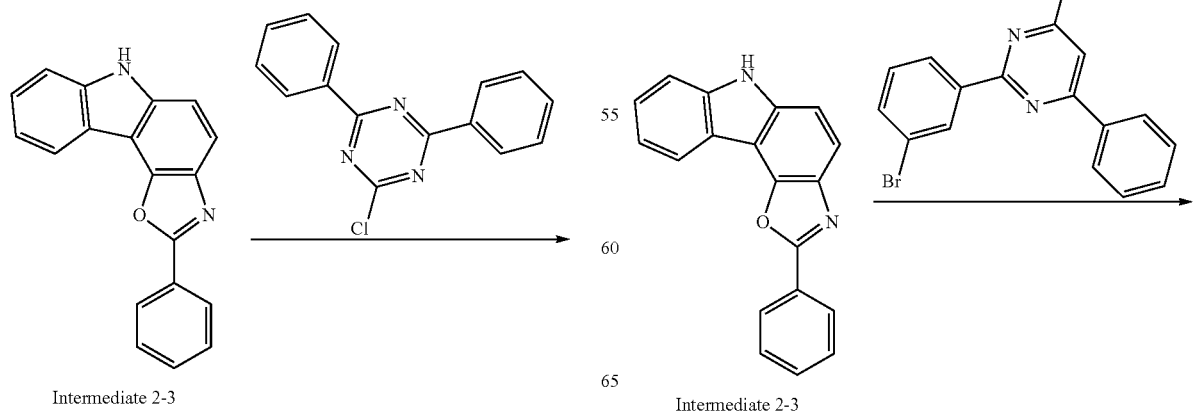

Intermediate 2-3

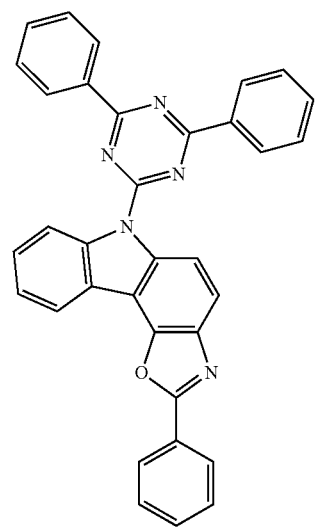

Compound 436

After 11.82 g (41.56 mmol) of Intermediate 2-3 and 2.49 g (62.35 mmol) of sodium hydride were added to 100 mL of dimethylformamide and stirred for about 30 minutes, a solution of 13.35 g (49.88 mmol) of 2-chloro-4,6-diphenyltriazine dissolved in 150 mL of dimethylformamide was dropwise added thereto and stirred for about 8 hours. The resulting reaction product was poured into water to obtain a solid, which was filtered, and then recrystallized using chlorobenzene to obtain 18.3 g of Compound 436 (Yield: 85%).

calcd. $C_{34}H_{21}N_5O$: C, 79.21; H, 4.11; N, 13.58; 0, 3.10. found: C, 79.34; H, 4.13; N, 13.45.

1H-NMR (300 MHz, CDCl$_3$) (ppm) δ=7.56~7.73 (10H, m), 7.96~7.99 (1H, d), 8.41~8.46 (3H, m), 8.77~8.80 (4H, m), 9.18~9.26 (2H, m)

Synthesis Example 5: Synthesis of Compound 438

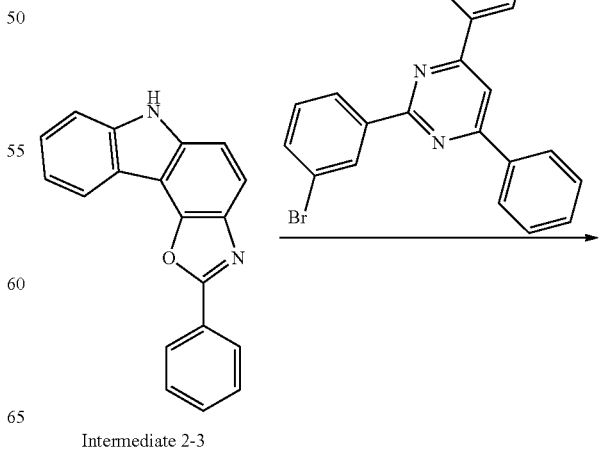

Intermediate 2-3

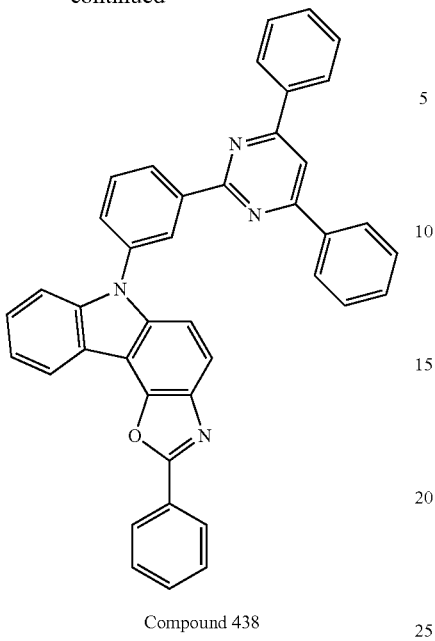

Compound 438

12.03 g (42.32 mmol) of Intermediate 2-3, 19.67 g (50.79 mmol) of 2-(3-bromophenyl)-4,6-diphenylpyrimidine, 1.217 g (2.12 mmol) of bis(dibenzylideneacetone)palladium, 6.102 g (63.49 mmol) of sodium-tert-butoxide, 4.107 g (8.46 mmol) of tri-tert-butylphosphine (50% toluene), and 170 mL of toluene were put into a reaction vessel, and stirred in a nitrogen atmosphere at about 110° C. for about 12 hours. After termination of the reaction, the resulting reaction solution was filtered, and recrystallized using chlorobenzene to obtain 17.4 g of Compound 438 (Yield: 70%).

calcd. $C_{41}H_{26}N_4O$: C, 83.37; H, 4.44; N, 9.49; O, 2.71. found: C, 83.41; H, 4.32; N, 9.42.

1H-NMR (300 MHz, $CDCl_3$) (ppm) δ=7.45~7.65 (13H, m), 7.74~7.77 (1H, m), 7.81~7.86 (2H, m), 8.10 (1H, s), 8.27~8.31 (4H, m), 8.41~8.45 (2H, m), 8.51~8.54 (1H, m), 8.89~8.93 (1H, m), 8.97~8.98 (1H, m)

Synthesis Example 6: Synthesis of Compound 440

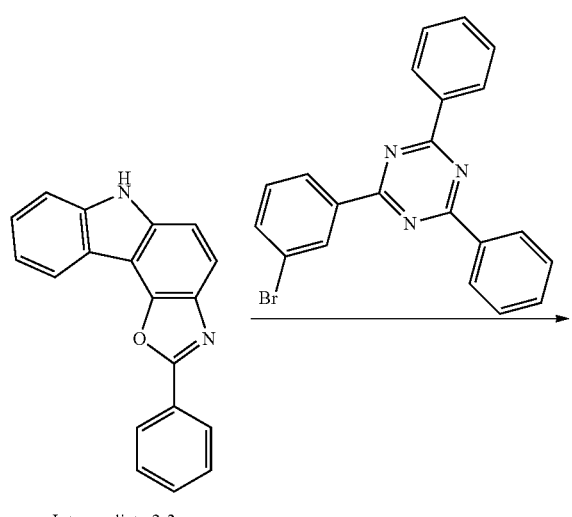

Intermediate 2-3

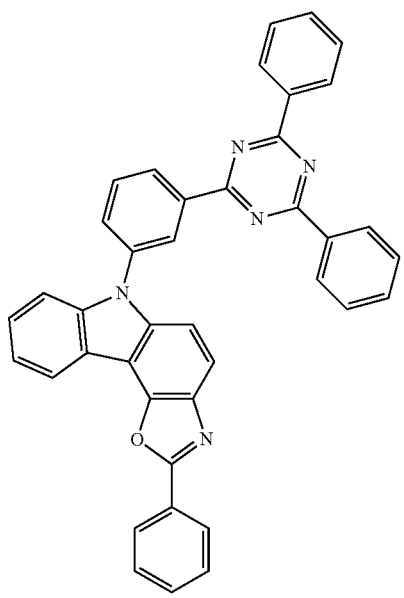

Compound 440

16.02 g (56.43 mmol) of Intermediate 2-3, 26.25 g (67.34 mmol) of 2-(3-bromophenyl)-4,6-diphenyltriazine, 1.620 g (2.82 mmol) of bis(dibenzylideneacetone)palladium, 8.122 g (84.51 mmol) of sodium-tert-butoxide, 5.47 g (11.27 mmol) of tri-tert-butylphosphine (50% toluene), and 225 mL of toluene were put into a reaction vessel, and stirred in a nitrogen atmosphere at about 110° C. for about 12 hours. After termination of the reaction, the resulting reaction solution was filtered, and recrystallized using chlorobenzene to obtain 22.8 g of Compound 440 (Yield: 68%).

calcd. $C_{40}H_{25}N_5O$: C, 81.20; H, 4.26; N, 11.84; O, 2.70. found: C, 81.14; H, 4.28; N, 11.81.

1H-NMR (300 MHz, $CDCl_3$) (ppm) δ=7.42~7.63 (13H, m), 7.80~7.88 (3H, m), 8.38~8.42 (2H, m), 8.49~8.52 (1H, m), 8.73~8.77 (4H, m), 8.91~8.97 (1H, m), 9.00 (1H, s)

Evaluation Example 1: Evaluation of HOMO, LUMO, and T1 Energy Levels

The highest occupied molecular orbital (HOMO), lowest unoccupied molecular orbital (LUMO), and triplet (T1) energy levels of Compounds 290, 292, 434, 436, 438, and 440 were evaluated according to the methods described in Table 2 below. The results are shown in Table 3.

TABLE 2

| | |
|---|---|
| HOMO energy level evaluation method | A potential (V)-current (A) plot of each of the compounds was obtained using cyclic voltammetry (CV) (Electrolyte: 0.1M Bu$_4$NClO$_4$/Solvent: CH$_2$Cl$_2$/ Electrode: 3-electrode system (working electrode: GC, reference electrode: Ag/AgCl, auxiliary electrode: Pt)), and a HOMO energy level of the compound was calculated based on the reduction onset potential in the potential-current plot. |
| LUMO energy level evaluation method | Each of the compounds was diluted in CHCl$_3$ to a concentration of 1 × 10$^{-5}$M, and then UV absorption spectra thereof were measured at room temperature using a spectrometer (Shimadzu UV-350 Spectrometer). A LUMO energy level of the compound was calculated based on the optical band gap (Eg) of the absorption spectrum edge. |
| T1 energy level evaluation method | A mixture of each of the compounds and toluene (prepared by dissolving 1 mg of the compound in 3 cc of toluene) was put in a quartz cell, which was then placed in liquid nitrogen (77 K) for photoluminescence spectroscopy. Photoluminescence spectra of the compounds were measured using a photoluminescence spectrometer, and then compared with those at room temperature to analyze only peaks appearing at low temperature. A T1 energy level of each of the compounds was calculated based on the low-temperature peaks. |

TABLE 3

| Compound No. | HOMO (eV) (found) | LUMO (eV) (found) | T$_1$ Energy Level (eV) |
|---|---|---|---|
| 290 | −5.83 | −2.45 | 2.32 |
| 292 | −5.96 | −2.61 | 2.33 |
| 434 | −5.97 | −2.57 | 2.57 |
| 436 | −5.66 | −2.27 | 2.59 |
| 438 | −5.97 | −2.60 | 2.54 |
| 440 | −5.69 | −2.34 | 2.53 |

Referring to Table 3, Compounds 290, 292, 434, 436, 438, and 440 were found to have electrical characteristics suitable for use as materials for organic light-emitting devices.

Evaluation Example 2: Thermal Characteristics Evaluation

Thermal analysis of each of the synthesized compounds was performed using thermo gravimetric analysis (TGA) and differential scanning calorimetry (DSC) (N$_2$ atmosphere, temperature range: room temperature to 800° C. (10° C./min)-TGA, room temperature to 400° C.-DSC, Pan Type: Pt Pan in disposable Al Pan (TGA), disposable Al pan (DSC)). The results are shown in Table 4. Referring to Table 4, Compounds 290, 292, 434, 436, 438, and 440 were found to have good thermal stabilities.

TABLE 4

| Compound No. | Tc (° C.) | Tm (° C.) | Tg (° C.) | Td$_{5\%}$ (° C.) |
|---|---|---|---|---|
| 290 | 217.6 | 245.7 | 121.5 | 446 |
| 292 | 213.6 | 262.4 | 126.5 | 448 |
| 434 | 160, 189 | 233.8 | 96.8 | 425 |
| 436 | 247 | 306 | ND | 424 |
| 438 | 269.4 | 293.1 | 123.2 | 442 |
| 440 | 260.8 | 315.2 | ND | 440 |

Example 1

After a glass substrate with an indium tin oxide (ITO) electrode (first electrode, anode) having a thickness of about 1,500 Å was ultrasonically washed with distilled water, and then with a solvent such as isopropyl alcohol, acetone, and methanol, the washed glass substrate was dried, moved to a plasma cleaning system, and then cleaned using oxygen plasma for about 5 minutes. The glass substrate was then loaded into a vacuum deposition device.

Compound HT5 was vacuum-deposited on the ITO electrode of the glass substrate to form a HTL having a thickness of about 1,200 Å and form a hole transport region.

Compound 434 (host) and PhGD (dopant, 10 percent by weight (wt %), see Compound PD75) were co-deposited on the hole transport region to form an EML having a thickness of about 300 Å.

Subsequently, BAlq was vacuum-deposited on the EML to form a first ETL having a thickness of about 50 Å, and then Alq$_3$ was vacuum-deposited on the first ETL to form a second ETL having a thickness of about 250 Å. Then, LiF was deposited on the second ETL to form an EIL having a thickness of about 5 Å, and Al was deposited on the EIL to a thickness of about 1,000 Å to form a second electrode (cathode), thereby completing the manufacture of an organic light-emitting device.

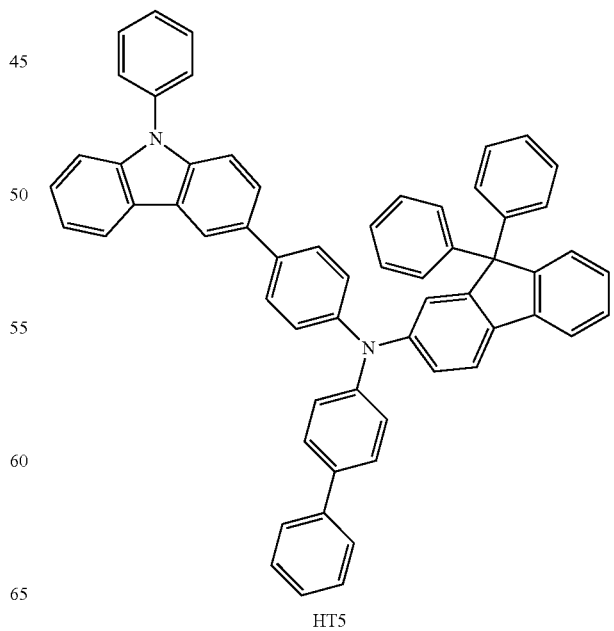

HT5

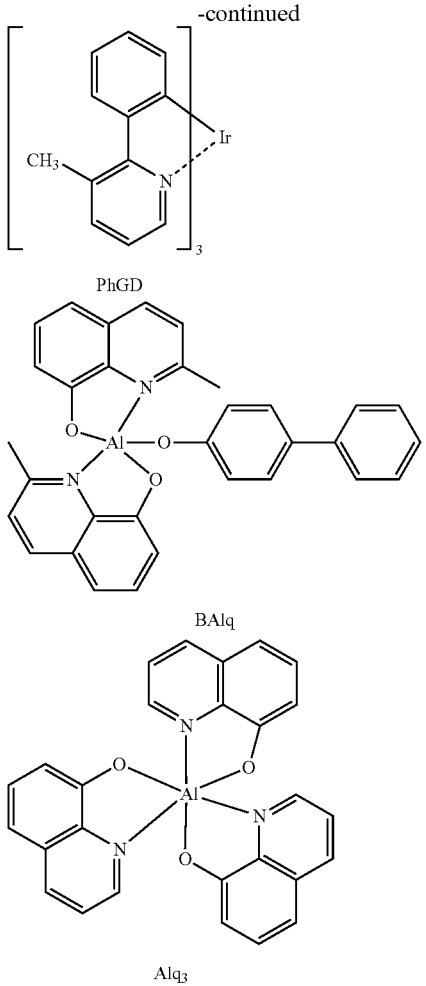

PhGD

BAlq

Alq₃

Example 2

An organic light-emitting device was manufactured in the same manner as in Example 1, except that Compound 436, instead of Compound 434, was used as a host to form the EML.

Example 3

An organic light-emitting device was manufactured in the same manner as in Example 1, except that Compound 438, instead of Compound 434, was used as a host to form the EML.

Example 4

An organic light-emitting device was manufactured in the same manner as in Example 1, except that Compound 440, instead of Compound 434, was used as a host to form the EML.

Comparative Example 1

An organic light-emitting device was manufactured in the same manner as in Example 1, except that CBP, instead of Compound 434, was used to form the EML.

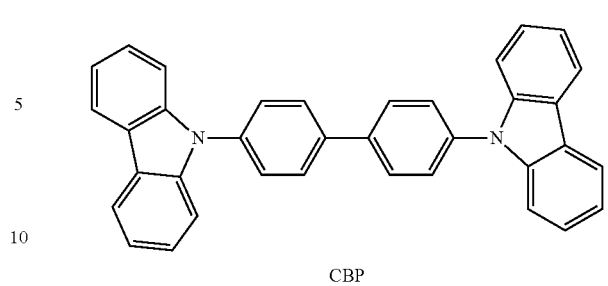

CBP

Evaluation Example 3: Characteristics Evaluation of Organic Light-Emitting Devices Current density changes with respect to voltage, luminance changes, and emission efficiencies in the organic light-emitting devices of Examples 1 to 4 and Comparative Example 1 were measured according to the following methods. The results are shown in Table 5 below.

(1) Measurement of Current Density Changes with Respect to Voltage Changes

A current value flowing through each of the organic light-emitting devices was measured while increasing a voltage from 0 volts (V) to about 10 V by using a current-voltage source meter (Keithley 2400), and then was divided by the area of the corresponding light-emitting device to obtain a current density.

(2) Measurement of Luminance Changes with Respect to Voltage Changes

The luminances of the organic light-emitting devices were measured while increasing a voltage from about 0 V to about 10 V by using a Minolta CS-1000A spectroradiometer.

(3) Measurement of Emission Efficiency

Current efficiencies at a certain current density of 10 milliamperes per square centimeter ($mA/cm^2$) of the organic light-emitting devices were calculated based on the current densities, voltages, and luminances obtained from the above-described measurements (1) and (2).

TABLE 5

| Example | Host | Dopant | Driving voltage (V) | Efficiency (cd/A) | Color coordinates CIE x | CIE y |
|---|---|---|---|---|---|---|
| Example 1 | 434 | PhGD | 4.0 | 57.9 | 0.374 | 0.591 |
| Example 2 | 436 | PhGD | 4.2 | 49.4 | 0.371 | 0.593 |
| Example 3 | 438 | PhGD | 4.2 | 45.2 | 0.373 | 0.592 |
| Example 4 | 440 | PhGD | 4.1 | 51.4 | 0.372 | 0.594 |
| Comparative Example 1 | CBP | PhGD | 8 | 45.1 | 0.33 | 0.62 |

Referring to Table 5, the organic light-emitting devices of Examples 1 to 4 were found to have lower driving voltages and higher efficiencies, compared to those of the organic light-emitting device of Comparative Example 1.

Synthesis Example 7: Synthesis of Compound A1

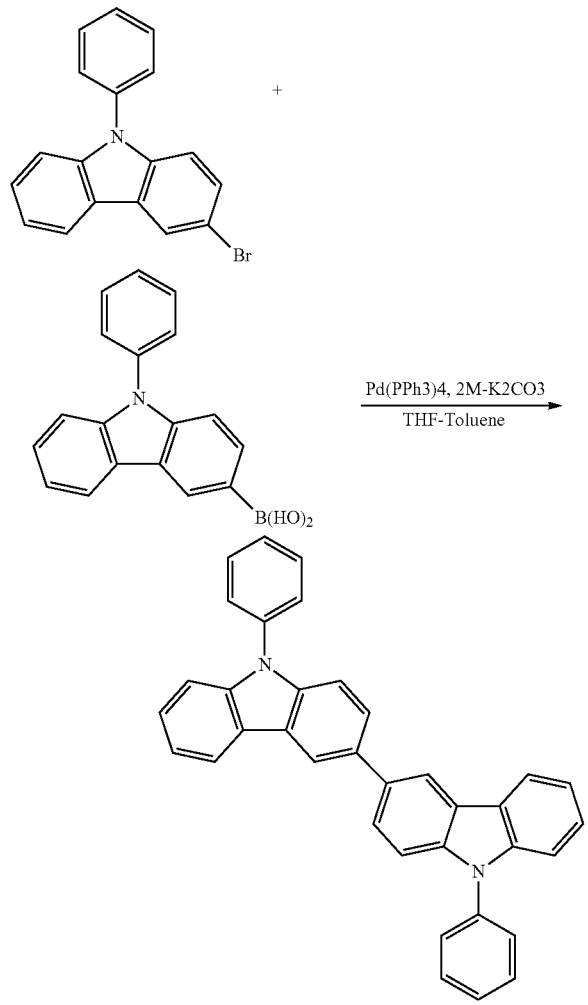

Compound A1

16.62 g (51.59 mmol) of 3-bromo-N-phenylcarbazole, 17.77 g (61.91 mmol) of N-phenylcarbazole-3-ylboronic acid, and 200 mL of a mixture of tetrahydrofuran (THF) and toluene (1:1), and 100 mL of an aqueous solution of 2 M potassium carbonate were mixed in a 500-mL round-bottom flask equipped with a stirrer in a nitrogen atmosphere, and 2.98 g (2.58 mmol) of tetrakis(triphenylphosphine)palladium(0) was added thereto, and heated under reflux in a nitrogen atmosphere for about 12 hours. After completion of the reaction, the reaction product was added to methanol to obtain a solid by filtering. This solid was thoroughly washed with water and methanol, and then dried. The resulting product was dissolved in 1 L of chlorobenzene by heating, followed by filtration using silica gel and removing the solvent. The resulting product was dissolved in 500 mL of toluene by heating, followed by recrystallization to obtain Compound A1 (16.05 g, Yield: 64%).

calcd. $C_{36}H_{24}N_2$: C, 89.23; H, 4.99; N, 5.78. found: C, 89.45; H, 4.89; N, 5.65.

Synthesis Example 8: Synthesis of Compound A2

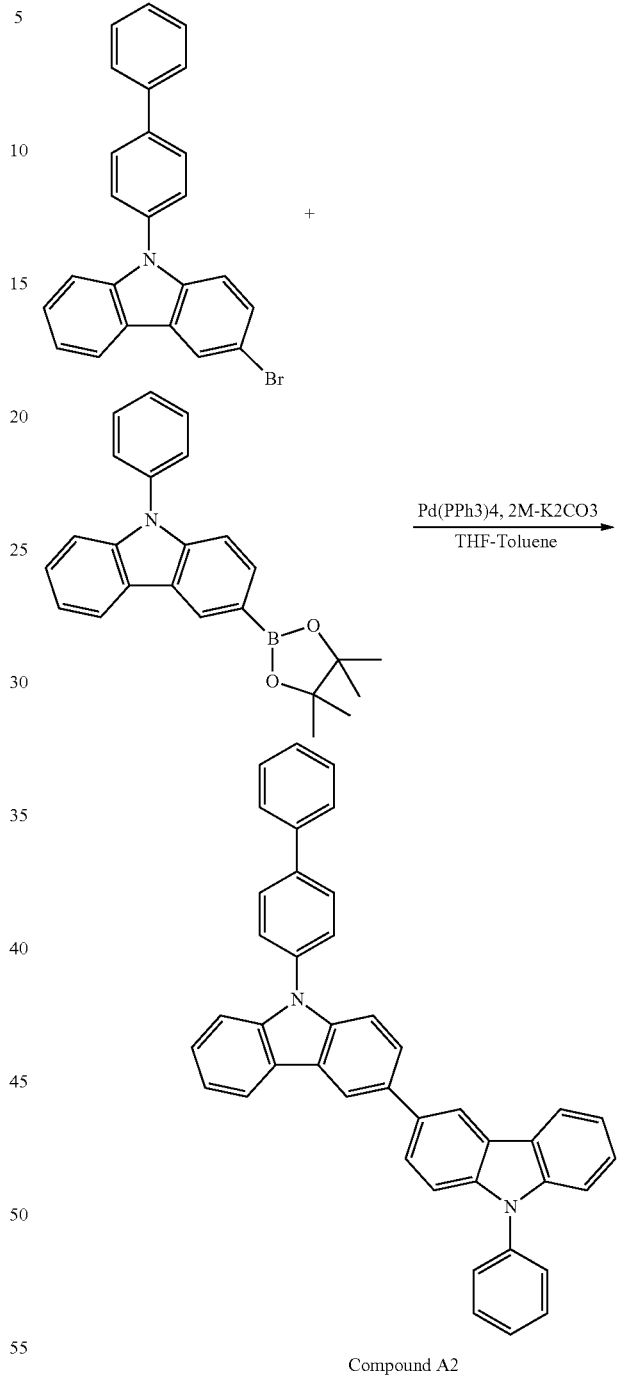

Compound A2

20.00 g (50.21 mmol) of 3-bromo-N-biphenylcarbazole, 18.54 g (50.21 mmol) of N-phenylcarbazole-3-boronic ester, and 175 mL of a mixture of tetrahydrofuran (THF) and toluene (1:1), and 75 mL of an aqueous solution of 2 M potassium carbonate were mixed in a 500-mL round-bottom flask equipped with a stirrer in a nitrogen atmosphere, and 2.90 g (2.51 mmol) of tetrakis(triphenylphosphine)palladium(0) was added thereto, and heated under reflux in a nitrogen atmosphere for about 12 hours. After completion of the reaction, the reaction product was added to methanol to obtain a solid by filtering. This solid was thoroughly washed with water and methanol, and then dried. The resulting product was dissolved in 700 mL of chlorobenzene by heating, followed by filtration using silica gel and removing the solvent. The resulting product was dissolved in 400 mL of chlorobenzene by heating, followed by recrystallization to obtain Compound A2 (19.15 g, Yield: 68%).

calcd. $C_{42}H_{28}N_2$: C, 89.97; H, 5.03; N, 5.00. found: C, 89.53; H, 4.92; N, 4.89.

Synthesis Example 9: Synthesis of Compound A5

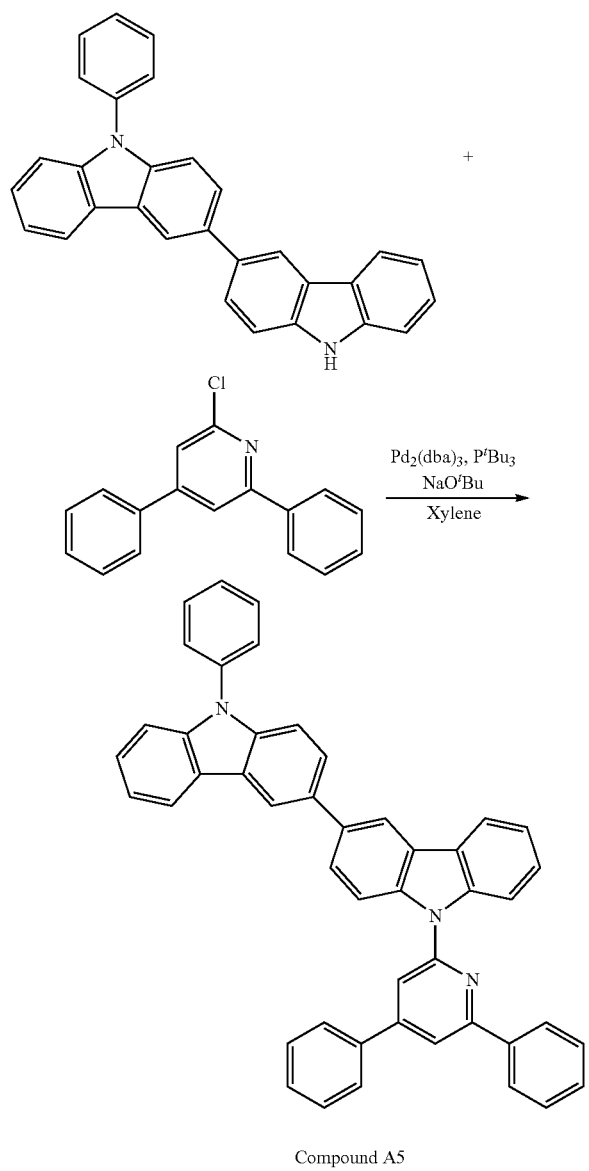

Compound A5

12.81 g (31.36 mmol) of N-phenyl-3,3-bicarbazole, 8.33 g (31.36 mmol) of 2-chloro-di-4,6-phenylpyridine, 6.03 g (62.72 mmol) of sodium t-butoxide, 1.80 g (3.14 mmol) of tris(dibenzylideneacetone)dipalladium, and 2.6 mL of tri-t-butylphosphine (50% in toluene) were added to 200 mL of xylene in a 500-mL round-bottom flask, and heated under reflux in a nitrogen atmosphere for about 15 hours. The resulting mixture was added to 600 mL of methanol to obtain crystalline solid powder by filtering. The resulting product was dissolved in dichlorobenzene and filtered using Silica gel/Celite, followed by removing an appropriate amount of the organic solvent and recrystallization with methanol to obtain Compound A5 (13.5 g, Yield: 68%).

calcd. $C_{47}H_{31}N_3$: C, 88.51; H, 4.90; N, 6.59. found: C, 88.39; H, 4.64; N, 6.43.

Synthesis Example 10: Synthesis of Compound A15

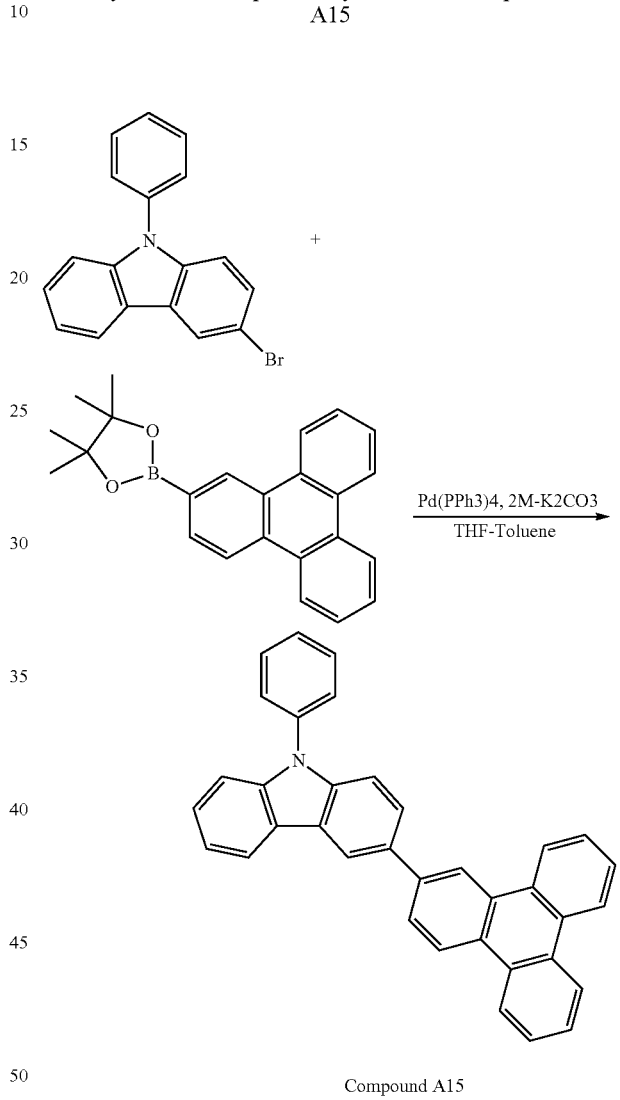

Compound A15

10.00 g (31.04 mmol) of 3-bromo-N-phenylcarbazole, 10.99 g (31.04 mmol) of 2-triphenylene boronic ester, 150 mL of a mixture of tetrahydrofuran (THF) and toluene (1:1), and 75 mL of an aqueous solution of 2 M potassium carbonate were mixed in a 500-mL round-bottom flask equipped with a stirrer in a nitrogen atmosphere, and 1.79 g (1.55 mmol) of tetrakis(triphenylphosphine)palladium(0) was added thereto, and heated under reflux in a nitrogen atmosphere for about 12 hours. After completion of the reaction, the reaction product was added to methanol to obtain a solid by filtering. This solid was thoroughly washed with water and methanol, and then dried. The resulting product was dissolved in 400 mL of chlorobenzene by heating, followed by filtration using silica gel and removing the solvent. The resulting product was dissolved in 300 mL of toluene by heating, followed by recrystallization to obtain Compound A15 (8.74 g, Yield: 60%).

calcd. $C_{36}H_{23}N$: C, 92.08; H, 4.94; N, 2.98. found: C, 92.43; H, 4.63; N, 2.84.

Synthesis Example 11: Synthesis of Compound A17

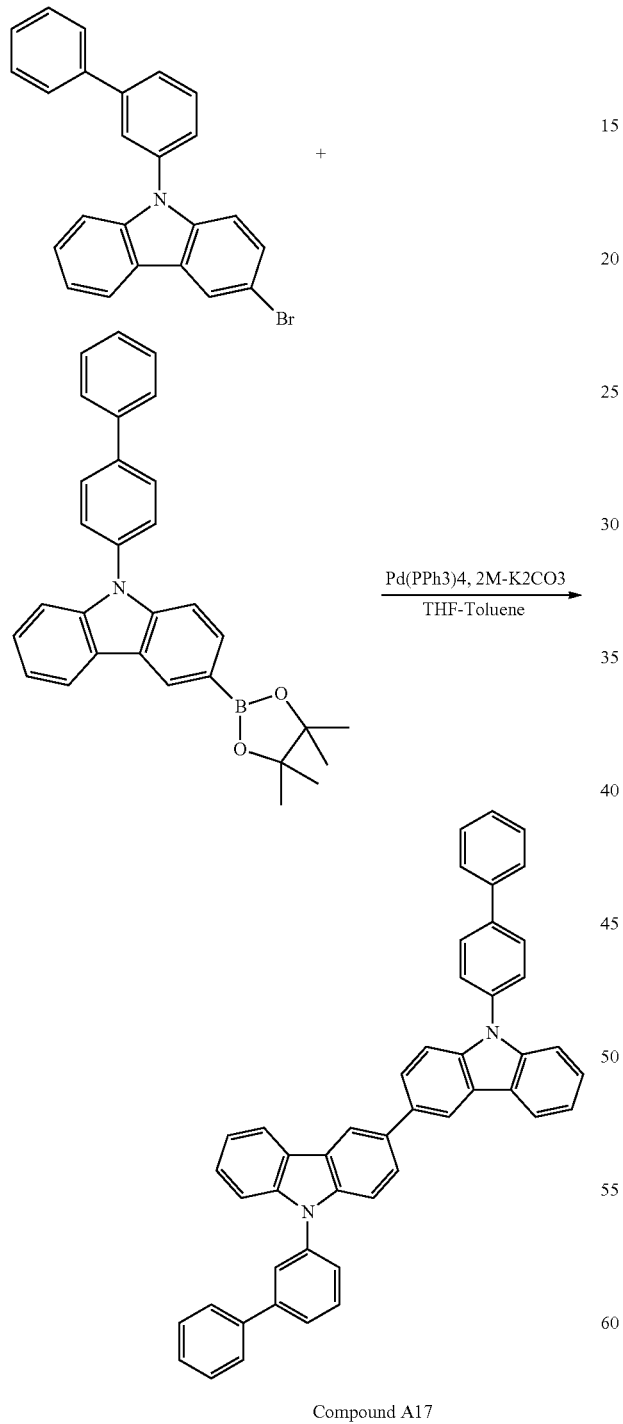

Compound A17

15.00 g (37.66 mmol) of 3-bromo-N-meta-biphenylcarbazole, 16.77 g (37.66 mmol) of 3-boronic ester-N-biphenyl carbazole, 200 mL of a mixture of tetrahydrofuran (THF) and toluene (1:1), and 100 mL of an aqueous solution of 2 M potassium carbonate were mixed in a 500-mL round-bottom flask equipped with a stirrer in a nitrogen atmosphere, and 2.18 g (1.88 mmol) of tetrakis(triphenylphosphine)palladium(0) was added thereto, and heated under reflux in a nitrogen atmosphere for about 12 hours. After completion of the reaction, the reaction product was added to methanol to obtain a solid by filtering. This solid was thoroughly washed with water and methanol, and then dried. The resulting product was dissolved in 500 mL of chlorobenzene by heating, followed by filtration using silica gel and removing the solvent. The resulting product was dissolved in 400 mL of toluene by heating, followed by recrystallization to obtain Compound A17 (16.07 g, Yield: 67%).

calcd. $C_{48}H_{32}N_2$: C, 90.54; H, 5.07; N, 4.40. found: C, 90.71; H, 5.01; N, 4.27.

Synthesis Example 12: Synthesis of Compound B2

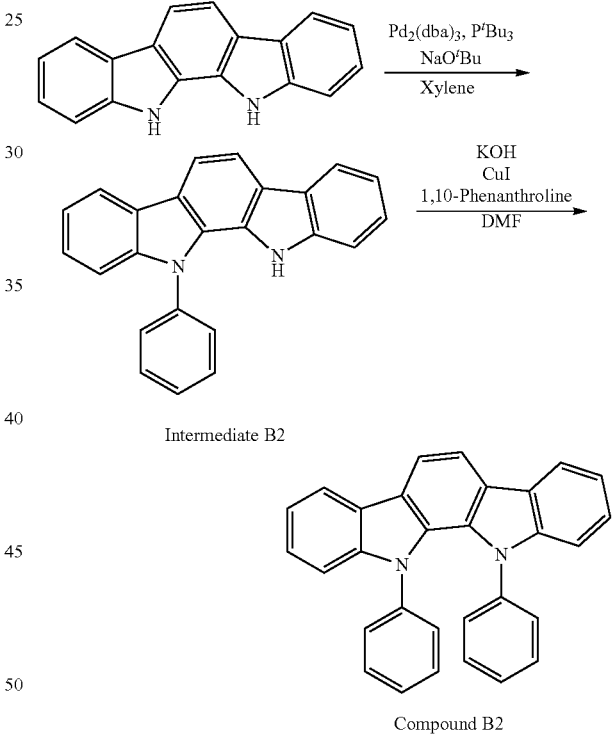

Compound B2

Synthesis of Intermediate B2

39.99 g (156.01 mmol) of indolocarbazole, 26.94 g (171.61 mmol) of bromobenzene, 22.49 g (234.01 mmol) of sodium t-butoxide, 4.28 g (4.68 mmol) of tris(dibenzylideneacetone)dipalladium, and 2.9 mL of tri-t-butylphosphine (50% in toluene) were added to 500 mL of xylene in a 1,000-mL round-bottom flask, and mixed and heated under reflux in a nitrogen atmosphere for about 15 hours. The resulting mixture was added to 1,000 mL of methanol to obtain crystalline solid powder by filtering. The resulting product was dissolved in dichlorobenzene and filtered using Silica gel/Celite, followed by removing an appropriate amount of the organic solvent and recrystallization with methanol to obtain Intermediate B2 (23.01 g, Yield: 44%).

calcd. $C_{24}H_{16}N_2$: C, 86.72; H, 4.85; N, 8.43. found: C, 86.72; H, 4.85; N, 8.43.

Synthesis of Compound B2

22.93 g (69.03 mmol) of Intermediate B2, 11.38 g (72.49 mmol) of bromobenzene, 4.26 g (75.94 mmol) of potassium hydroxide, 13.14 g (69.03 mmol) of cooper iodide, and 6.22 g (34.52 mmol) of 1,10-phenanthroline were added to 230 mL of dimethylformamide (DMF) in a 500-mL round-bottom flask, and heated under reflux in a nitrogen atmosphere for about 15 hours. The resulting mixture was added to 1,000 mL of methanol to obtain crystalline solid powder by filtering. The resulting product was dissolved in dichlorobenzene and filtered using Silica gel/Celite, followed by removing an appropriate amount of the organic solvent and recrystallization with methanol to obtain Compound B2 (12.04 g, Yield: 43%).

calcd. $C_{30}H_{20}N_2$: C, 88.21; H, 4.93; N, 6.86. found: C, 88.21; H, 4.93; N, 6.86.

Example 5

An organic light-emitting device was manufactured in the same manner as in Example 1, except that Compound 434 and Compound A1 (in a weight ratio of 50:50), instead of Compound 434, were used as hosts to form the EML.

Example 6

An organic light-emitting device was manufactured in the same manner as in Example 1, except that Compound 436 and Compound A1 (in a weight ratio of 50:50), instead of Compound 434, were used as hosts to form the EML.

Example 7

An organic light-emitting device was manufactured in the same manner as in Example 1, except that Compound 438 and Compound A1 (in a weight ratio of 50:50), instead of Compound 434, were used as hosts to form the EML.

Example 8

An organic light-emitting device was manufactured in the same manner as in Example 1, except that Compound 440 and Compound A1 (in a weight ratio of 50:50), instead of Compound 434, were used as hosts to form the EML.

Example 9

An organic light-emitting device was manufactured in the same manner as in Example 1, except that Compound 440 and Compound A15 (in a weight ratio of 50:50), instead of Compound 434, were used as hosts to form the EML.

Example 10

An organic light-emitting device was manufactured in the same manner as in Example 1, except that Compound 436 and Compound A5 (in a weight ratio of 50:50), instead of Compound 434, were used as hosts to form the EML.

Example 11

An organic light-emitting device was manufactured in the same manner as in Example 1, except that Compound 436 and Compound A2 (in a weight ratio of 50:50), instead of Compound 434, were used as hosts to form the EML.

Example 12

An organic light-emitting device was manufactured in the same manner as in Example 1, except that Compound 436 and Compound A17 (in a weight ratio of 50:50), instead of Compound 434, were used as hosts to form the EML.

Example 13

An organic light-emitting device was manufactured in the same manner as in Example 1, except that Compound 436 and Compound B2 (in a weight ratio of 50:50), instead of Compound 434, were used as hosts to form the EML.

Evaluation Example 4: Characteristics Evaluation of Organic Light-Emitting Devices Current density changes with respect to voltage, luminance changes, and emission efficiencies in the organic light-emitting devices of Examples 5 to 13 were measured in the same manner as in Evaluation Example 3. The results are shown in Table 6.

TABLE 6

| Example | Host compound No. (weight ratio) | Dopant | Driving voltage (V) | Efficiency (cd/A) | Color coordinate CIE x | CIE y |
|---|---|---|---|---|---|---|
| Example 5 | 434:A1(5:5) | PhGD | 4.7 | 62.3 | 0.374 | 0.596 |
| Example 6 | 436:A1(5:5) | PhGD | 4.0 | 64.5 | 0.372 | 0.594 |
| Example 7 | 438:A1(5:5) | PhGD | 4.1 | 59.6 | 0.376 | 0.596 |
| Example 8 | 440:A1(5:5) | PhGD | 4.3 | 64.0 | 0.376 | 0.593 |
| Example 9 | 440:A15(5:5) | PhGD | 4.2 | 53.8 | 0.375 | 0.596 |
| Example 10 | 436:A5(5:5) | PhGD | 4.1 | 57.4 | 0.372 | 0.594 |
| Example 11 | 436:A2(5:5) | PhGD | 4.3 | 58.0 | 0.369 | 0.597 |
| Example 12 | 436:A17(5:5) | PhGD | 4.0 | 64.1 | 0.371 | 0.598 |
| Example 13 | 436:B2(5:5) | PhGD | 4.0 | 56.8 | 0.370 | 0.595 |

Referring to Table 6, the organic light-emitting devices of Examples 5 to 13 were found to have low driving voltages and high efficiencies.

As described above, according to the one or more of the above embodiments of the present disclosure, a condensed cyclic compound represented by Formula 1 above may have improved electrical and thermal characteristics. Thus, an organic light-emitting device including the condensed cyclic compound of Formula 1 above may have a low driving voltage, a high efficiency, a high luminance, and long lifetime characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula 1:

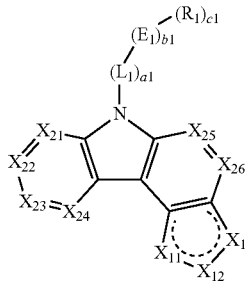

Formula 1 wherein, in Formula 1, $X_{11}$ is O and $X_{13}$ is N, or $X_{11}$ is N and $X_{13}$ is O;
$X_{12}$ is S, O, N, C-[$(L_{12})_{a12}$-$(E_{12})_{b12}$-$(R_{12})_{c12}$], or Si-[$(L_{12})_{a12}$-$(E_{12})_{b12}$-$(R_{12})_{c12}$];
$X_{21}$ is N or C-[$(L_{21})_{a21}$-$(E_{21})_{b21}$-$(R_{21})_{c21}$],
$X_{22}$ is N or C-[$(L_{22})_{a22}$-$(E_{22})_{b22}$-$(R_{22})_{c22}$],
$X_{23}$ is N or C-[$(L_{23})_{a23}$-$(E_{23})_{b23}$-$(R_{23})_{c23}$],
$X_{24}$ is N or C-[$(L_{24})_{a24}$-$(E_{24})_{b24}$-$(R_{24})_{c24}$],
$X_{25}$ is N or C-[$(L_{25})_{a25}$-$(E_{25})_{b25}$-$(R_{25})_{c25}$],
$X_{26}$ is N or C-[$(L_{26})_{a26}$-$(E_{26})_{b26}$-$(R_{26})_{c26}$],
$L_1$, $L_{12}$, and $L_{21}$ to $L_{26}$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent nonaromatic condensed polycyclic group, and a substituted or unsubstituted divalent nonaromatic condensed heteropolycyclic group;
$a_1$, $a_{12}$, and $a_{21}$ to $a_{26}$ are each independently an integer selected from 0 to 5;
$E_1$, $E_{12}$, and $E_{21}$ to $E_{26}$ are each independently selected from a substituted or unsubstituted nitrogen-containing electron transporting moiety;
b1, b12, and b21 to b26 are each independently an integer selected from 0 to 5, provided that at least one of $E_1$, $E_{12}$, and $E_{21}$ to $E_{26}$ is present in Formula 1;
$R_1$, $R_{12}$, and $R_{21}$ to $R_{26}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent nonaromatic condensed polycyclic group, a substituted or unsubstituted monovalent nonaromatic condensed heteropolycyclic group, —N($Q_1$)($Q_2$), —Si($Q_3$)($Q_4$)($Q_5$), and —B($Q_6$)($Q_7$);
c1, c12, and c21 to c26 are each independently an integer selected from 1 to 5;
wherein at least one of substituents of the substituted nitrogen-containing electron transporting moiety, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent nonaromatic condensed polycyclic group, and the substituted monovalent nonaromatic condensed heteropolycyclic group is selected from
a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent nonaromatic condensed polycyclic group, and a monovalent nonaromatic condensed heteropolycyclic group.

2. The condensed cyclic compound of claim 1, wherein $X_{11}$ is O; and $X_{13}$ is N.

3. The condensed cyclic compound of claim 1, wherein $L_1$, $L_{12}$, and $L_{21}$ to $L_{26}$ are each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group, each substituted with at least one of a deuterium atom, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a $C_1$-$C_{20}$ heteroaryl group, a monovalent nonaromatic condensed polycyclic group, a monovalent nonaromatic condensed heteropolycyclic group, and —Si($Q_{33}$)($Q_3$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

4. The condensed cyclic compound of claim 1, wherein $L_1$, $L_{12}$, and $L_{21}$ to $L_{26}$ are each independently represented by one of Formulae 2-1 to 2-34:

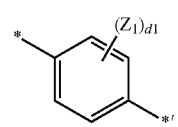

Formula 2-1

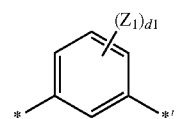

Formula 2-2

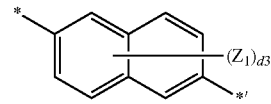

Formula 2-3

-continued

Formula 2-4

Formula 2-5

Formula 2-6

Formula 2-7

Formula 2-8

Formula 2-9

Formula 2-10

Formula 2-11

Formula 2-12

Formula 2-13

-continued

Formula 2-14

Formula 2-15

Formula 2-16

Formula 2-17

Formula 2-18

Formula 2-19

Formula 2-20

Formula 2-21

Formula 2-22

Formula 2-23

Formula 2-24

Formula 2-25

-continued

Formula 2-26

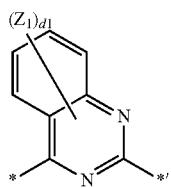

Formula 2-27

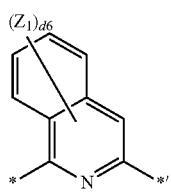

Formula 2-28

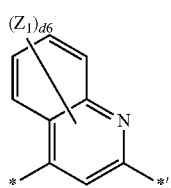

Formula 2-29

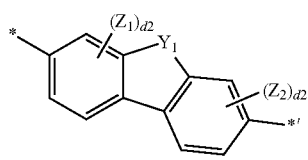

Formula 2-30

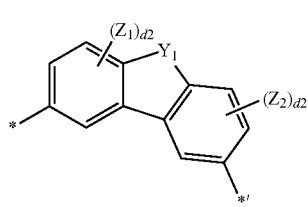

Formula 2-31

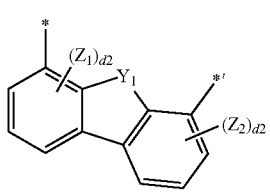

Formula 2-32

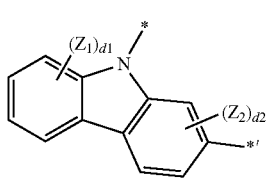

Formula 2-33

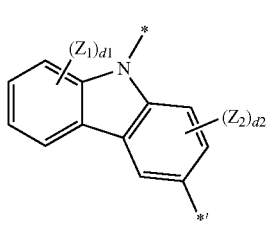

Formula 2-34

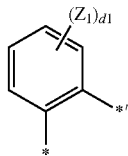

wherein, in Formulae 2-1 to 2-34, $Y_1$ is O, S, S(=O), S(=O)$_2$, C($Z_3$)($Z_4$), N($Z_5$), or Si($Z_6$)($Z_7$);

$Z_1$ to $Z_7$ are each independently selected from a hydrogen, a deuterium, —F, —Cl, —Br, —I, a hydroxyl group, a cyano group, a nitro group, an amino group, an amidino groups, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —Si($Q_{33}$)($Q_{34}$)($Q_{35}$), where $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 is an integer of 1 to 4;
d2 is an integer of 1 to 3;
d3 is an integer of 1 to 6;
d4 is an integer of 1 to 8;
d5 is 1 or 2;
d6 is an integer of 1 to 5; and
\* and \*' indicate a binding site with an adjacent atom.

5. The condensed cyclic compound of claim 1, wherein $L_1$, $L_{12}$, and $L_{21}$ to $L_{26}$ are each independently represented by one of Formulae 3-1 to 3-21:

Formula 3-1

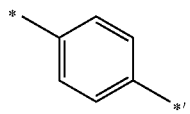

Formula 3-2

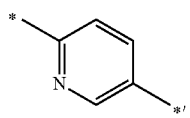

Formula 3-3

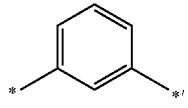

-continued
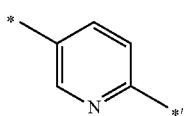
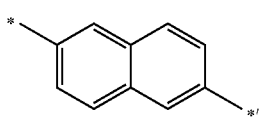
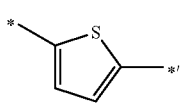
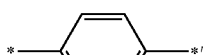
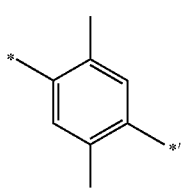
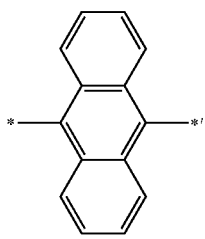
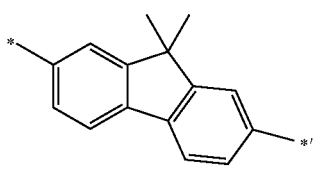
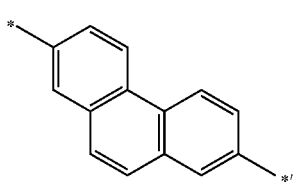
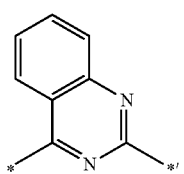
-continued
Formula 3-4
Formula 3-5
Formula 3-6
Formula 3-7
Formula 3-8
Formula 3-9
Formula 3-10
Formula 3-11
Formula 3-12
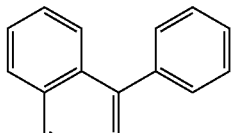
Formula 3-13
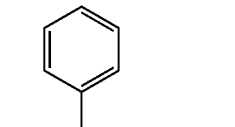
Formula 3-14
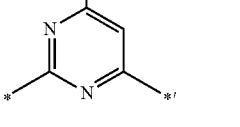
Formula 3-15
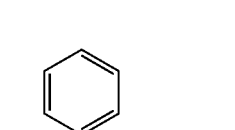
Formula 3-16
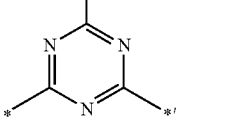
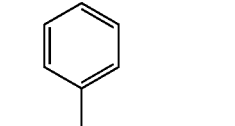
Formula 3-17
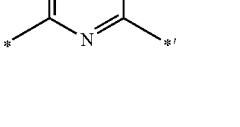
Formula 3-18
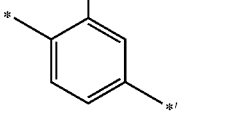
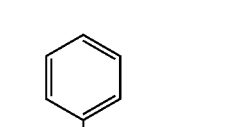
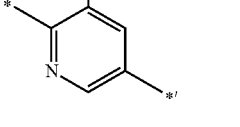

Formula 3-19

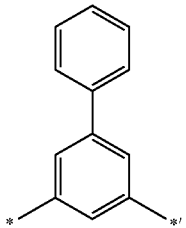

Formula 3-20

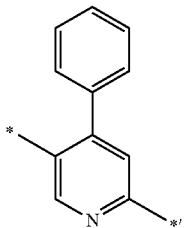

Formula 3-21

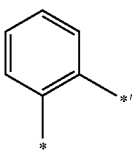

wherein, in Formulae 3-1 to 3-21,
* indicates a binding site with a core in Formula 1 or a binding site with an adjacent group of $L_1$, $L_{11}$ to $L_{13}$, and $L_{21}$ to $L_{26}$ in Formula 1; and
*' indicates a binding site with an adjacent group of $L_1$, $L_{11}$ to $L_{13}$, and $L_{21}$ to $L_{26}$ in Formula 1, a binding site with an adjacent group of $E_1$, $E_{11}$ to $E_{13}$, and $E_{21}$ to $E_2$ in Formula 1, or a binding site with one of $R_1$, $R_{11}$ to $R_{13}$, and $R_{21}$ to $R_{26}$ in Formula 1.

6. The condensed cyclic compound of claim 1, wherein a1, a12, and a21 to a26 are each independently 0, 1, or 2.

7. The condensed cyclic compound of claim 1, wherein $E_1$, $E_{12}$, and $E_{21}$ to $E_{26}$ are each independently selected from a substituted or unsubstituted pyrrolylene group, a substituted or unsubstituted imidazolylene group, a substituted or unsubstituted pyrazolylene group, a substituted or unsubstituted thiazolylene group, a substituted or unsubstituted isothiazolylene group, a substituted or unsubstituted oxazolylene group, a substituted or unsubstituted isooxazolylene group, a substituted or unsubstituted pyridinylene group, a substituted or unsubstituted pyrazinylene group, a substituted or unsubstituted pyrimidinylene group, a substituted or unsubstituted pyridazinylene group, a substituted or unsubstituted isoindolylene group, a substituted or unsubstituted indolylene group, a substituted or unsubstituted indazolylene group, a substituted or unsubstituted quinolinylene group, a substituted or unsubstituted isoquinolinylene group, a substituted or unsubstituted benzoquinolinylene group, a substituted or unsubstituted quinoxalinylene group, a substituted or unsubstituted quinazolinylene group, a substituted or unsubstituted phenanthridinylene group, a substituted or unsubstituted acridinylene group, a substituted or unsubstituted phenanthrolinylene group, a substituted or unsubstituted phenazinylene group, a substituted or unsubstituted benzoimidazolylene group, a substituted or unsubstituted isobenzothiazolylene group, a substituted or unsubstituted benzooxazolylene group, a substituted or unsubstituted isobenzooxazolylene group, a substituted or unsubstituted triazolylene group, a substituted or unsubstituted oxadiazolylene group, a substituted or unsubstituted thiadiazolylene group, a substituted or unsubstituted triazinylene group, a substituted or unsubstituted imidazopyridinylene group, and a substituted or unsubstituted imidazopyrimidinylene group, wherein at least one of substituents of the substituted pyrrolylene group, the substituted imidazolylene group, the substituted pyrazolylene group, the substituted thiazolylene group, the substituted isothiazolylene group, the substituted oxazolylene group, the substituted isooxazolylene group, the substituted pyridinylene group, the substituted pyrazinylene group, the substituted pyrimidinylene group, the substituted pyridazinylene group, the substituted isoindolylene group, the substituted indolylene group, the substituted indazolylene group, the substituted quinolinylene group, the substituted isoquinolinylene group, the substituted benzoquinolinylene group, the substituted quinoxalinylene group, the substituted quinazolinylene group, the substituted phenanthridinylene group, the substituted acridinylene group, the substituted phenanthrolinylene group, the substituted phenazinylene group, the substituted benzoimidazolylene group, the substituted isobenzothiazolylene group, the substituted benzooxazolylene group, the substituted isobenzooxazolylene group, the substituted triazolylene group, the substituted oxadiazolylene group, the substituted thiadiazolylene group, the substituted triazinylene group, the substituted imidazopyridinylene group, and the substituted imidazopyrimidinylene group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{23}$)($Q_{24}$)($Q_{25}$), and —Si($Q_{33}$)($Q_{34}$)($Q_{35}$), wherein $Q_{23}$ to $Q_{25}$, and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

8. The condensed cyclic compound of claim 1, wherein $E_1$, $E_{12}$, and $E_{21}$ to $E_{26}$ are each independently selected from a substituted or unsubstituted imidazolylene group, a substituted or unsubstituted pyridinylene group, a substituted or unsubstituted pyrimidinylene group, a substituted or unsubstituted quinolinylene group, a substituted or unsubstituted isoquinolinylene group, a substituted or unsubstituted quinazolinylene group, a substituted or unsubstituted phenanthrolinylene group, a substituted or unsubstituted benzoimidazolylene group, a substituted or unsubstituted triazolylene group, a substituted or unsubstituted oxadiazolylene group, a substituted or unsubstituted thiadiazolylene group, a substituted or unsubstituted triazinylene group, a substituted or unsubstituted imidazopyridinylene group, and a substituted or unsubstituted imidazopyrimidinylene group, wherein at least one of substituents of the substituted imidazolylene group, the substituted pyridinylene group, the substituted pyrimidinylene group, the substituted quinolinylene group, the substituted isoquinolinylene group, the substituted quinazolinylene group, the substituted phenanthrolinylene group, the substituted benzoimidazolylene group, the substituted triazolylene group, the substituted oxadiazolylene group, the substituted thiadiazolylene group, the substituted triazinylene group, the substituted imidazopyridinylene group, and the substituted imidazopyrimidinylene group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{23}$)($Q_{24}$)($Q_{25}$), and —Si($Q_{33}$)($Q_{34}$)($Q_{35}$), wherein $Q_{23}$ to $Q_{25}$, and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

9. The condensed cyclic compound of claim 1, wherein $E_1$, $E_{12}$, and $E_{21}$ to $E_{26}$ are each independently represented by one of Formulae 10-1 to 10-27:

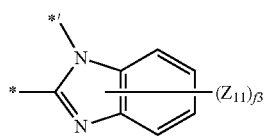

Formula 10-13

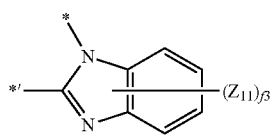

Formula 10-14

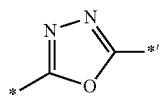

Formula 10-15

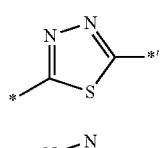

Formula 10-16

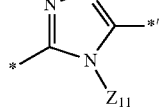

Formula 10-17

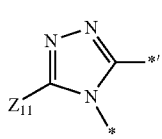

Formula 10-18

-continued

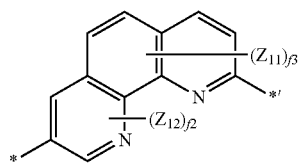

Formula 10-19

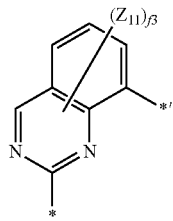

Formula 10-20

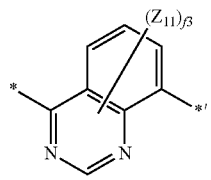

Formula 10-21

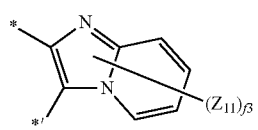

Formula 10-22

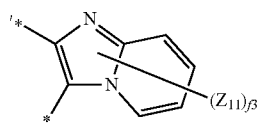

Formula 10-23

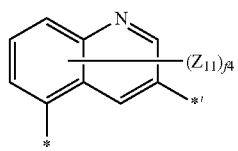

Formula 10-24

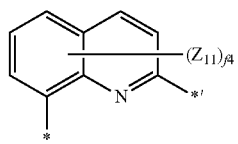

Formula 10-25

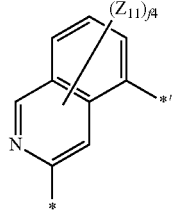

Formula 10-26

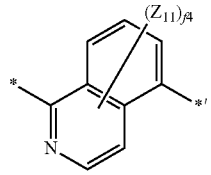

Formula 10-27 wherein, in Formulae 10-1 to 10-27, $Z_{11}$ and $Z_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{23}$)($Q_{24}$)($Q_{25}$); and —Si($Q_{33}$)($Q_{34}$)($Q_{35}$), wherein $Q_{23}$ to $Q_{25}$, and $Q_{33}$ to $Q_{35}$ are each independently selected from a hydrogen, a $C_1$-$C_{20}$alkyl group, a $C_1$-$C_{20}$alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

f1 is an integer selected from 1 to 3;
f2 is 1 or 2;
f3 is an integer selected from 1 to 4;
f4 is an integer selected from 1 to 5;
* indicates a binding site with a core in Formula 1, a binding site with an adjacent group of $L_1$, $L_{11}$ to $L_{13}$, and $L_{21}$ to $L_{26}$ in Formula 1, or a binding site with an adjacent group of $E_1$, $E_{11}$ to $E_{13}$, and $E_{21}$ to $E_{26}$ in Formula 1; and
*' indicates a binding site with an adjacent group of $E_1$, $E_{11}$ to $E_{13}$, and $E_{21}$ to $E_{26}$ in Formula 1, or a binding site with an adjacent group of $R_1$, $R_{11}$ to $R_{13}$, and $R_{21}$ to $R_{26}$ in Formula 1.

10. The condensed cyclic compound of claim 1, wherein b1 is 1 or 2.

11. The condensed cyclic compound of claim 1, wherein $R_1$, $R_{12}$, and $R_{21}$ to $R_{26}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium atom, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{35}$), and —Si($Q_3$)($Q_4$)($Q_5$), wherein $R_{11}$ to $R_{13}$ are not —Si($Q_3$)($Q_4$)($Q_5$); and $Q_3$ to $Q_5$, and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

12. The condensed cyclic compound of claim 1, wherein $R_1$, $R_{12}$, and $R_{21}$ to $R_{26}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a group represented by one of Formulae 4-1 to 4-31, and —Si($Q_3$)($Q_4$)($Q_5$), wherein $Q_3$ to $Q_5$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

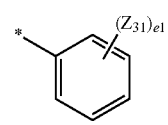

Formula 4-1

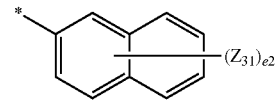

Formula 4-2

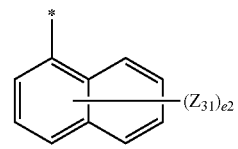

Formula 4-3

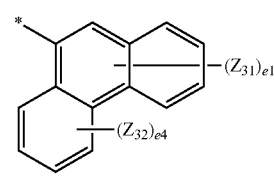

Formula 4-4

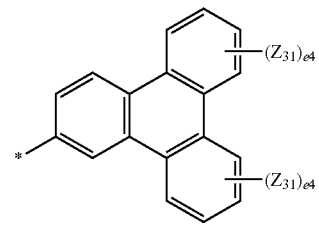

Formula 4-5

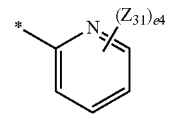

Formula 4-6

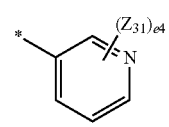

Formula 4-7

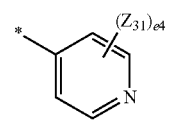

Formula 4-8

Formula 4-9
Formula 4-10
Formula 4-11
Formula 4-12
Formula 4-13
Formula 4-14
Formula 4-15
Formula 4-16
Formula 4-17
Formula 4-18
Formula 4-19
Formula 4-20

Formula 4-21
Formula 4-22
Formula 4-23
Formula 4-24
Formula 4-25
Formula 4-26
Formula 4-27
Formula 4-28
Formula 4-29
Formula 4-30

-continued

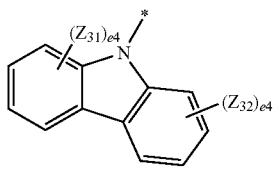

Formula 4-31 wherein, in Formula 4-1 to 4-31, $Y_{31}$ is O, S, $C(Z_{33})(Z_{34})$, $N(Z_{35})$, or $Si(Z_{36})(Z_{37})$;

$Z_{31}$ to $Z_{37}$ are each independently selected from a hydrogen, a deuterium, —F, —Cl, —Br, —I, a hydroxyl group, a cyano group, a nitro group, an amino group, an amidino groups, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —$Si(Q_{33})(Q_{34})(Q_{35})$, wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 is an integer of 1 to 5;
e2 is an integer of 1 to 7;
e3 is an integer of 1 to 3;
e4 is an integer of 1 to 4;
e5 is 1 or 2;
e6 is an integer of 1 to 6;
* indicates a binding site with a core in Formula 1, a binding site with an adjacent group of $L_1$, $L_{11}$ to $L_{13}$, and $L_{21}$ to $L_{26}$ in Formula 1, or a binding site with an adjacent group of $E_1$, $E_{11}$ to $E_{13}$, and $E_{21}$ to $E_2$ in Formula 1.

13. The condensed cyclic compound of claim 1, wherein $R_1$, $R_{12}$, and $R_{21}$ to $R_{26}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a group represented by one of Formulae 5-1 to 5-27, and —$Si(Q_3)(Q_4)(Q_5)$, wherein $Q_3$ to $Q_5$ are each independently selected from a hydrogen, a $C_1$-$C_{20}$ alkyl group, a $C_1$-$C_{20}$ alkoxy group, a phenyl group, and a naphthyl group:

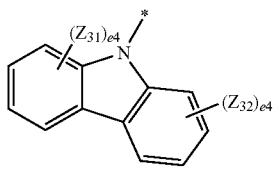

Formula 5-1

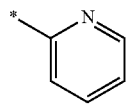

Formula 5-2

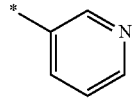

Formula 5-3

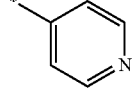

Formula 5-4

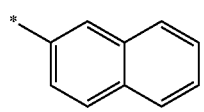

Formula 5-5

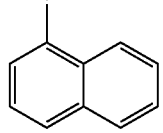

Formula 5-6

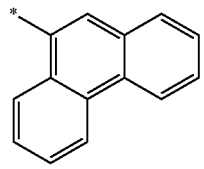

Formula 5-7

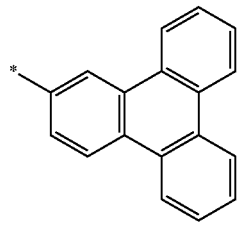

Formula 5-8

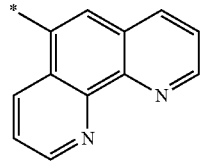

Formula 5-9

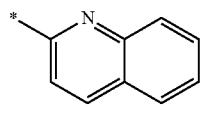

Formula 5-10

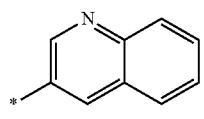

Formula 5-11

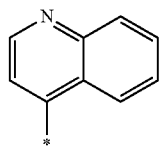

Formula 5-12

Formula 5-13
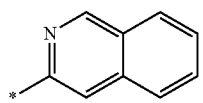

Formula 5-14
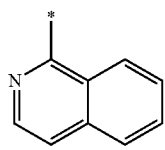

Formula 5-15
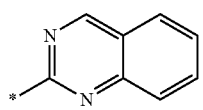

Formula 5-16
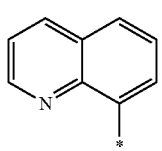

Formula 5-17
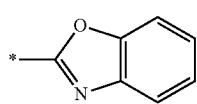

Formula 5-18
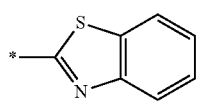

Formula 5-19
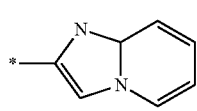

Formula 5-20
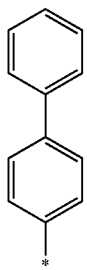

Formula 5-21
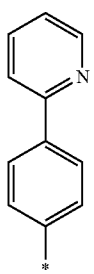

Formula 5-22
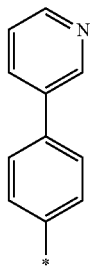

Formula 5-23
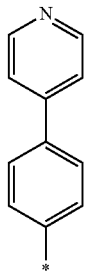

Formula 5-24
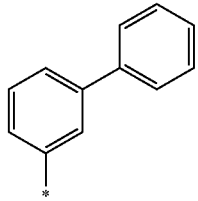

Formula 5-25
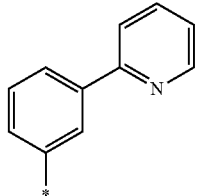

Formula 5-26
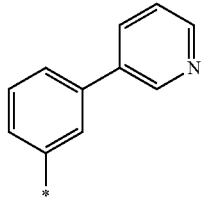

Formula 5-27
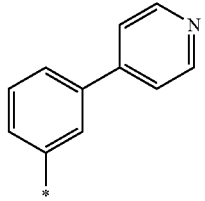

wherein, in Formulae 5-1 to 5-27,
* indicates a binding site with a core in Formula 1, a binding site with an adjacent group of $L_1$, $L_{11}$ to $L_{13}$, and $L_{21}$ to $L_{26}$ in Formula 1, or a binding site with an adjacent group of $E_1$, $E_{11}$ to $E_{13}$, and $E_{21}$ to $E_{26}$ in Formula 1.

14. The condensed cyclic compound of claim 1, wherein
$X_{21}$ is C-[$(L_{21})_{a21}$-$(E_{21})_{b21}$-$(R_{21})_{c21}$];
$X_{22}$ is C-[$(L_{22})_{a22}$-$(E_{22})_{b22}$-$(R_{22})_{c22}$];

$X_{23}$ is C-[(L$_{23}$)$_{a23}$-(E)$_{b23}$-(R$_{23}$)$_{c23}$];

$X_{24}$ is C-[(L$_{24}$)$_{a24}$-(E$_{24}$)$_{b24}$-(R$_{24}$)$_{c24}$];

$X_{25}$ is C-[(L$_{25}$s)$_{a25}$-(E$_2$s)$_{b25}$-(R$_{25}$)$_{c25}$s];

$X_{26}$ is C-[(L$_{26}$)$_{a26}$-(E$_{26}$)$_{b26}$-(R$_{26}$)$_{c26}$];

a21 to a26, and b21 to b26 are 0;

$R_{21}$ to $R_{26}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group a naphthyl group, and —Si(Q$_3$)(Q$_4$)(Q$_5$);

c21 to c26 are 1;

wherein Q$_3$ to Q$_5$ are each independently selected from a hydrogen, a C$_1$-C$_{20}$ alkyl group, a C$_1$-C$_{20}$ alkoxy group, a phenyl group, and a naphthyl group.

15. The condensed cyclic compound of claim 1, wherein, in Formula 1, b1 is 1, and at least one of c1 number of groups R$_1$ is selected from a substituted or unsubstituted C$_6$-C$_{20}$ aryl group, a substituted or unsubstituted C$_1$-C$_{20}$ heteroaryl group, a substituted or unsubstituted monovalent nonaromatic condensed polycyclic group, and a substituted or unsubstituted monovalent nonaromatic condensed heteropolycyclic group.

16. The condensed cyclic compound of claim 1, wherein the condensed cyclic compound is represented by Formula 1D:

Formula 1D wherein, in Formula 1D, L$_1$, a1, E$_1$, R$_1$, R$_{21}$ to R$_{26}$, and c1 are the same as in claim 1; and b1 is 1 or 2.

17. The condensed cyclic compound of claim 1, wherein the condensed cyclic compound of Formula 1 is one of Compounds 433 to 504:

373
-continued
374
-continued
436
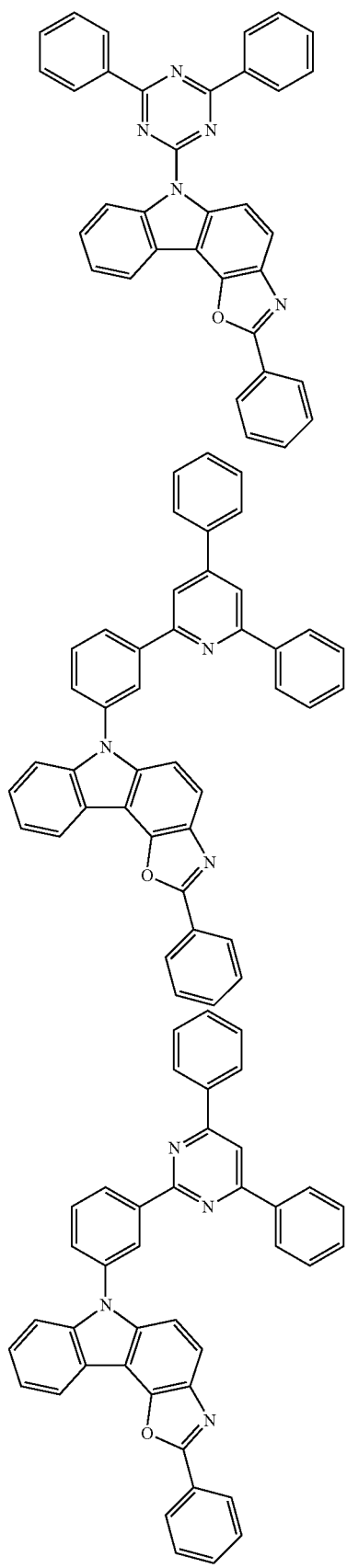
437
438
439
440

375
-continued
441
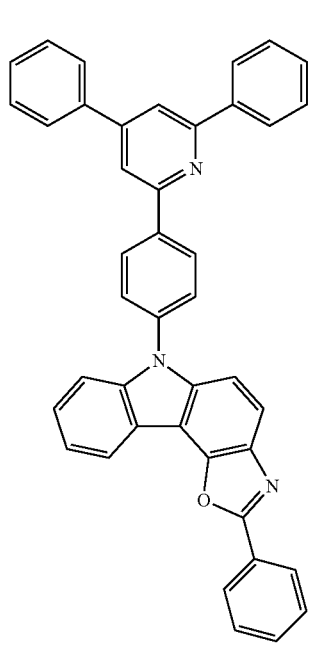
442
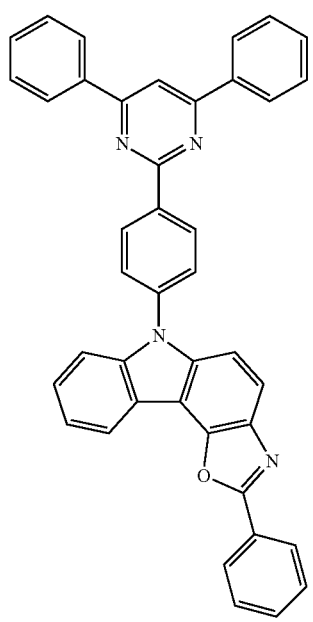
376
-continued
443
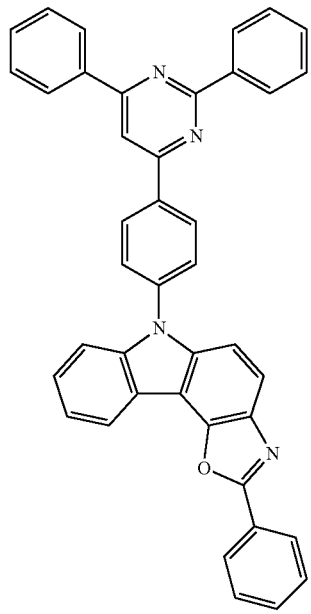
444

377
-continued
445
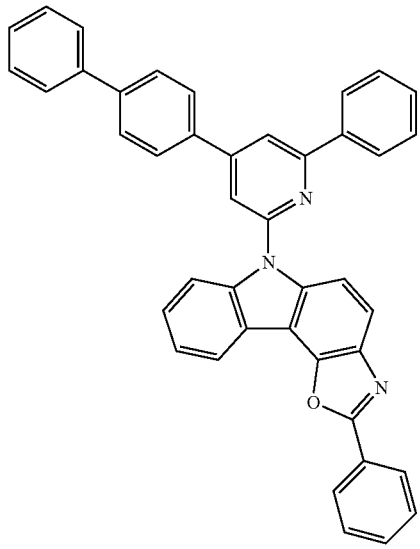
446
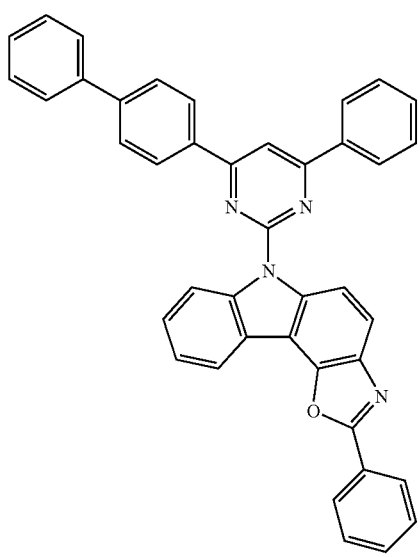
447
378
-continued
448
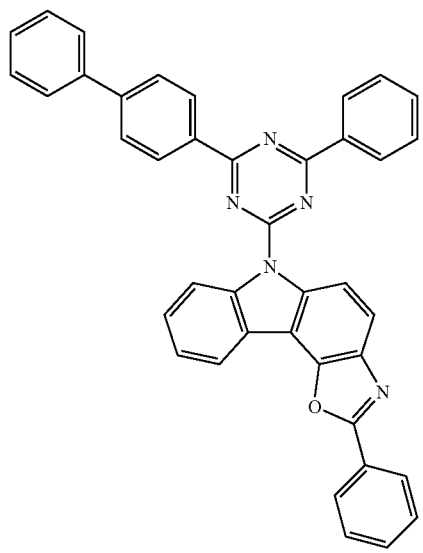
449
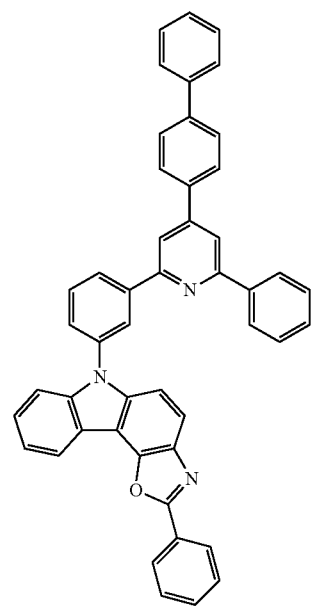

379
-continued
450 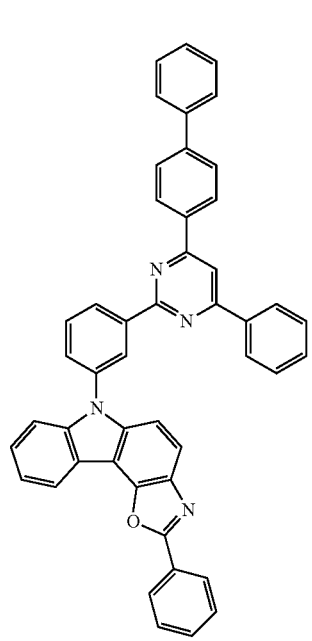
451 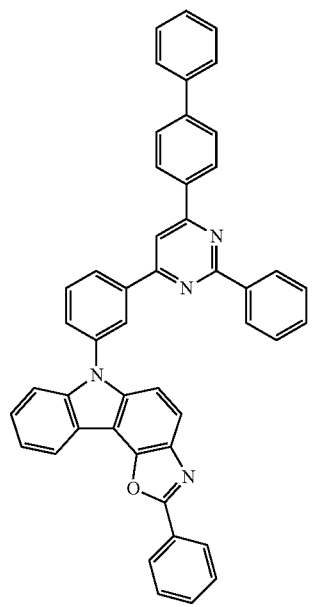
380
-continued
452 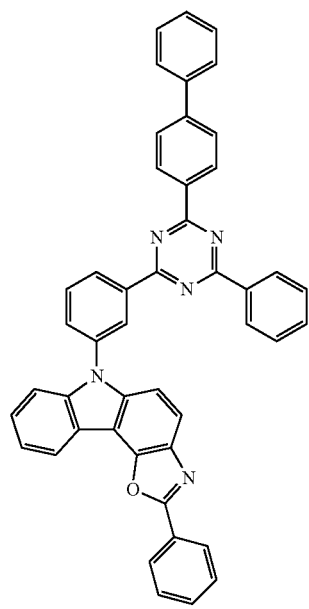
453 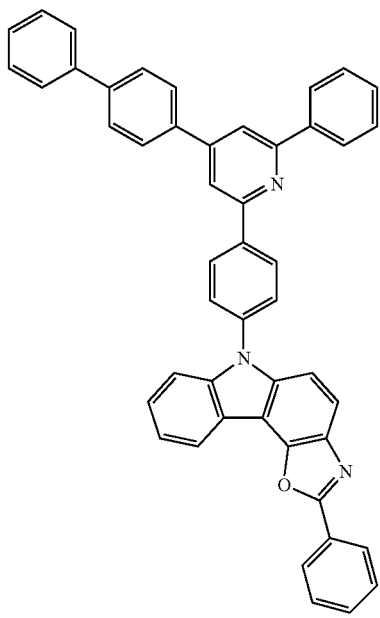

381
-continued
454
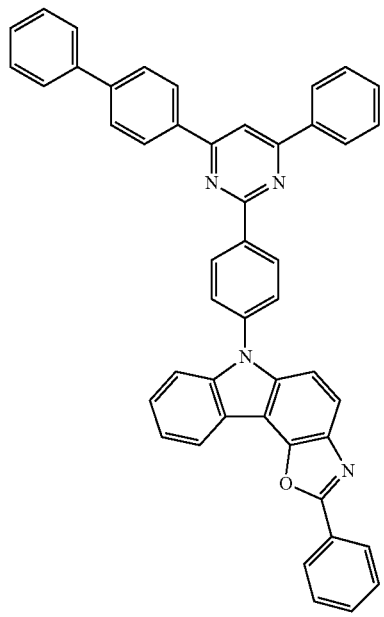
455
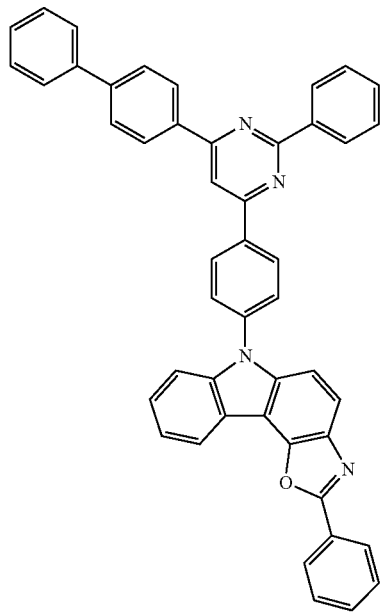
382
-continued
456
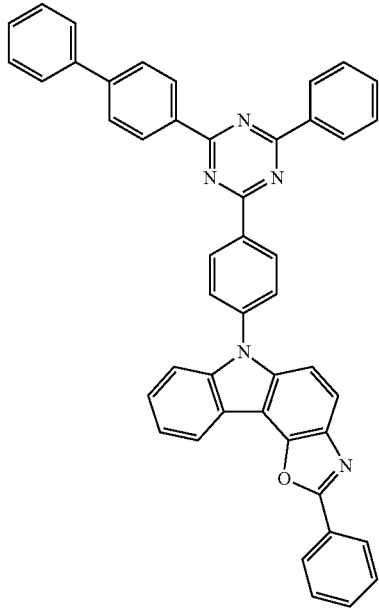
457
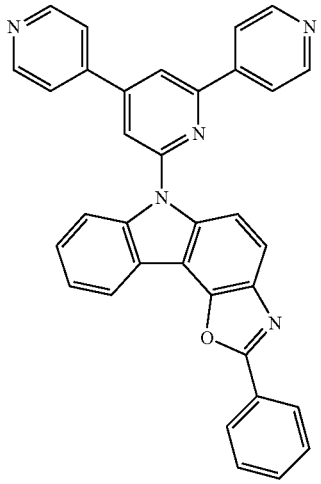
458
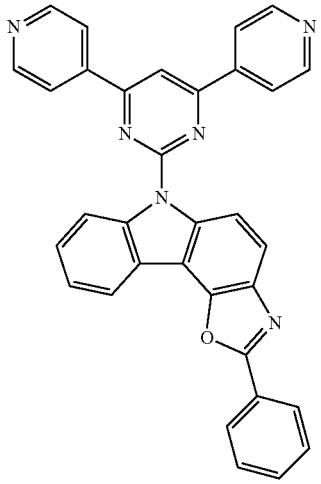

383
-continued
459
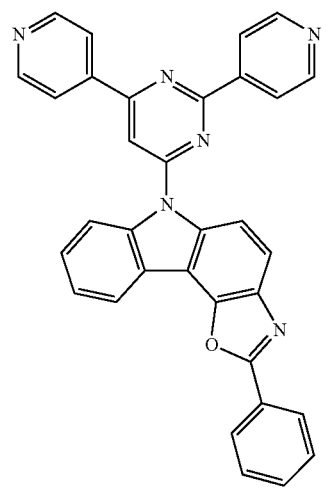
460
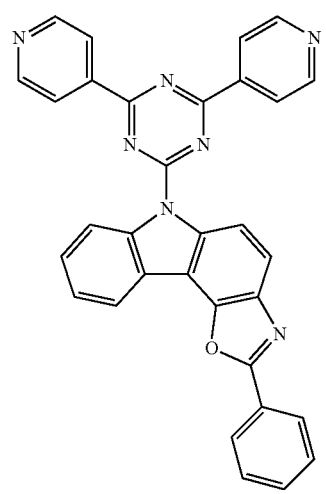
461
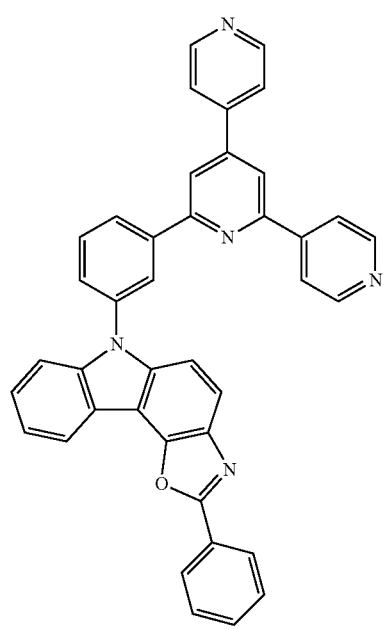
384
-continued
462
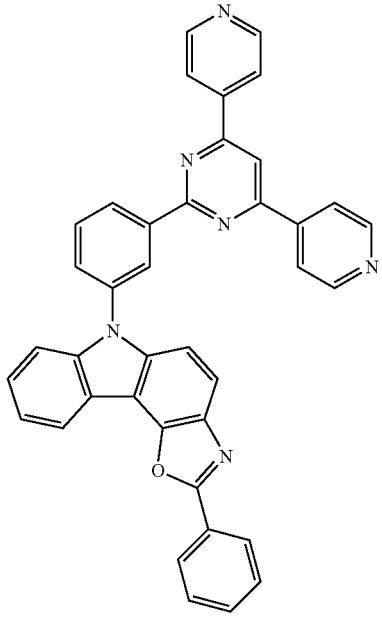
463
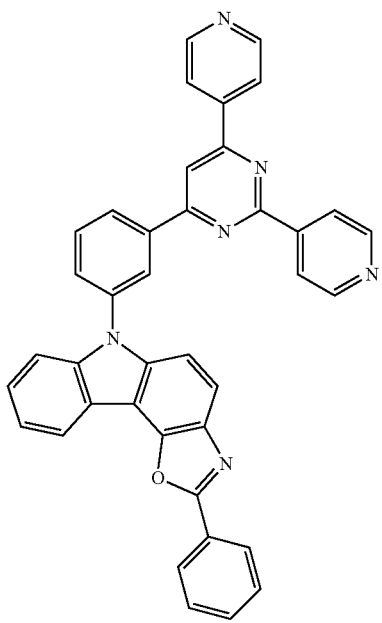

385
-continued
464
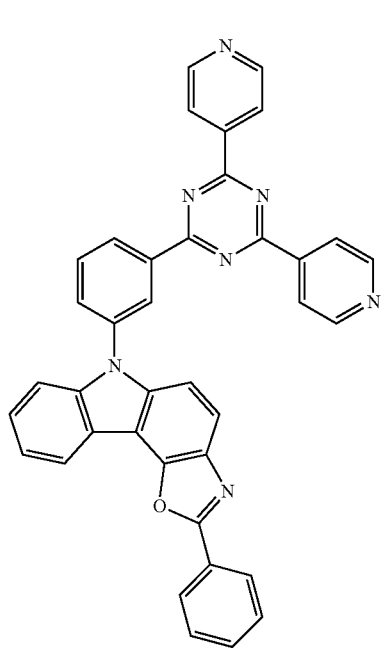
465
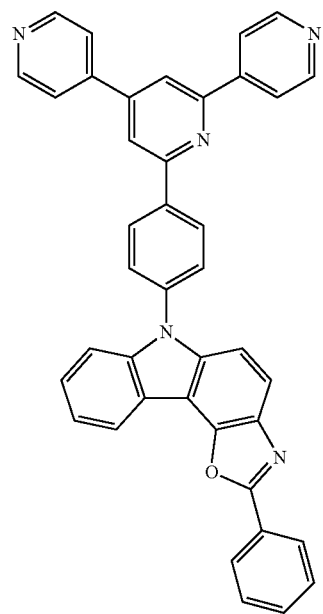
386
-continued
466
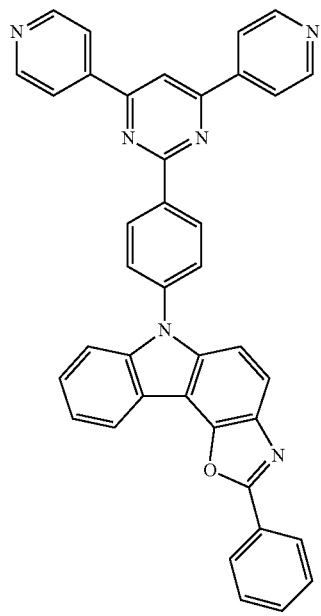
467
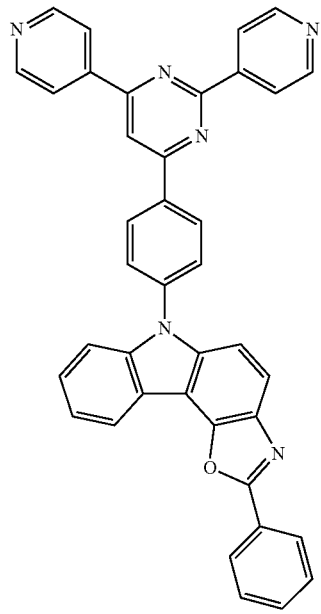

387
-continued
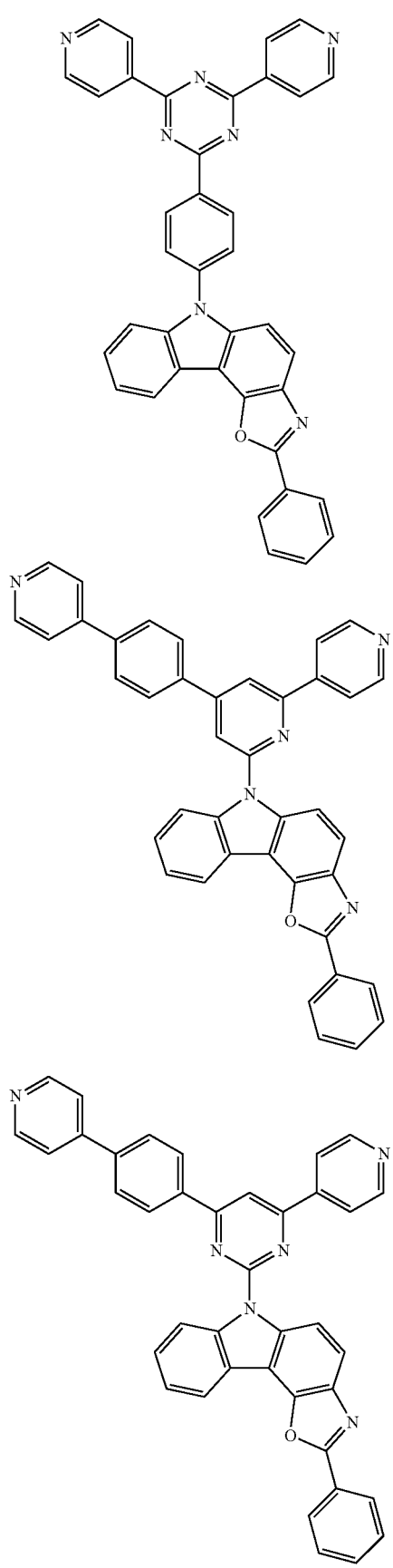
388
-continued
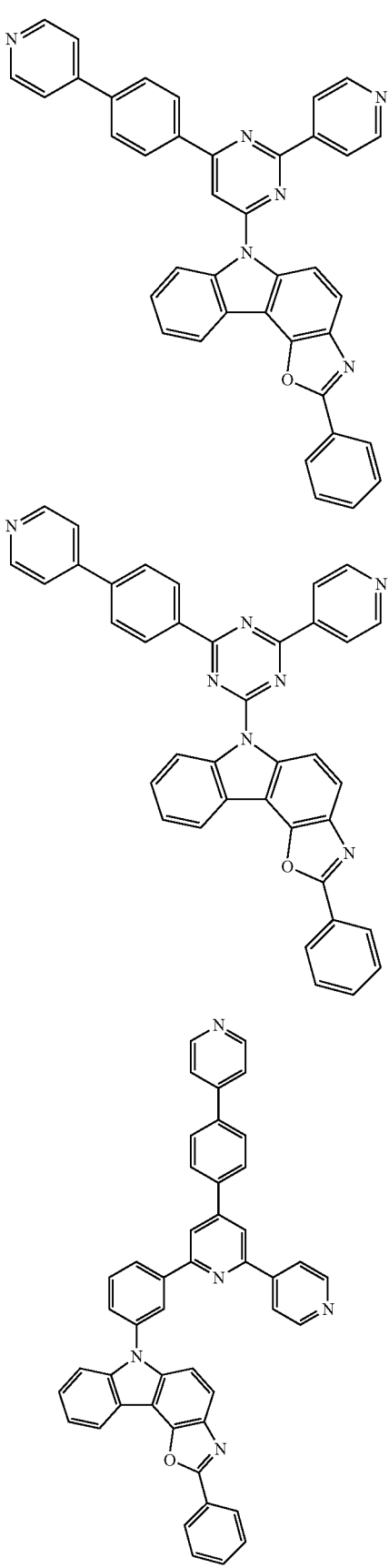

389
-continued
390
-continued
474 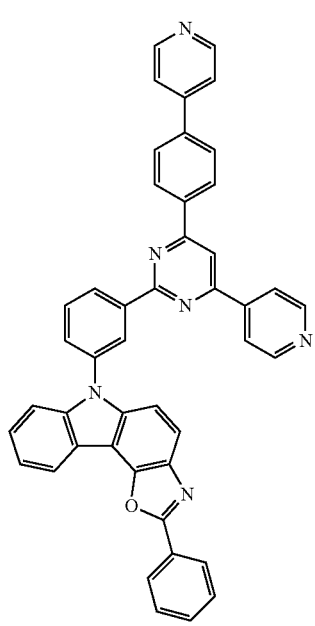
476 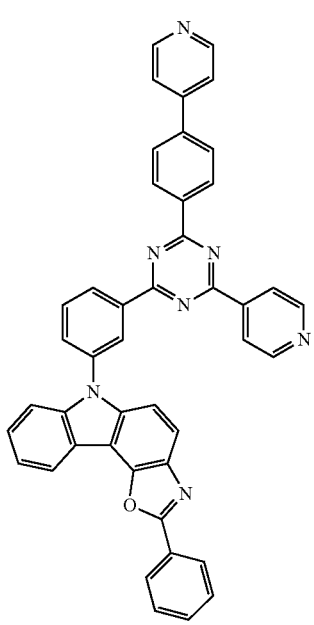
475
477 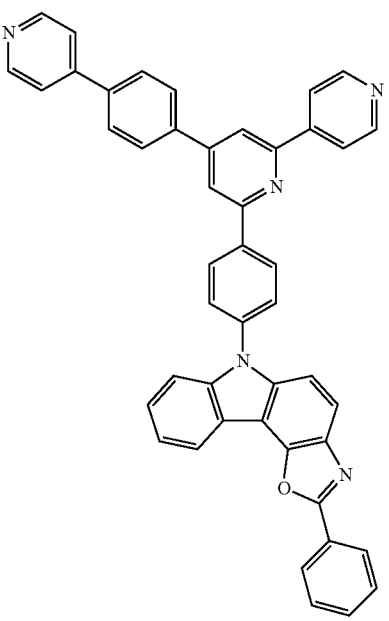

391
-continued
478
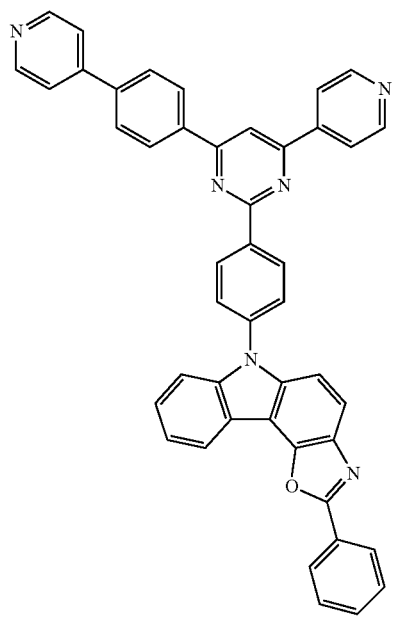
479
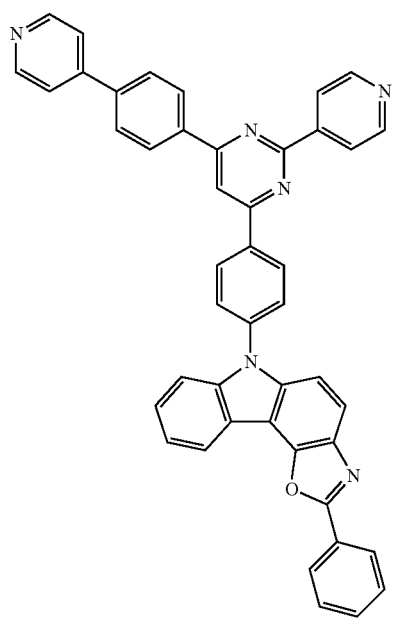
392
-continued
480
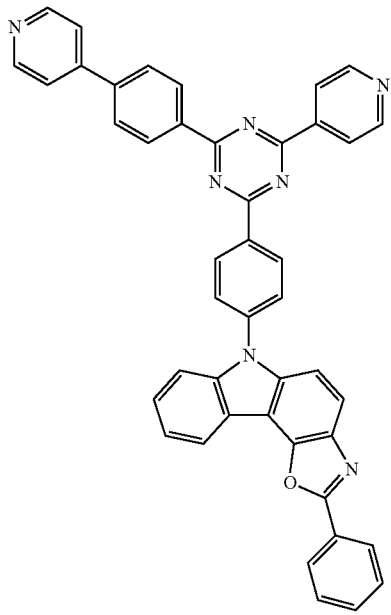
481
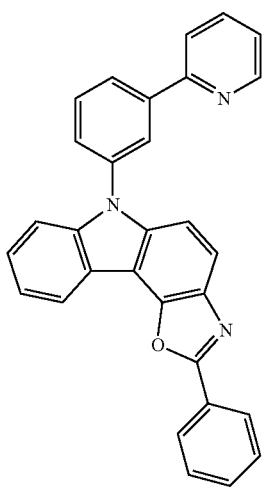
482
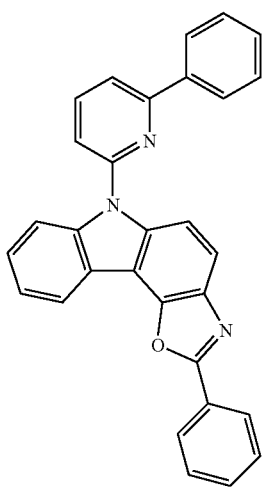

393
-continued
483
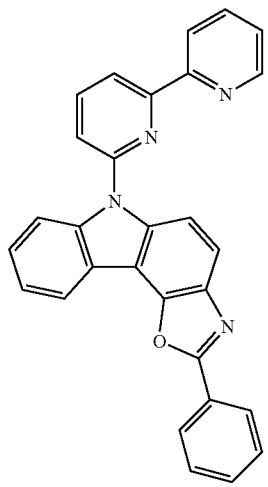
484
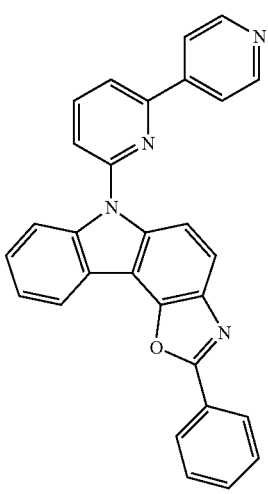
485
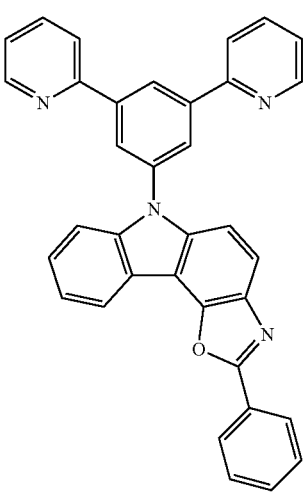
394
-continued
486
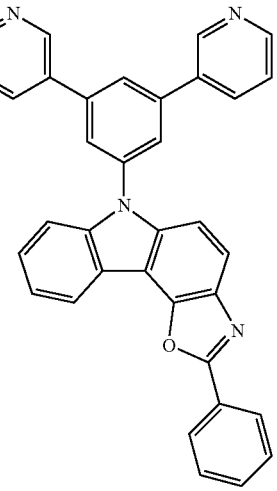
487
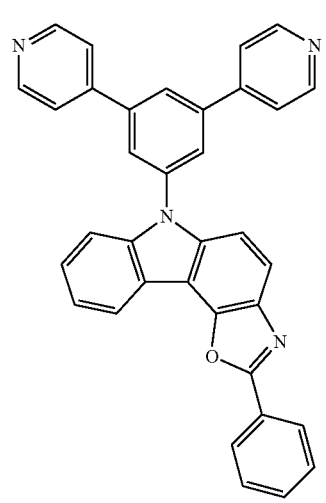
488
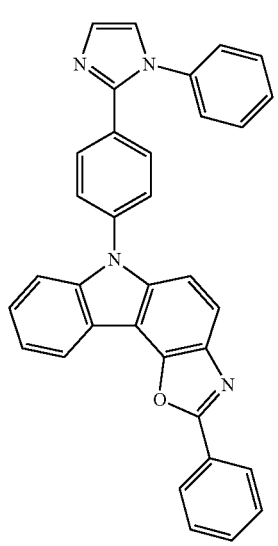

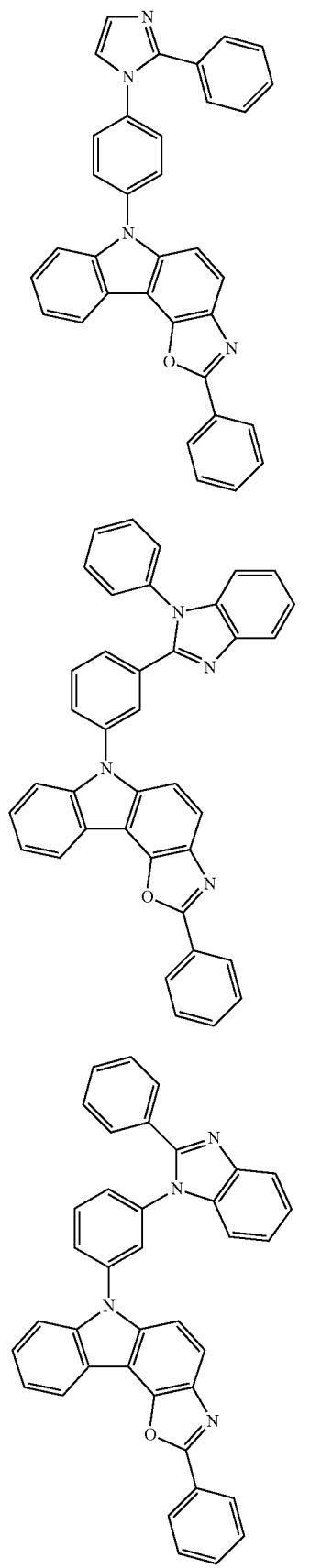

397
-continued
494
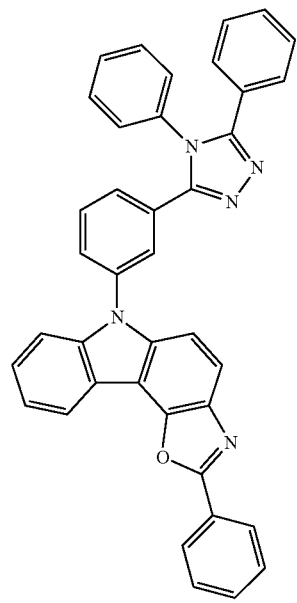
495
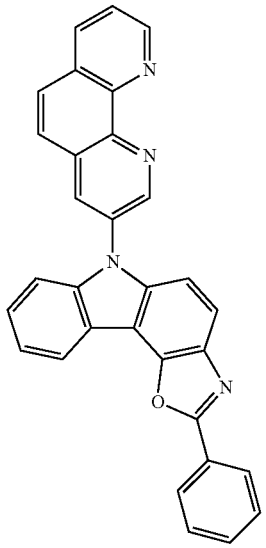
398
-continued
496
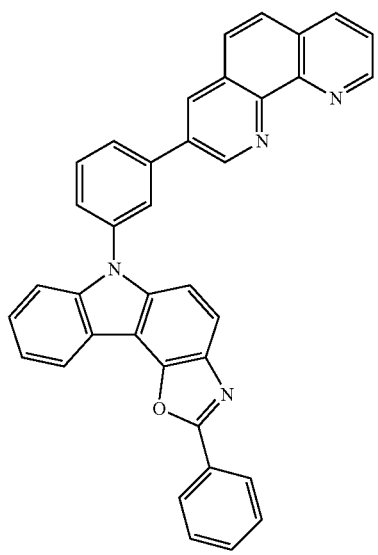
497
498
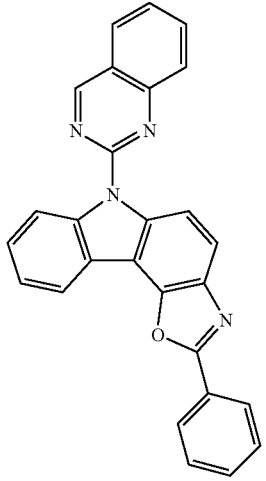

399
-continued
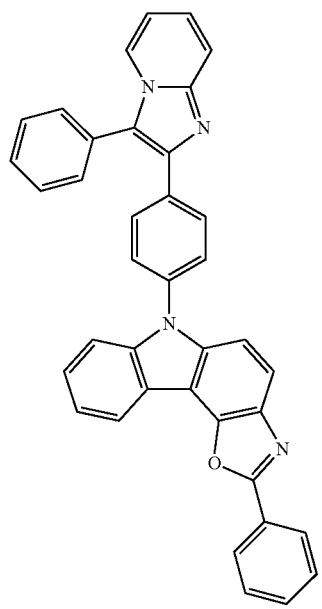
499
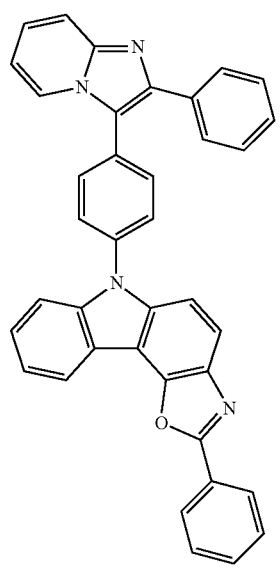
500
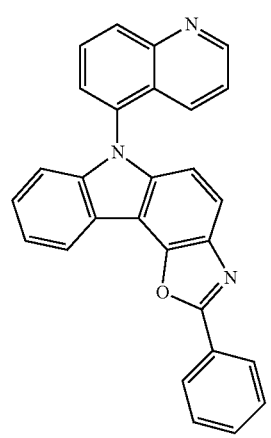
501
400
-continued
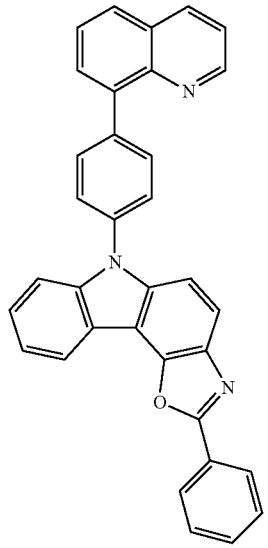
502
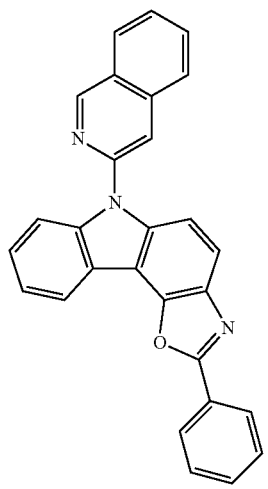
503
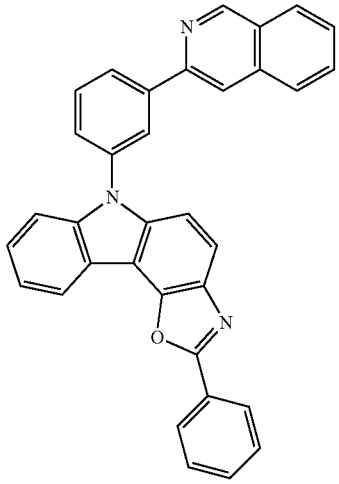
504
18. An organic light-emitting device comprising:
a first electrode;
a second electrode; and
an organic layer disposed between the first electrode and the second electrode, wherein the organic layer comprises an emission layer and at least one condensed cyclic compound of Formula 1 according to claim 1.

19. The organic light-emitting device of claim 18, wherein the first electrode is an anode,
the second electrode is a cathode, and
the organic layer comprises
i) a hole transport region disposed between the first electrode and the emission layer, wherein the hole transport region comprises at least one of a hole injection layer, a hole transport layer, and an electron blocking layer; and
ii) an electron transport region disposed between the emission layer and the second electrode, wherein the electron transport region comprises at least one of a hole blocking layer, an electron transport layer, and an electron injection layer.

20. The organic light-emitting device of claim 18, wherein the emission layer comprises the at least one condensed cyclic compound of Formula 1, and the emission layer further comprises a phosphorescent dopant.

21. The organic light-emitting device of claim 18, wherein the emission layer comprises a first host, a second host, and a dopant, provided that
the first host and the second host are different from each other,
the emission layer comprises the at least one condensed cyclic compound represented by Formula 1,
the first host comprises the at least one condensed cyclic compound of Formula 1, and
the second host comprises at least one of a first compound represented by Formula 41, a second compound represented by Formula 61, and a third compound represented by Formula 31:

Formula 41

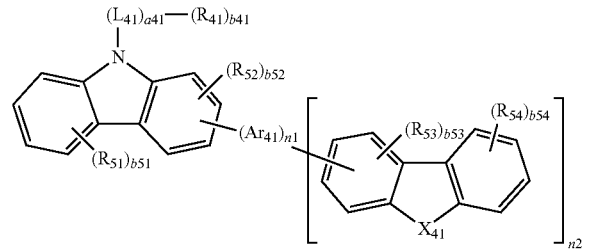

Formula 61

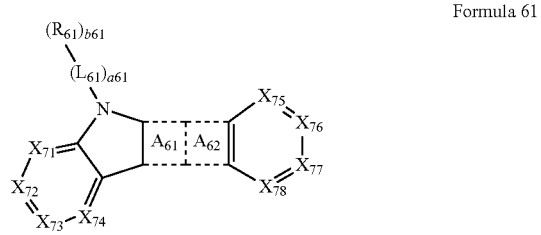

Formula 61A

Formula 61B

Formula 31

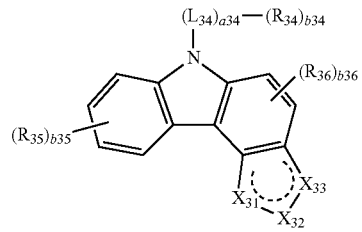

wherein, in Formulae 41, 61, 61A, 61B, and 31,
$X_{41}$ is N-[$(L_{42})_{a42}$-$(R_{42})_{b42}$], S, O, S(=O), S(=O)$_2$, C(=O), C($R_{43}$)($R_{44}$), Si($R_{43}$)($R_{44}$), P($R_{43}$), P(=O)($R_{43}$), or C=N($R_{43}$);
ring $A_{61}$ in Formula 61 is represented by Formula 61A;
ring $A_{62}$ in Formula 61 is represented by Formula 61B;
$X_{61}$ is N-[$(L_{62})_{a62}$-$(R_{62})_{b62}$], S, O, S(=O), S(=O)$_2$, C(=O), C($R_{63}$)($R_{64}$), Si($R_{63}$)($R_{64}$), P($R_{63}$), P(=O)($R_{63}$), or C=N($R_{63}$);
$X_{71}$ is C($R_{71}$) or N;
$X_{72}$ is C($R_{72}$) or N;
$X_{73}$ is C($R_{73}$) or N;
$X_{74}$ is C($R_{74}$) or N;
$X_{75}$ is C($R_{75}$) or N;
$X_{76}$ is C($R_{76}$) or N;
$X_{77}$ is C($R_{77}$) or N;
$X_{78}$ is C($R_{78}$) or N;
$X_{31}$ is S, O, N, C-[$(L_{31})_{a31}$-$(R_{31})_{b31}$], or Si-[$(L_{31})_{a31}$-$(R_{31})_{b31}$];
$X_{32}$ is S, O, N, C-[$(L_{32})_{a32}$-$(R_{32})_{c32}$], or Si-[$(L_{32})_{a32}$-$(R_{32})_{b32}$];
$X_{33}$ is S, O, N, C-[$(L_{33})_{a33}$-$(R_{33})_{b33}$], or Si-[$(L_{33})_{a33}$-$(R_{33})_{c33}$];
$Ar_{41}$, $L_{41}$, $L_{42}$, $L_{61}$, and $L_{62}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_3$-$C_{10}$ arylene group, a substituted or unsubstituted $C_1$-$C_{60}$ heteroarylene group, a substituted or unsubstituted divalent nonaromatic condensed polycyclic group, and a substituted or unsubstituted divalent nonaromatic condensed heteropolycyclic group;
$L_{31}$ to $L_{34}$ are each independently selected from a substituted or unsubstituted $C_3$-$C_{10}$ cycloalkylene group, a substituted or unsubstituted $C_3$-$C_{10}$ cycloalkenylene group, a substituted or unsubstituted Co-Coo arylene group, and a substituted or unsubstituted divalent nonaromatic condensed polycyclic group;
n1 and n2 are each independently an integer selected from 0 to 3;
a41, a42, a61, a62, and a31 to a34 are each independently an integer selected from 0 to 3;
$R_{41}$ to $R_{44}$, $R_{51}$ to $R_{54}$, $R_{61}$ to $R_{64}$, and $R_{71}$ to $R_{79}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent nonaromatic condensed polycyclic group, a substituted or unsubstituted monovalent nonaromatic condensed heteropolycyclic group, —N($Q_1$)($Q_2$), —Si($Q_3$)($Q_4$)($Q_5$), and —B($Q_6$)($Q_7$);

$R_{31}$ to $R_{36}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group, and a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group, and a dibenzocarbazolyl group;

b41, b42, b51 to b54, b61, b62, b79, and b31 to b34 are each independently an integer selected from 1 to 3;

b35 is an integer selected from 1 to 3; and b36 is 1 or 2, wherein at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent nonaromatic condensed polycyclic group, and the substituted monovalent nonaromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, and a monovalent nonaromatic condensed heteropolycyclic group, each substituted with at least one of a deuterium atom, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent nonaromatic condensed polycyclic group, a monovalent nonaromatic condensed heteropolycyclic group, —N(Q$_{21}$)(Q$_{22}$), —Si(Q$_{23}$)(Q$_{24}$)(Q$_{25}$), and —B(Q$_{26}$)(Q$_{27}$), and —N(Q$_{31}$)(Q$_{32}$), —Si(Q$_{33}$)(Q$_{34}$)(Q$_{35}$), and —B(Q$_{36}$)(Q$_{37}$), wherein Q$_1$ to Q$_7$, Q$_{11}$ to Q$_{17}$, Q$_{21}$ to Q$_{27}$, and Q$_{31}$ to Q$_{37}$ are each independently selected from a hydrogen, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent nonaromatic condensed polycyclic group, and a monovalent nonaromatic condensed heteropolycyclic group.

22. The organic light-emitting device of claim 21, wherein the first compound is represented by one of Formulae 41-1 to 41-12, and the second compound is represented by one of Formulae 61-1 to 61-6:

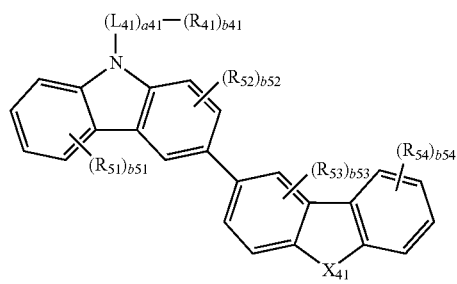

Formula 41-1

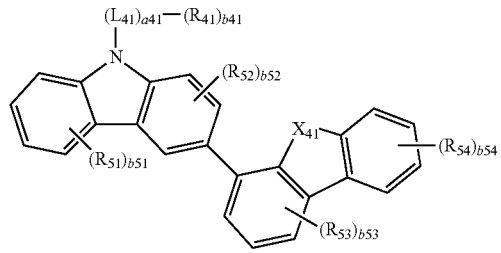

Formula 41-2

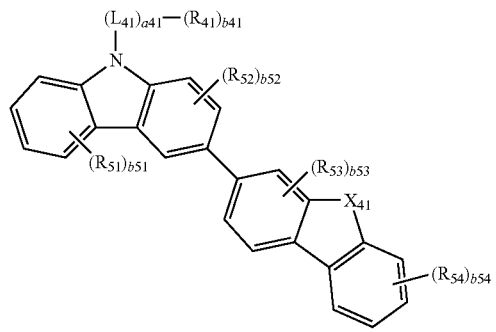

Formula 41-3

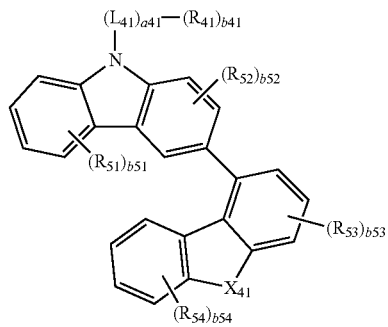

Formula 41-4

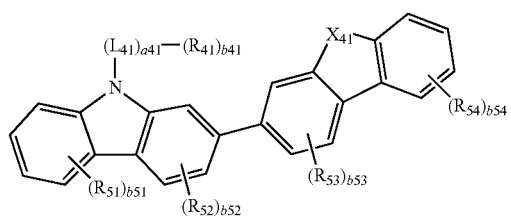

Formula 41-5

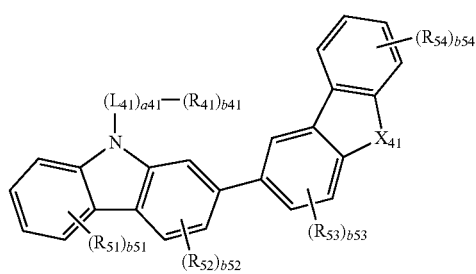

Formula 41-6

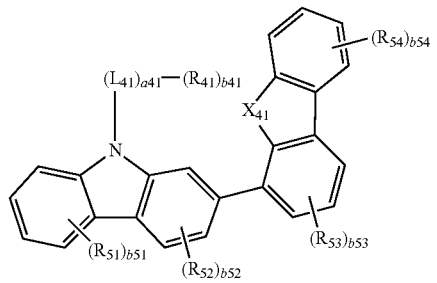

Formula 41-7

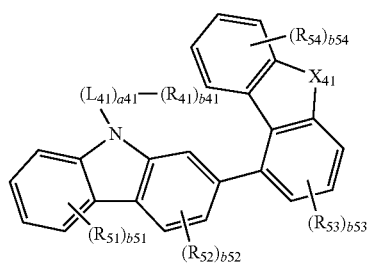

Formula 41-8

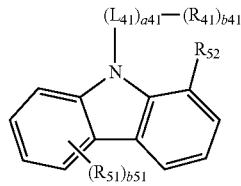

Formula 41-9

-continued

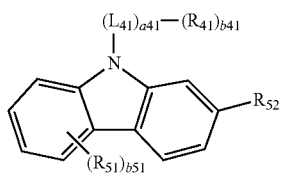
Formula 41-10

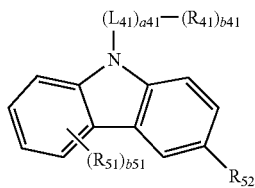
Formula 41-11

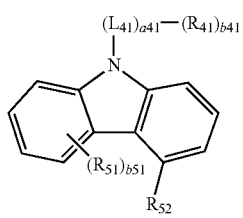
Formula 41-12

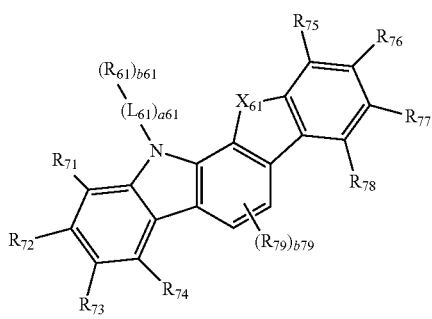
Formula 61-1

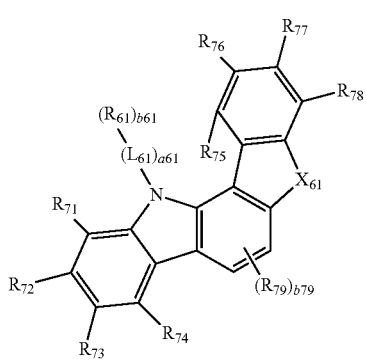
Formula 61-2

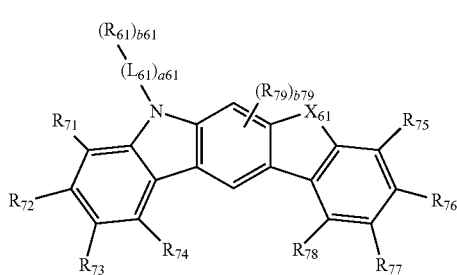
Formula 61-3

-continued

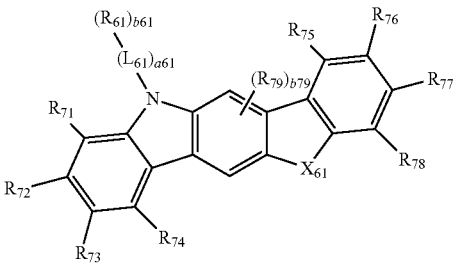
Formula 61-4

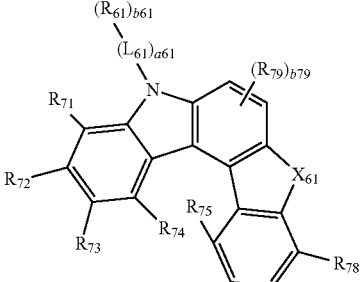
Formula 61-5

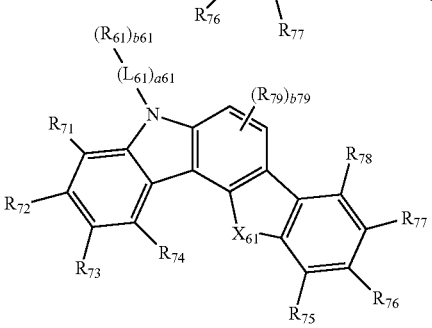
Formula 61-6 wherein, in Formulae 41-1 to 41-12 and Formulae 61-1 to 61-6, $X_{41}$, $X_{61}$, $L_{41}$, $L_{42}$, a41, a42, $L_{61}$, $L_{62}$, a61, a62, $R_{41}$ to $R_{44}$, b41, b42, $R_{61}$ to $R_{64}$, b61, b62, $R_{71}$ to $R_{79}$, and b79 are the same as in claim 21.

23. The organic light-emitting device of claim 21, wherein the first compound of Formula 41 comprises one of Compounds A1 to A83, the second compound of Formula 61 comprises one of Compounds B1 to B20, and the third compound of Formula 31 comprises one of Compounds 601 to 656:

A1

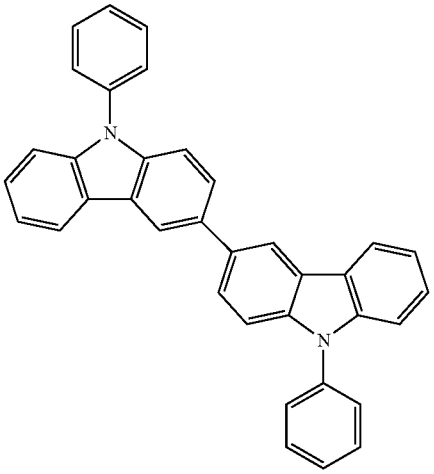

409
-continued
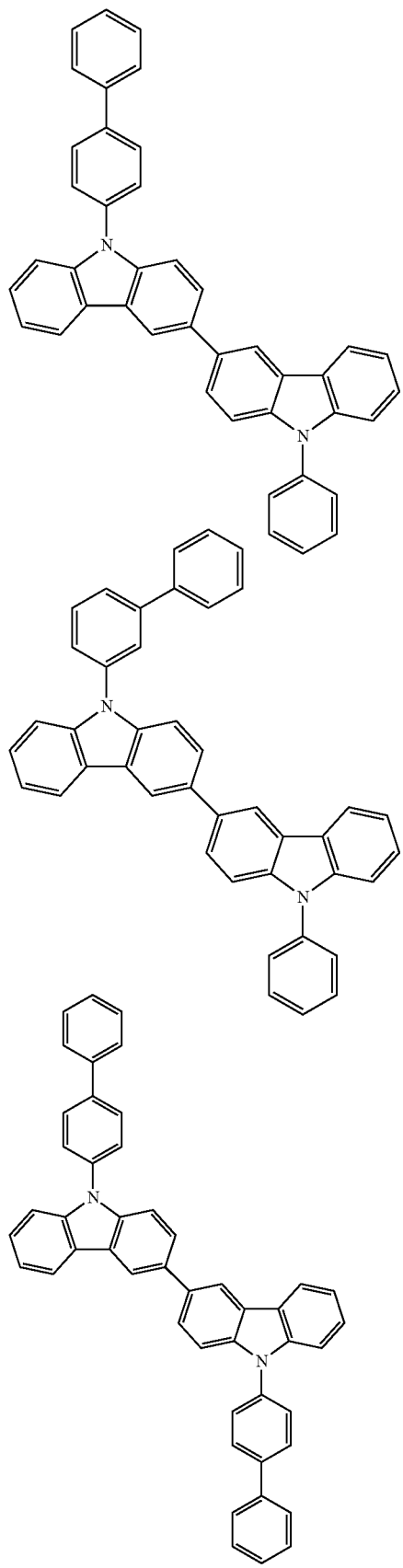
A2
A3
A4
410
-continued
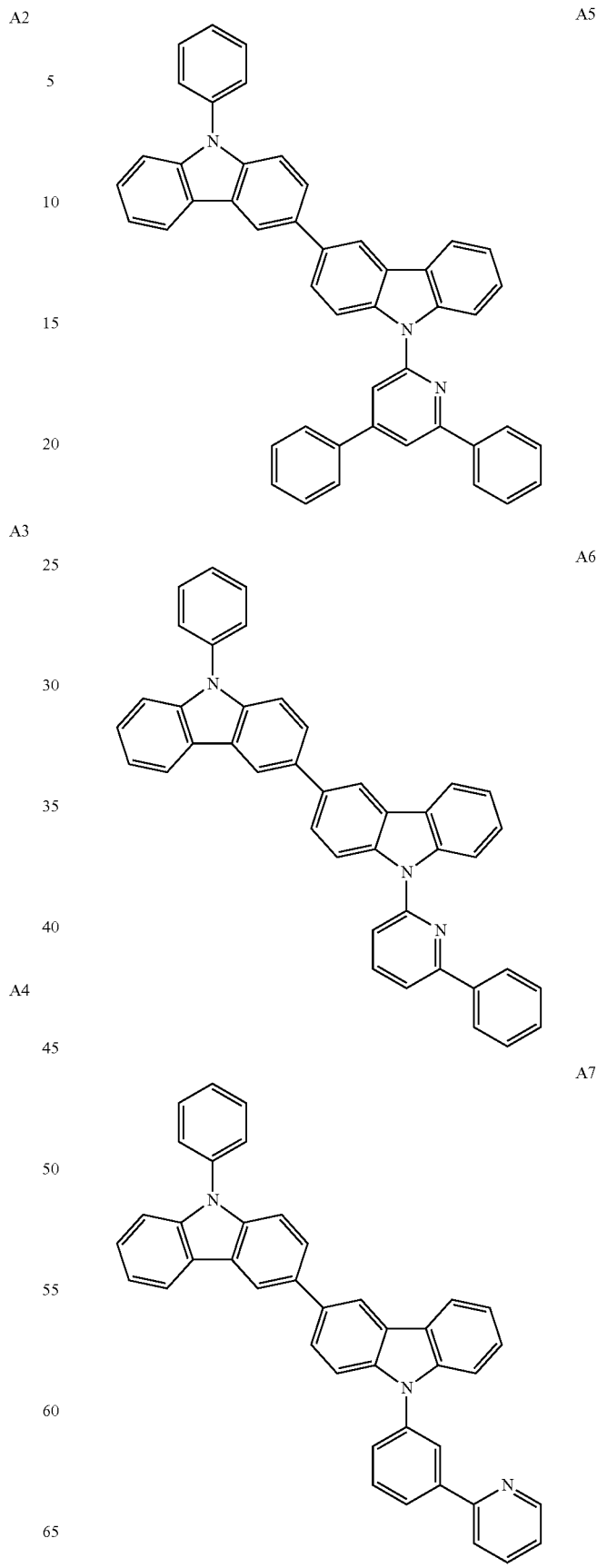
A5
A6
A7

411
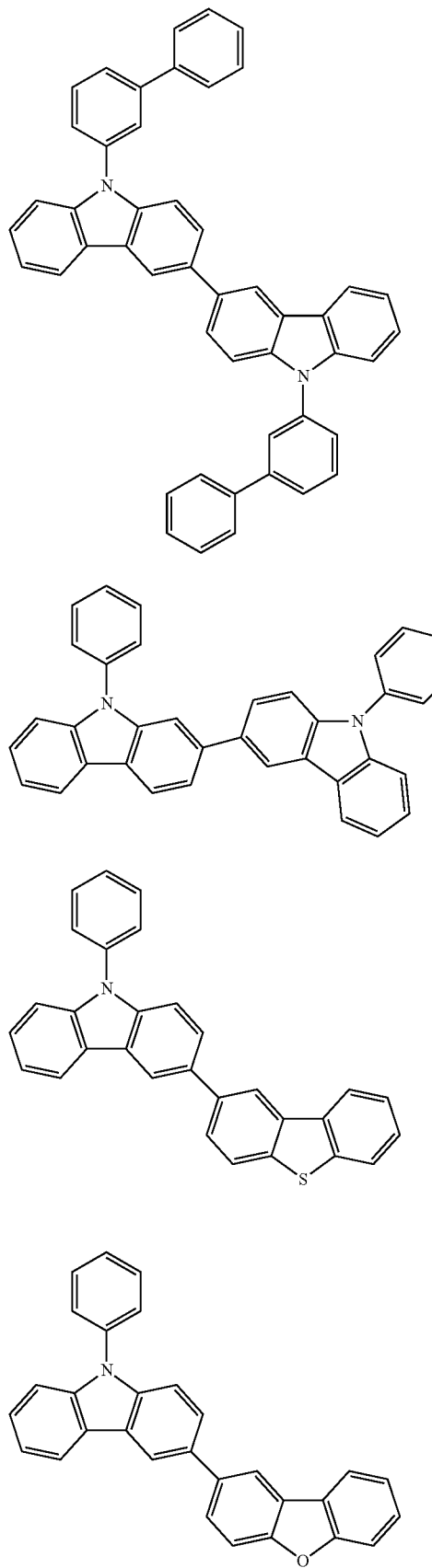
A8
A9
A10
A11
412
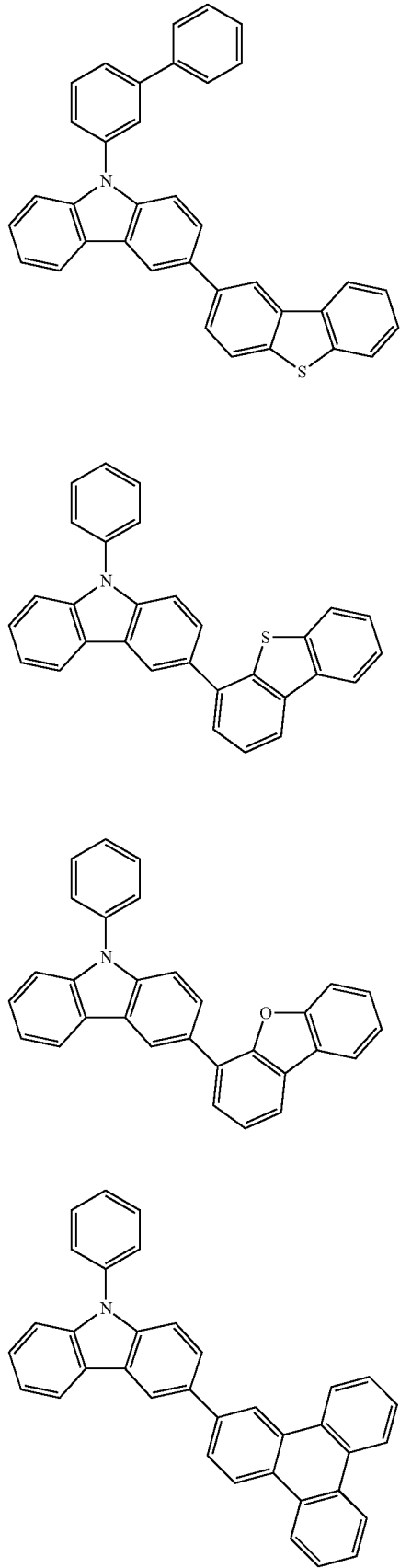
A12
A13
A14
A15

A16 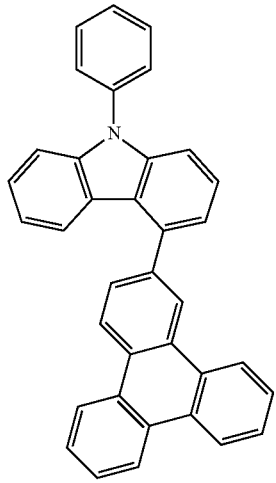
A19 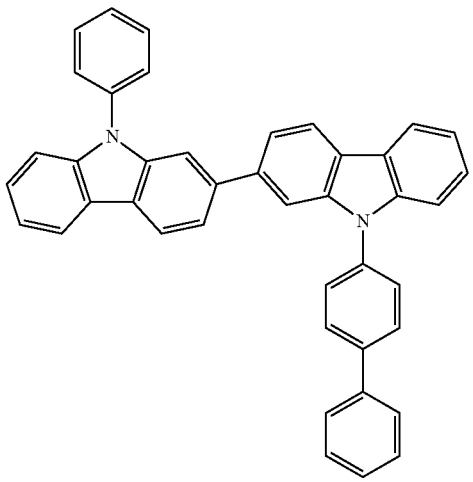
A17 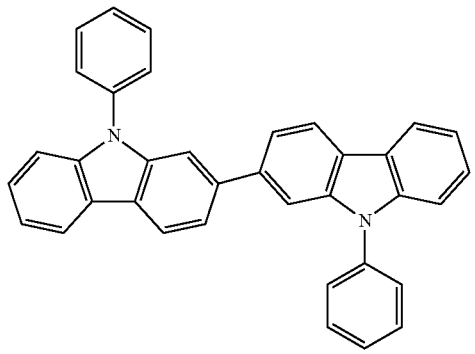
A20 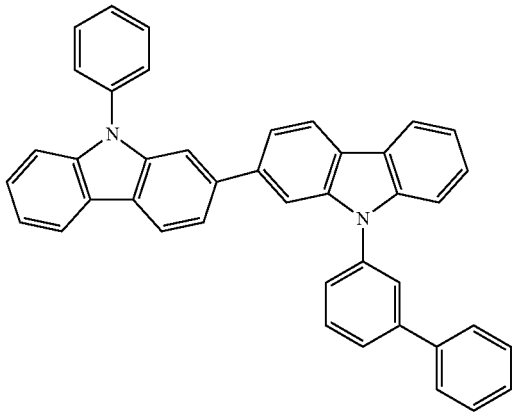
A18
A21 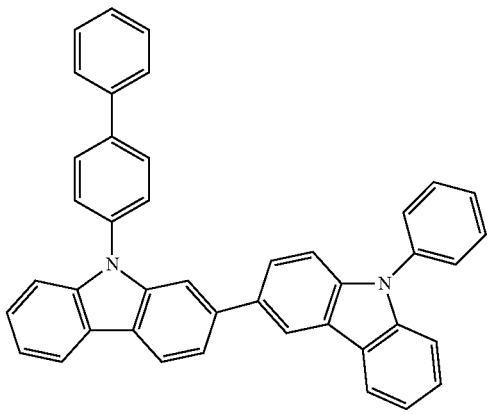

A22
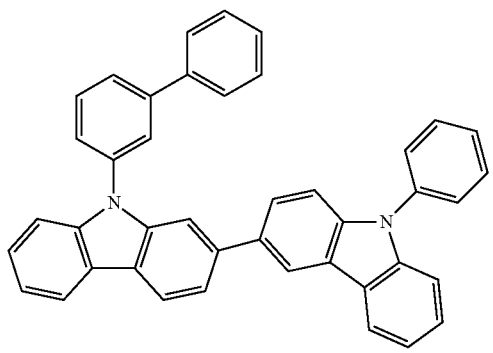
A23
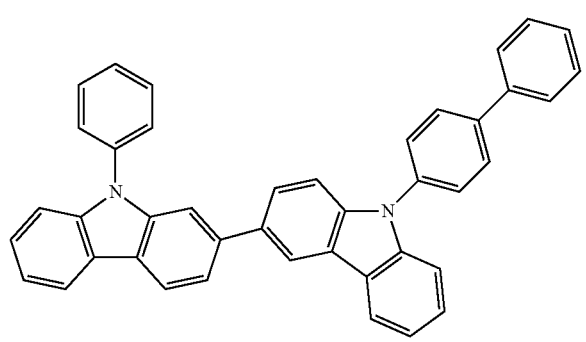
A24
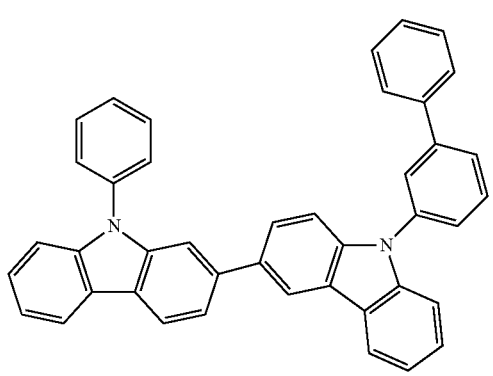
A25
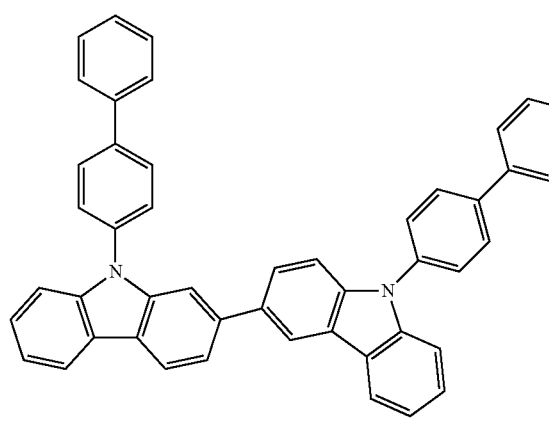
A26
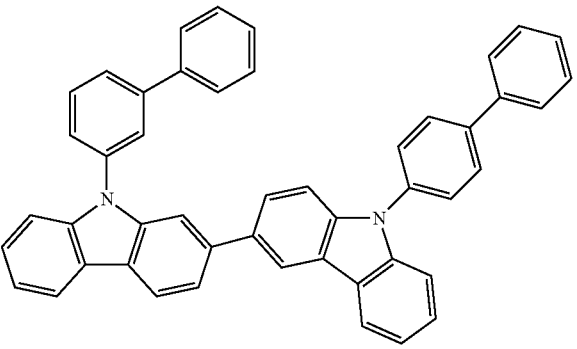
A27
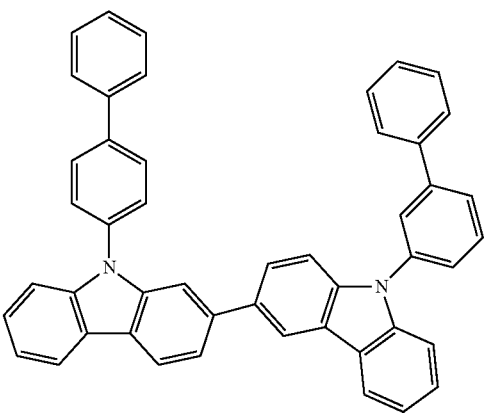
A28
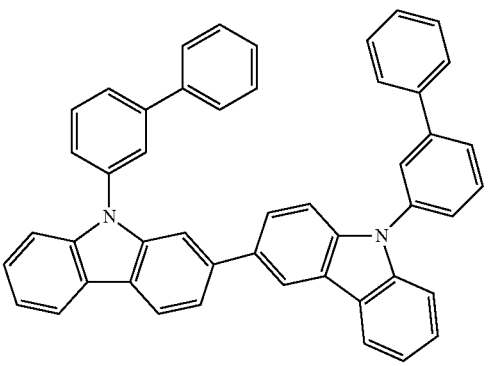

417
-continued
418
-continued
A29
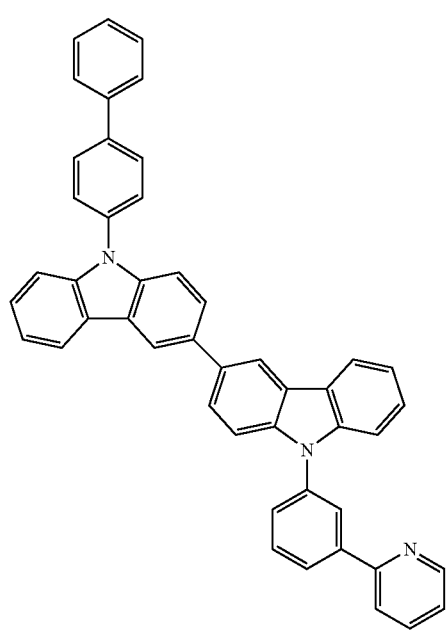
A31
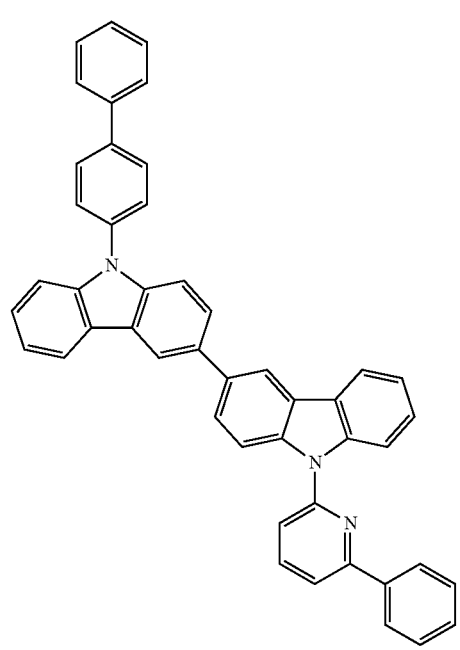
A30
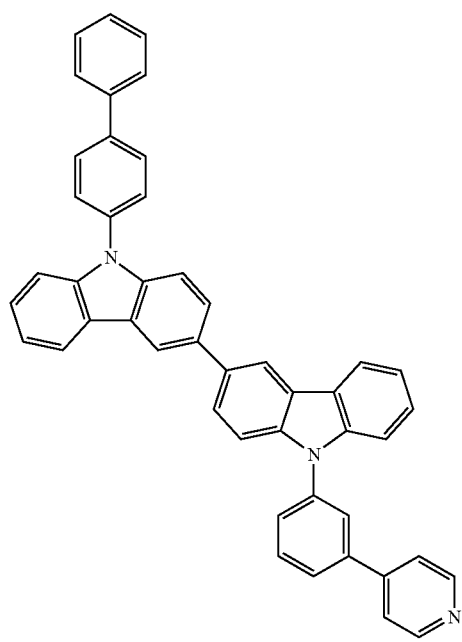
A32
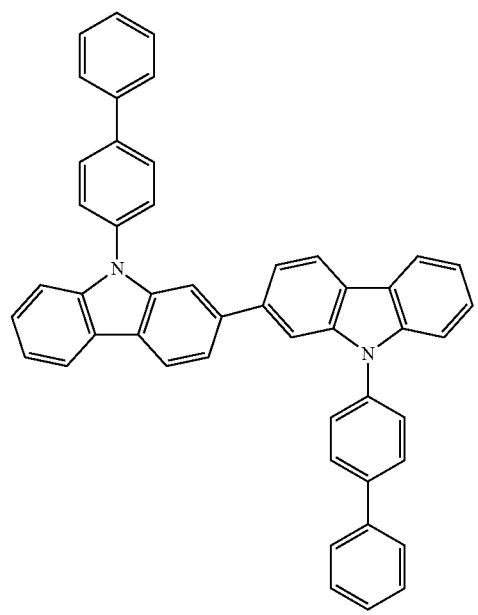

A33
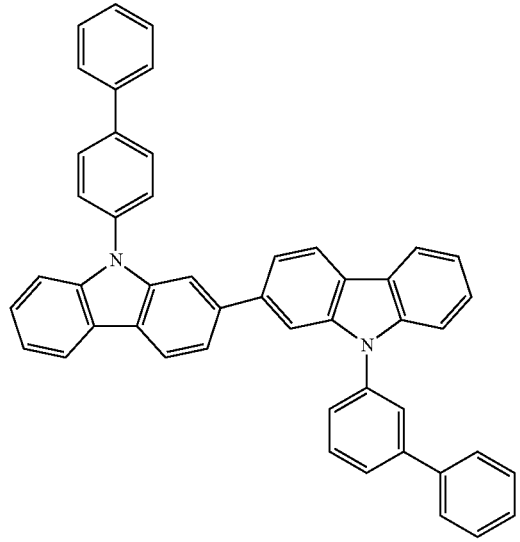
A34
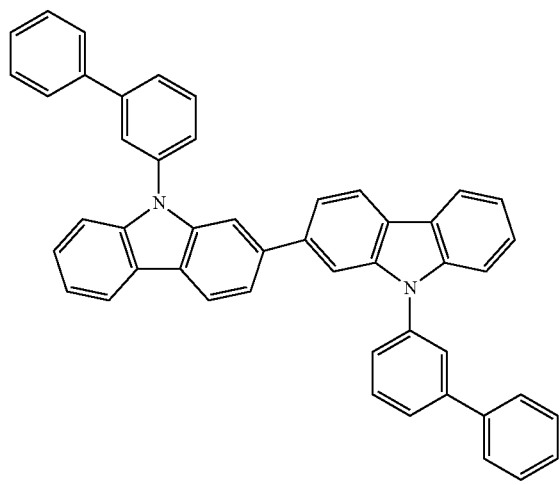
A35
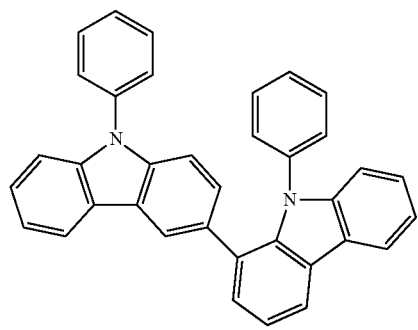
A36
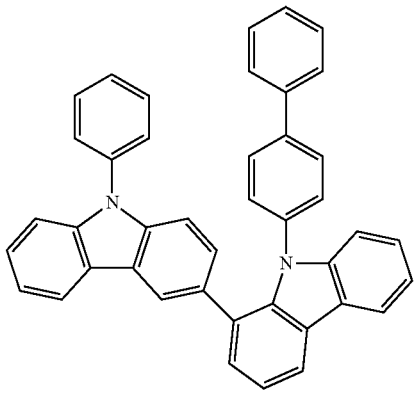
A37
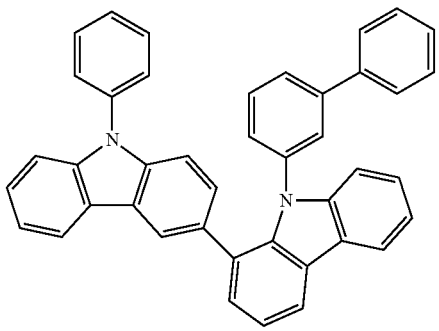
A38
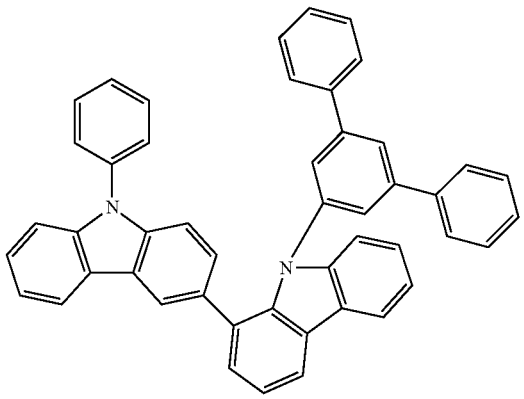
A39
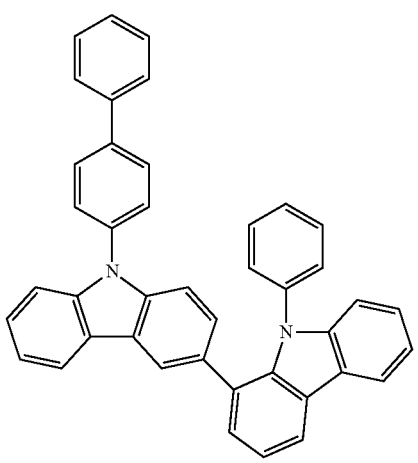

A40
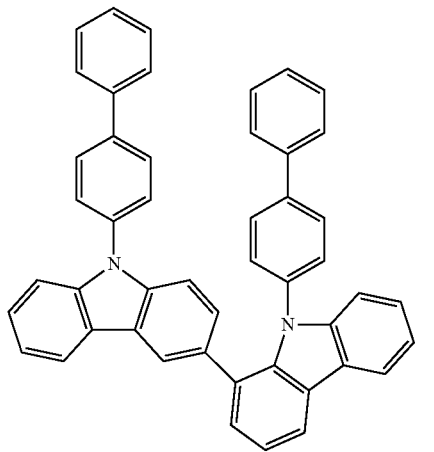
A41
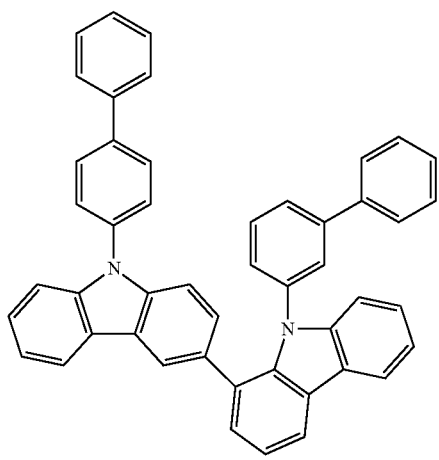
A42
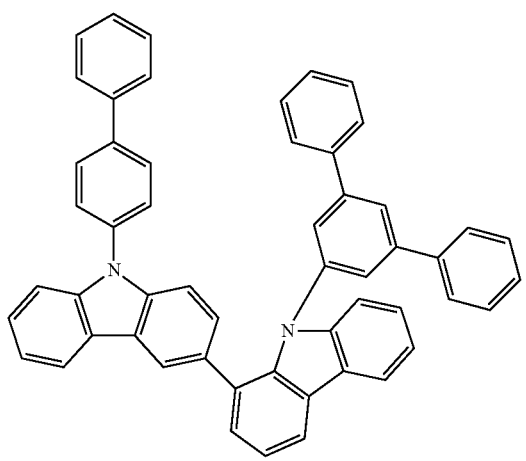
A43
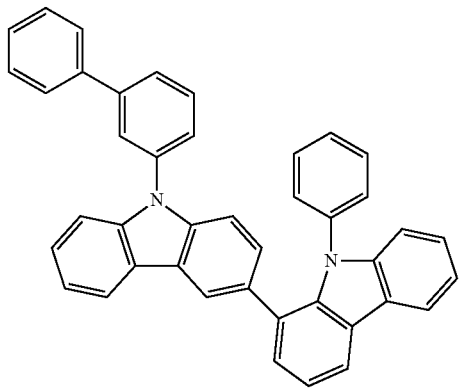
A44
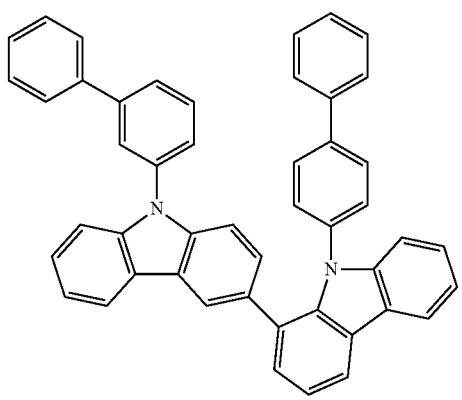
A45
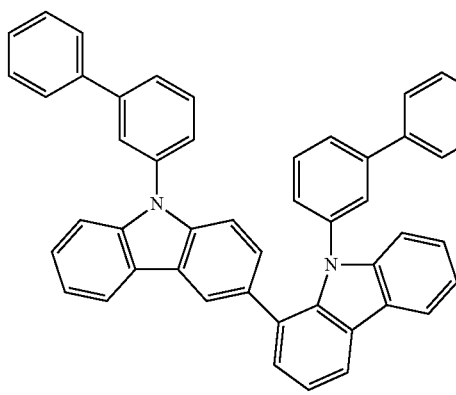
A46
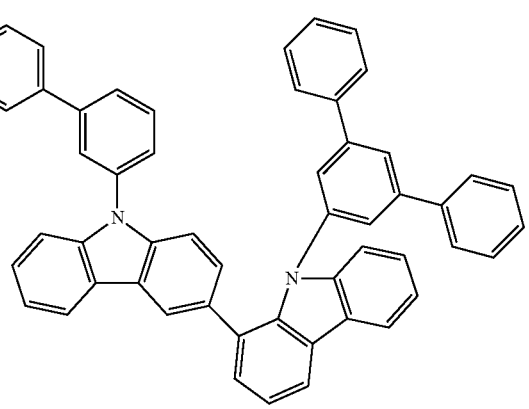

A47
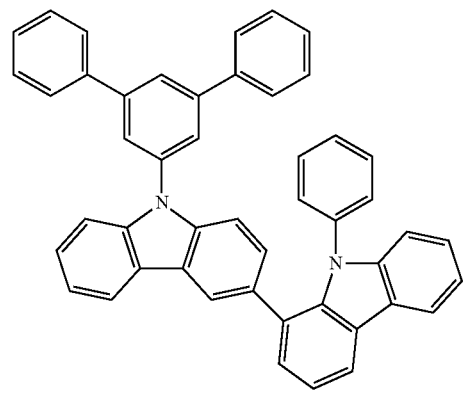
A48
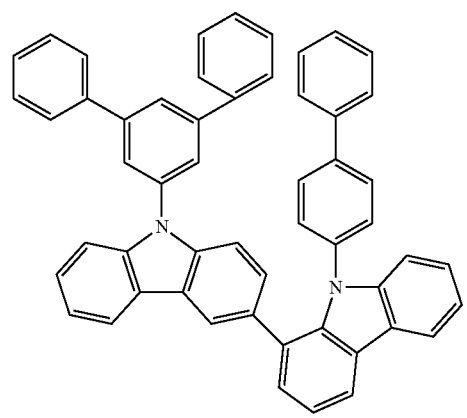
A49
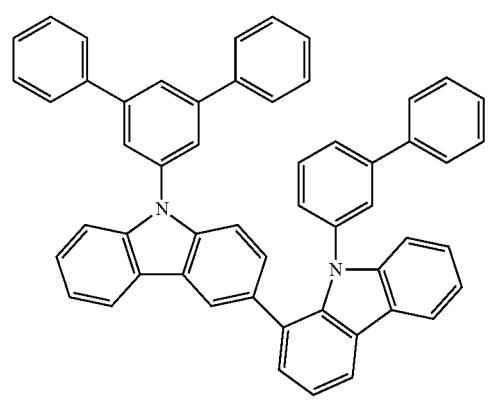
A50
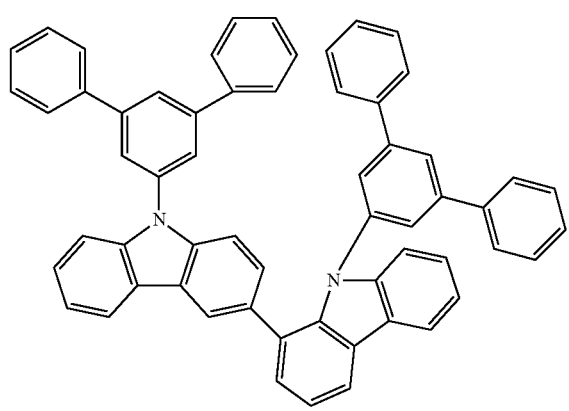
A51
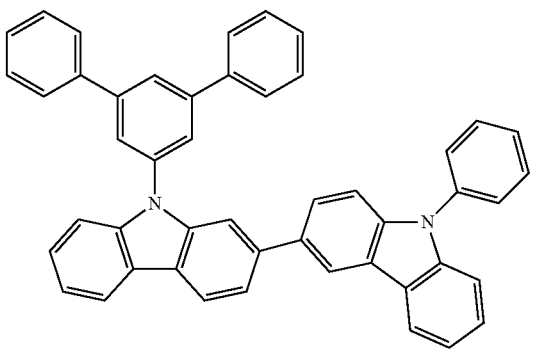
A52
A53
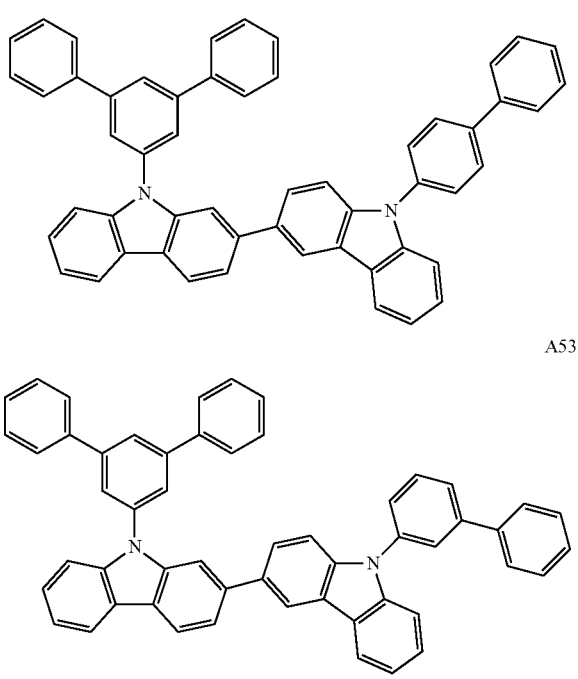
A54
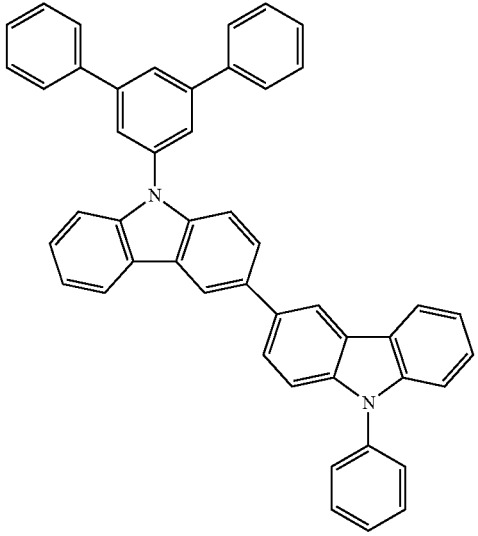

425
-continued
A55
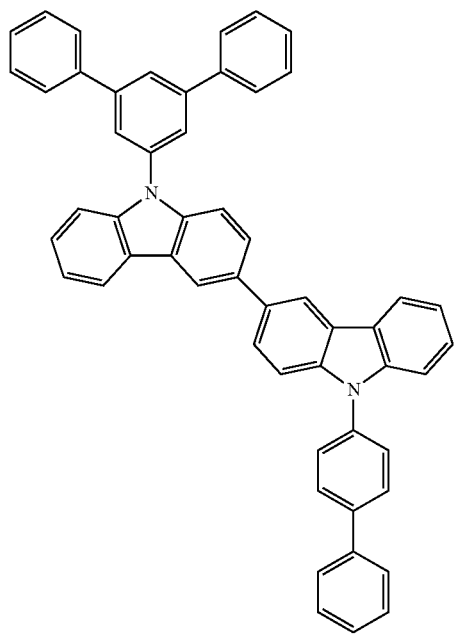
A56
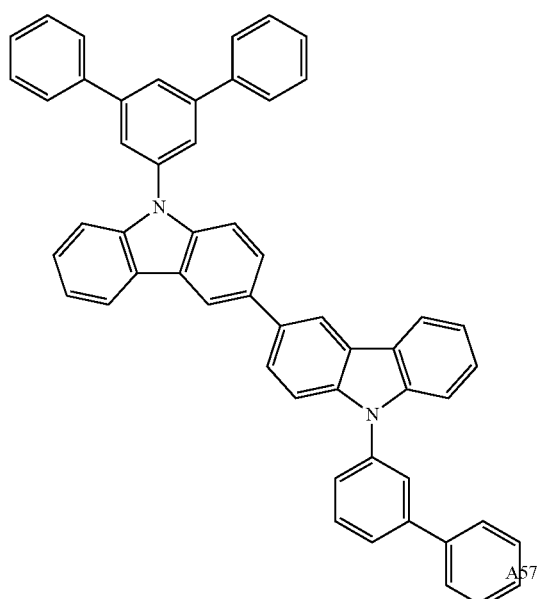
A57
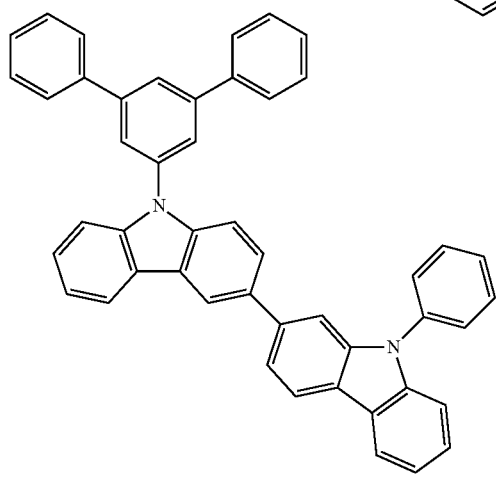
426
-continued
A58
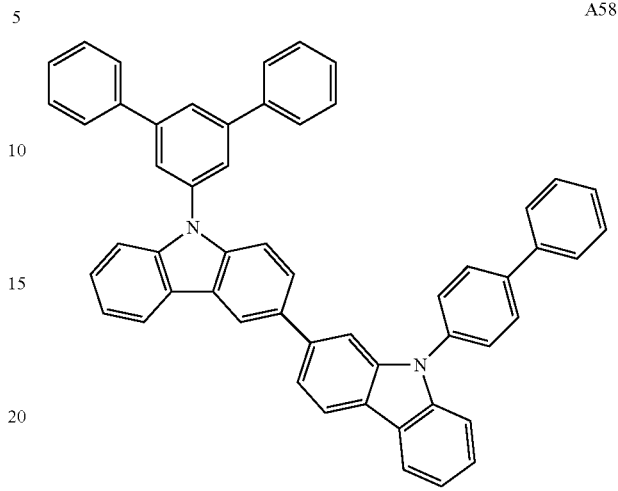
A59
A60
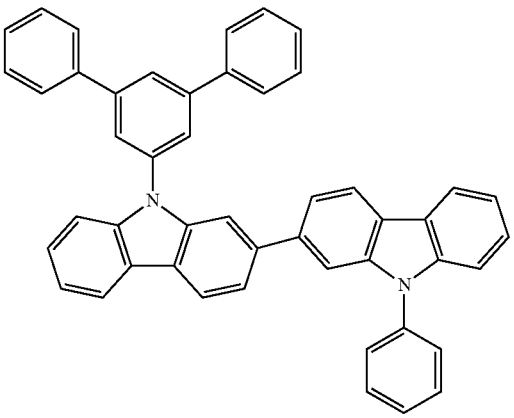

427
-continued
428
-continued
A61
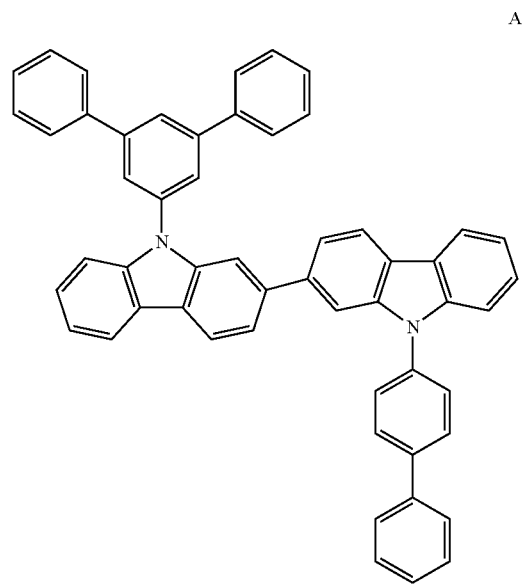
A64
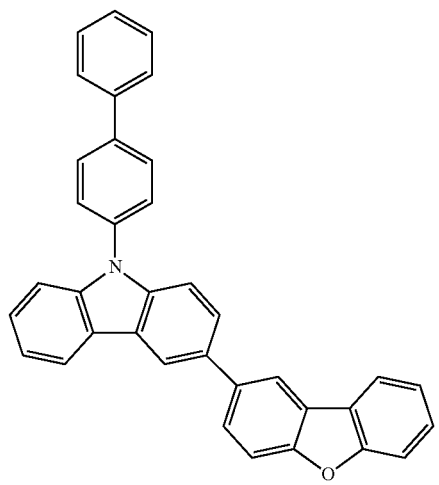
A62
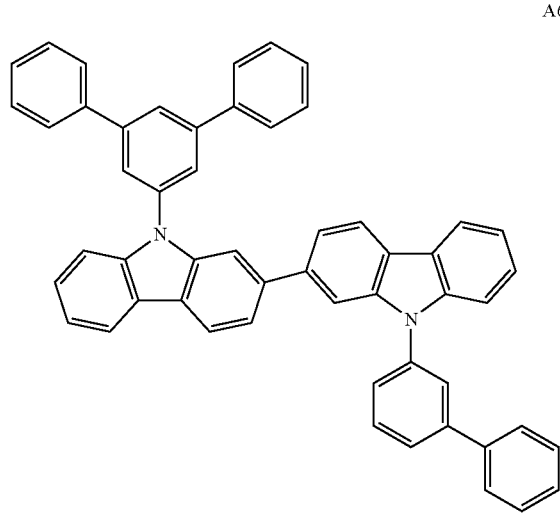
A65
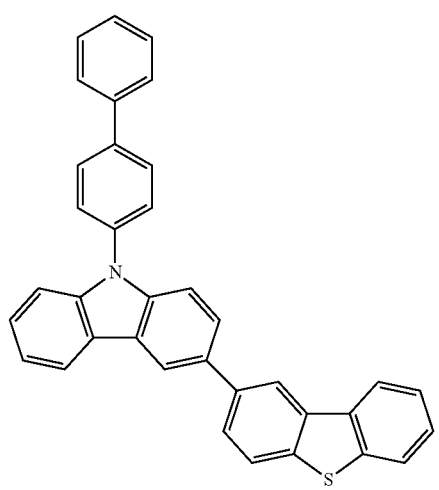
A63
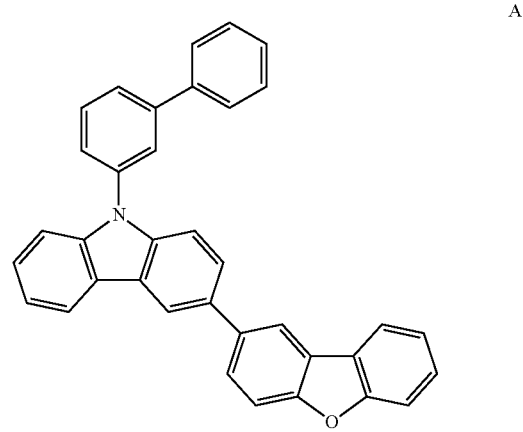
A66
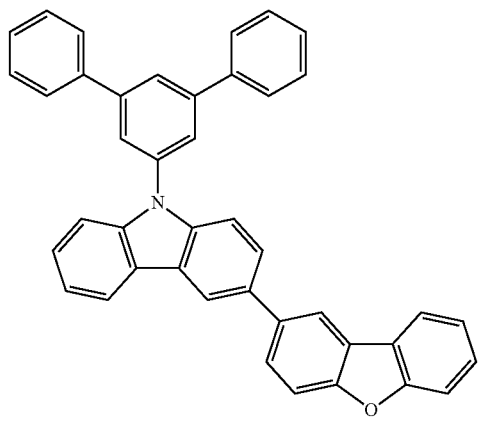

-continued
A67
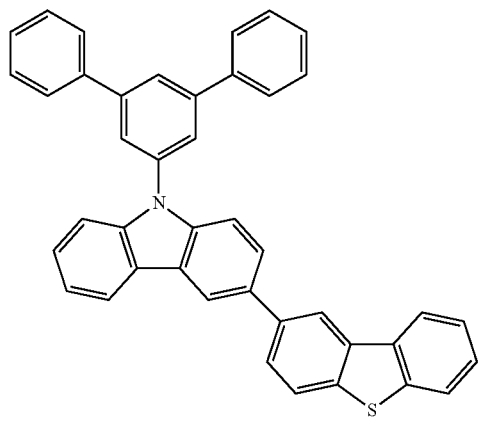
A68
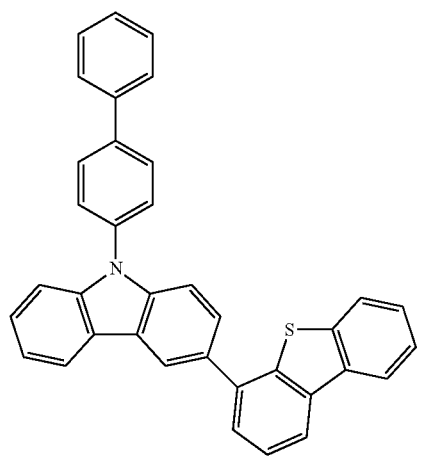
A69
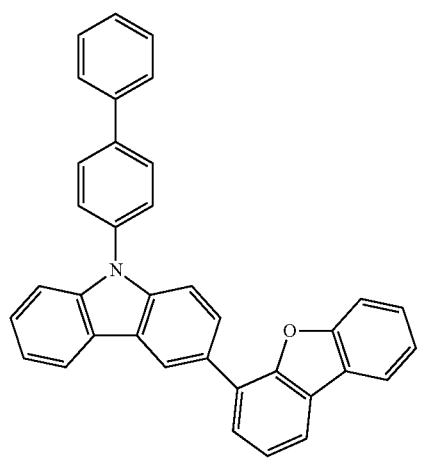
-continued
A70
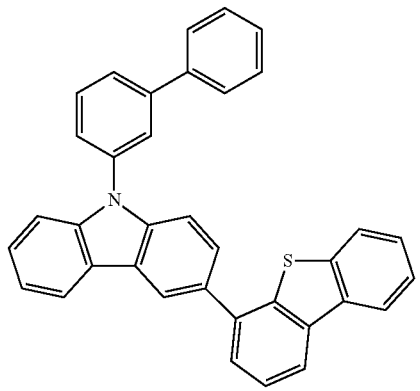
A71
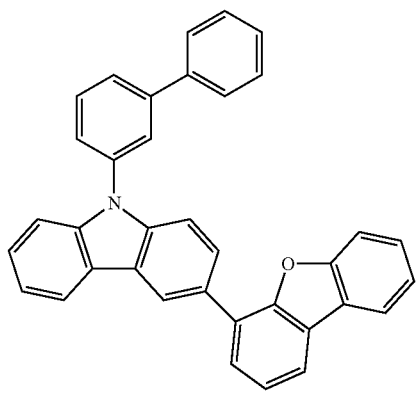
A72
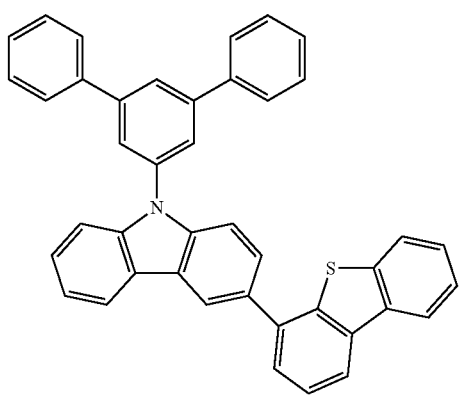
A73
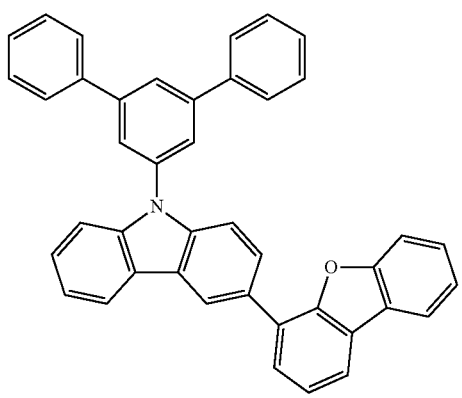

A74
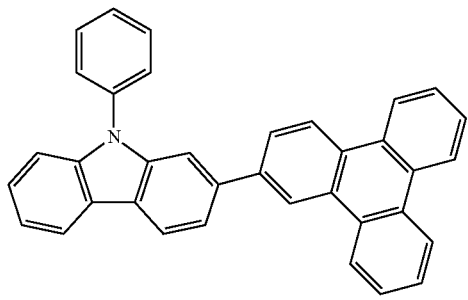
A75
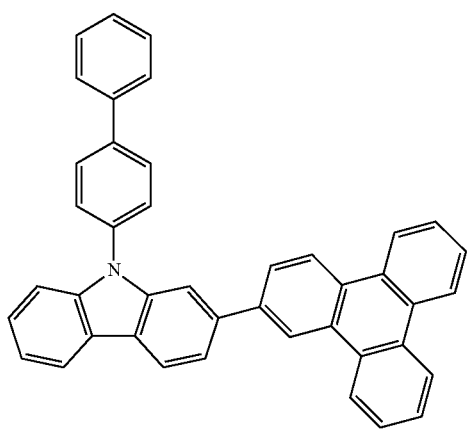
A76
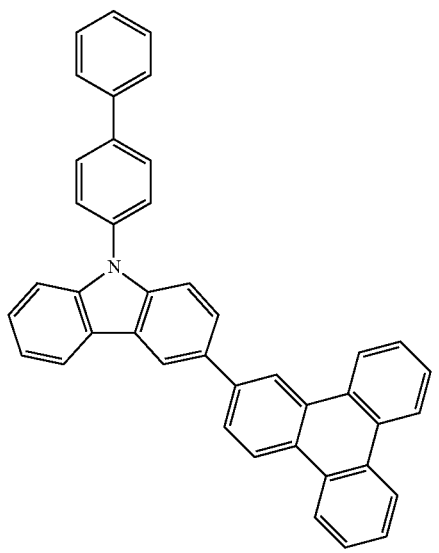
A77
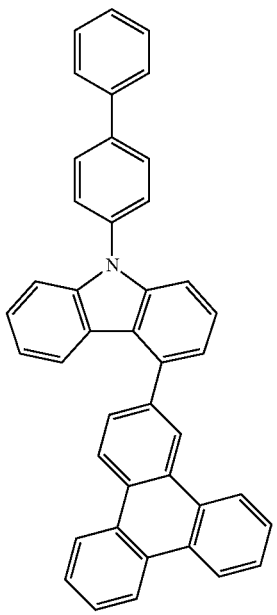
A78
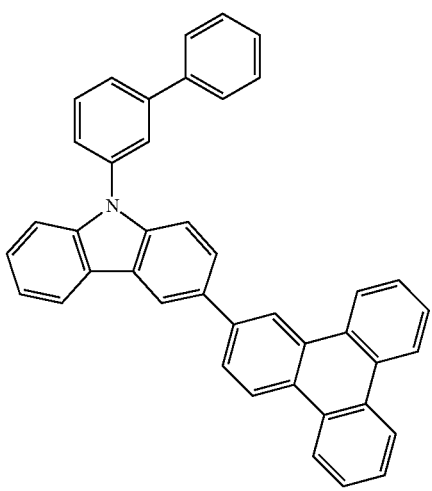
A79
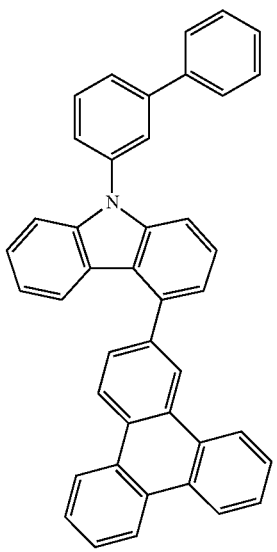

433
-continued
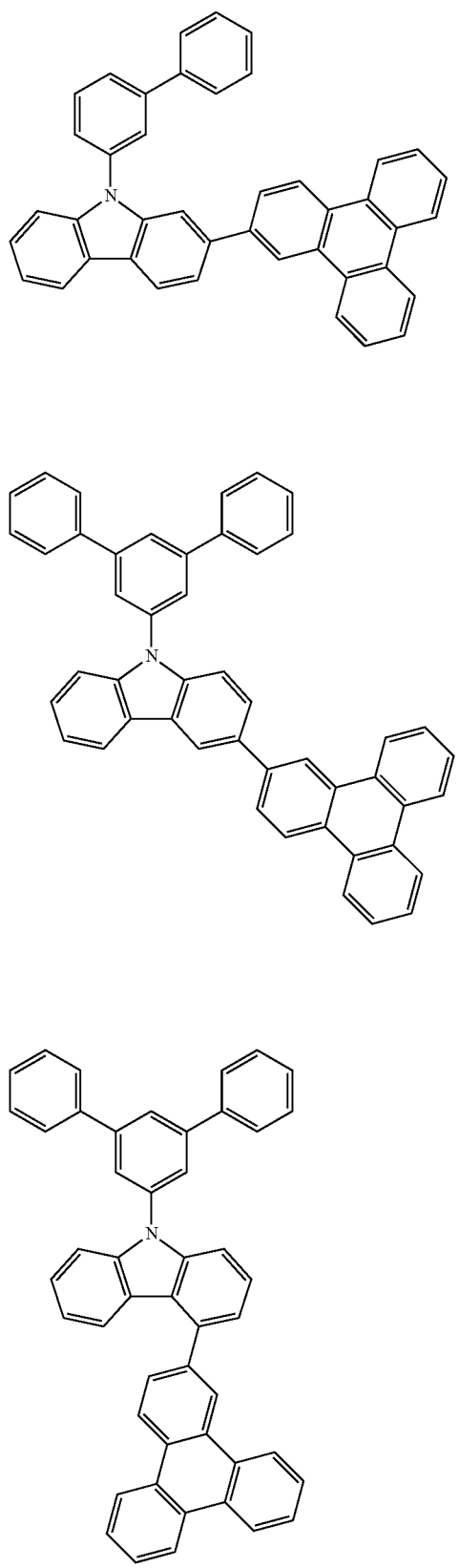
A80
A81
A82
434
-continued
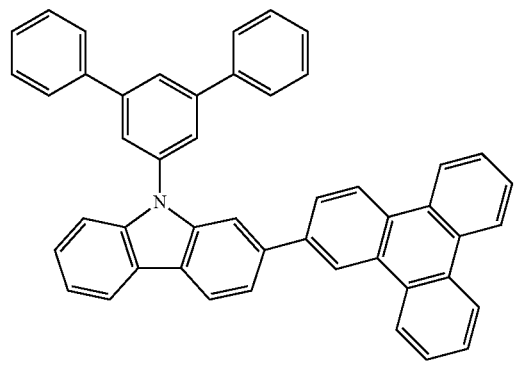
A83
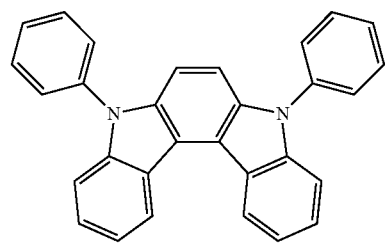
B1
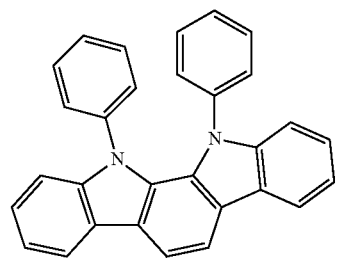
B2
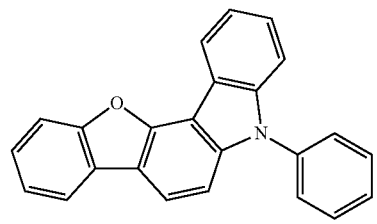
B3
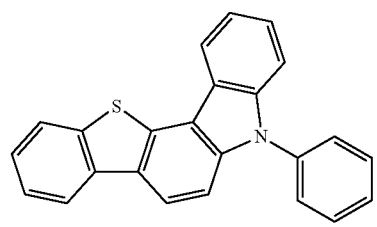
B4
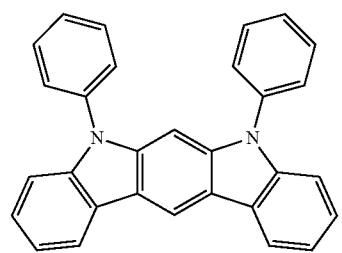
B5

-continued
B6
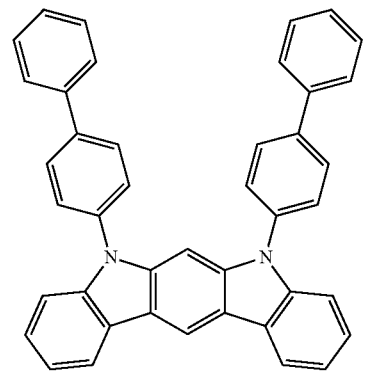
B7
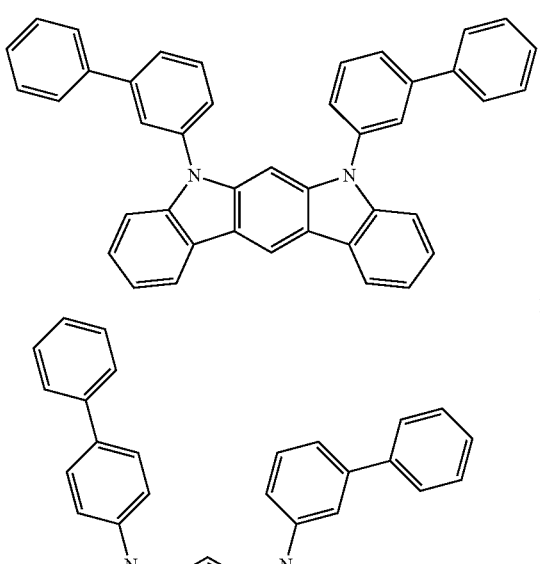
B8
B9
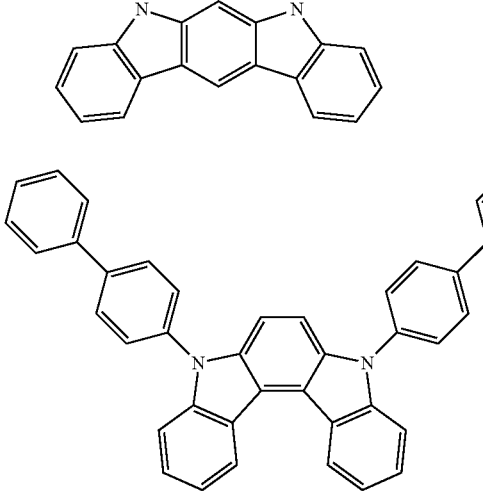
B10
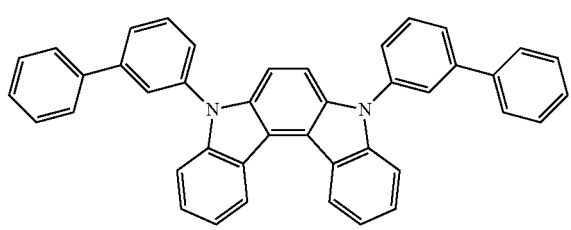
-continued
B11
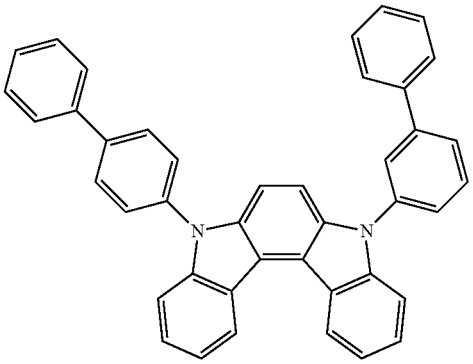
B12
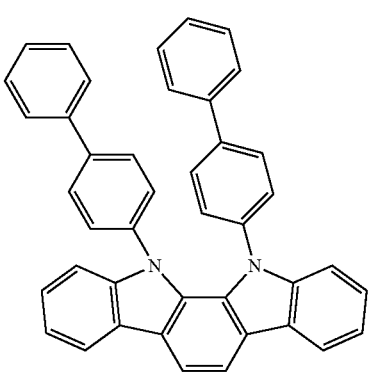
B13
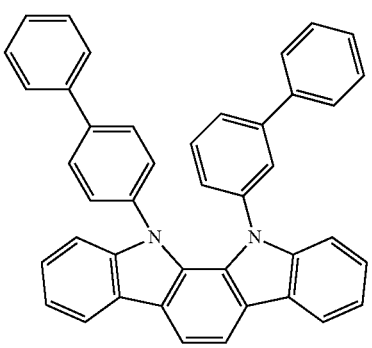
B14
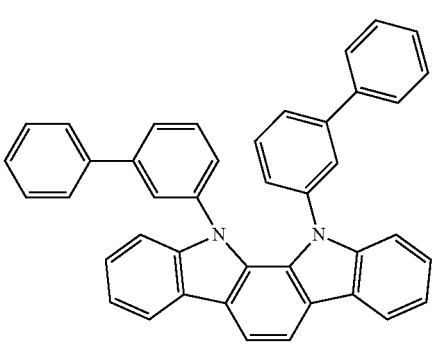

B15
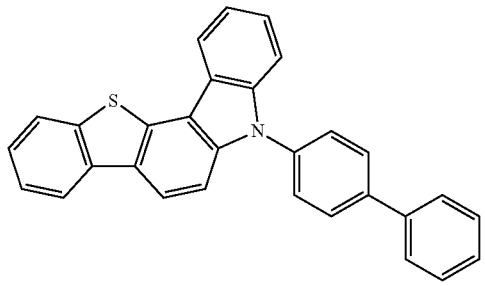
B16
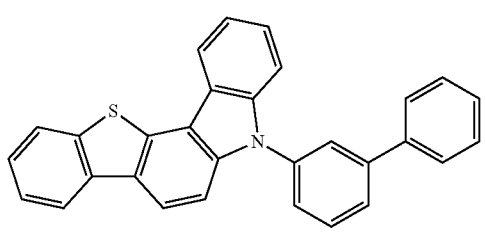
B17
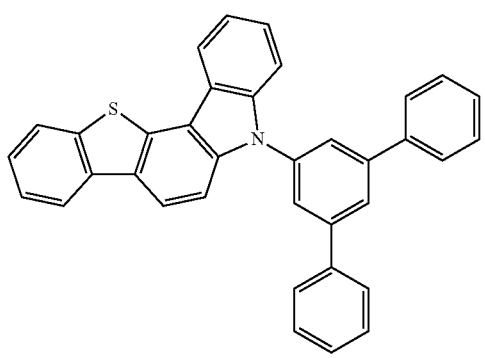
B18
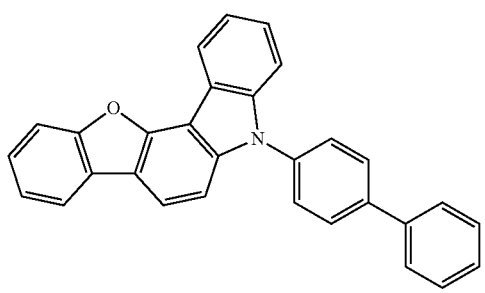
B19
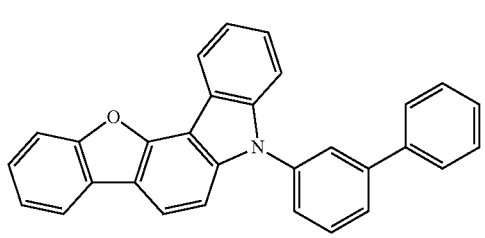
B20
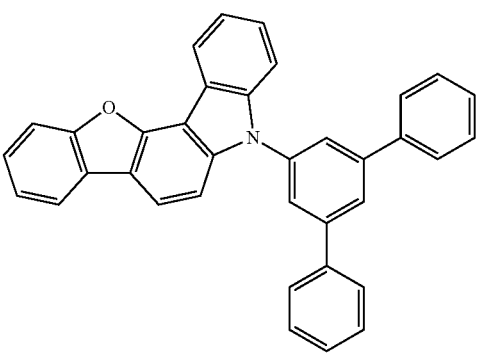
601
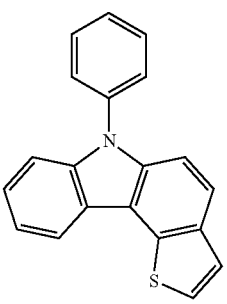
602
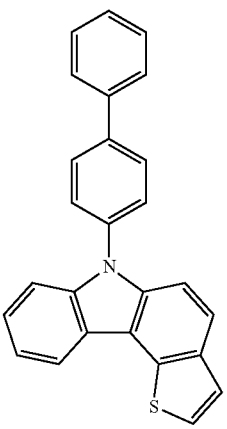
603
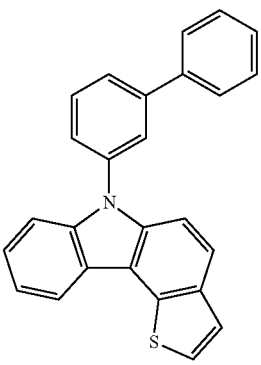

439
-continued
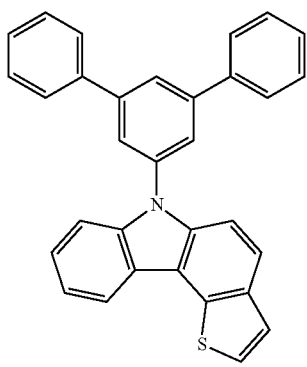
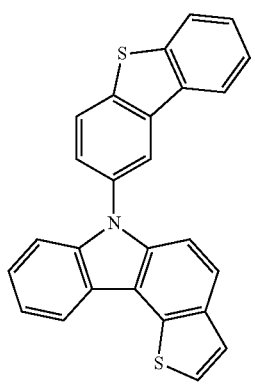
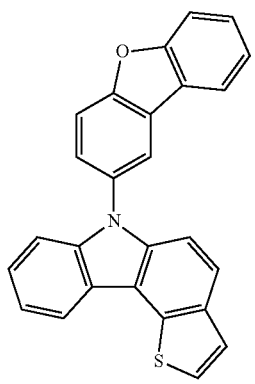
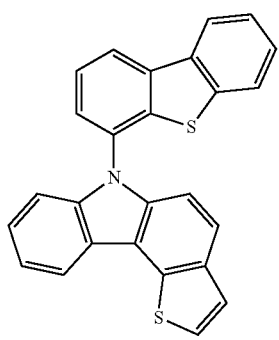
440
-continued
604
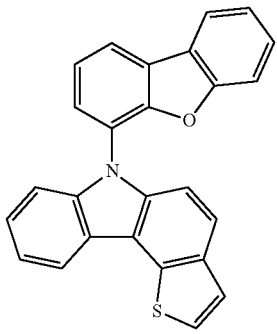
605
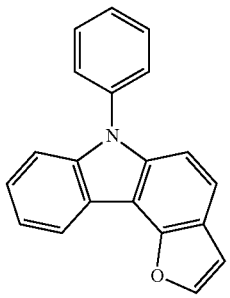
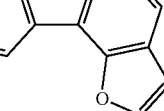
606
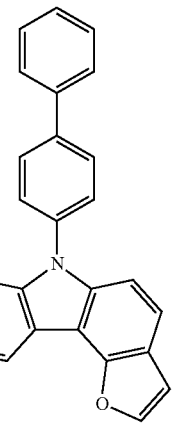
607
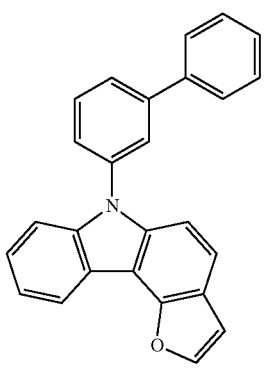
608
609
610
611

441
-continued
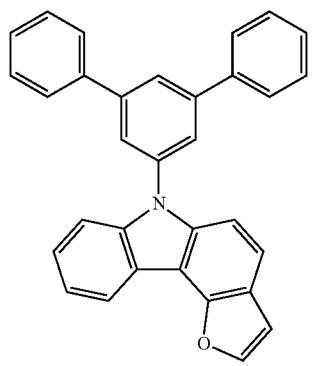
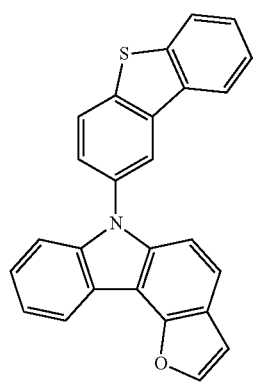
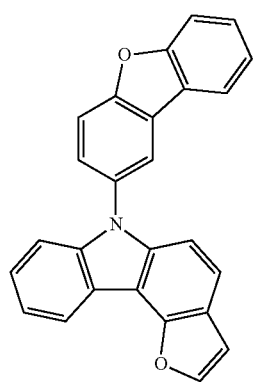
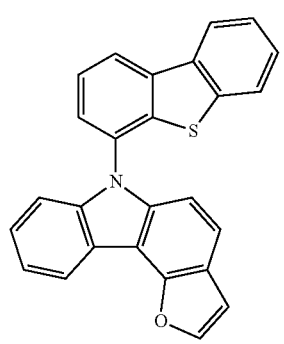
442
-continued
612
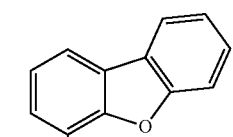
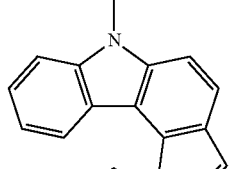
613
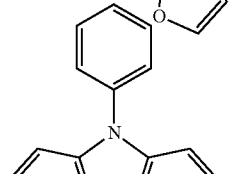
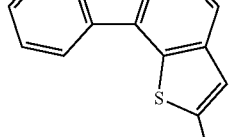
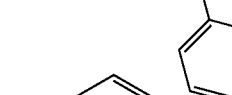
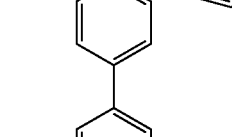
614
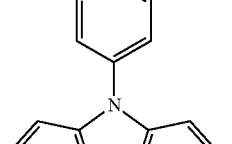
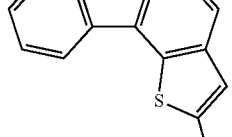
615
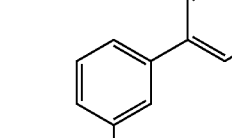
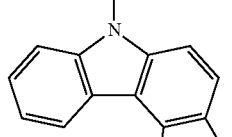
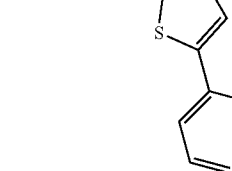
616
617
618
619

443
-continued
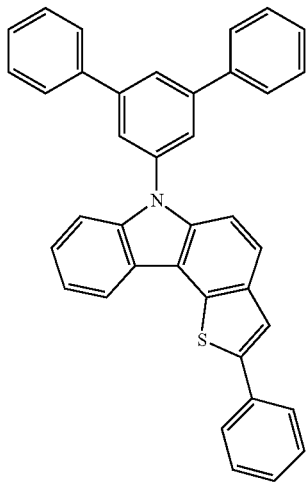
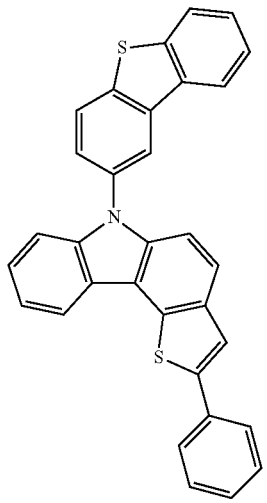
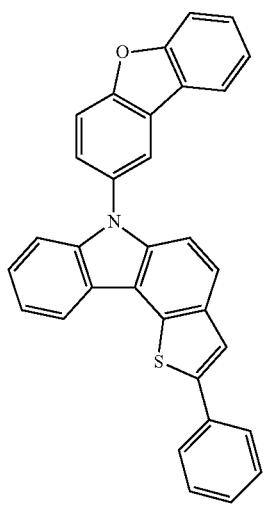
444
-continued
620
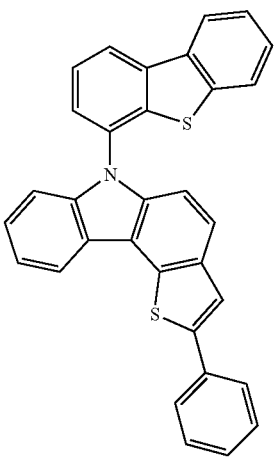
621
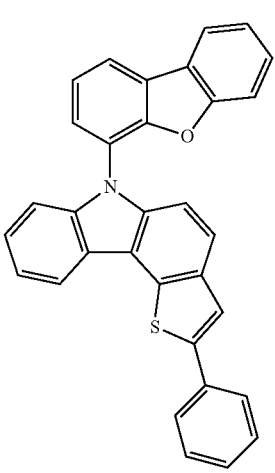
622
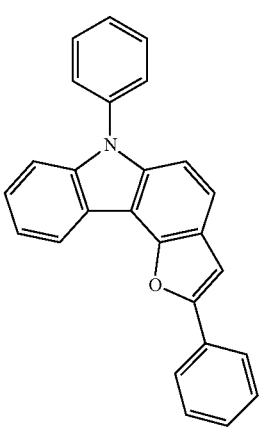
623
624
625

445
-continued
626
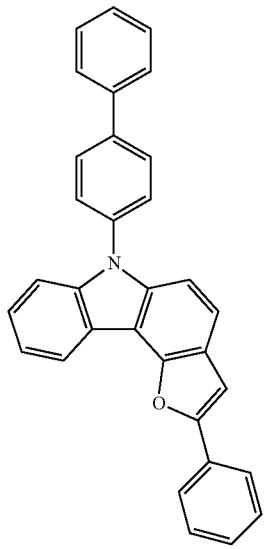
627
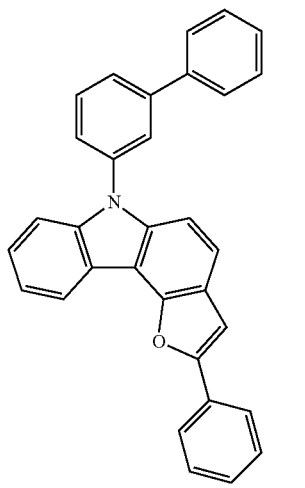
628
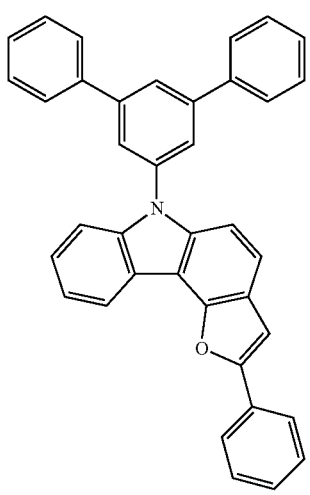
446
-continued
629
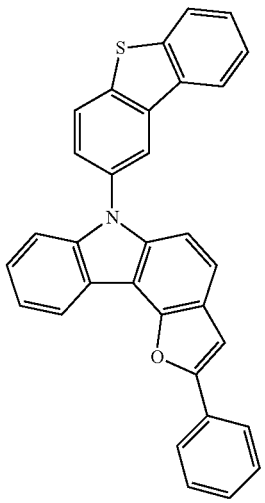
630
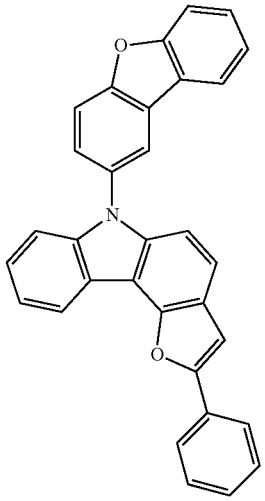
631
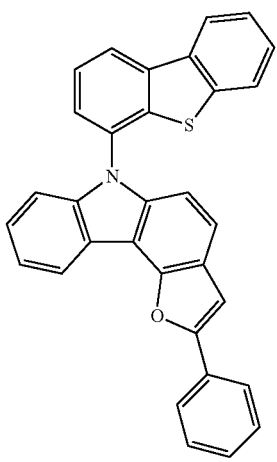

632 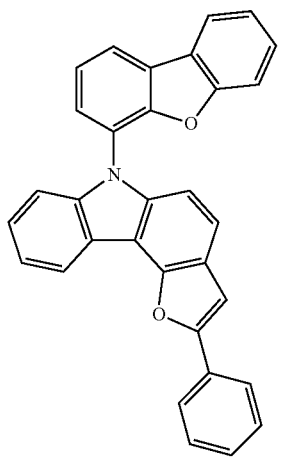
635 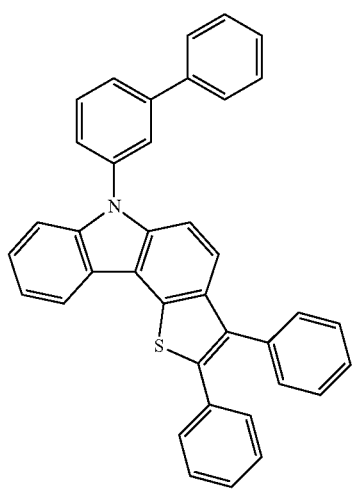
633 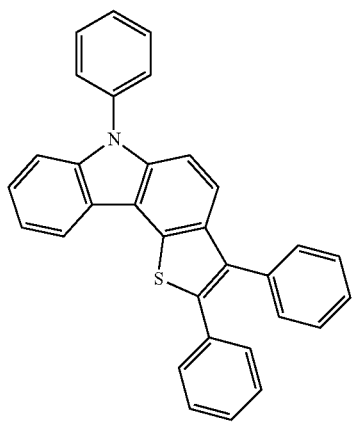
636
634 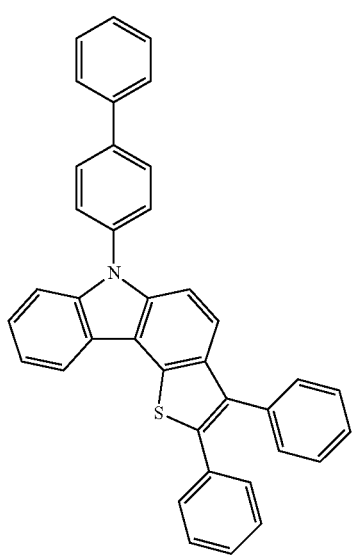
637 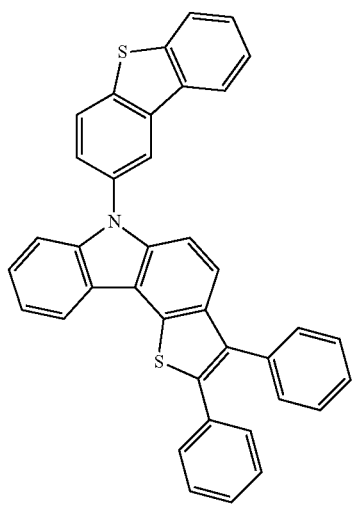

449
-continued
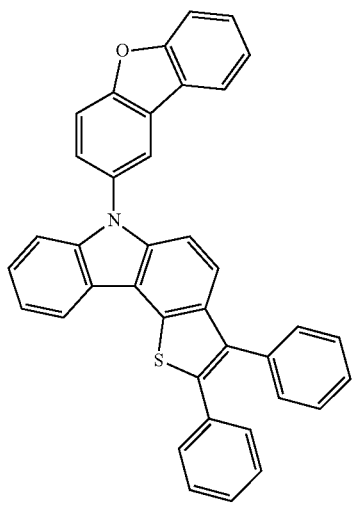
638
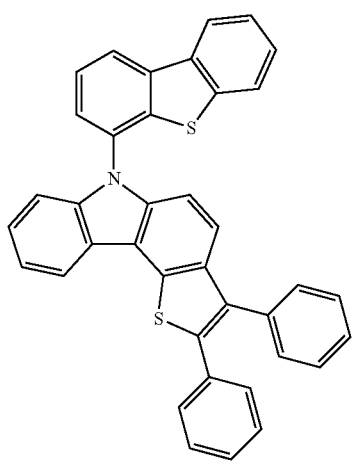
639
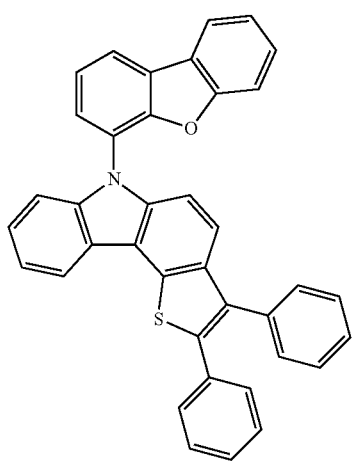
640
450
-continued
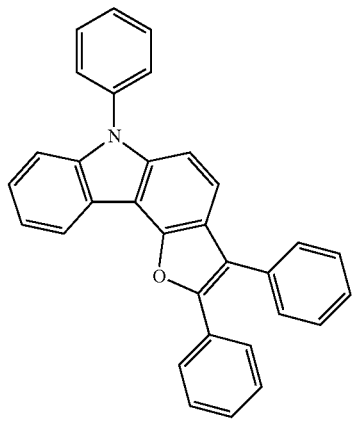
641
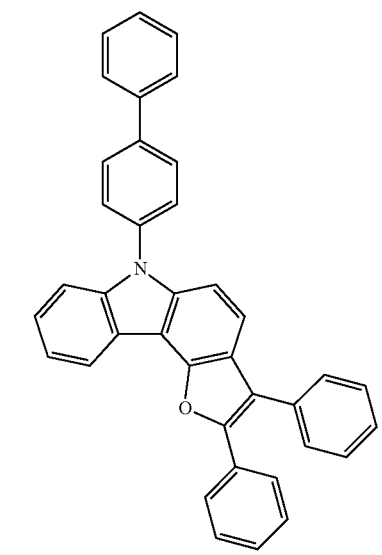
642
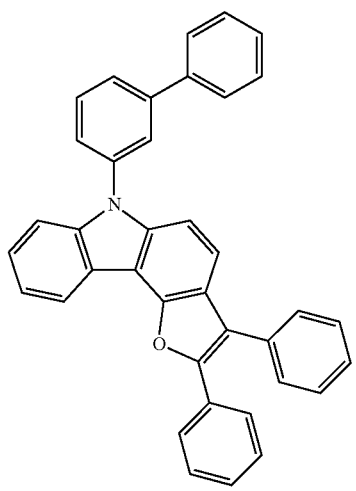
643

451
-continued
644
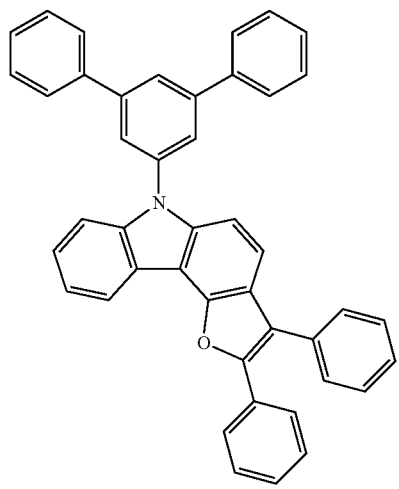
645
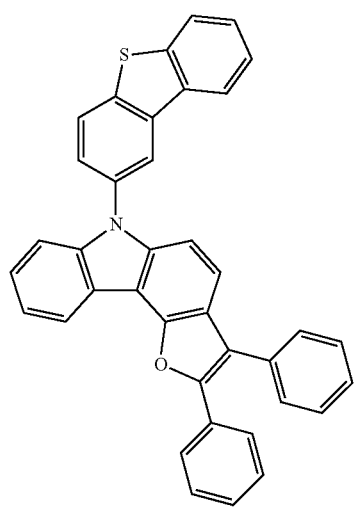
646
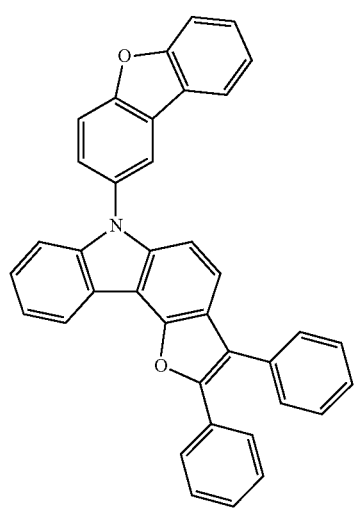
452
-continued
647
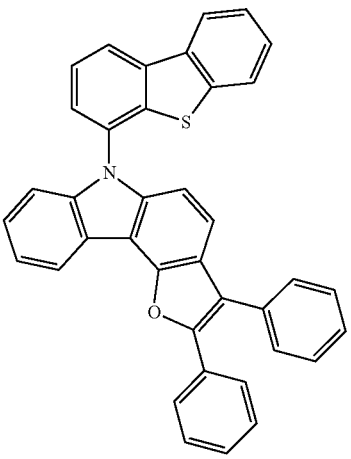
648
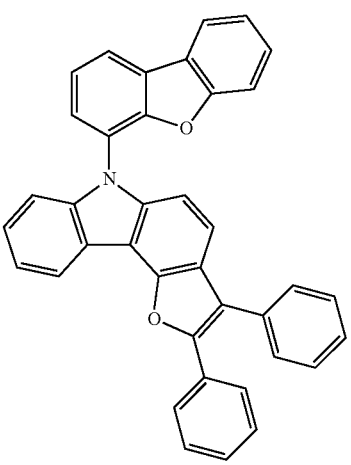
649
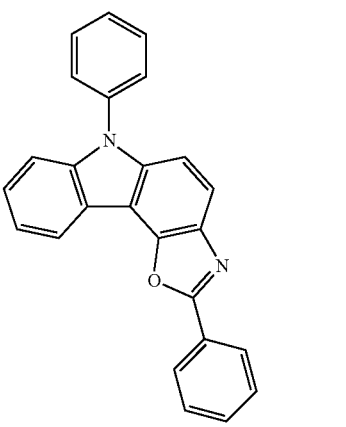

453
-continued
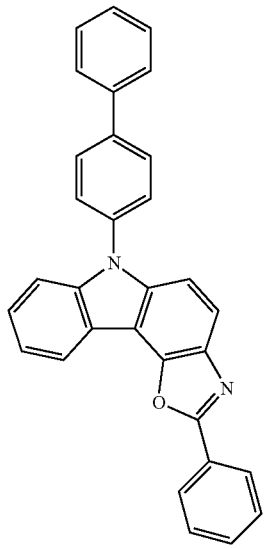
650
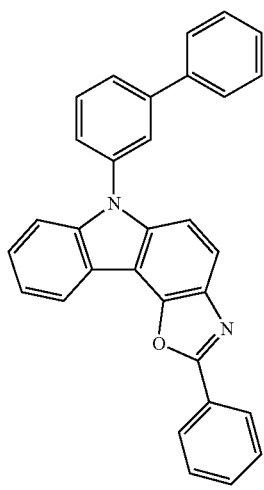
651
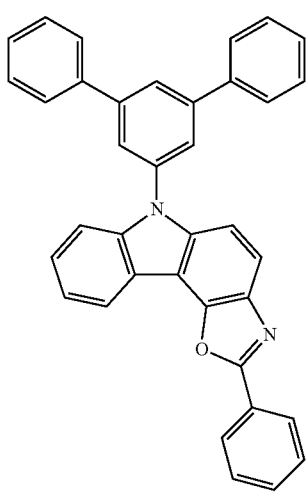
652
454
-continued
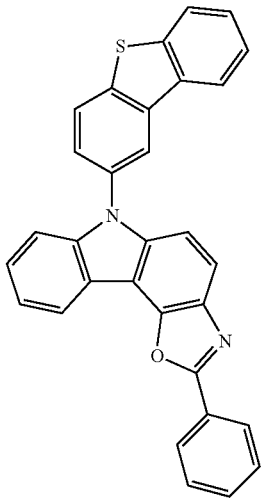
653
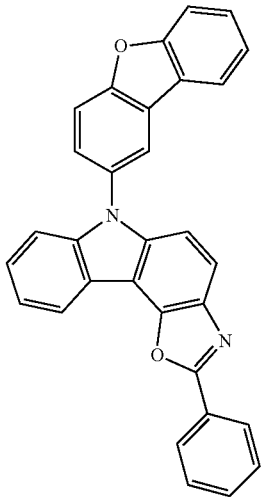
654
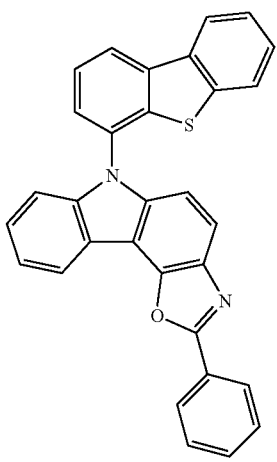
655

656

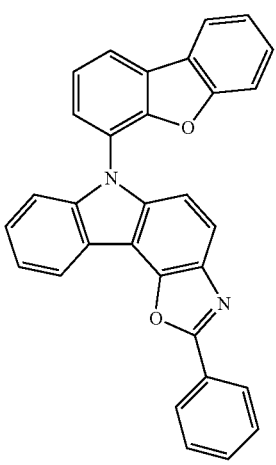

24. The organic light-emitting device of claim 18, wherein the emission layer comprises a dopant, and wherein the dopant is an organometallic compound represented by Formula 81:

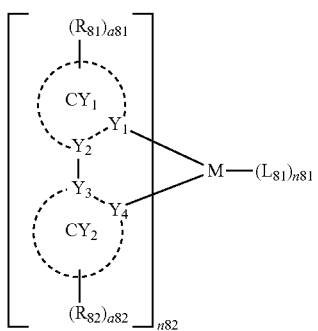

Formula 81 wherein, in Formula 81,

M is Ir, Pt, Os, Ti, Zr, Hf, Eu, Tb, or Tm;

$Y_1$ to $Y_4$ are each independently C or N; provided that $Y_1$ and $Y_2$ are linked to each other via a single bond or a double bond, and $Y_3$ and $Y_4$ are linked to each other via a single bond or a double bond;

$CY_1$ and $CY_2$ are each independently benzene, naphthalene, fluorene, spiro-fluorene, indene, pyrrole, thiophene, furan, imidazole, pyrazole, thiazole, isothiazole, oxazole, isooxazole, pyridine, pyrazine, pyrimidine, pyridazine, quinoline, isoquinoline, benzoquinoline, quinoxaline, quinazoline, carbazole, benzoimidazole, benzofuran, benzothiophene, isobenzothiophene, benzooxazole, isobenzooxazole, triazole, tetrazole, oxadiazole, triazine, dibenzofuran, or dibenzothiophene, wherein $CY_1$ and $CY_2$ are optionally linked to each other via a single bond or an organic linking group;

$R_{81}$ and $R_{82}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent nonaromatic condensed polycyclic group, a substituted or unsubstituted monovalent nonaromatic condensed heteropolycyclic group, —$N(Q_1)(Q_2)$, —$Si(Q_3)(Q_4)(Q_5)$, and —$B(Q_6)(Q_7)$;

a81 and a82 are each independently an integer selected from 1 to 5;

n81 is an integer selected from 0 to 4;

n82 is 1, 2, or 3; and $L_{81}$ is a monovalent organic ligand, a divalent organic ligand, or a trivalent organic ligand.

* * * * *